United States Patent
Dryer et al.

(10) Patent No.: US 11,209,957 B2
(45) Date of Patent: Dec. 28, 2021

(54) USER INTERFACES FOR CYCLE TRACKING

(71) Applicant: Apple Inc., Cupertino, CA (US)

(72) Inventors: Allison Dryer, San Francisco, CA (US); Gracee Agrawal, Sunnyvale, CA (US); Roxanne B. Brittain, Berkeley, CA (US); Vera Carr, San Francisco, CA (US); Dmitri Cavander, San Francisco, CA (US); Christine Lynette Curry, Sunnyvale, CA (US); Christine Eun, Palo Alto, CA (US); Charmian Bondoc Naguit, Richmond, CA (US); Shunan Zhang, Mountain View, CA (US)

(73) Assignee: Apple Inc., Cupertino, CA (US)

( * ) Notice: Subject to any disclaimer, the term of this patent is extended or adjusted under 35 U.S.C. 154(b) by 0 days.

(21) Appl. No.: 16/586,154

(22) Filed: Sep. 27, 2019

(65) Prior Publication Data

US 2020/0379611 A1    Dec. 3, 2020

Related U.S. Application Data

(60) Provisional application No. 62/856,024, filed on Jun. 1, 2019.

(51) Int. Cl.
| | | |
|---|---|---|
| *G06F 3/0482* | (2013.01) | |
| *G06F 3/0484* | (2013.01) | |
| *G16H 10/60* | (2018.01) | |
| *G06F 3/0488* | (2013.01) | |
| *G06Q 10/10* | (2012.01) | |

(52) U.S. Cl.
CPC .......... *G06F 3/0482* (2013.01); *G06F 3/0484* (2013.01); *G06F 3/04883* (2013.01); *G16H 10/60* (2018.01); *G06Q 10/1093* (2013.01)

(58) Field of Classification Search
CPC .. G06F 3/0482; G06F 3/04883; G06F 3/0484; G16H 10/60; G06Q 10/1093
See application file for complete search history.

(56) References Cited

U.S. PATENT DOCUMENTS

| | | | | |
|---|---|---|---|---|
| 5,515,344 A | * | 5/1996 | Ng | ..................... A61B 10/0012 368/10 |
| 5,642,731 A | | 7/1997 | Kehr | |

(Continued)

FOREIGN PATENT DOCUMENTS

| | | |
|---|---|---|
| CA | 2815518 A1 | 5/2012 |
| CN | 101107619 A | 1/2008 |

(Continued)

OTHER PUBLICATIONS

Vitti,MyFlotracker, https://web.archive.org/web/20170127104125/https://myflotracker.com/, 2017, 1-14 (Year: 2017).*

(Continued)

*Primary Examiner* — Ryan F Pitaro
(74) *Attorney, Agent, or Firm* — Dentons US LLP

(57) ABSTRACT

The present disclosure generally relates to cycle tracking. A notification for a respective recurrence of the recurring event is displayed. Representations of days are displayed with affordances for initiating processes for recording information corresponding to various days.

33 Claims, 71 Drawing Sheets

(56) References Cited

U.S. PATENT DOCUMENTS

| | | | |
|---|---|---|---|
| 6,416,471 B1 | 7/2002 | Kumar et al. | |
| 6,600,696 B1* | 7/2003 | Lynn | A61B 10/0012 368/10 |
| 6,705,972 B1 | 3/2004 | Takano et al. | |
| 6,950,839 B1* | 9/2005 | Green | A61B 10/0012 606/119 |
| 7,020,514 B1 | 3/2006 | Wiesel | |
| 7,128,693 B2 | 10/2006 | Brown et al. | |
| 7,166,078 B2* | 1/2007 | Saini | A61B 10/0012 600/551 |
| 7,739,148 B2 | 6/2010 | Suzuki et al. | |
| 8,321,006 B1 | 11/2012 | Snyder et al. | |
| 8,475,339 B2 | 7/2013 | Hwang et al. | |
| 8,676,170 B2 | 3/2014 | Porrati et al. | |
| 8,725,527 B1 | 5/2014 | Kahn et al. | |
| 8,758,262 B2 | 6/2014 | Rhee et al. | |
| 8,784,115 B1 | 7/2014 | Chuang | |
| 9,026,927 B2 | 5/2015 | Brumback et al. | |
| 9,224,291 B2 | 12/2015 | Moll-Carrillo et al. | |
| 9,579,060 B1 | 2/2017 | Lisy et al. | |
| 9,589,445 B2 | 3/2017 | White et al. | |
| 9,672,715 B2* | 6/2017 | Roberts | H04L 67/28 |
| 9,712,629 B2 | 7/2017 | Molettiere et al. | |
| 9,721,066 B1 | 8/2017 | Funaro et al. | |
| 9,730,621 B2 | 8/2017 | Cohen et al. | |
| 9,801,562 B1 | 10/2017 | Host-Madsen | |
| 9,808,206 B1 | 11/2017 | Zhao et al. | |
| 9,813,642 B1 | 11/2017 | Chen et al. | |
| 9,940,682 B2 | 4/2018 | Hoffman et al. | |
| 10,175,781 B2 | 1/2019 | Karagozler et al. | |
| 10,254,911 B2 | 4/2019 | Yang | |
| 10,339,830 B2 | 7/2019 | Han et al. | |
| 10,576,327 B2 | 3/2020 | Kim et al. | |
| 10,602,964 B2 | 3/2020 | Kerber | |
| 10,635,267 B2 | 4/2020 | Williams | |
| 10,674,942 B2 | 6/2020 | Williams et al. | |
| 10,762,990 B1 | 9/2020 | Schilling et al. | |
| 10,764,700 B1 | 9/2020 | Felton | |
| 10,796,549 B2 | 10/2020 | Roberts et al. | |
| 11,107,580 B1 | 8/2021 | Felton et al. | |
| 2001/0039503 A1 | 11/2001 | Chan et al. | |
| 2002/0095292 A1 | 7/2002 | Mittal et al. | |
| 2003/0126114 A1 | 7/2003 | Tedesco | |
| 2003/0181291 A1 | 9/2003 | Ogawa | |
| 2003/0191609 A1 | 10/2003 | Bernardi et al. | |
| 2003/0200483 A1 | 10/2003 | Sutton | |
| 2003/0216971 A1 | 11/2003 | Sick et al. | |
| 2003/0226695 A1 | 12/2003 | Mault | |
| 2004/0017300 A1 | 1/2004 | Kotzin et al. | |
| 2004/0034288 A1 | 2/2004 | Hennessy et al. | |
| 2004/0077958 A1 | 4/2004 | Kato et al. | |
| 2004/0190729 A1 | 9/2004 | Yonovitz et al. | |
| 2004/0193069 A1* | 9/2004 | Takehara | A61B 5/0537 600/551 |
| 2004/0236189 A1 | 11/2004 | Hawthorne et al. | |
| 2005/0010117 A1 | 1/2005 | Agutter et al. | |
| 2005/0027208 A1* | 2/2005 | Shiraishi | E03D 9/08 600/551 |
| 2005/0075214 A1 | 4/2005 | Brown et al. | |
| 2005/0079905 A1 | 4/2005 | Martens | |
| 2005/0149362 A1* | 7/2005 | Peterson | G06F 19/326 705/3 |
| 2005/0187794 A1 | 8/2005 | Kimak | |
| 2005/0228735 A1 | 10/2005 | Duquette | |
| 2005/0244013 A1 | 11/2005 | Battenberg et al. | |
| 2005/0272564 A1 | 12/2005 | Pyles et al. | |
| 2006/0094969 A1 | 5/2006 | Nissila | |
| 2006/0098109 A1 | 5/2006 | Ooki | |
| 2006/0106741 A1 | 5/2006 | Janarthanan | |
| 2006/0136173 A1 | 6/2006 | Case, Jr. et al. | |
| 2006/0149144 A1 | 7/2006 | Lynn et al. | |
| 2006/0152372 A1 | 7/2006 | Stout | |
| 2006/0182287 A1 | 8/2006 | Schulein et al. | |
| 2006/0205564 A1 | 9/2006 | Peterson | |
| 2006/0235319 A1 | 10/2006 | Belohlavek et al. | |
| 2006/0274908 A1 | 12/2006 | Choi | |
| 2007/0016440 A1 | 1/2007 | Stroup | |
| 2007/0056727 A1 | 3/2007 | Newman | |
| 2008/0005106 A1 | 1/2008 | Schumacher et al. | |
| 2008/0012701 A1 | 1/2008 | Kass et al. | |
| 2008/0021884 A1 | 1/2008 | Jones et al. | |
| 2008/0058626 A1 | 3/2008 | Miyata et al. | |
| 2008/0146892 A1 | 6/2008 | Leboeuf et al. | |
| 2008/0159547 A1 | 7/2008 | Schuler et al. | |
| 2008/0200312 A1 | 8/2008 | Tagliabue | |
| 2008/0205660 A1 | 8/2008 | Goldstein | |
| 2008/0228045 A1 | 9/2008 | Gao et al. | |
| 2008/0240519 A1 | 10/2008 | Nagamitsu | |
| 2008/0243885 A1 | 10/2008 | Harger et al. | |
| 2008/0300110 A1 | 12/2008 | Smith et al. | |
| 2009/0007596 A1 | 1/2009 | Goldstein et al. | |
| 2009/0052677 A1 | 2/2009 | Smith | |
| 2009/0065578 A1 | 3/2009 | Peterson et al. | |
| 2009/0105552 A1 | 4/2009 | Nishiyama et al. | |
| 2009/0118100 A1 | 5/2009 | Oliver et al. | |
| 2009/0172773 A1 | 7/2009 | Moore | |
| 2009/0180631 A1 | 7/2009 | Michael et al. | |
| 2009/0210078 A1 | 8/2009 | Crowley | |
| 2009/0216556 A1 | 8/2009 | Martin et al. | |
| 2009/0240521 A1 | 9/2009 | Simons et al. | |
| 2009/0245537 A1 | 10/2009 | Morin | |
| 2009/0259134 A1 | 10/2009 | Levine | |
| 2009/0262088 A1 | 10/2009 | Moll-Carrillo et al. | |
| 2009/0287103 A1 | 11/2009 | Pillai | |
| 2009/0287327 A1 | 11/2009 | Hsu et al. | |
| 2009/0290721 A1 | 11/2009 | Goldstein et al. | |
| 2009/0307105 A1 | 12/2009 | Lemay et al. | |
| 2010/0003951 A1 | 1/2010 | Ray et al. | |
| 2010/0010832 A1 | 1/2010 | Boute et al. | |
| 2010/0017489 A1 | 1/2010 | Birnbaum et al. | |
| 2010/0027807 A1 | 2/2010 | Jeon | |
| 2010/0046767 A1 | 2/2010 | Bayley et al. | |
| 2010/0062905 A1 | 3/2010 | Rottler et al. | |
| 2010/0076331 A1 | 3/2010 | Chan et al. | |
| 2010/0094658 A1 | 4/2010 | Mok et al. | |
| 2010/0099539 A1 | 4/2010 | Haataja | |
| 2010/0119093 A1 | 5/2010 | Uzuanis et al. | |
| 2010/0121700 A1 | 5/2010 | Wigder et al. | |
| 2010/0150378 A1 | 6/2010 | Lee et al. | |
| 2010/0222645 A1 | 9/2010 | Nadler et al. | |
| 2010/0292600 A1 | 11/2010 | Dibenedetto et al. | |
| 2010/0312138 A1* | 12/2010 | Regas | A61B 10/0012 600/551 |
| 2011/0010195 A1 | 1/2011 | Cohn | |
| 2011/0066051 A1 | 3/2011 | Moon et al. | |
| 2011/0093481 A1 | 4/2011 | Hussam | |
| 2011/0098928 A1 | 4/2011 | Hoffman et al. | |
| 2011/0119088 A1 | 5/2011 | Gunn | |
| 2011/0152656 A1* | 6/2011 | Weinert | G16H 10/20 600/365 |
| 2011/0166631 A1* | 7/2011 | Breining | A61N 5/0613 607/88 |
| 2011/0214162 A1 | 9/2011 | Brakensiek et al. | |
| 2011/0245623 A1 | 10/2011 | Chutani et al. | |
| 2011/0307821 A1 | 12/2011 | Martens | |
| 2012/0002510 A1 | 1/2012 | Berman, Jr. | |
| 2012/0023586 A1 | 1/2012 | Flickner et al. | |
| 2012/0029303 A1 | 2/2012 | Shaya | |
| 2012/0038651 A1 | 2/2012 | Case et al. | |
| 2012/0041767 A1 | 2/2012 | Hoffman et al. | |
| 2012/0059664 A1 | 3/2012 | Georgiev et al. | |
| 2012/0065480 A1 | 3/2012 | Badilini et al. | |
| 2012/0071770 A1 | 3/2012 | Grey et al. | |
| 2012/0112908 A1 | 5/2012 | Prykaeri et al. | |
| 2012/0116550 A1 | 5/2012 | Hoffman et al. | |
| 2012/0185267 A1 | 7/2012 | Kamen et al. | |
| 2012/0203124 A1 | 8/2012 | Lim | |
| 2012/0215115 A1 | 8/2012 | Takahashi | |
| 2012/0232929 A1 | 9/2012 | Experton | |
| 2012/0245447 A1 | 9/2012 | Karan et al. | |
| 2012/0283587 A1 | 11/2012 | Gosh et al. | |
| 2012/0283855 A1 | 11/2012 | Hoffman et al. | |
| 2012/0317167 A1 | 12/2012 | Rahman et al. | |

(56) References Cited

U.S. PATENT DOCUMENTS

| | | |
|---|---|---|
| 2012/0321094 A1 | 12/2012 | Schiller et al. |
| 2013/0002425 A1 | 1/2013 | Hatch et al. |
| 2013/0011819 A1 | 1/2013 | Horseman |
| 2013/0012788 A1 | 1/2013 | Horseman |
| 2013/0013331 A1 | 1/2013 | Horseman |
| 2013/0033376 A1 | 2/2013 | Seyed et al. |
| 2013/0065569 A1 | 3/2013 | Leipzig et al. |
| 2013/0073960 A1 | 3/2013 | Eppolito et al. |
| 2013/0095459 A1 | 4/2013 | Tran |
| 2013/0110264 A1 | 5/2013 | Weast et al. |
| 2013/0114100 A1 | 5/2013 | Torii et al. |
| 2013/0115583 A1 | 5/2013 | Gordon et al. |
| 2013/0144653 A1 | 6/2013 | Poe et al. |
| 2013/0151285 A1 | 6/2013 | Mclaren et al. |
| 2013/0158416 A1 | 6/2013 | Hatlestad et al. |
| 2013/0191647 A1 | 7/2013 | Ferrara et al. |
| 2013/0197679 A1 | 8/2013 | Balakrishnan et al. |
| 2013/0202121 A1 | 8/2013 | Georgiou et al. |
| 2013/0215042 A1 | 8/2013 | Messerschmidt et al. |
| 2013/0231575 A1 | 9/2013 | Erkkila et al. |
| 2013/0231947 A1 | 9/2013 | Shusterman |
| 2013/0262155 A1 | 10/2013 | Hinkamp |
| 2013/0268398 A1* | 10/2013 | Agami ............... G06Q 30/0631 705/26.7 |
| 2013/0274628 A1 | 10/2013 | Fausti et al. |
| 2013/0304510 A1 | 11/2013 | Chen et al. |
| 2013/0304616 A1* | 11/2013 | Raleigh ................. H04M 15/66 705/34 |
| 2013/0317380 A1 | 11/2013 | Liley et al. |
| 2013/0325396 A1 | 12/2013 | Yuen et al. |
| 2013/0325511 A1 | 12/2013 | Neagle, III |
| 2013/0332286 A1 | 12/2013 | Medelius et al. |
| 2014/0019162 A1 | 1/2014 | Skowronski et al. |
| 2014/0037107 A1 | 2/2014 | Marino et al. |
| 2014/0038781 A1 | 2/2014 | Foley et al. |
| 2014/0046926 A1 | 2/2014 | Walton |
| 2014/0073486 A1 | 3/2014 | Ahmed et al. |
| 2014/0081118 A1 | 3/2014 | Reinhold et al. |
| 2014/0088995 A1 | 3/2014 | Damani |
| 2014/0100885 A1 | 4/2014 | Stern |
| 2014/0127996 A1 | 5/2014 | Park et al. |
| 2014/0129007 A1 | 5/2014 | Utter, II |
| 2014/0129243 A1 | 5/2014 | Utter, II |
| 2014/0135592 A1 | 5/2014 | Ohnemus et al. |
| 2014/0142403 A1 | 5/2014 | Brumback et al. |
| 2014/0143678 A1 | 5/2014 | Mistry et al. |
| 2014/0164611 A1 | 6/2014 | Molettiere et al. |
| 2014/0176335 A1 | 6/2014 | Brumback et al. |
| 2014/0176475 A1 | 6/2014 | Myers et al. |
| 2014/0180595 A1 | 6/2014 | Brumback et al. |
| 2014/0184422 A1 | 7/2014 | Mensinger et al. |
| 2014/0189510 A1 | 7/2014 | Ozcan |
| 2014/0197946 A1 | 7/2014 | Park et al. |
| 2014/0200426 A1 | 7/2014 | Taub et al. |
| 2014/0240122 A1 | 8/2014 | Roberts et al. |
| 2014/0240349 A1 | 8/2014 | Tuukkanen |
| 2014/0266776 A1 | 9/2014 | Miller et al. |
| 2014/0275852 A1 | 9/2014 | Hong et al. |
| 2014/0275856 A1 | 9/2014 | Kohlrausch et al. |
| 2014/0278220 A1 | 9/2014 | Yuen |
| 2014/0297217 A1 | 10/2014 | Yuen |
| 2014/0327527 A1 | 11/2014 | Goldstein et al. |
| 2014/0336796 A1 | 11/2014 | Agnew |
| 2014/0344687 A1 | 11/2014 | Durham et al. |
| 2014/0354494 A1 | 12/2014 | Katz |
| 2014/0358012 A1 | 12/2014 | Richards et al. |
| 2014/0371887 A1 | 12/2014 | Hoffman et al. |
| 2015/0081210 A1 | 3/2015 | Yeh et al. |
| 2015/0089536 A1 | 3/2015 | Byerley |
| 2015/0099991 A1 | 4/2015 | Yamaguchi et al. |
| 2015/0106025 A1 | 4/2015 | Keller et al. |
| 2015/0110277 A1 | 4/2015 | Pidgeon et al. |
| 2015/0110279 A1 | 4/2015 | Tejerina |
| 2015/0120633 A1 | 4/2015 | Norlander et al. |
| 2015/0124067 A1 | 5/2015 | Bala et al. |
| 2015/0125832 A1 | 5/2015 | Tran |
| 2015/0127365 A1 | 5/2015 | Rizvi et al. |
| 2015/0142689 A1 | 5/2015 | Squires |
| 2015/0179186 A1 | 6/2015 | Swierk et al. |
| 2015/0181314 A1 | 6/2015 | Swanson |
| 2015/0182843 A1 | 7/2015 | Esposito et al. |
| 2015/0185967 A1 | 7/2015 | Ly et al. |
| 2015/0196804 A1 | 7/2015 | Koduri et al. |
| 2015/0205947 A1 | 7/2015 | Berman et al. |
| 2015/0216448 A1 | 8/2015 | Lotan et al. |
| 2015/0217163 A1 | 8/2015 | Amis et al. |
| 2015/0220883 A1 | 8/2015 | B'far et al. |
| 2015/0230717 A1 | 8/2015 | Wan |
| 2015/0262499 A1 | 9/2015 | Wicka et al. |
| 2015/0286800 A1 | 10/2015 | Kanagala et al. |
| 2015/0287421 A1 | 10/2015 | Benway et al. |
| 2015/0288944 A1 | 10/2015 | Nistico et al. |
| 2015/0289823 A1 | 10/2015 | Rack-Gomer et al. |
| 2015/0297134 A1 | 10/2015 | Albert et al. |
| 2015/0324751 A1 | 11/2015 | Orenstein et al. |
| 2015/0347711 A1 | 12/2015 | Soli et al. |
| 2015/0350799 A1 | 12/2015 | Schnaare et al. |
| 2015/0350861 A1 | 12/2015 | Soli et al. |
| 2016/0019360 A1 | 1/2016 | Pahwa et al. |
| 2016/0055420 A1 | 2/2016 | Karanam et al. |
| 2016/0058313 A1 | 3/2016 | Sato |
| 2016/0058336 A1 | 3/2016 | Blahnik et al. |
| 2016/0058337 A1 | 3/2016 | Blahnik et al. |
| 2016/0062582 A1 | 3/2016 | Wilson et al. |
| 2016/0063215 A1 | 3/2016 | Zamer |
| 2016/0085937 A1 | 3/2016 | Dettinger et al. |
| 2016/0086500 A1 | 3/2016 | Kaleal, III |
| 2016/0098522 A1 | 4/2016 | Weinstein |
| 2016/0106398 A1* | 4/2016 | Kuppuswami ......... G16H 50/20 705/2 |
| 2016/0109961 A1 | 4/2016 | Parshionikar |
| 2016/0132046 A1 | 5/2016 | Beoughter et al. |
| 2016/0135719 A1 | 5/2016 | Von Kraus et al. |
| 2016/0135731 A1 | 5/2016 | Drennan |
| 2016/0150978 A1 | 6/2016 | Yuen et al. |
| 2016/0166181 A1 | 6/2016 | Shennib |
| 2016/0174857 A1 | 6/2016 | Eggers et al. |
| 2016/0189051 A1 | 6/2016 | Mahmood |
| 2016/0196635 A1 | 7/2016 | Cho et al. |
| 2016/0210099 A1 | 7/2016 | Hampapuram et al. |
| 2016/0210434 A1 | 7/2016 | Al-Sharif |
| 2016/0235325 A1 | 8/2016 | Chou |
| 2016/0235374 A1 | 8/2016 | Miller et al. |
| 2016/0249857 A1 | 9/2016 | Choi et al. |
| 2016/0250517 A1 | 9/2016 | Tilvis et al. |
| 2016/0256082 A1 | 9/2016 | Ely et al. |
| 2016/0263435 A1 | 9/2016 | Venkatraman et al. |
| 2016/0270717 A1 | 9/2016 | Luna et al. |
| 2016/0275310 A1 | 9/2016 | Tribble et al. |
| 2016/0275990 A1 | 9/2016 | Vassort |
| 2016/0287177 A1 | 10/2016 | Huppert et al. |
| 2016/0292373 A1 | 10/2016 | Spors et al. |
| 2016/0299769 A1 | 10/2016 | Hunter et al. |
| 2016/0301761 A1 | 10/2016 | Sanchez-sandoval et al. |
| 2016/0301794 A1 | 10/2016 | Schlakman et al. |
| 2016/0302666 A1 | 10/2016 | Shaya |
| 2016/0314670 A1 | 10/2016 | Roberts et al. |
| 2016/0314683 A1 | 10/2016 | Felch et al. |
| 2016/0317341 A1 | 11/2016 | Galvan |
| 2016/0324457 A1 | 11/2016 | Dagum |
| 2016/0324488 A1 | 11/2016 | Olsen |
| 2016/0328991 A1 | 11/2016 | Simpson et al. |
| 2016/0332025 A1 | 11/2016 | Repka |
| 2016/0346607 A1 | 12/2016 | Rapfogel |
| 2016/0360100 A1 | 12/2016 | Kim et al. |
| 2017/0000348 A1 | 1/2017 | Karsten et al. |
| 2017/0000359 A1 | 1/2017 | Kohli et al. |
| 2017/0007159 A1 | 1/2017 | Dieffenderfer et al. |
| 2017/0007167 A1 | 1/2017 | Kostic et al. |
| 2017/0032168 A1 | 2/2017 | Kim |
| 2017/0039327 A1 | 2/2017 | Bitran et al. |
| 2017/0043214 A1 | 2/2017 | Higashi |
| 2017/0046024 A1 | 2/2017 | Dascola et al. |
| 2017/0053542 A1 | 2/2017 | Wilson et al. |

(56) References Cited

U.S. PATENT DOCUMENTS

| | | |
|---|---|---|
| 2017/0071551 A1 | 3/2017 | Jain et al. |
| 2017/0075551 A1 | 3/2017 | Robinson et al. |
| 2017/0086693 A1 | 3/2017 | Peterson et al. |
| 2017/0127997 A1 | 5/2017 | Hyde et al. |
| 2017/0132395 A1 | 5/2017 | Futch |
| 2017/0136297 A1 | 5/2017 | Penie |
| 2017/0150917 A1* | 6/2017 | Brief .................. A61B 5/4318 |
| 2017/0156593 A1 | 6/2017 | Ferber et al. |
| 2017/0161014 A1 | 6/2017 | Kikugawa et al. |
| 2017/0172522 A1 | 6/2017 | Insler et al. |
| 2017/0177797 A1 | 6/2017 | Kurniawan et al. |
| 2017/0181645 A1 | 6/2017 | Mahalingam et al. |
| 2017/0188841 A1 | 7/2017 | Ma et al. |
| 2017/0188893 A1 | 7/2017 | Venkatraman et al. |
| 2017/0188979 A1 | 7/2017 | Volpe |
| 2017/0202496 A1 | 7/2017 | Ramanathan |
| 2017/0235443 A1* | 8/2017 | Suzuki .................. G16H 10/20 715/780 |
| 2017/0237694 A1 | 8/2017 | Choudhary et al. |
| 2017/0243508 A1 | 8/2017 | Cheng et al. |
| 2017/0258455 A1* | 9/2017 | Qi ..................... A61B 10/0012 |
| 2017/0274149 A1 | 9/2017 | Aeschlimann |
| 2017/0274267 A1 | 9/2017 | Blahnik |
| 2017/0293727 A1 | 10/2017 | Klaassen et al. |
| 2017/0294174 A1 | 10/2017 | Albadawi et al. |
| 2017/0300186 A1 | 10/2017 | Kuhar et al. |
| 2017/0303844 A1 | 10/2017 | Baker et al. |
| 2017/0319184 A1* | 11/2017 | Sano .................. A61B 10/0012 |
| 2017/0330297 A1 | 11/2017 | Cronin et al. |
| 2017/0348562 A1 | 12/2017 | Jung et al. |
| 2017/0354845 A1 | 12/2017 | Williams et al. |
| 2017/0357329 A1 | 12/2017 | Park et al. |
| 2017/0357520 A1 | 12/2017 | De vries et al. |
| 2018/0000426 A1 | 1/2018 | Li |
| 2018/0001184 A1 | 1/2018 | Tran et al. |
| 2018/0011686 A1 | 1/2018 | Zhao et al. |
| 2018/0032234 A1 | 2/2018 | Michalske |
| 2018/0042559 A1 | 2/2018 | Cabrera et al. |
| 2018/0047277 A1 | 2/2018 | Thyroff |
| 2018/0049659 A1 | 2/2018 | Briante et al. |
| 2018/0049696 A1 | 2/2018 | Eom et al. |
| 2018/0055490 A1* | 3/2018 | Lee .................... A61B 5/14546 |
| 2018/0060522 A1 | 3/2018 | Petterson et al. |
| 2018/0064356 A1 | 3/2018 | Mendenhall et al. |
| 2018/0064388 A1 | 3/2018 | Heneghan et al. |
| 2018/0065025 A1 | 3/2018 | Toda et al. |
| 2018/0070861 A1 | 3/2018 | Eastman et al. |
| 2018/0074462 A1 | 3/2018 | Helder et al. |
| 2018/0074464 A1 | 3/2018 | Essery et al. |
| 2018/0081918 A1 | 3/2018 | Gravenites et al. |
| 2018/0096739 A1* | 4/2018 | Sano .................. G06F 16/9535 |
| 2018/0107962 A1 | 4/2018 | Lundin et al. |
| 2018/0117414 A1 | 5/2018 | Miyasaka et al. |
| 2018/0120985 A1 | 5/2018 | Wallace et al. |
| 2018/0132768 A1 | 5/2018 | Sasahara et al. |
| 2018/0137937 A1 | 5/2018 | Gass et al. |
| 2018/0140211 A1 | 5/2018 | Nakazawa et al. |
| 2018/0140927 A1 | 5/2018 | Kito et al. |
| 2018/0154212 A1 | 6/2018 | Park et al. |
| 2018/0157864 A1 | 6/2018 | Tribble et al. |
| 2018/0189077 A1 | 7/2018 | Gupta et al. |
| 2018/0211020 A1 | 7/2018 | Fukuda |
| 2018/0239869 A1 | 8/2018 | Laing et al. |
| 2018/0255159 A1* | 9/2018 | Cohen .................. H04L 63/10 |
| 2018/0256036 A1 | 9/2018 | Kogure et al. |
| 2018/0256078 A1 | 9/2018 | Vaterlaus |
| 2018/0256095 A1 | 9/2018 | Arnold et al. |
| 2018/0263510 A1 | 9/2018 | Cronin et al. |
| 2018/0263517 A1 | 9/2018 | Kubo |
| 2018/0279885 A1 | 10/2018 | Bulut |
| 2018/0336530 A1 | 11/2018 | Johnson et al. |
| 2018/0350451 A1 | 12/2018 | Ohnemus et al. |
| 2018/0368814 A1* | 12/2018 | R. Kudtarkar ....... A61B 5/7435 |
| 2018/0376107 A1 | 12/2018 | Shibaev et al. |
| 2019/0012898 A1 | 1/2019 | Wittrup |
| 2019/0014205 A1 | 1/2019 | Miloseski et al. |
| 2019/0034050 A1 | 1/2019 | Williams et al. |
| 2019/0034494 A1 | 1/2019 | Bradley et al. |
| 2019/0043337 A1 | 2/2019 | Liu et al. |
| 2019/0073618 A1 | 3/2019 | Kanukurthy et al. |
| 2019/0090800 A1 | 3/2019 | Bosworth et al. |
| 2019/0090816 A1 | 3/2019 | Horseman |
| 2019/0104951 A1 | 4/2019 | Valys et al. |
| 2019/0122523 A1 | 4/2019 | Roberts et al. |
| 2019/0138696 A1 | 5/2019 | Carpenter et al. |
| 2019/0150854 A1 | 5/2019 | Chung et al. |
| 2019/0192086 A1 | 6/2019 | Menon et al. |
| 2019/0206538 A1 | 7/2019 | Xing et al. |
| 2019/0223843 A1* | 7/2019 | Vitti .................... A61B 5/7435 |
| 2019/0228179 A1 | 7/2019 | Rakshit et al. |
| 2019/0228640 A1 | 7/2019 | Freedman et al. |
| 2019/0228847 A1 | 7/2019 | Soli |
| 2019/0240534 A1 | 8/2019 | Black |
| 2019/0252054 A1 | 8/2019 | Dirani et al. |
| 2019/0274562 A1 | 9/2019 | Soli et al. |
| 2019/0274563 A1 | 9/2019 | Soli et al. |
| 2019/0274564 A1 | 9/2019 | Soli et al. |
| 2019/0274565 A1 | 9/2019 | Soli et al. |
| 2019/0278556 A1 | 9/2019 | Usher et al. |
| 2019/0298230 A1 | 10/2019 | Nicholson et al. |
| 2019/0336044 A1 | 11/2019 | Williams et al. |
| 2019/0336045 A1 | 11/2019 | Williams et al. |
| 2019/0339849 A1 | 11/2019 | Williams et al. |
| 2019/0365332 A1 | 12/2019 | Fedichev et al. |
| 2019/0380624 A1 | 12/2019 | Ota et al. |
| 2020/0000441 A1* | 1/2020 | Lafon .................... A61B 5/01 |
| 2020/0069258 A1 | 3/2020 | Grinberg |
| 2020/0100693 A1 | 4/2020 | Velo |
| 2020/0126673 A1 | 4/2020 | Tanabe et al. |
| 2020/0245928 A1 | 8/2020 | Kang et al. |
| 2020/0261011 A1 | 8/2020 | Seppänen et al. |
| 2020/0273566 A1 | 8/2020 | Bhowmik et al. |
| 2020/0297249 A1 | 9/2020 | Williams et al. |
| 2020/0315544 A1 | 10/2020 | Levine |
| 2020/0356687 A1 | 11/2020 | Salzman et al. |
| 2020/0374682 A1 | 11/2020 | Newman et al. |
| 2020/0381099 A1 | 12/2020 | Crowley et al. |
| 2020/0381123 A1 | 12/2020 | Dryer et al. |
| 2020/0382866 A1 | 12/2020 | Felton |
| 2020/0382867 A1 | 12/2020 | Felton |
| 2020/0384314 A1 | 12/2020 | Lee et al. |
| 2021/0068714 A1 | 3/2021 | Crowley et al. |
| 2021/0113137 A1 | 4/2021 | Soli et al. |
| 2021/0225482 A1 | 7/2021 | Crowley et al. |

FOREIGN PATENT DOCUMENTS

| | | |
|---|---|---|
| CN | 102448555 A | 5/2012 |
| CN | 102790761 A | 11/2012 |
| CN | 103403627 A | 11/2013 |
| CN | 104720765 A | 6/2015 |
| CN | 106164808 A | 11/2016 |
| CN | 106537397 A | 3/2017 |
| CN | 106709235 A | 5/2017 |
| CN | 106725384 A | 5/2017 |
| CN | 107278138 A | 10/2017 |
| CN | 107361755 A | 11/2017 |
| CN | 107591211 A | 1/2018 |
| CN | 107713981 A | 2/2018 |
| EP | 2391004 A1 | 11/2011 |
| EP | 2568409 A1 | 3/2013 |
| EP | 2921899 A2 | 9/2015 |
| EP | 3042606 A1 | 7/2016 |
| EP | 3096235 A1 | 11/2016 |
| EP | 3101882 A2 | 12/2016 |
| EP | 3557590 A1 | 10/2019 |
| JP | 2005-79814 A | 3/2005 |
| JP | 2008-11865 A | 1/2008 |
| JP | 2010-517725 A | 5/2010 |
| JP | 2010-162297 A | 7/2010 |
| JP | 2010-181280 A | 8/2010 |
| JP | 2012-524640 A | 10/2012 |
| JP | 2013-544140 A | 12/2013 |
| JP | 2016-502875 A | 2/2016 |

(56) References Cited

FOREIGN PATENT DOCUMENTS

| | | |
|---|---|---|
| JP | 2016-528016 A | 9/2016 |
| JP | 2016-177151 A | 10/2016 |
| JP | 2016-202751 A | 12/2016 |
| JP | 2017-134689 A | 8/2017 |
| JP | 2017-211994 A | 11/2017 |
| JP | 2017-532069 A | 11/2017 |
| KR | 10-2012-0023657 A | 3/2012 |
| KR | 10-2013-0093837 A | 8/2013 |
| KR | 10-2013-0111569 A | 10/2013 |
| KR | 10-2013-0111570 A | 10/2013 |
| KR | 10-1594486 B1 | 2/2016 |
| KR | 10-2016-0028351 A | 3/2016 |
| KR | 10-2017-0003608 A | 1/2017 |
| KR | 10-2019-0094795 A | 8/2019 |
| WO | 2001/096986 A2 | 12/2001 |
| WO | 2003/067202 A2 | 8/2003 |
| WO | 2006/046648 A1 | 5/2006 |
| WO | 2008/073359 A2 | 6/2008 |
| WO | 2010/126825 A1 | 11/2010 |
| WO | 2012/060588 A2 | 5/2012 |
| WO | 2012/061438 A2 | 5/2012 |
| WO | 2012/061440 A2 | 5/2012 |
| WO | 2013/109916 A1 | 7/2013 |
| WO | 2014/015378 A1 | 1/2014 |
| WO | 2015/027133 A1 | 2/2015 |
| WO | 2015/153803 A1 | 10/2015 |
| WO | 2015/187799 A1 | 12/2015 |
| WO | 2015/198488 A1 | 12/2015 |
| WO | 2016/036582 A2 | 3/2016 |
| WO | 2016/151479 A1 | 9/2016 |
| WO | 2016/161152 A1 | 10/2016 |
| WO | 2016/164475 A1 | 10/2016 |
| WO | 2017/003045 A1 | 1/2017 |
| WO | 2017/037242 A1 | 3/2017 |
| WO | 2017/062621 A1 | 4/2017 |
| WO | 2017/087642 A1 | 5/2017 |
| WO | 2017/090810 A1 | 6/2017 |
| WO | 2017/215203 A1 | 12/2017 |
| WO | 2018/148356 A1 | 8/2018 |
| WO | 2019/020977 A1 | 1/2019 |
| WO | 2019/168956 A1 | 9/2019 |

OTHER PUBLICATIONS

James Cook, German period tracking app Clue has over 2.5 million active users—but it's still not sure how it's going to make money, 2016,Insider, www.businessinsider.com/interview-with-clue-ceo-ida-tin-period-tracking-app-apple-2016-1 (Year: 2016).*

Advisory Action received for U.S. Appl. No. 16/143,909, dated Nov. 7, 2019, 5 pages.

Decision to Grant received for Danish Patent Application No. PA201870600, dated Oct. 17, 2019, 2 pages.

Notice of Allowance received for U.S. Appl. No. 16/143,959, dated Oct. 31, 2019, 10 pages.

Advisory Action received for U.S. Appl. No. 16/144,864, dated Jul. 29, 2019, 6 pages.

Advisory Action received for U.S. Appl. No. 16/144,849, dated Aug. 12, 2019, 5 pages.

Certificate of Examination received for Australian Patent Application No. 2019100222, dated Aug. 29, 2019, 2 pages.

Decision to Grant received for Danish Patent Application No. PA201870379, dated Jul. 5, 2019, 2 pages.

Final Office Action received for U.S. Appl. No. 15/167,699, dated Jun. 30, 2017, 8 pages.

Final Office Action received for U.S. Appl. No. 16/143,909, dated Aug. 28, 2019, 20 pages.

Final Office Action received for U.S. Appl. No. 16/143,997, dated Sep. 30, 2019, 16 pages.

Final Office Action received for U.S. Appl. No. 16/144,030, dated Oct. 1, 2019, 13 pages.

Final Office Action received for U.S. Appl. No. 16/144,849, dated Jun. 7, 2019, 29 pages.

Final Office Action received for U.S. Appl. No. 16/144,864, dated May 17, 2019, 24 pages.

"Fitbit App", Available online at: <http://web.archive.org/web/20180114083150/https://www.fitbit.com/au/app>, Jan. 14, 2018, 8 pages.

"Graphs and Charts", Online available at: <https://www.teachervision.com/lesson-planning/graph-chart-teacher-resources>, retrieved on Dec. 12, 2018, 4 pages.

Intention to Grant received for Danish Patent Application No. PA201870379, dated May 2, 2019, 2 pages.

Intention to Grant received for Danish Patent Application No. PA201870600, dated Jul. 10, 2019, 2 pages.

International Search Report and Written Opinion received for PCT Patent Application No. PCT/US2019/019694, dated Sep. 2, 2019, 17 pages.

International Search Report and Written Opinion received for PCT Patent Application No. PCT/US2019/024570, dated Aug. 8, 2019, 18 pages.

Invitation to Pay Additional Fees received for PCT Patent Application No. PCT/US2019/019694, mailed on Jul. 10, 2019, 12 pages.

"Multi-Set Bar Chart", The Data Visualization Catalogue, Available Online at: https://datavizcatalogue.com/methods/multiset_barchart.html, Feb. 8, 2014, 3 pages.

Non-Final Office Action Received for U.S. Appl. No. 16/144,864, dated Dec. 18, 2018, 19 pages.

Non-Final Office Action received for U.S. Appl. No. 15/167,699, dated Oct. 21, 2016, 13 pages.

Non-Final Office Action received for U.S. Appl. No. 16/143,909, dated Apr. 19, 2019, 16 pages.

Non-Final Office Action received for U.S. Appl. No. 16/143,959, dated Apr. 17, 2019, 15 pages.

Non-Final Office Action received for U.S. Appl. No. 16/143,997, dated May 21, 2019, 15 pages.

Non-Final Office Action received for U.S. Appl. No. 16/144,030, dated Apr. 12, 2019, 8 pages.

Non-Final Office Action received for U.S. Appl. No. 16/144,849, dated Dec. 31, 2018, 28 pages.

Non-Final Office Action received for U.S. Appl. No. 16/144,849, dated Sep. 17, 2019, 9 pages.

Notice from the European Patent Office dated Oct. 1, 2007 Concerning Business Methods, Official Journal EPO, available online at <http://archive.epo.org/epo/pubs/oj007/11_07/11_5927.pdf>, Nov. 2007, pp. 592-593.

Notice of Acceptance received for Australian Patent Application No. 2013406817, dated Nov. 21, 2017, 3 pages.

Notice of Allowance received for Chinese Patent Application No. 201380081315.7, dated Jan. 4, 2019, 2 pages (1 page of English Translation and 1 page of Official Copy).

Notice of Allowance received for Korean Patent Application No. 10-2016-7014353, dated Aug. 2, 2018, 3 pages (Official Copy Only) {See Communication under 37 CFR § 1.98(a) (3)}.

Notice of Allowance received for Korean Patent Application No. 10-2018-7032096, dated Dec. 12, 2018, 4 pages (1 page of English Translation and 3 pages of Official copy).

Notice of Allowance received for U.S. Appl. No. 15/167,699, dated Oct. 27, 2017, 8 pages.

Office Action received for Australian Patent Application No. 2013406817, dated Aug. 1, 2017, 3 pages.

Office Action received for Australian Patent Application No. 2013406817, dated Nov. 14, 2016, 4 pages.

Office Action received for Australian Patent Application No. 2018201260, dated Feb. 12, 2019, 6 pages.

Office Action received for Australian Patent Application No. 2018201260, dated Jul. 17, 2019, 3 pages.

Office Action received for Australian Patent Application No. 2018201260, dated Sep. 5, 2019, 5 pages.

Office Action received for Australian Patent Application No. 2019100222, dated May 24, 2019, 6 pages.

Office Action received for Australian Patent Application No. 2019100495, dated Sep. 17, 2019, 7 pages.

Office Action received for Australian Patent Application No. 2019222943, dated Oct. 3, 2019, 3 Pages.

(56) References Cited

OTHER PUBLICATIONS

Office Action received for Chinese Patent Application No. 201380081315.7, dated Aug. 16, 2018, 6 pages (3 pages of English Translation and 3 pages of Official Copy).
Office Action received for Chinese Patent Application No. 201380081315.7, dated Mar. 2, 2018, 12 pages (5 pages of English Translation and 7 pages of Official Copy).
Office Action received for Danish Patent Application No. PA201870378, dated Feb. 25, 2019, 3 pages.
Office Action received for Danish Patent Application No. PA201870379, dated Feb. 28, 2019, 3 pages.
Office Action received for Danish Patent Application No. PA201870380, dated Mar. 27, 2019, 4 pages.
Office Action received for Danish Patent Application No. PA201870380, dated Sep. 11, 2018, 9 pages.
Office Action received for Danish Patent Application No. PA201870600, dated May 8, 2019, 3 pages.
Office Action received for Danish Patent Application No. PA201870601, dated Dec. 13, 2018, 8 pages.
Office Action received for Danish Patent Application No. PA201870601, dated Jun. 25, 2019, 3 pages.
Office Action received for Danish Patent Application No. PA201870602, dated Jun. 26, 2019, 3 pages.
Office Action received for European Patent Application No. 13812320,3, dated Mar. 28, 2018, 7 pages.
Office Action received for Korean Patent Application No. 10-2016-7014353, dated Mar. 21, 2018, 11 pages (5 pages of English Translation and 6 pages of Official Copy).
Search Report and Opinion received for Danish Patent Application No. PA201870378, dated Sep. 10, 2018, 9 pages.
Search Report and Opinion received for Danish Patent Application No. PA201870379, dated Sep. 14, 2018, 9 pages.
Search Report and Opinion received for Danish Patent Application No. PA201870599, dated Dec. 21, 2018, 9 pages.
Search Report and Opinion received for Danish Patent Application No. PA201870600, dated Jan. 31, 2019, 8 pages.
Search Report and Opinion received for Danish Patent Application No. PA201870602, dated Dec. 19, 2018, 8 pages.
"Suunto Spartan Trainer Wrist HR 1.12", Online Available at :–https://web.archive.org/web/20180127155200/https://ns.suunto.com/Manuals/Spartan_Trainer_WristHR/Userguides/Suunto_Spartan_Trainer_WristHR_UserGuide_EN.pdf, Jan. 17, 2018, 47 pages.
"Visual Pace Alarm app", Available Online at: <https://apps.garmin.com/en-US/apps/3940f3a2-4847-4078-a911-d77422966c82>, Oct. 19, 2016, 1 page.
Casella Cel Casella, "The Casella dBadge2—World's First Truly Wireless Noise Dosimeter and Airwave App!", Retrieved from URL: <https://www.youtube.com/watch?v=Xvy2fl3cgYo>, May 27, 2015, 3 pages.
CNET, "Google Fit's automatic activity tracking is getting smarter on Android Wear", Available online at: <https://www.youtube.com/watch?v=IttzlCid_d8>, May 18, 2016, 1 page.
Evergreen, et al., "Bar Chart", Better Evaluation, Available Online at: <https://www.betterevaluation.org/en/evaluation-options/BarChart>, Oct. 31, 2014, 8 pages.
Garmin, "Fenix 5x Owner's Manual", Online Available at :–https://web.archive.org/web/20180127170640/https://static.garmin.com/pumac/fenix5x_OM_EN.pdf, Jan. 27, 2018, 42 pages.
Megadepot, "Casella dBadge2 Noise Dosimeter", Retrieved from URL: <https://www.youtube.com/watch?v=pHiHLiYCD08>, Jun. 12, 2018, 3 pages.
International Preliminary Report on Patentability received for PCT Patent Application No. PCT/US2013/073188, dated Jun. 16, 2016, 6 pages.
International Search Report and Written Opinion received for PCT Patent Application No. PCT/US2013/073188, dated Feb. 24, 2014, 8 pages.
Rainmaker, "Garmin Fenix3 New Auto Climb Functionality", Available online at: https://www.youtube.com/watch?v=iuavOSNpVRc, Feb. 19, 2015, 1 page.

Rizknows, "Tom Tom Multisport Cardio Review", Online available at :–https://www.youtube.com/watch?v=WoVCzLrSN9A, Sep. 4, 2015, 1 page.
Smith, "Garmin Fenix 5 Activity/Smart Watch Review", Online Available at :–<https://www.youtube.com/watch?v=6PkQxXQxpoU>, Sep. 2, 2017, 1 page.
SportsTechGuides, "Garmin Fenix 5: How to Add Power Data Fields", Online Available at :–<https://www.youtube.com/watch?v=ZkPptnnXEiQ>, Apr. 29, 2017, 2 pages.
SportsTechGuides, "Garmin Fenix 5: How To Set Up Run Alerts", Online Available at :–<https://www.youtube.com/watch?v=gSMwv8vlhB4>, May 13, 2017, 2 pages.
StudioSixDigital, "Dosimeter", Retrieved from URL: <https://www.youtube.com/watch?v=CZ4jkgutp3l>, Mar. 3, 2017, 3 pages.
Suunto, "Suunto Spartan—Heart Rate Zones", Online Available at :–<https://www.youtube.com/watch?v=aixfoCnS0OU>, Mar. 19, 2018, 2 pages.
Teunmo, "Data field: Visual Pace Alarm", Garmin Forum; Available online at: <https://forums.garmin.com/forum/developers/connect-iq/connect-iq-showcase/115996-data-field-visual-pace-alarm>, Nov. 17, 2015, 10 pages.
TomTom, "TomTom Runner & Multi-Sport Reference Guide", Online available at :–<https://web.archive.org/web/20150908075934/http://download.tomtom.com/open/manuals/Runner_Multi-Sport/refman/TomTom-Runner-Multi-Sport-RG-en-gb.pdf>, Sep. 8, 2015, 44 pages.
Weiyu, Jiang, et al., A Multi-Identities Authentication and Authorization Schema in Cloud Computing, Aug. 20, 2012, pp. 7-10 (English Abstract Submitted).
Zlelik, "Garmin Fenix 5 Open Water Swimming Activity Demo", Online Available at :–<https://www.youtube.com/watch?v=iSVhdvw2dcs>, Jun. 9, 2017, 1 page.
Corrected Notice of Allowance received for U.S. Appl. No. 16/143,909, dated Feb. 20, 2020, 3 pages.
Final Office Action received for U.S. Appl. No. 16/144,030, dated Feb. 13, 2020, 11 pages.
Invitation to Pay Search Fees received for European Patent Application No. 19726205.8, mailed on Feb. 14, 2020, 5 pages.
Non-Final Office Action received for U.S. Appl. No. 16/144,864, dated Jan. 31, 2020, 29 pages.
Office Action received for Danish Patent Application No. PA201870602, dated Feb. 5, 2020, 3 pages.
Advisory Action received for U.S. Appl. No. 16/143,997, dated Dec. 26, 2019, 7 pages.
Corrected Notice of Allowance received for U.S. Appl. No. 16/143,959, dated Dec. 13, 2019, 2 pages.
Office Action received for Danish Patent Application No. PA201870599, dated Dec. 20, 2019, 5 pages.
Office Action received for Australian Patent Application No. 2019100495, dated Mar. 16, 2020, 3 pages.
Supplemental Notice of Allowance received for U.S. Appl. No. 16/144,849, dated Mar. 31, 2020, 2 pages.
Applicant-Initiated Interview Summary received for U.S. Appl. No. 16/138,809, dated Jun. 9, 2020, 4 pages.
Notice of Allowance received for U.S. Appl. No. 15/885,448, dated Jun. 16, 2020, 5 pages.
Office Action received for European Patent Application No. 19721883.7, dated May 28, 2020, 11 pages.
Corrected Notice of Allowance received for U.S. Appl. No. 16/143,909, dated Mar. 18, 2020, 3 pages.
Non-Final Office Action received for U.S. Appl. No. 16/138,809, dated Feb. 28, 2020, 22 pages.
Notice of Allowance received for U.S. Appl. No. 16/144,849, dated Mar. 6, 2020, 9 pages.
Office Action received for Australian Patent Application No. 2019100495, dated Mar. 6, 2020, 3 pages.
Office Action received for Danish Patent Application No. PA201870380, dated Mar. 5, 2020, 2 pages.
Office Action received for Japanese Patent Application No. 2019-162293, dated Jan. 31, 2020, 8 pages (4 pages of English Translation and 4 pages of Official Copy).

(56) References Cited

OTHER PUBLICATIONS

Office Action received for Korean Patent Application No. 10-2019-7025538, dated Feb. 17, 2020, 12 pages (6 pages of English Translation and 6 pages of Official Copy).
Wesley, "Apple Watch Series 1", Online available at: http://toolbox.info/blog/archives/1737-unknown.html, May 28, 2015, 5 pages (Official copy only) (See Communication under 37 CFR § 1.98(a) (3)).
Youtube, "Apple Watch Series 3", Online available at: https://www.youtube.com/watch?v=iBPr9gEfkK8, Nov. 21, 2017, 15 pages (Official copy only) (See Communication under 37 CFR § 1.98(a) (3)).
Applicant Initiated Interview Summary received for U.S. Appl. No. 16/144,849, dated Jan. 21, 2020, 6 pages.
Notice of Acceptance received for Australian Patent Application No. 2018201260, dated Jan. 15, 2020, 3 pages.
Notice of Allowance received for U.S. Appl. No. 16/143,909, dated Jan. 21, 2020, 9 pages.
Office Action received for Danish Patent Application No. PA201870378, dated Jan. 6, 2020, 3 pages.
Office Action received for Danish Patent Application No. PA201870601, dated Jan. 14, 2020, 3 pages.
Office Action received for European Patent Application No. 19721883.7, dated Jan. 10, 2020, 4 pages.
Intention to Grant received for Danish Patent Application No. PA201870601, dated Apr. 24, 2020, 2 pages.
Intention to Grant received for Danish Patent Application No. PA201870602, dated Apr. 24, 2020, 2 pages.
Office Action received for Indian Patent Application No. 201617016494, dated Apr. 27, 2020, 7 pages.
Final Office Action received for U.S. Appl. No. 16/144,864, dated May 28, 2020, 29 pages.
Notice of Acceptance received for Australian Patent Application No. 2019222943, dated May 5, 2020, 3 pages.
Applicant Initiated Interview Summary received for U.S. Appl. No. 16/144,864, dated Apr. 29, 2020, 4 pages.
Non-Final Office Action received for U.S. Appl. No. 15/885,448, dated Apr. 16, 2020, 9 pages.
Notice of Allowance received for U.S. Appl. No. 16/144,849, dated Apr. 17, 2020, 2 pages.
Advisory Action received for U.S. Appl. No. 16/144,864, dated Jul. 6, 2020, 6 pages.
Applicant Initiated Interview Summary received for U.S. Appl. No. 16/143,997, dated Aug. 13, 2020, 3 pages.
Applicant-Initiated Interview Summary received for U.S. Appl. No. 16/144,864, dated Jun. 22, 2020, 3 pages.
Applicant-Initiated Interview Summary received for U.S. Appl. No. 16/584,186, dated Feb. 3, 2020, 4 pages.
Applicant-Initiated Interview Summary received for U.S. Appl. No. 16/880,552, dated Oct. 20, 2020, 6 pages.
Chatrzarrin Hanieh, "Feature Extraction for the Differentiation of Dry and Wet Cough Sounds", Carleton University, Sep. 2011, 144 pages.
Corrected Notice of Allowance received for U.S. Appl. No. 16/584,186, dated Jul. 31, 2020, 2 pages.
Decision to Grant received for Danish Patent Application No. PA201870601, dated Aug. 17, 2020, 2 pages.
Decision to Grant received for Danish Patent Application No. PA201870602, dated Aug. 18, 2020, 2 pages.
European Search Report received for European Patent Application No. 20182116.2, dated Oct. 21, 2020, 4 pages.
Extended European Search Report received for European Patent Application No. 20180581.9, dated Aug. 12, 2020, 9 pages.
Extended European Search Report received for European Patent Application No. 20180592.6, dated Aug. 11, 2020, 10 pages.
Final Office Action received for U.S. Appl. No. 16/138,809, dated Aug. 27, 2020, 24 pages.
Haslam Oliver, "Stop Coronavirus in its Tracks by Using This Apple Watch App to Time Hand Washes", Available Online at: <https://www.imore.com/stop-coronavirus-its-tracks-using-apple-watch-app-time-hand-washes>, Mar. 12, 2020, 12 pages.

International Preliminary Report on Patentability received for PCT Patent Application No. PCT/US2019/014215, dated Aug. 6, 2020, 14 pages.
International Preliminary Report on Patentability received for PCT Patent Application No. PCT/US2019/019694, dated Sep. 24, 2020, 12 pages.
International Preliminary Report on Patentability received for PCT Patent Application No. PCT/US2019/024570, dated Nov. 19, 2020, 10 pages.
International Search Report and Written Opinion received for PCT Patent Application No. PCT/US2019/014215, dated Jun. 4, 2019, 17 pages.
International Search Report and written Opinion received for PCT Patent Application No. PCT/US2020/025768, dated Aug. 10, 2020, 11 pages.
International Search Report and Written Opinion received for PCT Patent Application No. PCT/US2020/042439, dated Oct. 9, 2020, 14 pages.
Invitation to Pay Addition Fees and Partial International Search Report received for PCT Patent Application No. PCT/US2019/014215, dated Apr. 12, 2019, 13 pages.
Invitation to Pay Addition Fees received for PCT Patent Application No. PCT/US2020/035474, mailed on Oct. 2, 2020, 11 pages.
Liaqat et al., "Challenges with Real-World Smartwatch based Audio Monitoring", WearSys'18, Munich, Germany, Available Online at: <https://doi.org/10.1145/3211960.3211977>, Jun. 10, 2018, 6 pages.
Lyles Taylor, "Wear OS Smartwatches are Now Sending Reminders to Wash Your Hands", Available Online at: <https://www.theverge.com/2020/4/14/21221294/google-wear-os-smartwatches-reminders-wash-your-hands>, Apr. 14, 2020, 2 pages.
Non-Final Office Action received for U.S. Appl. No. 16/143,997, dated Jul. 27, 2020, 15 pages.
Non-Final Office Action received for U.S. Appl. No. 16/144,030, dated Nov. 5, 2020, 5 pages.
Non-Final Office Action received for U.S. Appl. No. 16/584,186, dated Dec. 6, 2019, 13 pages.
Non-Final Office Action received for U.S. Appl. No. 16/880,552, dated Jul. 23, 2020, 19 pages.
Non-Final Office Action received for U.S. Appl. No. 16/894,309, dated Oct. 15, 2020, 24 pages.
Non-Final Office Action received for U.S. Appl. No. 16/907,261, dated Sep. 30, 2020, 22 pages.
Non-Final Office Action received for U.S. Appl. No. 17/031,717, dated Nov. 19, 2020, 22 pages.
Notice of Acceptance received for Australian Patent Application No. 2020204153, dated Jul. 6, 2020, 3 pages.
Notice of Allowance received for Chinese Patent Application No. 201910972529.2, dated Sep. 14, 2020, 6 pages (3 pages of English Translation and 3 pages of Official Copy).
Notice of Allowance received for U.S. Appl. No. 16/144,864, dated Jul. 28, 2020, 27 pages.
Notice of Allowance received for U.S. Appl. No. 16/144,864, dated Sep. 10, 2020, 3 pages.
Notice of Allowance received for U.S. Appl. No. 16/144,864, dated Sep. 16, 2020, 2 pages.
Notice of Allowance received for U.S. Appl. No. 16/144,864, dated Sep. 29, 2020, 2 pages.
Notice of Allowance received for U.S. Appl. No. 16/584,186, dated Mar. 24, 2020, 10 pages.
Office Action received for Australian Patent Application No. 2019234289, dated Nov. 2, 2020, 6 pages.
Office Action received for Australian Patent Application No. 2020230340, dated Nov. 2, 2020, 5 pages.
Office Action received for Chinese Patent Application No. 201910858933.7, dated Aug. 18, 2020, 14 pages (7 pages of English Translation and 7 pages of Official Copy).
Office Action received for Chinese Patent Application No. 201910972529.2, dated Jun. 28, 2020, 8 pages (1 page of English Translation and 7 pages of Official Copy).
Office Action received for Danish Patent Application No. PA201970534, dated Jun. 29, 2020, 2 pages.
Office Action received for European Patent Application No. 19726205.8, dated Jun. 26, 2020, 9 pages.

(56) References Cited

OTHER PUBLICATIONS

Office Action received for European Patent Application No. 20182116.2, dated Nov. 6, 2020, 9 pages.
Office Action received for Japanese Patent Application No. 2019-162293, dated Jul. 27, 2020, 9 pages (5 pages of English Translation and 4 pages of Official Copy).
Office Action received for Japanese Patent Application No. 2020-104679, dated Sep. 18, 2020, 13 pages (7 pages of English Translation and 6 pages of Official Copy).
Office Action received for Korean Patent Application No. 10-2019-7025538, dated Aug. 15, 2020, 8 pages (4 pages of English Translation and 4 pages of Official Copy).
Peters Jay, "Samsung's Smartwatches Get a Hand-Washing Reminder and Timer App", Available Online at: <https://www.theverge.com/2020/4/17/21225205/samsung-smartwatch-galaxy-active-hand-washing-timer-reminder-app>, Apr. 17, 2020, 2 pages.
Result of Consultation received for European Patent Application No. 19721883.7, dated Oct. 7, 2020, 3 pages.
Schoon Ben, "Wear OS Now Sends a Reminder to Wash Your Hands Every Few Hours", Available Online at: <https://9to5google.com/2020/04/14/wear-os-wash-hands-reminder-coronavirus/>, Apr. 14, 2020, 7 pages.
Search Report and Opinion received for Danish Patent Application No. PA201970534, dated Sep. 23, 2019, 6 pages.
Summons to Attend Oral Proceedings received for European Patent Application No. 19726205.8, mailed on Oct. 29, 2020, 13 pages.
Epstein et al., "Examining Menstrual Tracking to Inform the Design of Personal Informatics Tools", Proceedings of the 2017 CHI Conference on Human Factors in Computing Systems, CHI '17, ACM Press, Denver, CO, USA, May 6-11, 2017, pp. 6876-6888.
International Search Report and Written Opinion received for PCT Patent Application No. PCT/US2020/035462, dated Sep. 11, 2020, 17 pages.
Moglia et al., "Evaluation of Smartphone Menstrual Cycle Tracking Applications Using an Adapted Applications Scoring System", Obstetrics and Gynecology, vol. 127, No. 6, Jun. 2016, pp. 1153-1160.
Applicant-Initiated Interview Summary received for U.S. Appl. No. 16/138,809, dated Dec. 16, 2020, 7 pages.
Applicant-Initiated Interview Summary received for U.S. Appl. No. 16/880,552, dated Dec. 16, 2020, 6 pages.
Applicant-Initiated Interview Summary received for U.S. Appl. No. 16/907,261, dated Dec. 16, 2020, 6 pages.
International Search Report and Written Opinion received for PCT Patent Application No. PCT/US2020/035474, dated Nov. 26, 2020, 16 pages.
Invitation to Pay Additional Fees and Partial International Search Report received for PCT Patent Application No. PCT/US2020/035164, dated Oct. 16, 2020, 14 pages.
Non-Final Office Action received for U.S. Appl. No. 16/880,714, dated Oct. 28, 2020, 11 pages.
Notice of Allowance received for U.S. Appl. No. 16/880,552, dated Dec. 1, 2020, 7 pages.
Search Report and Opinion received for Danish Patent Application No. PA202070335, dated Nov. 27, 2020, 10 pages.
Search Report and Opinion received for Danish Patent Application No. PA202070395, dated Nov. 24, 2020, 10 pages.
Gupta Rajat, "Disable High Volume Warning (no root) in Samsung S7, S8 / Android 7.0", Online available at: <https://www.youtube.com/watch?v=9fKwRBtk-x8>, Retrieved on Nov. 26, 2020; esp. 2:04, Aug. 6, 2017, 1 page.
Tech, Kalyani,"I See Some problems in Honor Band 5", Retrieved from: https://www.youtube.com/watch?v=5XPnYJFqajl, May 19, 2020, 1 page.
Ticks, Smartwatch,"Senbono S10 IP67 Waterproof Multi-Function Blood Pressure Sports Smartwatch: One Minute Overview", Retrieved from: https://www.youtube.com/watch?v=rMxLJvKIVBs, Oct. 30, 2019, 1 page.
Applicant-Initiated Interview Summary received for U.S. Appl. No. 16/880,552, dated Apr. 21, 2021, 3 pages.

Notice of Allowance received for Japanese Patent Application No. 2019-162293, dated Apr. 9, 2021, 4 pages (1 page of English Translation and 3 pages of Official Copy).
Notice of Allowance received for U.S. Appl. No. 16/138,809, dated Apr. 16, 2021, 11 pages.
Office Action received for Chinese Patent Application No. 202010618569.X, dated Mar. 12, 2021, 14 pages (7 pages of English Translation and 7 pages of Official Copy).
Applicant-Initiated Interview Summary received for U.S. Appl. No. 16/880,714, dated Feb. 26, 2021, 5 pages.
Final Office Action received for U.S. Appl. No. 16/894,309, dated Feb. 24, 2021, 30 pages.
International Search Report and Written Opinion received for PCT Patent Application No. PCT/US2020/035164, dated Feb. 8, 2021, 26 pages.
Non-Final Office Action received for U.S. Appl. No. 16/880,552, dated Feb. 19, 2021, 11 pages.
Office Action received for Danish Patent Application No. PA201970534, dated Feb. 16, 2021, 2 pages.
Office Action received for Korean Patent Application No. 10-2020-7026035, dated Feb. 19, 2021, 13 pages (6 pages of English Translation and 7 pages of Official Copy).
Notice of Allowance received for U.S. Appl. No. 16/144,030, dated Apr. 5, 2021, 8 pages.
Office Action received for European Patent Application No. 20180581.9, dated Apr. 1, 2021, 11 pages.
Office Action received for European Patent Application No. 20180592.6, dated Apr. 1, 2021, 11 pages.
Office Action received for Japanese Patent Application No. 2018-184532, dated Mar. 1, 2021, 11 pages (6 pages of English Translation and 5 pages of Official Copy).
International Search Report and Written Opinion received for PCT Patent Application No. PCT/US2020/070280, dated Nov. 30, 2020, 20 pages.
Invitation to Pay Additional Fees received for PCT Patent Application No. PCT/US2020/070280, mailed on Oct. 7, 2020, 12 pages.
Non-Final Office Action received for U.S. Appl. No. 16/249,627, dated Mar. 11, 2021, 21 pages.
Notice of Allowance received for U.S. Appl. No. 16/144,864, dated Mar. 12, 2021, 2 pages.
Office Action received for Australian Patent Application No. 2020230340, dated Mar. 2, 2021, 6 pages.
Office Action received for Chinese Patent Application No. 202010606407.4, dated Jan. 27, 2021, 16 pages (7 pages of English Translation and 9 pages of Official Copy).
Summons to Attend Oral Proceedings received for European Patent Application No. 13812320.3, mailed on Mar. 12, 2021, 9 pages.
Corrected Notice of Allowance received for U.S. Appl. No. 16/880,552, dated Dec. 23, 2020, 2 pages.
Search Report and Opinion received for Danish Patent Application No. PA202070620, dated Dec. 11, 2020, 9 pages.
Applicant-Initiated Interview Summary received for U.S. Appl. No. 16/907,261, dated Mar. 25, 2021, 2 pages.
Decision on Appeal received for Korean Patent Application No. 10-2019-7025538, mailed on Feb. 24, 2021, 20 pages (4 pages of English Translation and 16 pages of Official Copy).
Final Office Action received for U.S. Appl. No. 16/907,261, dated Mar. 18, 2021, 20 pages.
Notice of Allowance received for Korean Patent Application No. 10-2019-7025538, dated Mar. 10, 2021, 5 pages (2 pages of English Translation and 3 pages of Official Copy).
Notice of Allowance received for U.S. Appl. No. 16/144,864, dated Mar. 30, 2021, 2 pages.
Notice of Allowance received for U.S. Appl. No. 16/880,714, dated Mar. 19, 2021, 7 pages.
Office Action received for Australian Patent Application No. 2019234289, dated Mar. 16, 2021, 8 pages.
Result of Consultation received for European Patent Application No. 19726205.8, mailed on Mar. 15, 2021, 19 pages.
Applicant-Initiated Interview Summary received for U.S. Appl. No. 16/894,309, dated Jan. 26, 2021, 3 pages.
Extended European Search Report received for European Patent Application No. 20203526.7, dated Jan. 29, 2021, 13 pages.

(56) References Cited

OTHER PUBLICATIONS

Final Office Action received for U.S. Appl. No. 16/143,997, dated Feb. 9, 2021, 16 pages.
Lovejoy, Ben, "Apple Watch blood sugar measurement coming in Series 7, claims report", Available Online at: https://9to5mac.com/2021/01/25/apple-watch-blood-sugar-measurement/, Jan. 25, 2021, 6 pages.
Notice of Allowance received for U.S. Appl. No. 16/144,864, dated Feb. 9, 2021, 13 pages.
Office Action received for Korean Patent Application No. 10-2020-7026391, dated Jan. 27, 2021, 5 pages (2 pages of English Translation and 3 pages of Official Copy).
Office Action received for Korean Patent Application No. 10-2020-7026453, dated Jan. 27, 2021, 5 pages (2 pages of English Translation and 3 pages of Official Copy).
Notice of Allowance received for Japanese Patent Application No. 2020-104679, dated Jan. 4, 2021, 4 pages (1 page of English Translation and 3 pages of Official Copy).
Applicant-Initiated Interview Summary received for U.S. Appl. No. 16/143,997, dated May 3, 2021, 4 pages.
Applicant-Initiated Interview Summary received for U.S. Appl. No. 16/249,627, dated Jun. 2, 2021, 5 pages.
Applicant-Initiated Interview Summary received for U.S. Appl. No. 16/894,309, dated Jun. 25, 2021, 4 pages.
Applicant-Initiated Interview Summary received for U.S. Appl. No. 16/907,261, dated Jul. 16, 2021, 10 pages.
Applicant-Initiated Interview Summary received for U.S. Appl. No. 17/031,704, dated Feb. 9, 2021, 3 pages.
Applicant-Initiated Interview Summary received for U.S. Appl. No. 17/031,704, dated Jun. 25, 2021, 3 pages.
Applicant-Initiated Interview Summary received for U.S. Appl. No. 17/031,717, dated Jan. 29, 2021, 5 pages.
Applicant-Initiated Interview Summary received for U.S. Appl. No. 17/031,717, dated May 17, 2021, 5 pages.
Brief Communication Regarding Oral Proceedings received for European Patent Application No. 13812320.3, dated Sep. 16, 2021, 2 pages.
Corrected Notice of Allowance received for U.S. Appl. No. 16/143,997, dated Jul. 2, 2021, 2 pages.
Corrected Notice of Allowance received for U.S. Appl. No. 16/143,997, dated Jun. 4, 2021, 2 pages.
Corrected Notice of Allowance received for U.S. Appl. No. 16/880,552, dated Jul. 7, 2021, 2 pages.
Corrected Notice of Allowance received for U.S. Appl. No. 16/921,312, dated Sep. 24, 2021, 2 pages.
Final Office Action received for U.S. Appl. No. 17/031,704, dated Apr. 1, 2021, 31 pages.
Final Office Action received for U.S. Appl. No. 17/031,717, dated Feb. 24, 2021, 23 pages.
Non-Final Office Action received for U.S. Appl. No. 16/249,627, dated Aug. 31, 2021, 18 pages.
Non-Final Office Action received for U.S. Appl. No. 16/990,846, dated May 10, 2021, 16 pages.
Non-Final Office Action received for U.S. Appl. No. 17/031,704, dated Dec. 10, 2020, 30 pages.
Non-Final Office Action received for U.S. Appl. No. 17/031,717, dated Sep. 14, 2021, 35 pages.
Notice of Acceptance received for Australian Patent Application No. 2020256383, dated Aug. 3, 2021, 3 pages.
Notice of Allowance received for Japanese Patent Application No. 2020-153166, dated Sep. 13, 2021, 4 pages (1 page of English Translation and 3 pages of Official Copy).
Notice of Allowance received for Japanese Patent Application No. 2020-547369, dated Jul. 16, 2021, 4 pages (1 page of English Translation and 3 pages of Official Copy).
Notice of Allowance received for Korean Patent Application No. 10-2020-7026035, dated Aug. 23, 2021, 4 pages (2 pages of English Translation and 2 pages of Official Copy).
Notice of Allowance received for Korean Patent Application No. 10-2020-7026391, dated May 11, 2021, 3 pages (1 page of English Translation and 2 pages of Official Copy).
Notice of Allowance received for Korean Patent Application No. 10-2020-7026453, dated May 11, 2021, 3 pages (1 page of English Translation and 2 pages of Official Copy).
Notice of Allowance received for U.S. Appl. No. 16/138,809, dated Jul. 20, 2021, 6 pages.
Notice of Allowance received for U.S. Appl. No. 16/143,997, dated May 13, 2021, 10 pages.
Notice of Allowance received for U.S. Appl. No. 16/880,552, dated Jul. 23, 2021, 5 pages.
Notice of Allowance received for U.S. Appl. No. 16/880,552, dated May 12, 2021, 7 pages.
Notice of Allowance received for U.S. Appl. No. 16/880,714, dated Jun. 9, 2021, 6 pages.
Notice of Allowance received for U.S. Appl. No. 16/907,261, dated Aug. 13, 2021, 8 pages.
Notice of Allowance received for U.S. Appl. No. 16/907,261, dated Sep. 28, 2021, 6 pages.
Notice of Allowance received for U.S. Appl. No. 16/921,312, dated Sep. 14, 2021, 9 pages.
Notice of Allowance received for U.S. Appl. No. 16/990,846, dated Sep. 22, 2021, 9 pages.
Notice of Allowance received for U.S. Appl. No. 17/031,704, dated Jul. 21, 2021, 10 pages.
Notice of Allowance received for U.S. Appl. No. 17/031,727, dated Dec. 24, 2020, 12 pages.
Notice of Allowance received for U.S. Appl. No. 17/031,727, dated Jun. 25, 2021, 6 pages.
Notice of Allowance received for U.S. Appl. No. 17/031,727, dated Mar. 12, 2021, 7 pages.
Office Action received for Australian Patent Application No. 2019210192, dated May 25, 2021, 4 pages.
Office Action received for Australian Patent Application No. 2019210192, dated Sep. 9, 2021, 4 pages.
Office Action received for Australian Patent Application No. 2019234289, dated Jul. 20, 2021, 4 pages.
Office Action received for Australian Patent Application No. 2020230340, dated May 27, 2021, 5 pages.
Office Action received for Australian Patent Application No. 2020239692, dated Jul. 20, 2021, 5 pages.
Office Action received for Australian Patent Application No. 2020239740, dated Jul. 9, 2021, 4 pages.
Office Action received for Australian Patent Application No. 2020256383, dated Jun. 4, 2021, 3 pages.
Office Action received for Chinese Patent Application No. 201910858933.7, dated Jun. 29, 2021, 8 pages (3 pages of English Translation and 5 pages of Official Copy).
Office Action received for Chinese Patent Application No. 202010606407.4, dated Jun. 2, 2021, 12 pages (5 pages of English Translation and 7 pages of Official Copy).
Office Action received for Chinese Patent Application No. 202010618240.3, dated Mar. 29, 2021, 21 pages (11 pages of English Translation and 10 pages of Official Copy).
Office Action received for Chinese Patent Application No. 202010618569.X, dated Sep. 7, 2021, 7 pages (4 pages of English Translation and 3 pages of Official Copy).
Office Action received for Chinese Patent Application No. 202011220489.5, dated Jun. 1, 2021, 12 pages (6 pages of English Translation and 6 pages of Official Copy).
Office Action received for Danish Patent Application No. PA202070335, dated Jun. 11, 2021, 4 pages.
Office Action received for Danish Patent Application No. PA202070619, dated Aug. 27, 2021, 12 pages.
Office Action received for Danish Patent Application No. PA202070620, dated May 10, 2021, 5 pages.
Office Action received for European Patent Application No. 19721883.7, dated Jun. 15, 2021, 9 pages.
Office Action received for European Patent Application No. 20182116.2, dated May 25, 2021, 9 pages.

(56) References Cited

OTHER PUBLICATIONS

Office Action received for Japanese Patent Application No. 2020-153166, dated May 31, 2021, 6 pages (3 pages of English Translation and 3 pages of Official Copy).
Office Action received for Japanese Patent Application No. 2020-547369, dated Apr. 9, 2021, 4 pages (2 pages of English Translation and 2 pages of Official Copy).
Search Report and Opinion received for Danish Patent Application No. PA202070619, dated Dec. 2, 2020, 11 pages.
Summons to Attend Oral Proceedings received for European Patent Application No. 20180581.9, mailed on Aug. 18, 2021, 15 pages.
Summons to Attend Oral Proceedings received for European Patent Application No. 20180592.6, mailed on Aug. 11, 2021, 16 pages.
Supplemental Notice of Allowance received for U.S. Appl. No. 16/880,714, dated Sep. 16, 2021, 2 pages.
Supplemental Notice of Allowance received for U.S. Appl. No. 17/031,727, dated Jan. 15, 2021, 2 pages.

* cited by examiner

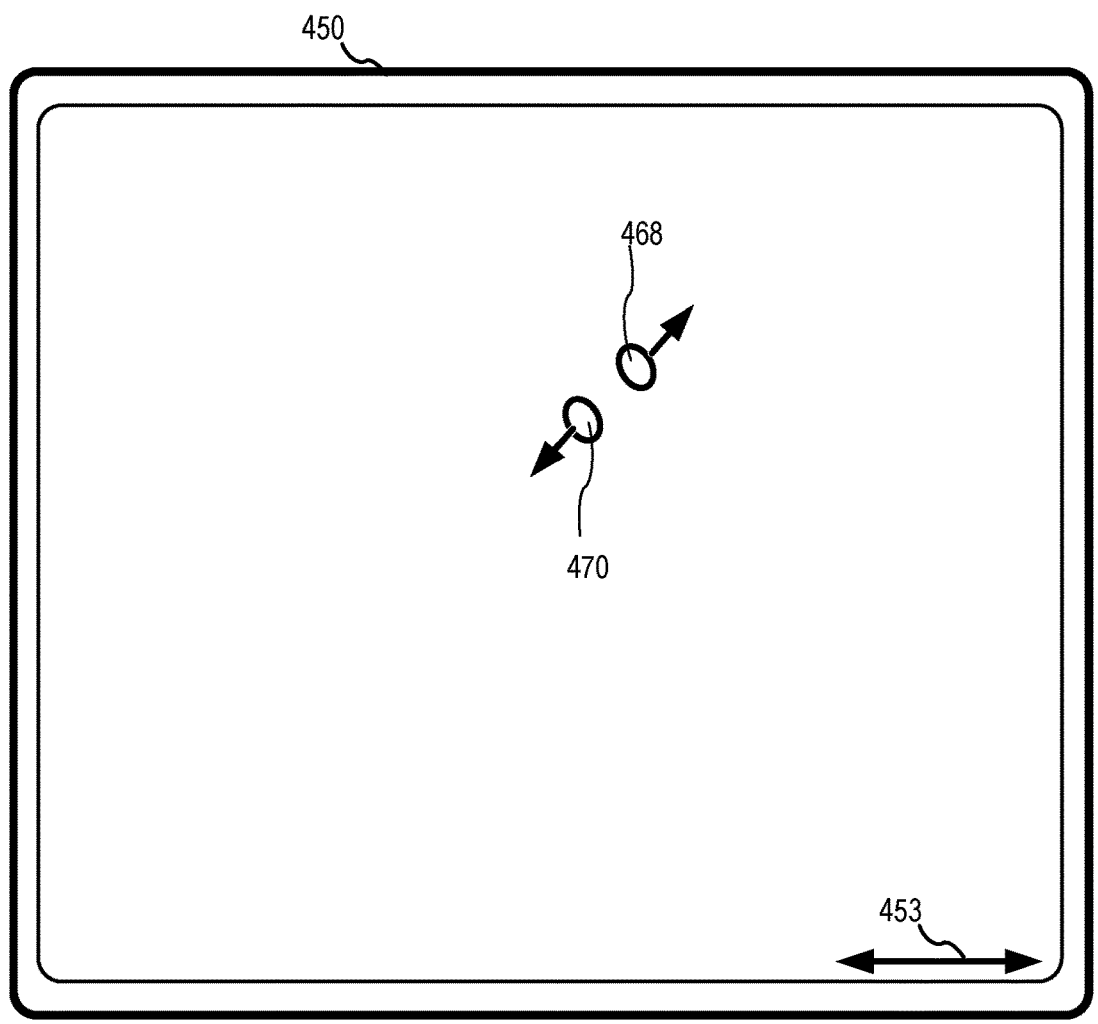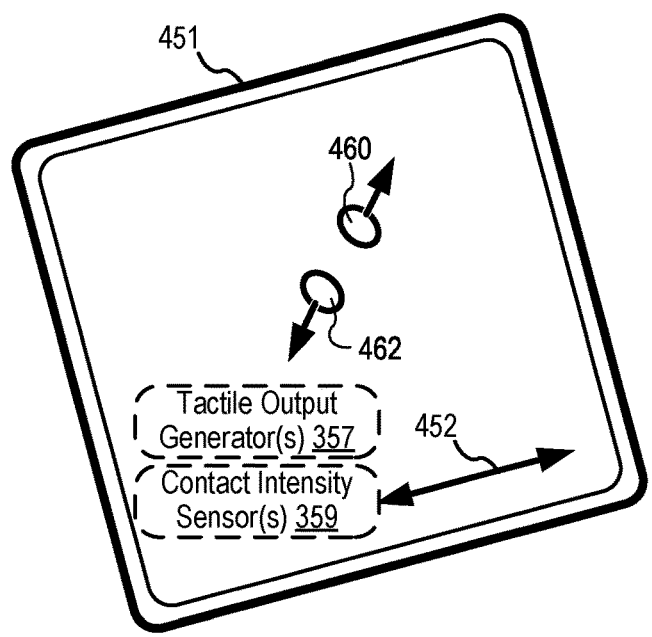
FIG. 4B

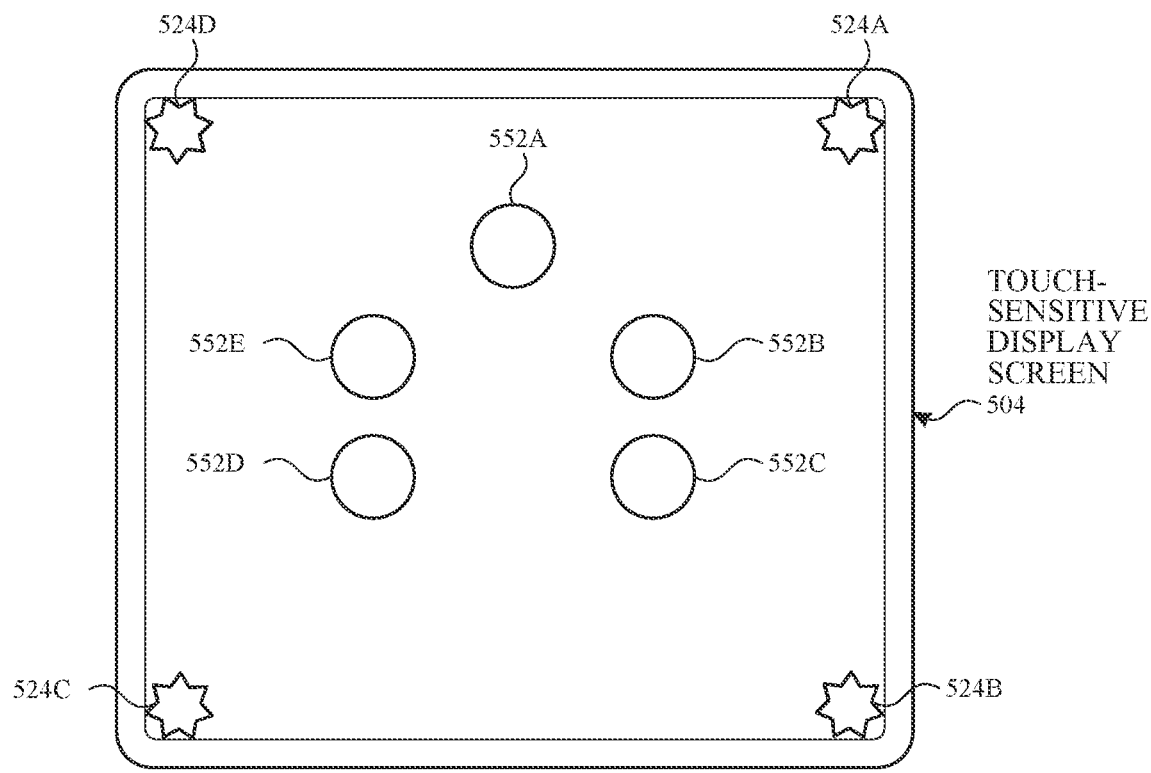
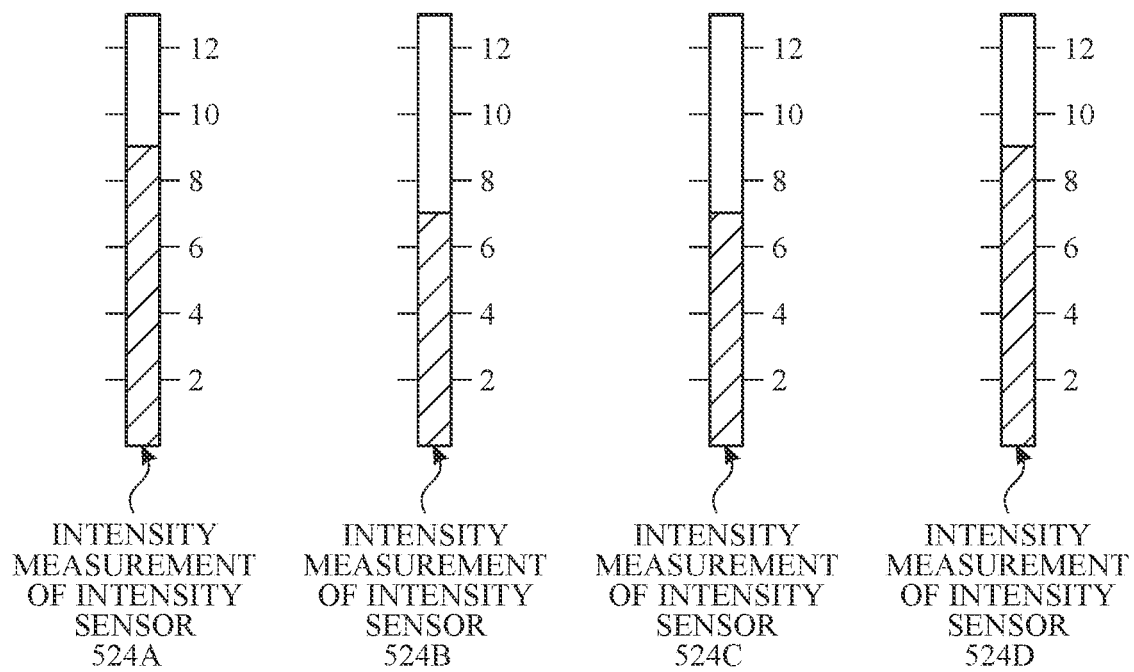
FIG. 5C

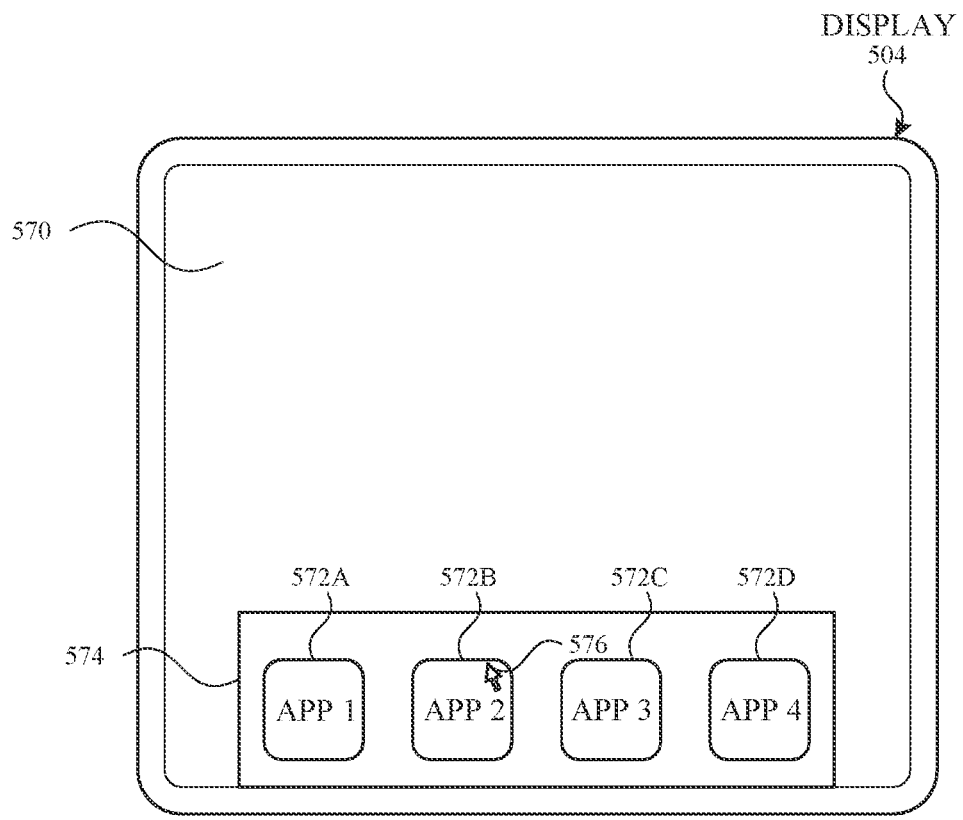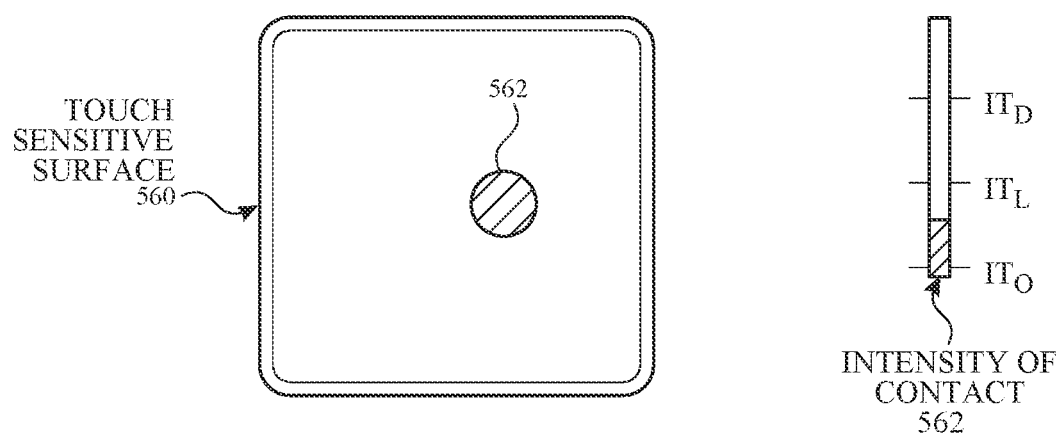
FIG. 5E

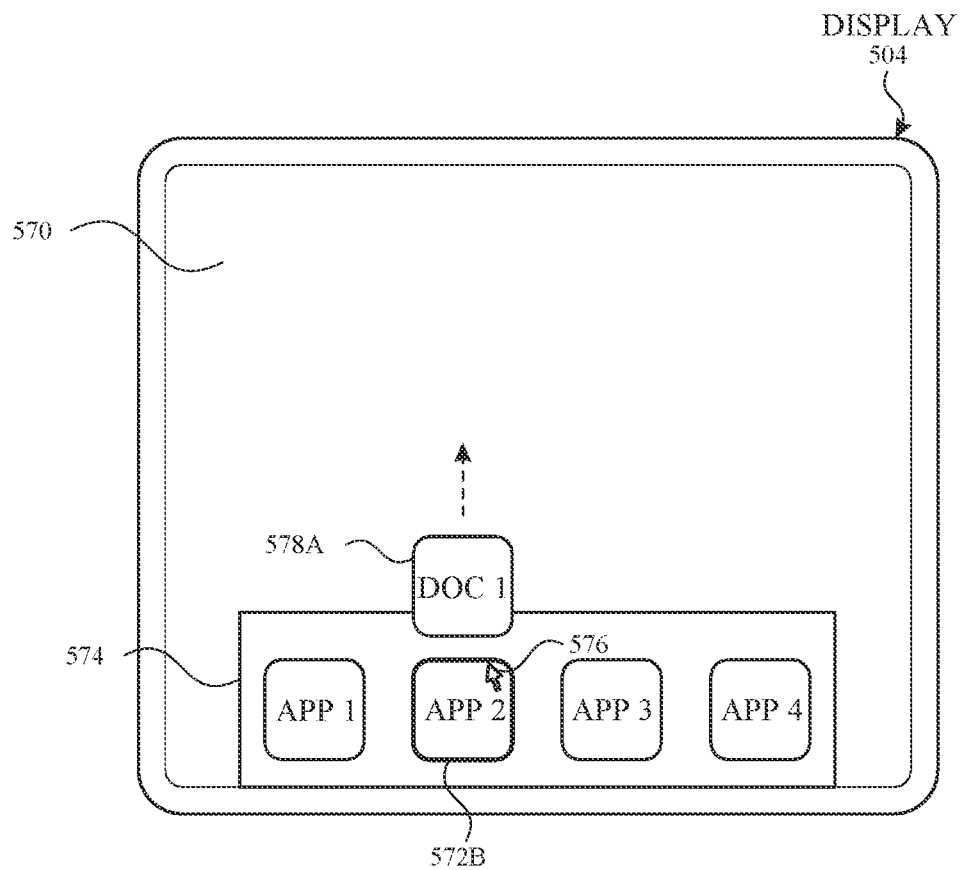
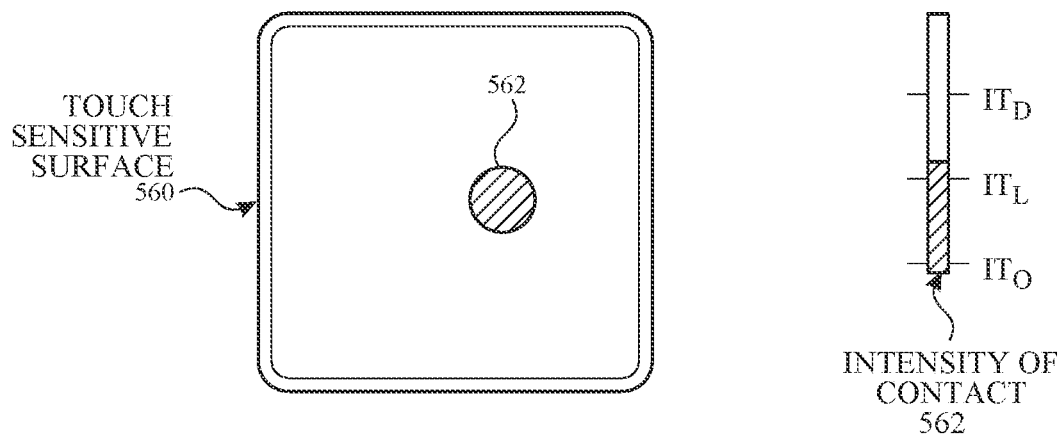
FIG. 5F

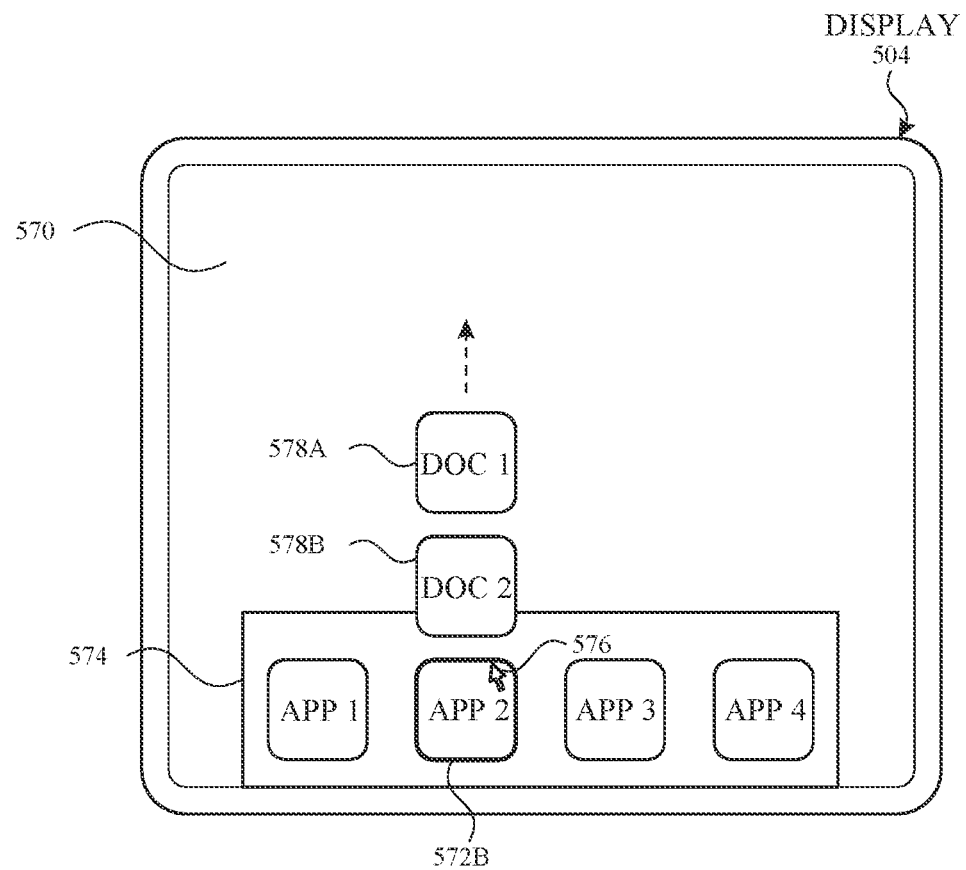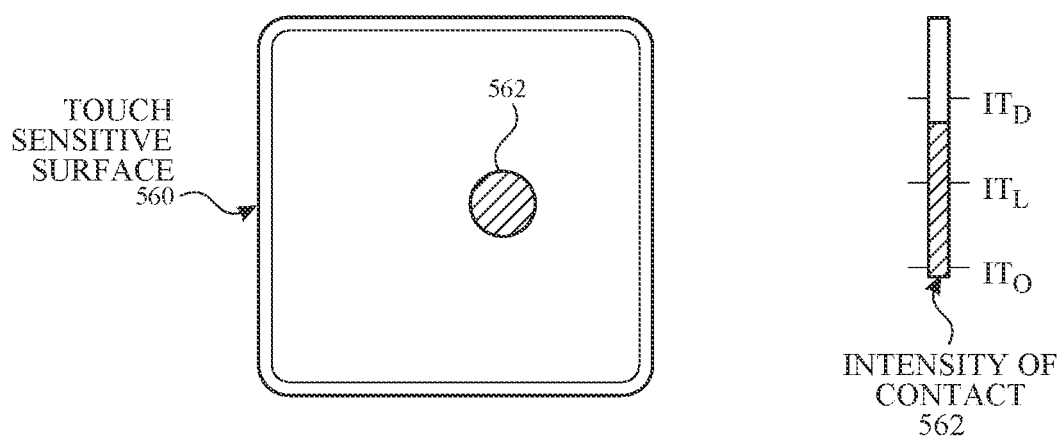
FIG. 5G

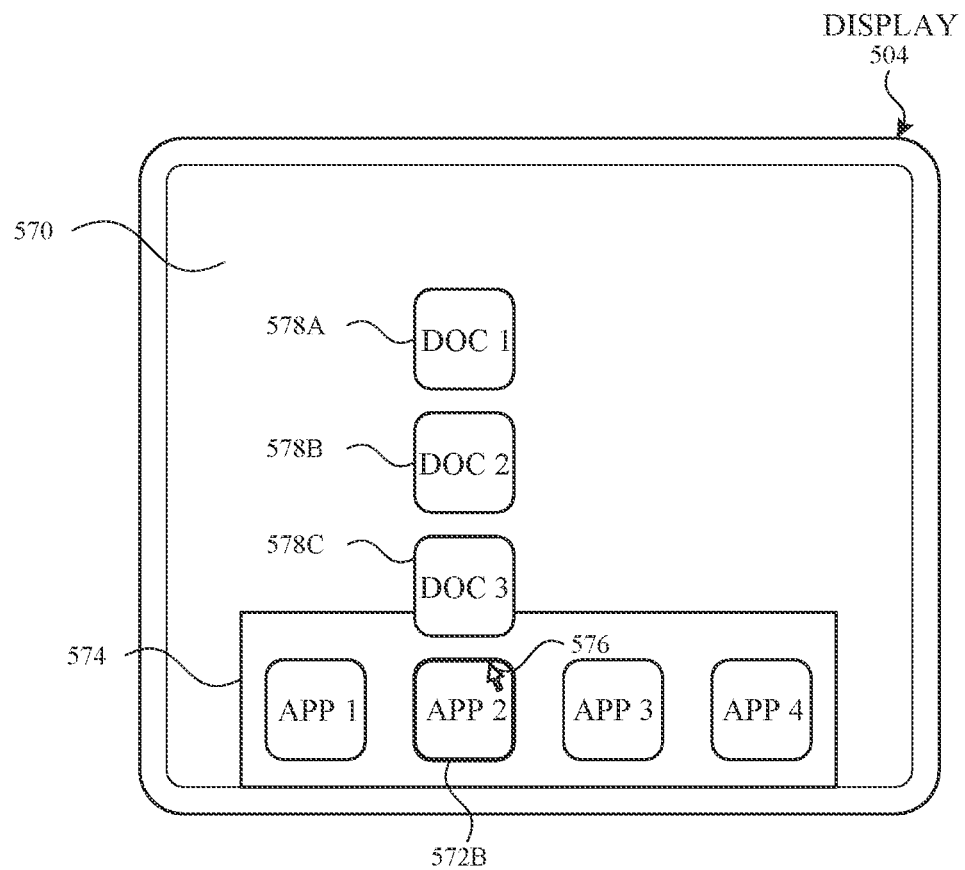
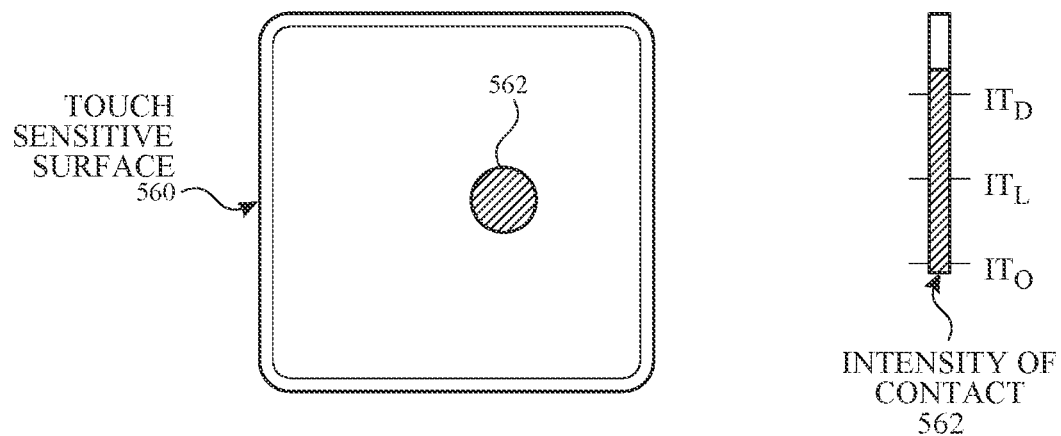
FIG. 5H

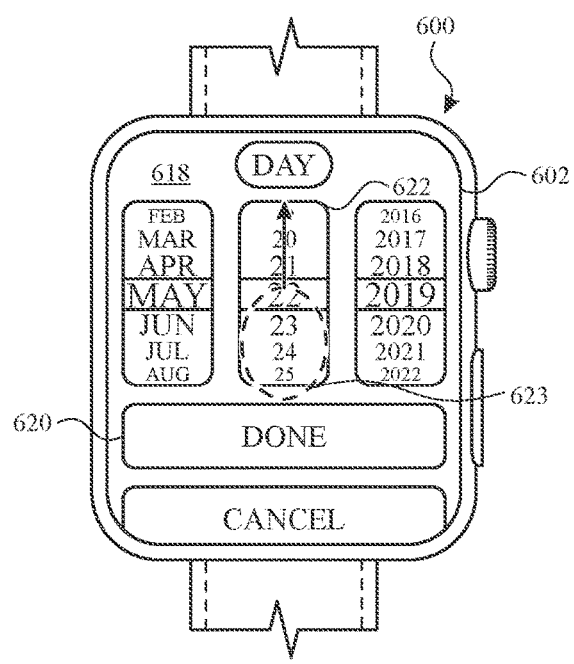 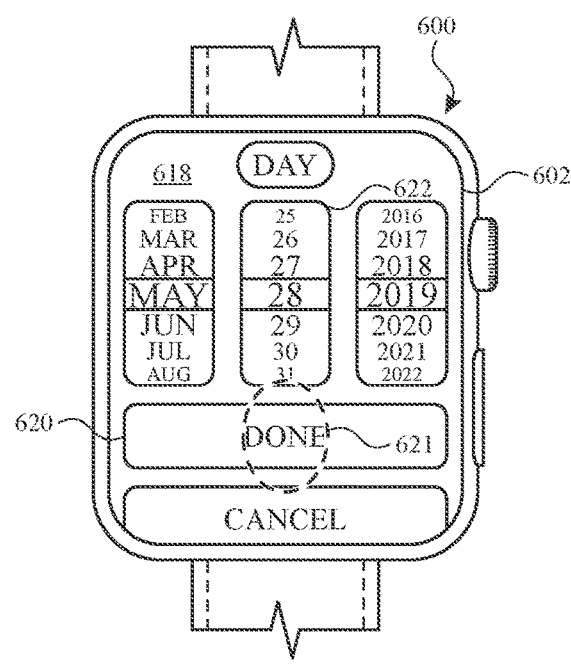
*FIG. 6E*  *FIG. 6F*

700

702
At a first time, display, via the display device:

704
In accordance with a determination that a first set of criteria is met, the first set of criteria including a criterion that is met when a current date corresponds to a predicted start date of a recurring event, a first notification that includes a first affordance that, when selected, initiates a process to record a start date for a respective recurrence of the recurring event.

706
In accordance with a determination that a second set of criteria are met, the second set of criteria including a criterion that is met when the current date corresponds to a predicted end date of the recurring event, a second notification that includes a second affordance that, when selected, initiates a process to record an end date for the respective recurrence of the recurring event.

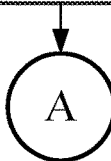

708
While displaying a respective notification selected from the group consisting of the first notification and the second notification, receive a first set of one or more inputs.

710
In response to receiving the first set of one or more inputs:

712
In accordance with a determination that the first set of one or more inputs includes a first input corresponding to selection of the first affordance, record a start date for the respective recurrence of the recurring event.

714
In accordance with a determination that the first set of one or more inputs includes a second input corresponding to selection of the second affordance, record an end date for the respective recurrence of the recurring event.

*FIG. 7B*

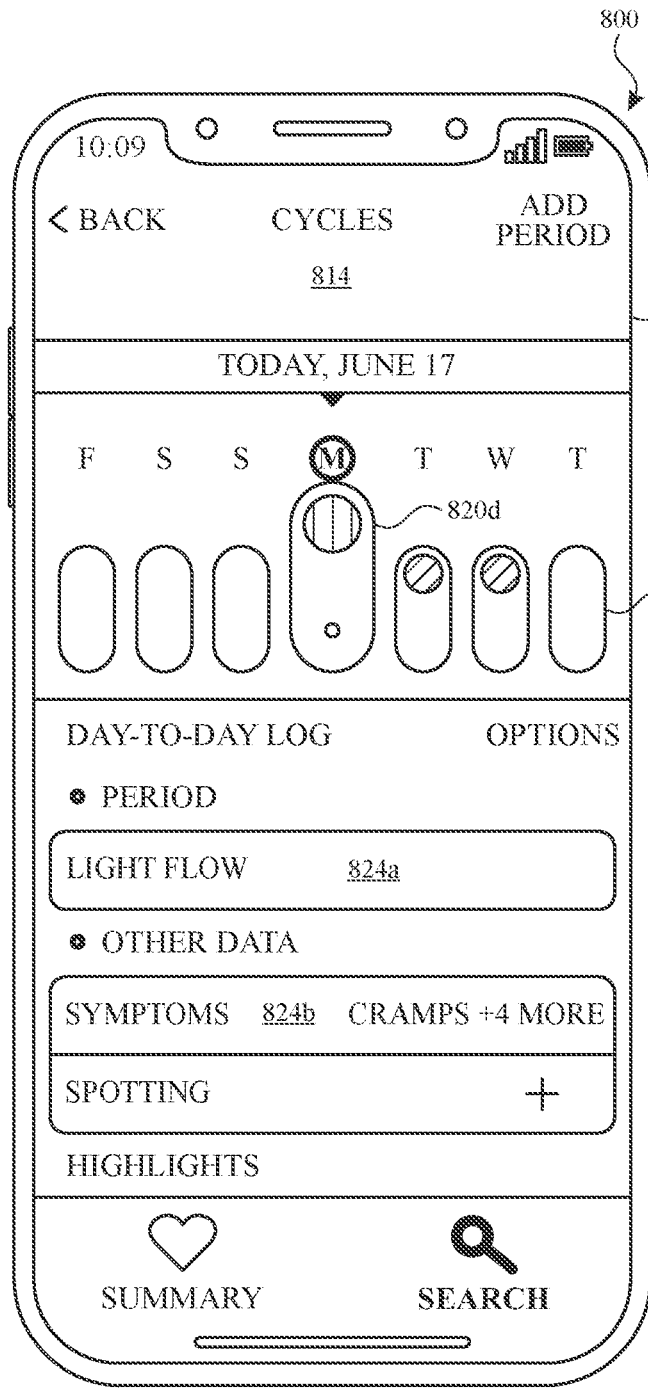
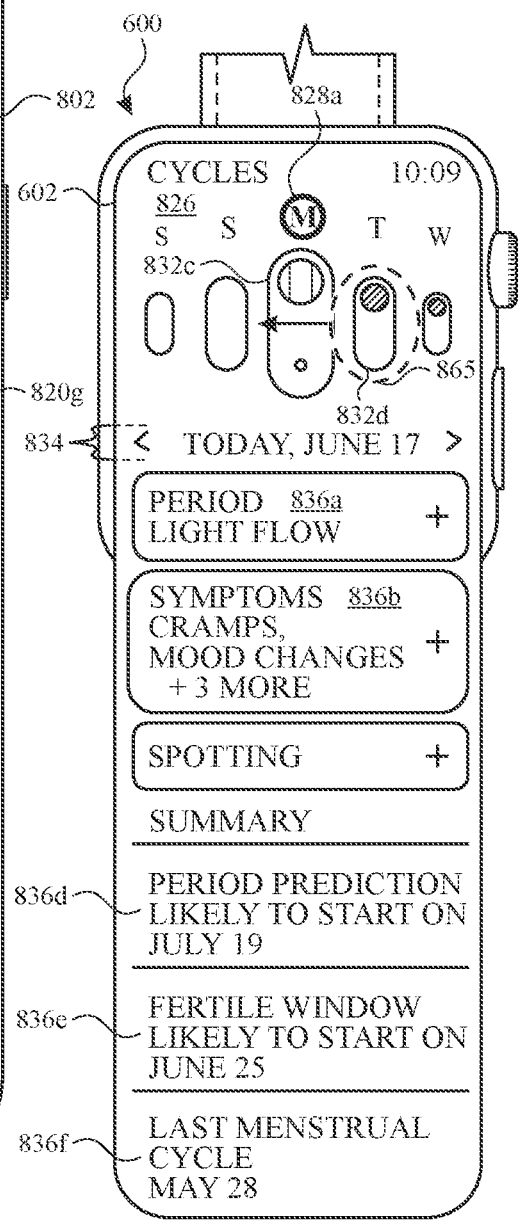
*FIG. 8L*  *FIG. 8M*

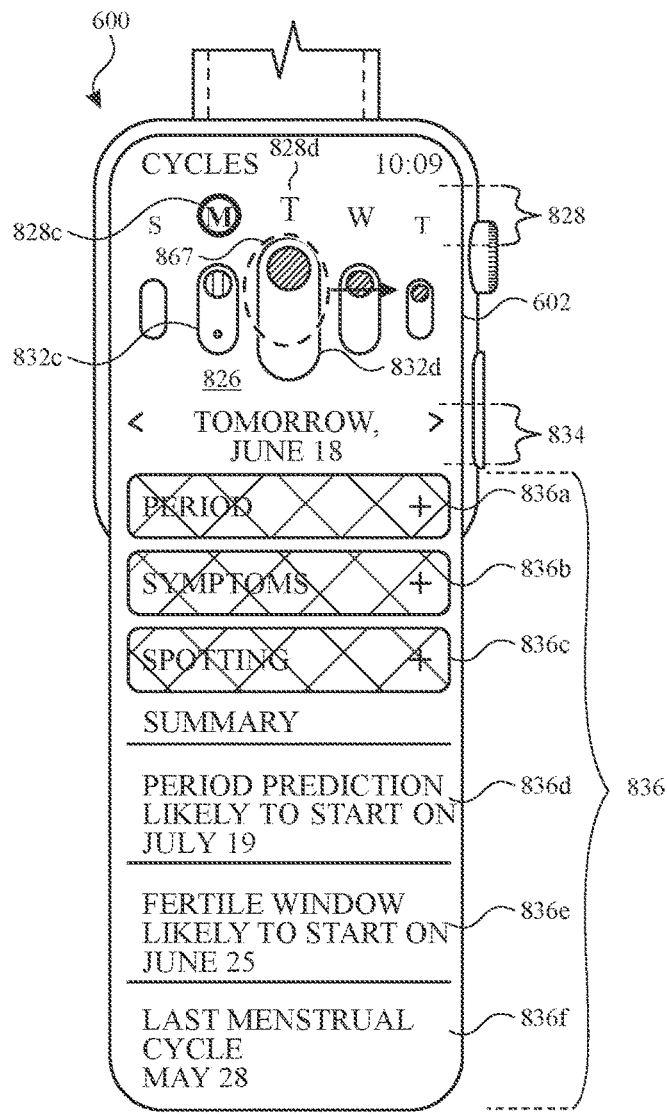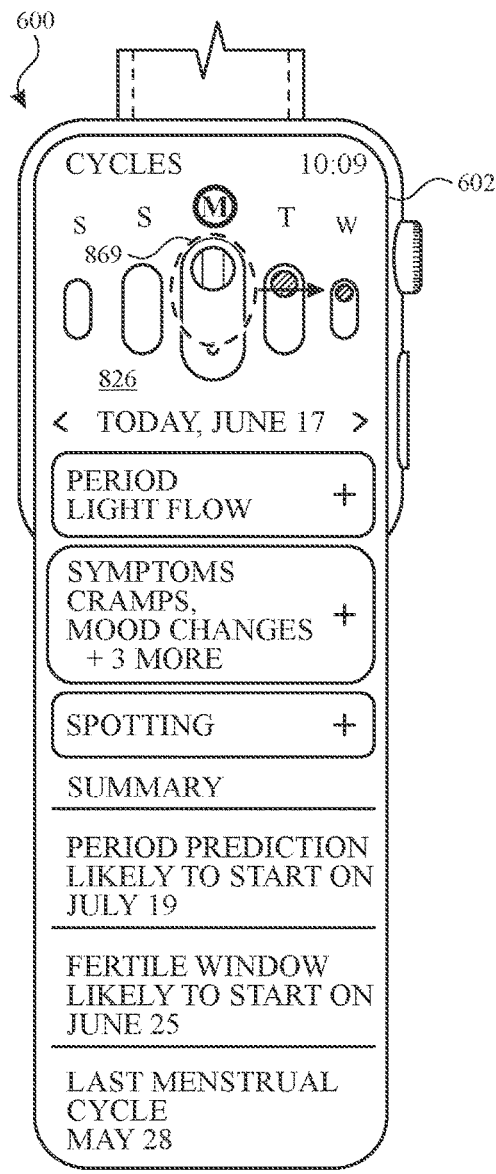
FIG. 8N
FIG. 8O

900

902
Display a first user interface that includes:

904
A first region that includes a plurality of representations of dates, including a first representation corresponding to a first date and a second representation corresponding to a second date.

906
A second region that includes:

908
In accordance with a determination that the first representation occupies a first predetermined position in the first region, a first affordance that, when selected, initiates a process for recording information corresponding to the first date.

910
In accordance with a determination that the second representation occupies the first predetermined position in the first region, a second affordance that, when selected, initiates a process for recording information corresponding to the second date.

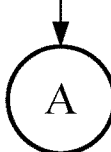

FIG. 9A

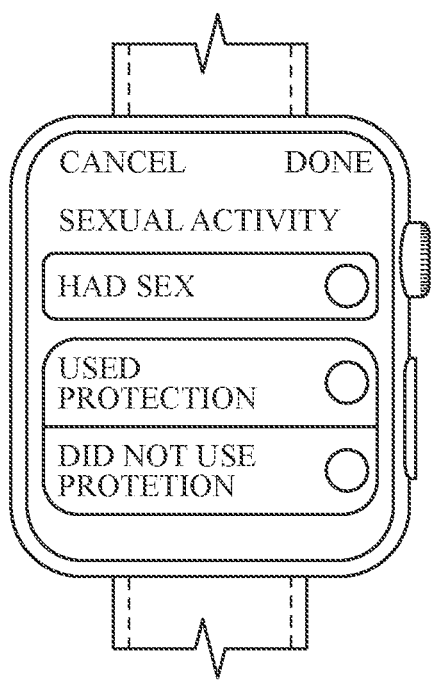
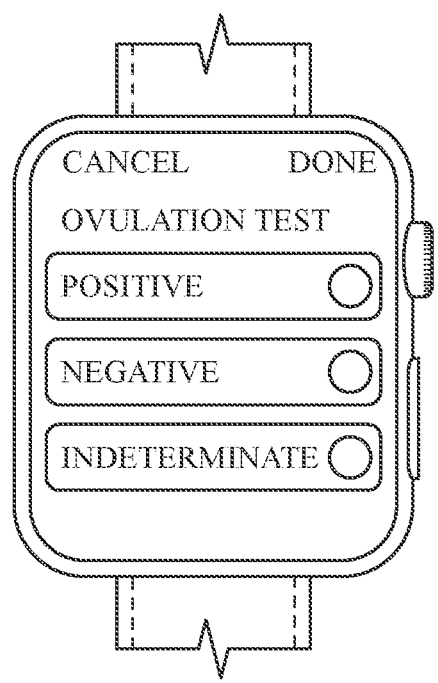
FIG. 10AH    FIG. 10AI

USER INTERFACES FOR CYCLE TRACKING

CROSS-REFERENCE TO RELATED APPLICATIONS

This application claims priority to U.S. Provisional Application No. 62/856,024, filed Jun. 1, 2019, entitled "USER INTERFACES FOR CYCLE TRACKING," the entire contents of which are hereby incorporated by reference.

FIELD

The present disclosure relates generally to computer user interfaces, and more specifically to user interfaces for tracking recurring events.

BACKGROUND

Recurring events, such as recurring health events can be tracked an electronic devices to log past events and to predict future events.

BRIEF SUMMARY

Some user interfaces for cycle tracking, however, are generally cumbersome and inefficient. For example, some existing user interfaces are complex and time-consuming, which may include multiple key presses, keystrokes, and/or touch inputs. Existing interfaces require more time than necessary, wasting user time and device energy. This latter consideration is particularly important in battery-operated devices.

Accordingly, the present user interfaces provide electronic devices with faster, more efficient methods and interfaces for cycle tracking. Such methods and interfaces optionally complement or replace other methods for cycle tracking. Such methods and interfaces reduce the cognitive burden on a user and produce a more efficient human-machine interface. For battery-operated computing devices, such methods and interfaces conserve power and increase the time between battery charges.

Example methods are disclosed herein. An example method includes, at an electronic device with a display device: at a first time, displaying, via the display device: in accordance with a determination that a first set of criteria is met, the first set of criteria including a criterion that is met when a current date corresponds to a predicted start date of a recurring event, a first notification that includes a first affordance that, when selected, initiates a process to record a start date for a respective recurrence of the recurring event; and in accordance with a determination that a second set of criteria is met, the second set of criteria including a criterion that is met when the current date corresponds to a predicted end date of the recurring event, a second notification that includes a second affordance that, when selected, initiates a process to record an end date for the respective recurrence of the recurring event.

Example non-transitory computer-readable storage media are described herein. An example non-transitory computer-readable storage medium stores one or more programs configured to be executed by one or more processors of an electronic device with a display device, the one or more programs including instructions for: at a first time, displaying, via the display device: in accordance with a determination that a first set of criteria is met, the first set of criteria including a criterion that is met when a current date corresponds to a predicted start date of a recurring event, a first notification that includes a first affordance that, when selected, initiates a process to record a start date for a respective recurrence of the recurring event; and in accordance with a determination that a second set of criteria is met, the second set of criteria including a criterion that is met when the current date corresponds to a predicted end date of the recurring event, a second notification that includes a second affordance that, when selected, initiates a process to record an end date for the respective recurrence of the recurring event.

Example transitory computer-readable storage media are described herein. An example transitory computer-readable storage medium stores one or more programs configured to be executed by one or more processors of an electronic device with a display device, the one or more programs including instructions for: at a first time, displaying, via the display device: in accordance with a determination that a first set of criteria is met, the first set of criteria including a criterion that is met when a current date corresponds to a predicted start date of a recurring event, a first notification that includes a first affordance that, when selected, initiates a process to record a start date for a respective recurrence of the recurring event; and in accordance with a determination that a second set of criteria is met, the second set of criteria including a criterion that is met when the current date corresponds to a predicted end date of the recurring event, a second notification that includes a second affordance that, when selected, initiates a process to record an end date for the respective recurrence of the recurring event.

Example electronic devices are described herein. An example electronic device includes a display device; one or more processors; and memory storing one or more programs configured to be executed by the one or more processors, the one or more programs including instructions for: at a first time, displaying, via the display device: in accordance with a determination that a first set of criteria is met, the first set of criteria including a criterion that is met when a current date corresponds to a predicted start date of a recurring event, a first notification that includes a first affordance that, when selected, initiates a process to record a start date for a respective recurrence of the recurring event; and in accordance with a determination that a second set of criteria is met, the second set of criteria including a criterion that is met when the current date corresponds to a predicted end date of the recurring event, a second notification that includes a second affordance that, when selected, initiates a process to record an end date for the respective recurrence of the recurring event.

An example electronic device includes a display device; and means for at a first time, displaying, via the display device: in accordance with a determination that a first set of criteria is met, the first set of criteria including a criterion that is met when a current date corresponds to a predicted start date of a recurring event, a first notification that includes a first affordance that, when selected, initiates a process to record a start date for a respective recurrence of the recurring event; and in accordance with a determination that a second set of criteria is met, the second set of criteria including a criterion that is met when the current date corresponds to a predicted end date of the recurring event, a second notification that includes a second affordance that, when selected, initiates a process to record an end date for the respective recurrence of the recurring event.

An example method includes, at an electronic device including a display device: displaying a first user interface that includes: a first region that includes a plurality of representations of dates, including a first representation corresponding to a first date and a second representation corresponding to a second date; and a second region that includes: in accordance with a determination that the first representation occupies a first predetermined position in the first region, a first affordance that, when selected, initiates a process for recording information corresponding to the first date; and in accordance with a determination that the second representation occupies the first predetermined position in the first region, a second affordance that, when selected, initiates a process for recording information corresponding to the second date.

An example non-transitory computer-readable storage medium stores one or more programs configured to be executed by one or more processors of an electronic device with a display device, the one or more programs including instructions for: displaying a first user interface that includes: a first region that includes a plurality of representations of dates, including a first representation corresponding to a first date and a second representation corresponding to a second date; and a second region that includes: in accordance with a determination that the first representation occupies a first predetermined position in the first region, a first affordance that, when selected, initiates a process for recording information corresponding to the first date; and in accordance with a determination that the second representation occupies the first predetermined position in the first region, a second affordance that, when selected, initiates a process for recording information corresponding to the second date.

An example transitory computer-readable storage medium stores one or more programs configured to be executed by one or more processors of an electronic device with a display device, the one or more programs including instructions for: displaying a first user interface that includes: a first region that includes a plurality of representations of dates, including a first representation corresponding to a first date and a second representation corresponding to a second date; and a second region that includes: in accordance with a determination that the first representation occupies a first predetermined position in the first region, a first affordance that, when selected, initiates a process for recording information corresponding to the first date; and in accordance with a determination that the second representation occupies the first predetermined position in the first region, a second affordance that, when selected, initiates a process for recording information corresponding to the second date.

An example electronic device includes a display device; one or more processors; and memory storing one or more programs configured to be executed by the one or more processors, the one or more programs including instructions for: displaying a first user interface that includes: a first region that includes a plurality of representations of dates, including a first representation corresponding to a first date and a second representation corresponding to a second date; and a second region that includes: in accordance with a determination that the first representation occupies a first predetermined position in the first region, a first affordance that, when selected, initiates a process for recording information corresponding to the first date; and in accordance with a determination that the second representation occupies the first predetermined position in the first region, a second affordance that, when selected, initiates a process for recording information corresponding to the second date.

An example electronic device includes a display device; and means for displaying a first user interface that includes: a first region that includes a plurality of representations of dates, including a first representation corresponding to a first date and a second representation corresponding to a second date; and a second region that includes: in accordance with a determination that the first representation occupies a first predetermined position in the first region, a first affordance that, when selected, initiates a process for recording information corresponding to the first date; and in accordance with a determination that the second representation occupies the first predetermined position in the first region, a second affordance that, when selected, initiates a process for recording information corresponding to the second date.

Executable instructions for performing these functions are, optionally, included in a non-transitory computer-readable storage medium or other computer program product configured for execution by one or more processors. Executable instructions for performing these functions are, optionally, included in a transitory computer-readable storage medium or other computer program product configured for execution by one or more processors.

Thus, devices are provided with faster, more efficient methods and interfaces for cycle tracking, thereby increasing the effectiveness, efficiency, and user satisfaction with such devices. Such methods and interfaces may complement or replace other methods related to user interfaces for cycle tracking.

DESCRIPTION OF THE FIGURES

For a better understanding of the various described embodiments, reference should be made to the Description of Embodiments below, in conjunction with the following drawings in which like reference numerals refer to corresponding parts throughout the figures.

FIG. 4B illustrates an exemplary user interface for a multifunction device with a touch-sensitive surface that is separate from the display in accordance with some embodiments.

FIGS. 5C-5D illustrate exemplary components of a personal electronic device having a touch-sensitive display and intensity sensors in accordance with some embodiments.

FIGS. 5E-5H illustrate exemplary components and user interfaces of a personal electronic device in accordance with some embodiments.

FIGS. 7A-7B is a flow diagram illustrating methods for cycle tracking, in accordance with some embodiments.

FIGS. 9A-9B is a flow diagram illustrating methods for cycle tracking, in accordance with some embodiments.

DESCRIPTION OF EMBODIMENTS

The following description sets forth exemplary methods, parameters, and the like. It should be recognized, however, that such description is not intended as a limitation on the scope of the present disclosure but is instead provided as a description of exemplary embodiments.

There is a need for electronic devices that provide efficient methods and interfaces for cycle tracking. Such devices and interfaces can reduce the cognitive burden on a user who views user interfaces for cycle tracking, thereby enhancing productivity. Further, such techniques can reduce processor and battery power otherwise wasted on redundant user inputs.

Figure 8A:
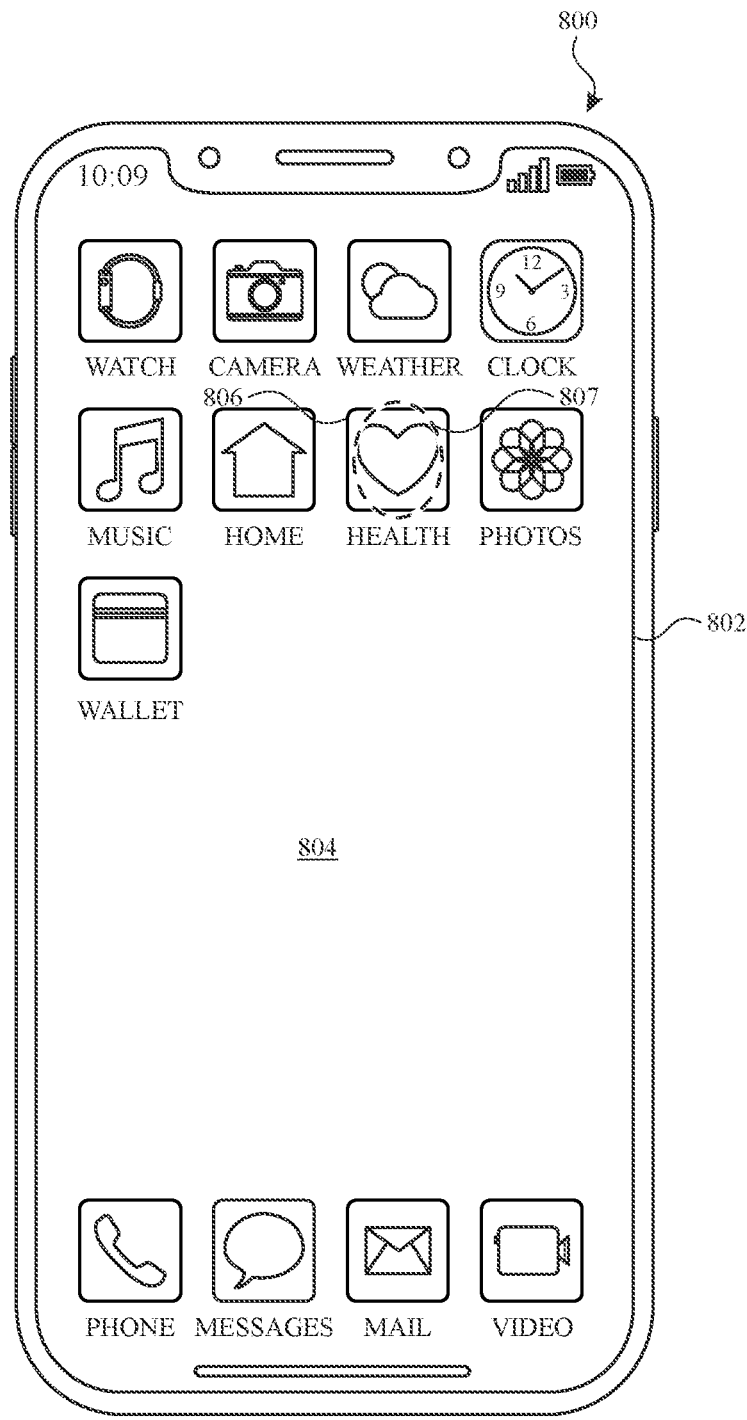
FIGS. 8A-8S illustrate exemplary user interfaces for cycle tracking, in accordance with some embodiments.
Figure 8S:
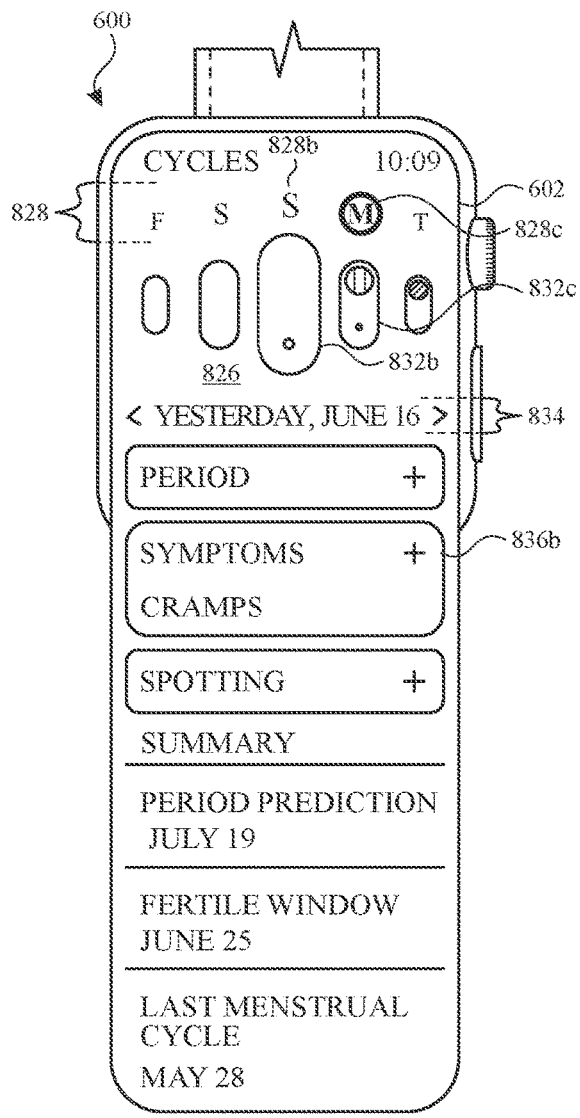
Figure 9B:
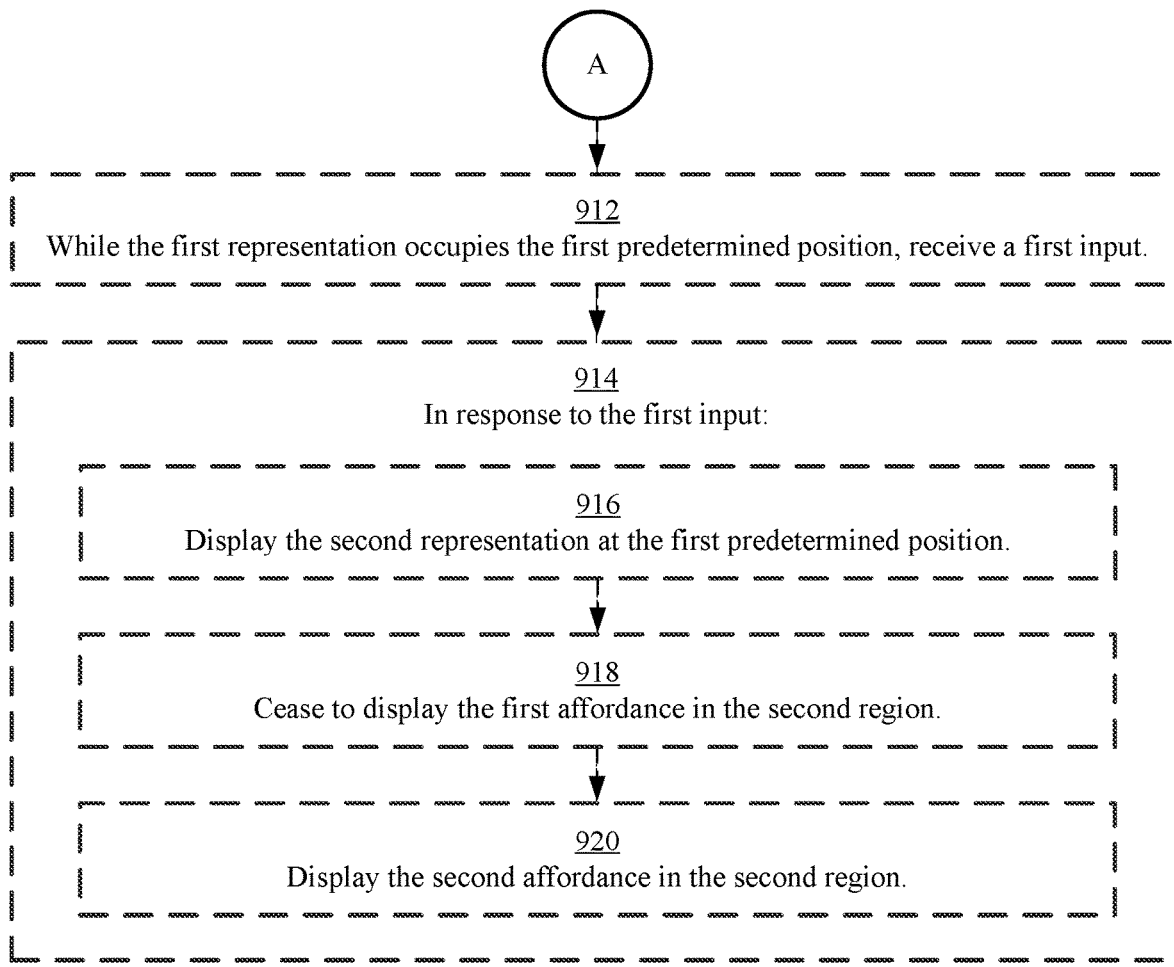
Figure 10A:
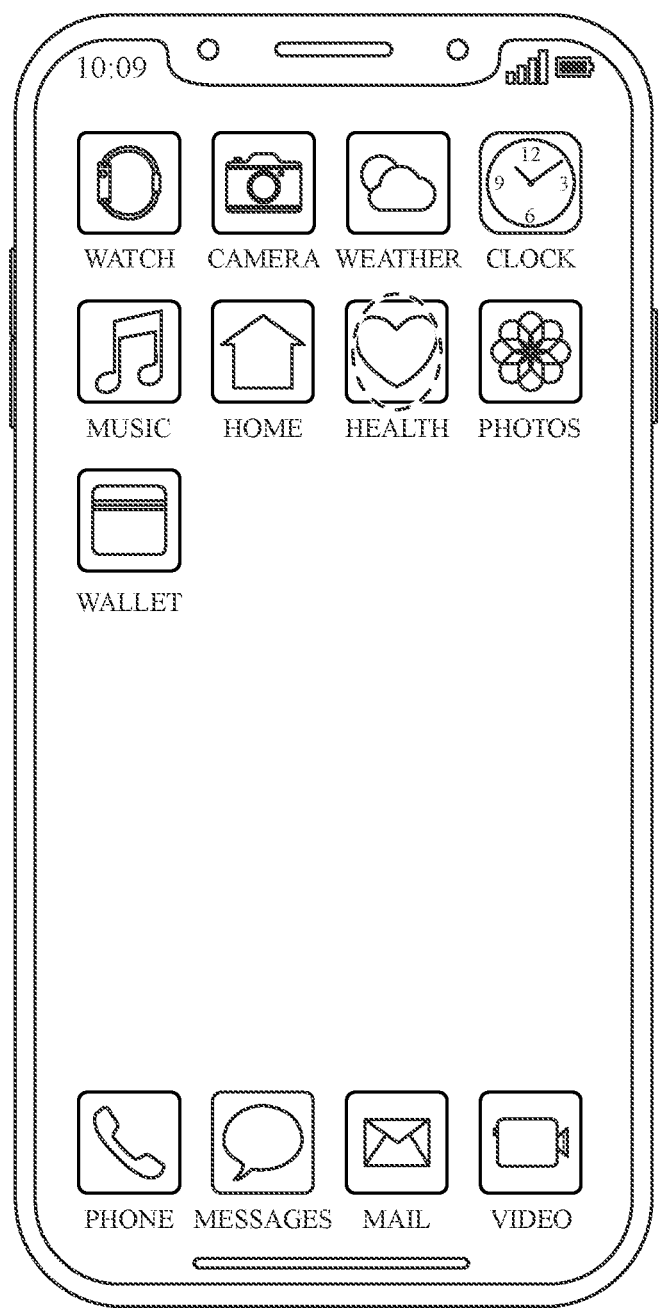
FIGS. 10A-10AK illustrate exemplary user interfaces for setting up a cycle tracking application, in accordance with some embodiments.
Figure 10B:
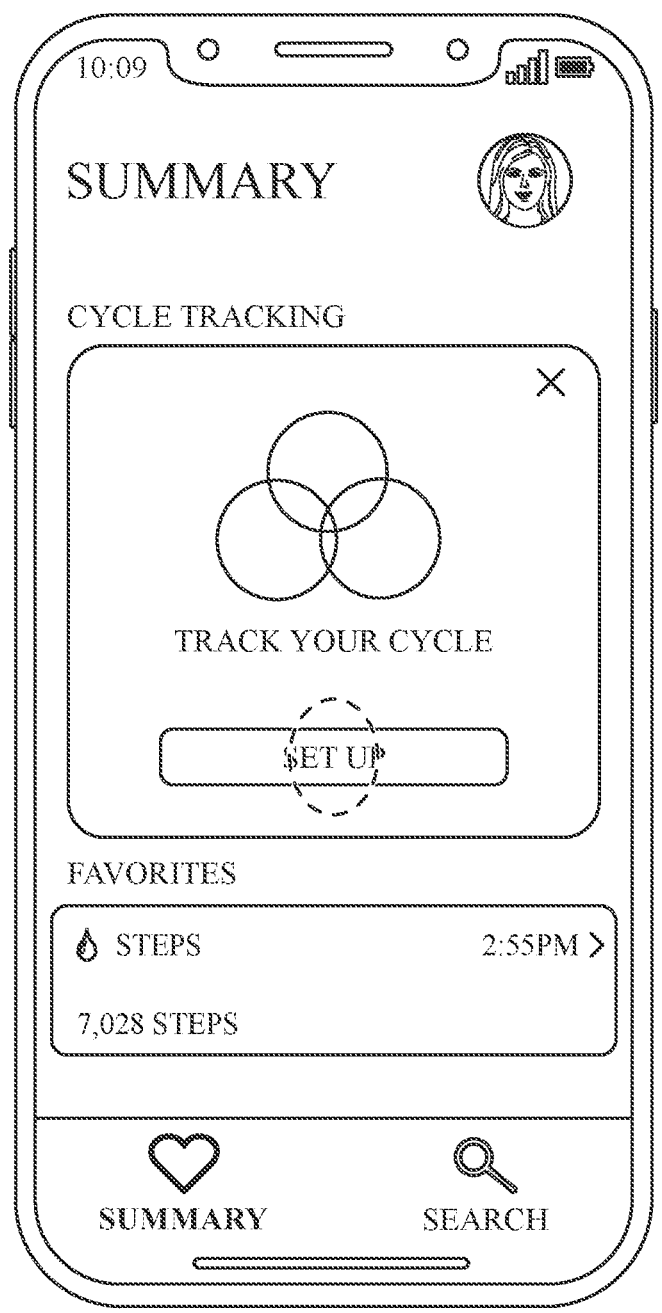
Figure 10C:
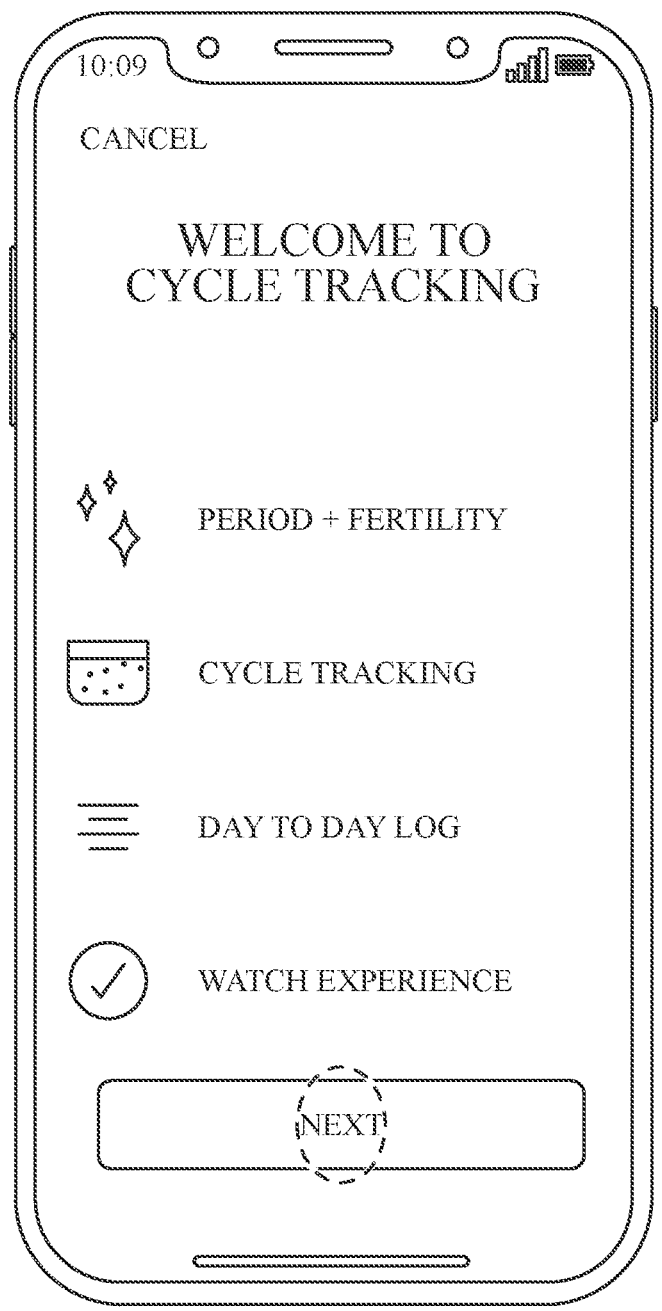
Figure 10D:
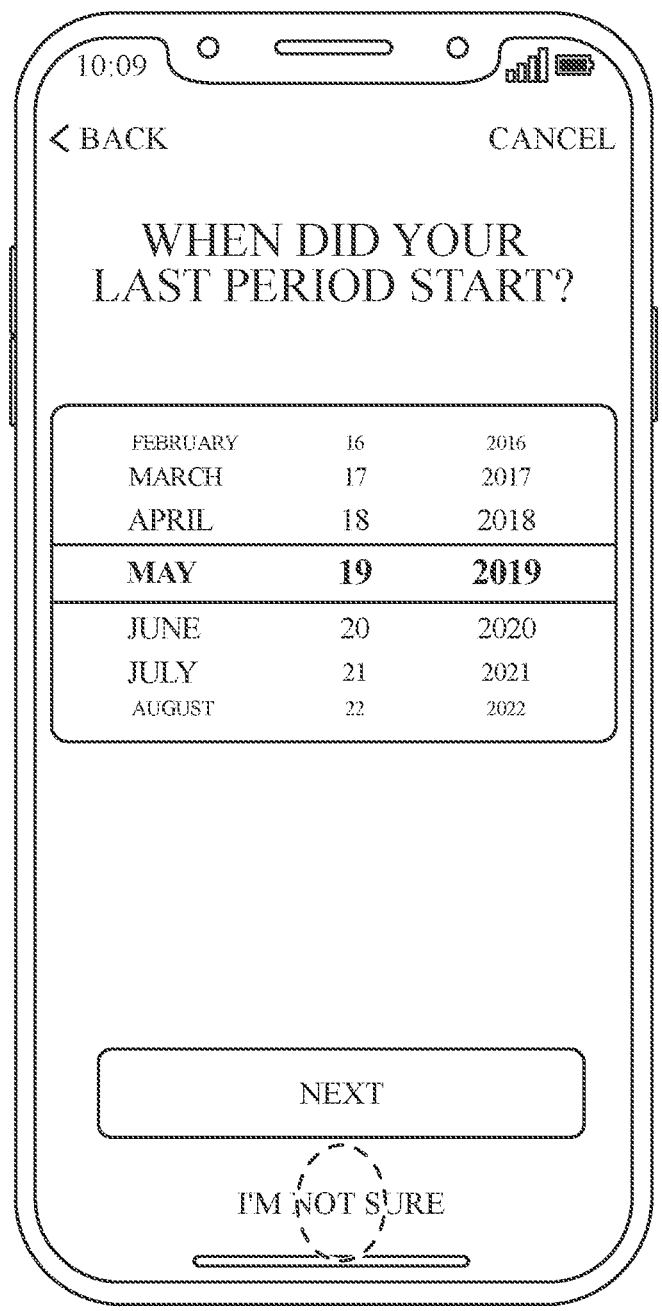
Figure 10E:
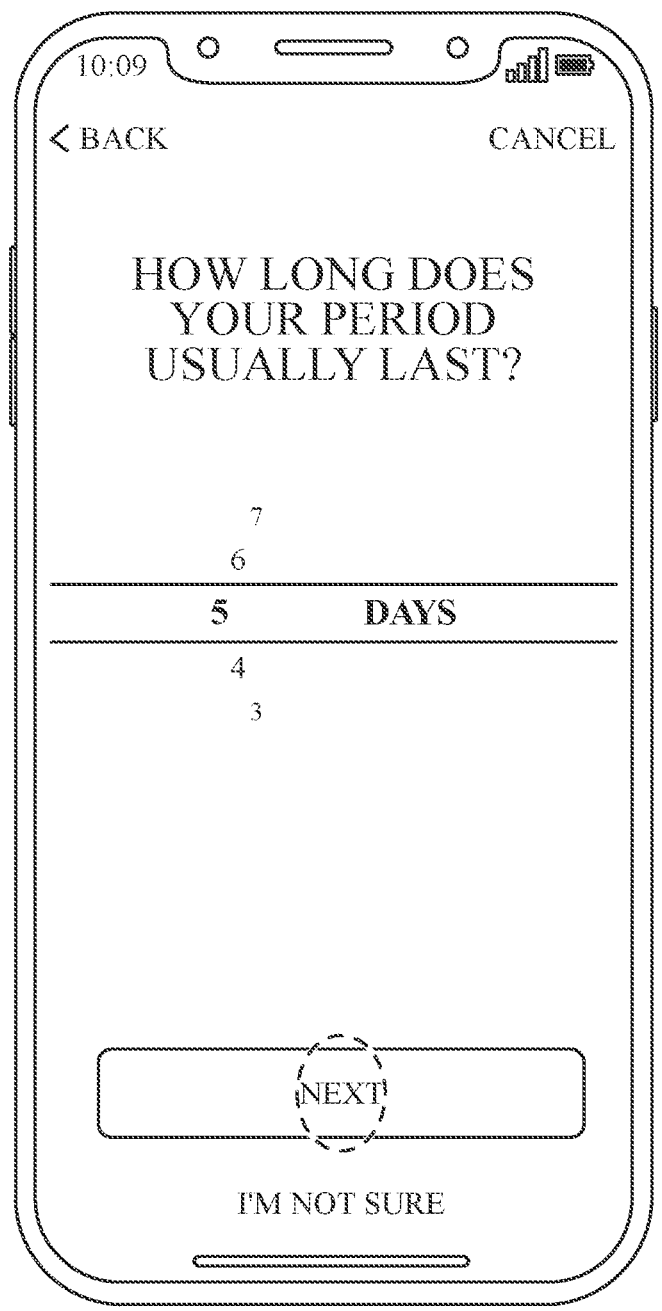
Figure 10F:
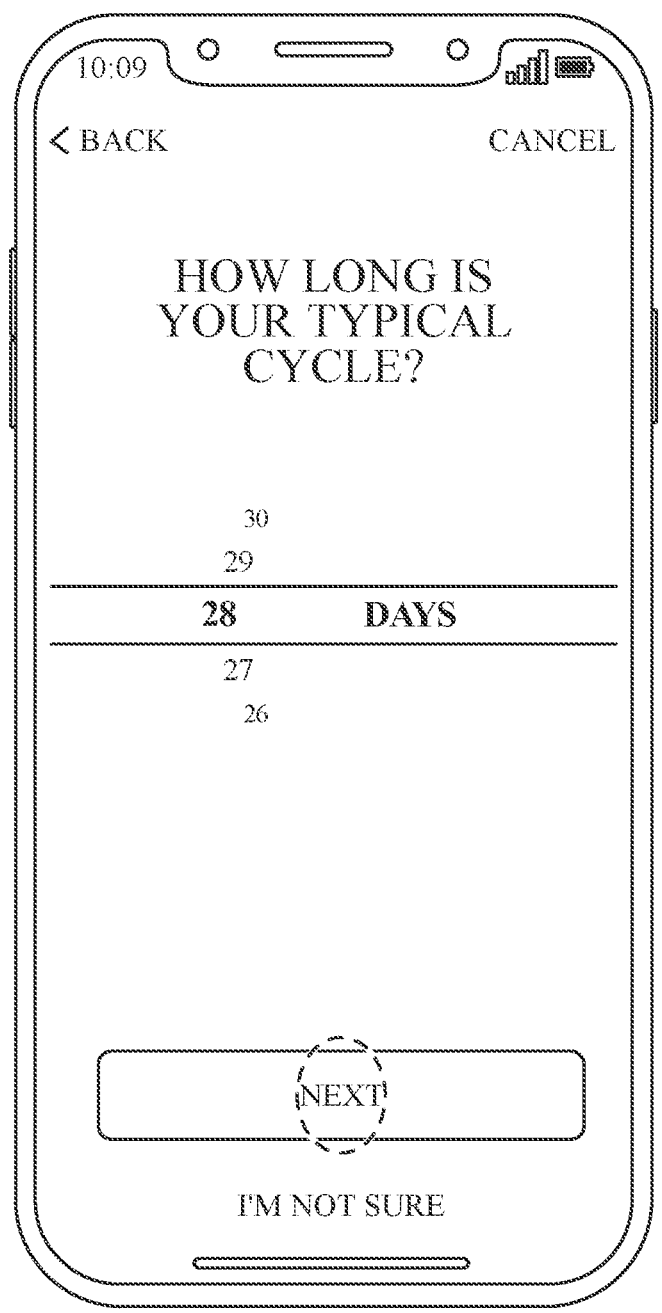
Figure 10G:
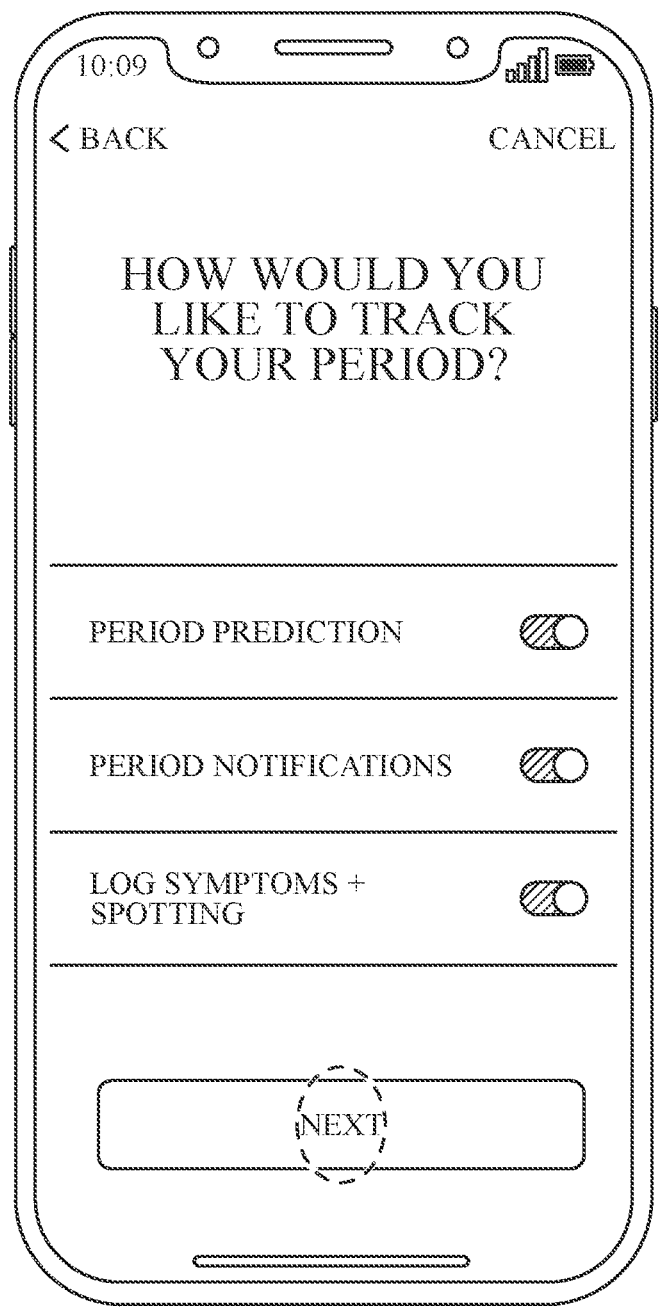
Figure 10H:
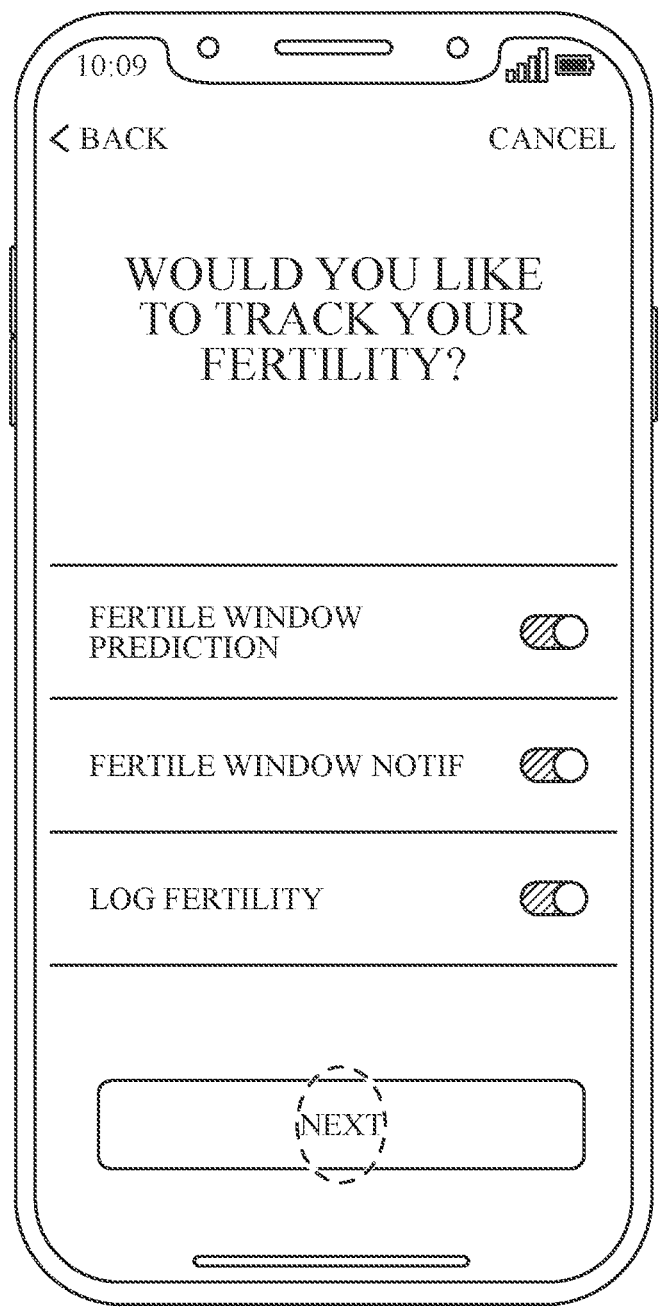
Figure 101:
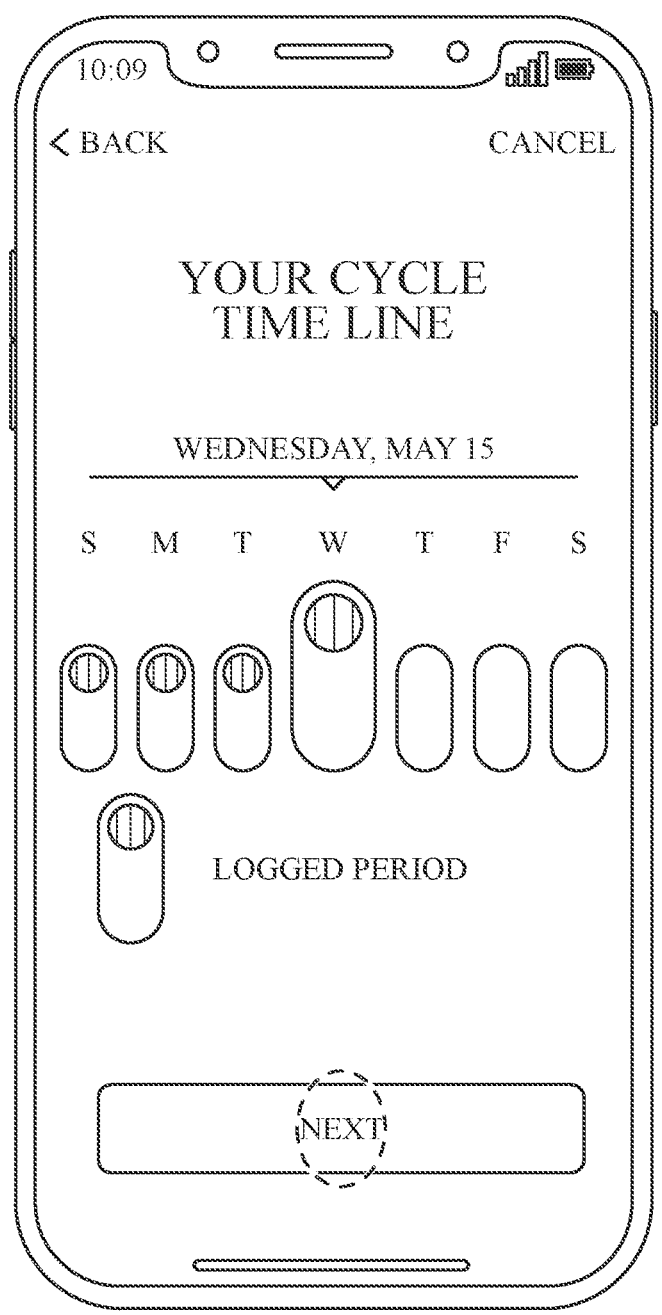
Figure 10J:
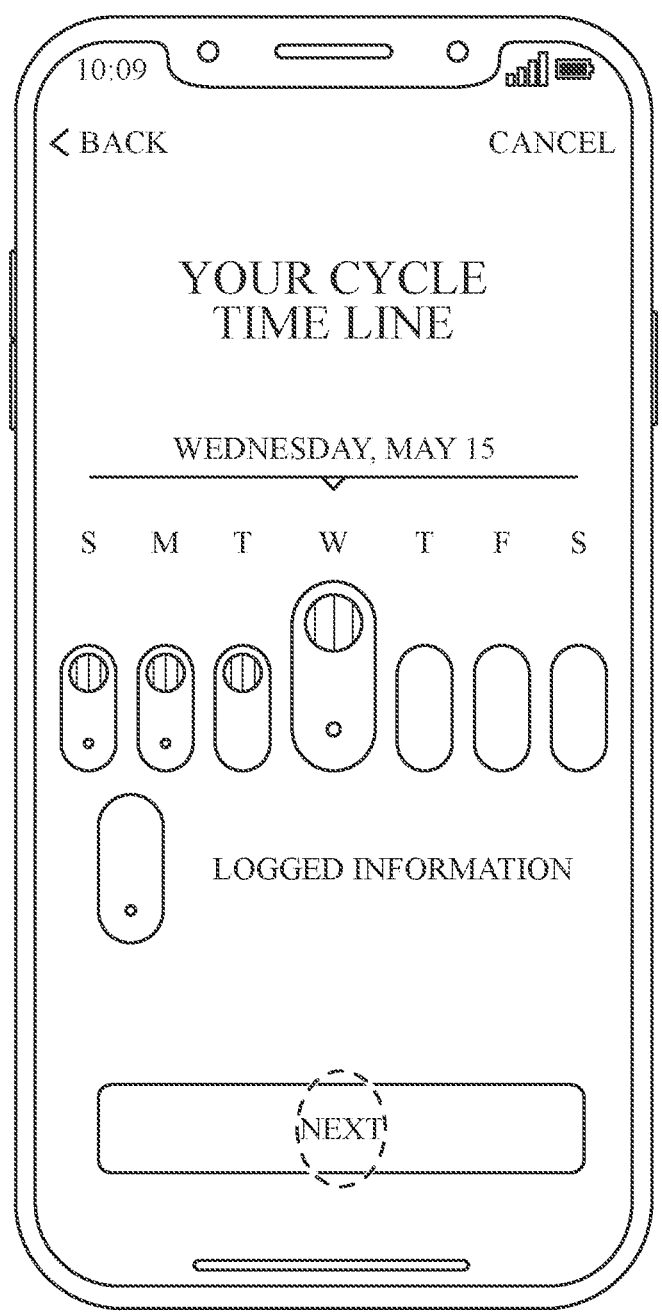
Figure 10K:
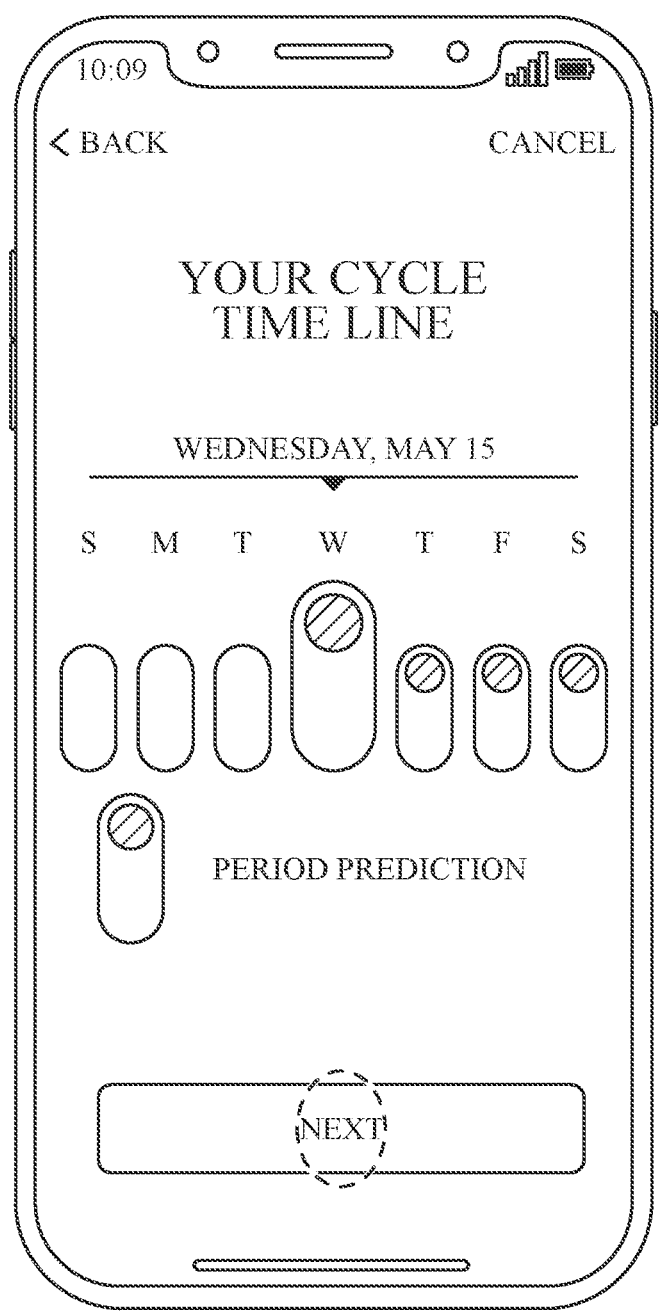

Below, FIGS. 1A-1B, 2, 3, 4A-4B, and 5A-5H provide a description of exemplary devices for performing the techniques for managing event notifications. FIGS. 6A-6O illustrate exemplary devices and user interfaces for cycle tracking. FIGS. 7A-7B are a flow diagram illustrating methods for cycle tracking, in accordance with some embodiments. The user interfaces in FIGS. 6A-6O are used to illustrate the processes described below, including the processes in FIGS. 7A-7B. FIGS. 8A-8S illustrate exemplary devices and user interfaces for cycle tracking. FIGS. 9A-9B are a flow diagram illustrating methods for cycle tracking, in accordance with some embodiments. The user interfaces in FIGS. 8A-8S are used to illustrate the processes described below, including the processes in FIGS. 9A-9B. FIGS. 10A-10AK illustrate exemplary devices and user interfaces for setting up a cycle tracking application.

Although the following description uses terms "first," "second," etc. to describe various elements, these elements should not be limited by the terms. These terms are only used to distinguish one element from another. For example, a first touch could be termed a second touch, and, similarly, a second touch could be termed a first touch, without departing from the scope of the various described embodiments. The first touch and the second touch are both touches, but they are not the same touch.

The terminology used in the description of the various described embodiments herein is for the purpose of describing particular embodiments only and is not intended to be limiting. As used in the description of the various described embodiments and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

The term "if" is, optionally, construed to mean "when" or "upon" or "in response to determining" or "in response to detecting," depending on the context. Similarly, the phrase "if it is determined" or "if [a stated condition or event] is detected" is, optionally, construed to mean "upon determining" or "in response to determining" or "upon detecting [the stated condition or event]" or "in response to detecting [the stated condition or event]," depending on the context.

Embodiments of electronic devices, user interfaces for such devices, and associated processes for using such devices are described. In some embodiments, the device is a portable communications device, such as a mobile telephone, that also contains other functions, such as PDA and/or music player functions. Exemplary embodiments of portable multifunction devices include, without limitation, the iPhone®, iPod Touch®, and iPad® devices from Apple Inc. of Cupertino, Calif. Other portable electronic devices, such as laptops or tablet computers with touch-sensitive surfaces (e.g., touch screen displays and/or touchpads), are, optionally, used. It should also be understood that, in some embodiments, the device is not a portable communications device, but is a desktop computer with a touch-sensitive surface (e.g., a touch screen display and/or a touchpad).

In the discussion that follows, an electronic device that includes a display and a touch-sensitive surface is described. It should be understood, however, that the electronic device optionally includes one or more other physical user-interface devices, such as a physical keyboard, a mouse, and/or a joystick.

The device typically supports a variety of applications, such as one or more of the following: a drawing application, a presentation application, a word processing application, a website creation application, a disk authoring application, a spreadsheet application, a gaming application, a telephone application, a video conferencing application, an e-mail application, an instant messaging application, a workout support application, a photo management application, a digital camera application, a digital video camera application, a web browsing application, a digital music player application, and/or a digital video player application.

The various applications that are executed on the device optionally use at least one common physical user-interface device, such as the touch-sensitive surface. One or more functions of the touch-sensitive surface as well as corresponding information displayed on the device are, optionally, adjusted and/or varied from one application to the next and/or within a respective application. In this way, a common physical architecture (such as the touch-sensitive surface) of the device optionally supports the variety of applications with user interfaces that are intuitive and transparent to the user.

Figure 1A:
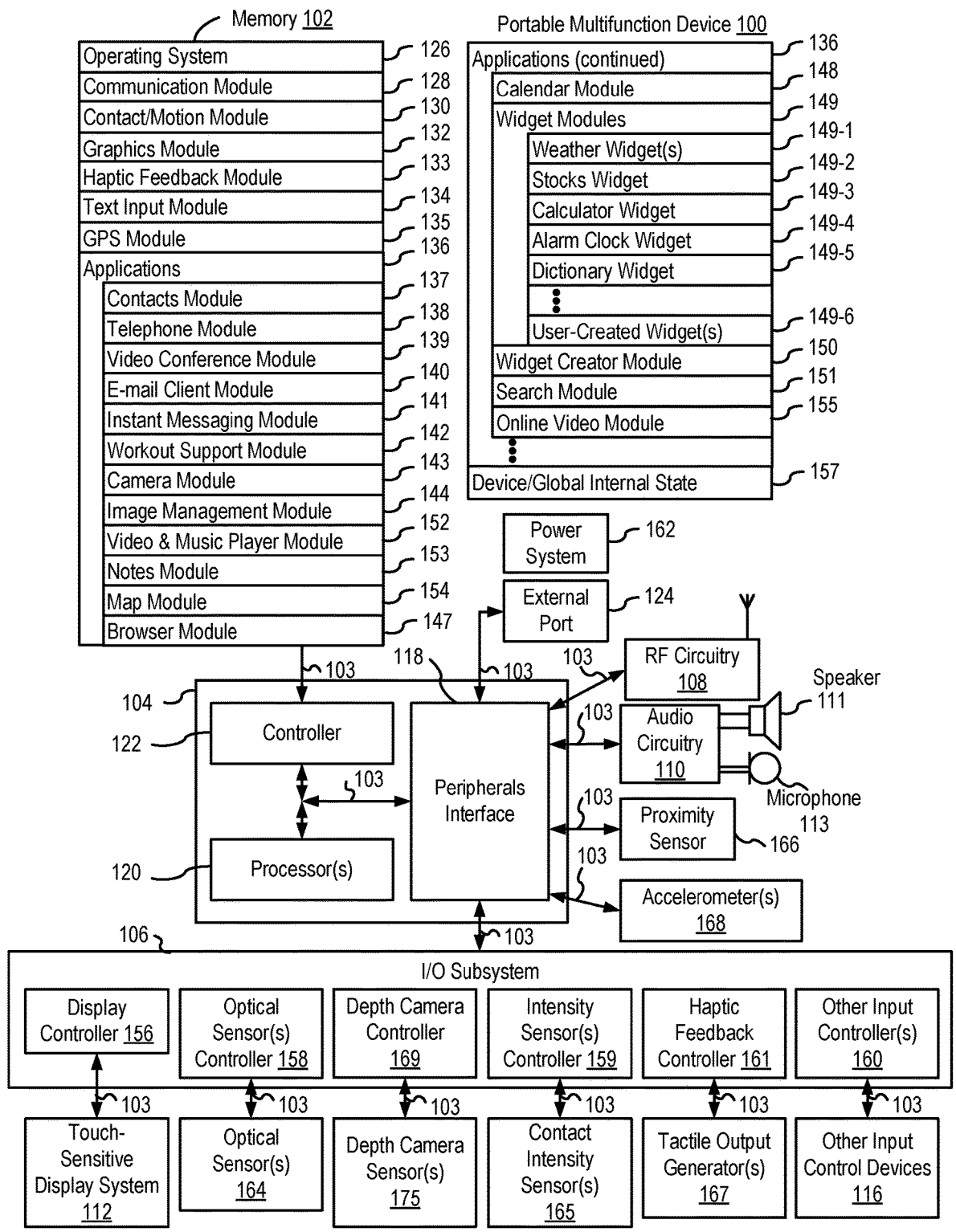
FIG. 1A is a block diagram illustrating a portable multifunction device with a touch-sensitive display in accordance with some embodiments.

Attention is now directed toward embodiments of portable devices with touch-sensitive displays. FIG. 1A is a block diagram illustrating portable multifunction device 100 with touch-sensitive display system 112 in accordance with some embodiments. Touch-sensitive display 112 is sometimes called a "touch screen" for convenience and is sometimes known as or called a "touch-sensitive display system." Device 100 includes memory 102 (which optionally includes one or more computer-readable storage mediums), memory controller 122, one or more processing units (CPUs) 120, peripherals interface 118, RF circuitry 108, audio circuitry 110, speaker 111, microphone 113, input/output (I/O) subsystem 106, other input control devices 116, and external port 124. Device 100 optionally includes one or more optical sensors 164. Device 100 optionally includes one or more contact intensity sensors 165 for detecting intensity of contacts on device 100 (e.g., a touch-sensitive surface such as touch-sensitive display system 112 of device 100). Device 100 optionally includes one or more tactile output generators 167 for generating tactile outputs on device 100 (e.g., generating tactile outputs on a touch-sensitive surface such as touch-sensitive display system 112 of device 100 or touchpad 355 of device 300). These components optionally communicate over one or more communication buses or signal lines 103.

As used in the specification and claims, the term "intensity" of a contact on a touch-sensitive surface refers to the force or pressure (force per unit area) of a contact (e.g., a finger contact) on the touch-sensitive surface, or to a substitute (proxy) for the force or pressure of a contact on the touch-sensitive surface. The intensity of a contact has a range of values that includes at least four distinct values and more typically includes hundreds of distinct values (e.g., at least 256). Intensity of a contact is, optionally, determined (or measured) using various approaches and various sensors or combinations of sensors. For example, one or more force sensors underneath or adjacent to the touch-sensitive surface are, optionally, used to measure force at various points on the touch-sensitive surface. In some implementations, force measurements from multiple force sensors are combined (e.g., a weighted average) to determine an estimated force of a contact. Similarly, a pressure-sensitive tip of a stylus is, optionally, used to determine a pressure of the stylus on the touch-sensitive surface. Alternatively, the size of the contact area detected on the touch-sensitive surface and/or changes thereto, the capacitance of the touch-sensitive surface proximate to the contact and/or changes thereto, and/or the resistance of the touch-sensitive surface proximate to the contact and/or changes thereto are, optionally, used as a substitute for the force or pressure of the contact on the touch-sensitive surface. In some implementations, the substitute measurements for contact force or pressure are used directly to determine whether an intensity threshold has been exceeded (e.g., the intensity threshold is described in units corresponding to the substitute measurements). In some implementations, the substitute measurements for contact force or pressure are converted to an estimated force or pressure, and the estimated force or pressure is used to determine whether an intensity threshold has been exceeded (e.g., the intensity threshold is a pressure threshold measured in units of pressure). Using the intensity of a contact as an attribute of a user input allows for user access to additional device functionality that may otherwise not be accessible by the user on a reduced-size device with limited real estate for displaying affordances (e.g., on a touch-sensitive display) and/or receiving user input (e.g., via a touch-sensitive display, a touch-sensitive surface, or a physical/mechanical control such as a knob or a button).

As used in the specification and claims, the term "tactile output" refers to physical displacement of a device relative to a previous position of the device, physical displacement of a component (e.g., a touch-sensitive surface) of a device relative to another component (e.g., housing) of the device, or displacement of the component relative to a center of mass of the device that will be detected by a user with the user's sense of touch. For example, in situations where the device or the component of the device is in contact with a surface of a user that is sensitive to touch (e.g., a finger, palm, or other part of a user's hand), the tactile output generated by the physical displacement will be interpreted by the user as a tactile sensation corresponding to a perceived change in physical characteristics of the device or the component of the device. For example, movement of a touch-sensitive surface (e.g., a touch-sensitive display or trackpad) is, optionally, interpreted by the user as a "down click" or "up click" of a physical actuator button. In some cases, a user will feel a tactile sensation such as an "down click" or "up click" even when there is no movement of a physical actuator button associated with the touch-sensitive surface that is physically pressed (e.g., displaced) by the user's movements. As another example, movement of the touch-sensitive surface is, optionally, interpreted or sensed by the user as "roughness" of the touch-sensitive surface, even when there is no change in smoothness of the touch-sensitive surface. While such interpretations of touch by a user will be subject to the individualized sensory perceptions of the user, there are many sensory perceptions of touch that are common to a large majority of users. Thus, when a tactile output is described as corresponding to a particular sensory perception of a user (e.g., an "up click," a "down click," "roughness"), unless otherwise stated, the generated tactile output corresponds to physical displacement of the device or a component thereof that will generate the described sensory perception for a typical (or average) user.

It should be appreciated that device 100 is only one example of a portable multifunction device, and that device 100 optionally has more or fewer components than shown, optionally combines two or more components, or optionally has a different configuration or arrangement of the components. The various components shown in FIG. 1A are implemented in hardware, software, or a combination of both hardware and software, including one or more signal processing and/or application-specific integrated circuits.

Memory 102 optionally includes high-speed random access memory and optionally also includes non-volatile memory, such as one or more magnetic disk storage devices, flash memory devices, or other non-volatile solid-state memory devices. Memory controller 122 optionally controls access to memory 102 by other components of device 100.

Peripherals interface 118 can be used to couple input and output peripherals of the device to CPU 120 and memory 102. The one or more processors 120 run or execute various software programs and/or sets of instructions stored in memory 102 to perform various functions for device 100 and to process data. In some embodiments, peripherals interface 118, CPU 120, and memory controller 122 are, optionally, implemented on a single chip, such as chip 104. In some other embodiments, they are, optionally, implemented on separate chips.

RF (radio frequency) circuitry 108 receives and sends RF signals, also called electromagnetic signals. RF circuitry 108 converts electrical signals to/from electromagnetic signals and communicates with communications networks and other communications devices via the electromagnetic signals. RF circuitry 108 optionally includes well-known circuitry for performing these functions, including but not limited to an antenna system, an RF transceiver, one or more amplifiers, a tuner, one or more oscillators, a digital signal processor, a CODEC chipset, a subscriber identity module (SIM) card, memory, and so forth. RF circuitry 108 optionally communicates with networks, such as the Internet, also referred to as the World Wide Web (WWW), an intranet and/or a wireless network, such as a cellular telephone network, a wireless local area network (LAN) and/or a metropolitan area network (MAN), and other devices by wireless communication. The RF circuitry 108 optionally includes well-known circuitry for detecting near field communication (NFC) fields, such as by a short-range communication radio. The wireless communication optionally uses any of a plurality of communications standards, protocols, and technologies, including but not limited to Global System for Mobile Communications (GSM), Enhanced Data GSM Environment (EDGE), high-speed downlink packet access (HSDPA), high-speed uplink packet access (HSUPA), Evolution, Data-Only (EV-DO), HSPA, HSPA+, Dual-Cell HSPA (DC-HSPDA), long term evolution (LTE), near field communication (NFC), wideband code division multiple access (W-CDMA), code division multiple access (CDMA), time division multiple access (TDMA), Bluetooth, Bluetooth Low Energy (BTLE), Wireless Fidelity (Wi-Fi) (e.g., IEEE 802.11a, IEEE 802.11b, IEEE 802.11g, IEEE 802.11n, and/or IEEE 802.11ac), voice over Internet Protocol (VoIP), Wi-MAX, a protocol for e-mail (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), Instant Messaging and Presence Service (IMPS)), and/or Short Message Service (SMS), or any other suitable communication protocol, including communication protocols not yet developed as of the filing date of this document.

Audio circuitry 110, speaker 111, and microphone 113 provide an audio interface between a user and device 100. Audio circuitry 110 receives audio data from peripherals interface 118, converts the audio data to an electrical signal, and transmits the electrical signal to speaker 111. Speaker 111 converts the electrical signal to human-audible sound waves. Audio circuitry 110 also receives electrical signals converted by microphone 113 from sound waves. Audio circuitry 110 converts the electrical signal to audio data and transmits the audio data to peripherals interface 118 for processing. Audio data is, optionally, retrieved from and/or transmitted to memory 102 and/or RF circuitry 108 by peripherals interface 118. In some embodiments, audio circuitry 110 also includes a headset jack (e.g., 212, FIG. 2). The headset jack provides an interface between audio circuitry 110 and removable audio input/output peripherals, such as output-only headphones or a headset with both output (e.g., a headphone for one or both ears) and input (e.g., a microphone).

I/O subsystem 106 couples input/output peripherals on device 100, such as touch screen 112 and other input control devices 116, to peripherals interface 118. I/O subsystem 106 optionally includes display controller 156, optical sensor controller 158, depth camera controller 169, intensity sensor controller 159, haptic feedback controller 161, and one or more input controllers 160 for other input or control devices. The one or more input controllers 160 receive/send electrical signals from/to other input control devices 116. The other input control devices 116 optionally include physical buttons (e.g., push buttons, rocker buttons, etc.), dials, slider switches, joysticks, click wheels, and so forth. In some alternate embodiments, input controller(s) 160 are, optionally, coupled to any (or none) of the following: a keyboard, an infrared port, a USB port, and a pointer device such as a mouse. The one or more buttons (e.g., 208, FIG. 2) optionally include an up/down button for volume control of speaker 111 and/or microphone 113. The one or more buttons optionally include a push button (e.g., 206, FIG. 2).

A quick press of the push button optionally disengages a lock of touch screen 112 or optionally begins a process that uses gestures on the touch screen to unlock the device, as described in U.S. patent application Ser. No. 11/322,549, "Unlocking a Device by Performing Gestures on an Unlock Image," filed Dec. 23, 2005, U.S. Pat. No. 7,657,849, which is hereby incorporated by reference in its entirety. A longer press of the push button (e.g., 206) optionally turns power to device 100 on or off. The functionality of one or more of the buttons are, optionally, user-customizable. Touch screen 112 is used to implement virtual or soft buttons and one or more soft keyboards.

Touch-sensitive display 112 provides an input interface and an output interface between the device and a user. Display controller 156 receives and/or sends electrical signals from/to touch screen 112. Touch screen 112 displays visual output to the user. The visual output optionally includes graphics, text, icons, video, and any combination thereof (collectively termed "graphics"). In some embodiments, some or all of the visual output optionally corresponds to user-interface objects.

Touch screen 112 has a touch-sensitive surface, sensor, or set of sensors that accepts input from the user based on haptic and/or tactile contact. Touch screen 112 and display controller 156 (along with any associated modules and/or sets of instructions in memory 102) detect contact (and any movement or breaking of the contact) on touch screen 112 and convert the detected contact into interaction with user-interface objects (e.g., one or more soft keys, icons, web pages, or images) that are displayed on touch screen 112. In an exemplary embodiment, a point of contact between touch screen 112 and the user corresponds to a finger of the user.

Touch screen 112 optionally uses LCD (liquid crystal display) technology, LPD (light emitting polymer display) technology, or LED (light emitting diode) technology, although other display technologies are used in other embodiments. Touch screen 112 and display controller 156 optionally detect contact and any movement or breaking thereof using any of a plurality of touch sensing technologies now known or later developed, including but not limited to capacitive, resistive, infrared, and surface acoustic wave technologies, as well as other proximity sensor arrays or other elements for determining one or more points of contact with touch screen 112. In an exemplary embodiment, projected mutual capacitance sensing technology is used, such as that found in the iPhone® and iPod Touch® from Apple Inc. of Cupertino, Calif.

A touch-sensitive display in some embodiments of touch screen 112 is, optionally, analogous to the multi-touch sensitive touchpads described in the following U.S. Pat. No. 6,323,846 (Westerman et al.), U.S. Pat. No. 6,570,557 (Westerman et al.), and/or U.S. Pat. No. 6,677,932 (Westerman), and/or U.S. Patent Publication 2002/0015024A1, each of which is hereby incorporated by reference in its entirety. However, touch screen 112 displays visual output from device 100, whereas touch-sensitive touchpads do not provide visual output.

A touch-sensitive display in some embodiments of touch screen 112 is described in the following applications: (1) U.S. patent application Ser. No. 11/381,313, "Multipoint Touch Surface Controller," filed May 2, 2006; (2) U.S. patent application Ser. No. 10/840,862, "Multipoint Touchscreen," filed May 6, 2004; (3) U.S. patent application Ser. No. 10/903,964, "Gestures For Touch Sensitive Input Devices," filed Jul. 30, 2004; (4) U.S. patent application Ser. No. 11/048,264, "Gestures For Touch Sensitive Input Devices," filed Jan. 31, 2005; (5) U.S. patent application Ser. No. 11/038,590, "Mode-Based Graphical User Interfaces For Touch Sensitive Input Devices," filed Jan. 18, 2005; (6) U.S. patent application Ser. No. 11/228,758, "Virtual Input Device Placement On A Touch Screen User Interface," filed Sep. 16, 2005; (7) U.S. patent application Ser. No. 11/228,700, "Operation Of A Computer With A Touch Screen Interface," filed Sep. 16, 2005; (8) U.S. patent application Ser. No. 11/228,737, "Activating Virtual Keys Of A Touch-Screen Virtual Keyboard," filed Sep. 16, 2005; and (9) U.S.

patent application Ser. No. 11/367,749, "Multi-Functional Hand-Held Device," filed Mar. 3, 2006. All of these applications are incorporated by reference herein in their entirety.

Touch screen 112 optionally has a video resolution in excess of 100 dpi. In some embodiments, the touch screen has a video resolution of approximately 160 dpi. The user optionally makes contact with touch screen 112 using any suitable object or appendage, such as a stylus, a finger, and so forth. In some embodiments, the user interface is designed to work primarily with finger-based contacts and gestures, which can be less precise than stylus-based input due to the larger area of contact of a finger on the touch screen. In some embodiments, the device translates the rough finger-based input into a precise pointer/cursor position or command for performing the actions desired by the user.

In some embodiments, in addition to the touch screen, device 100 optionally includes a touchpad for activating or deactivating particular functions. In some embodiments, the touchpad is a touch-sensitive area of the device that, unlike the touch screen, does not display visual output. The touchpad is, optionally, a touch-sensitive surface that is separate from touch screen 112 or an extension of the touch-sensitive surface formed by the touch screen.

Device 100 also includes power system 162 for powering the various components. Power system 162 optionally includes a power management system, one or more power sources (e.g., battery, alternating current (AC)), a recharging system, a power failure detection circuit, a power converter or inverter, a power status indicator (e.g., a light-emitting diode (LED)) and any other components associated with the generation, management and distribution of power in portable devices.

Device 100 optionally also includes one or more optical sensors 164. FIG. 1A shows an optical sensor coupled to optical sensor controller 158 in I/O subsystem 106. Optical sensor 164 optionally includes charge-coupled device (CCD) or complementary metal-oxide semiconductor (CMOS) phototransistors. Optical sensor 164 receives light from the environment, projected through one or more lenses, and converts the light to data representing an image. In conjunction with imaging module 143 (also called a camera module), optical sensor 164 optionally captures still images or video. In some embodiments, an optical sensor is located on the back of device 100, opposite touch screen display 112 on the front of the device so that the touch screen display is enabled for use as a viewfinder for still and/or video image acquisition. In some embodiments, an optical sensor is located on the front of the device so that the user's image is, optionally, obtained for video conferencing while the user views the other video conference participants on the touch screen display. In some embodiments, the position of optical sensor 164 can be changed by the user (e.g., by rotating the lens and the sensor in the device housing) so that a single optical sensor 164 is used along with the touch screen display for both video conferencing and still and/or video image acquisition.

Device 100 optionally also includes one or more depth camera sensors 175. FIG. 1A shows a depth camera sensor coupled to depth camera controller 169 in I/O subsystem 106. Depth camera sensor 175 receives data from the environment to create a three dimensional model of an object (e.g., a face) within a scene from a viewpoint (e.g., a depth camera sensor). In some embodiments, in conjunction with imaging module 143 (also called a camera module), depth camera sensor 175 is optionally used to determine a depth map of different portions of an image captured by the imaging module 143. In some embodiments, a depth camera sensor is located on the front of device 100 so that the user's image with depth information is, optionally, obtained for video conferencing while the user views the other video conference participants on the touch screen display and to capture selfies with depth map data. In some embodiments, the depth camera sensor 175 is located on the back of device, or on the back and the front of the device 100. In some embodiments, the position of depth camera sensor 175 can be changed by the user (e.g., by rotating the lens and the sensor in the device housing) so that a depth camera sensor 175 is used along with the touch screen display for both video conferencing and still and/or video image acquisition.

In some embodiments, a depth map (e.g., depth map image) contains information (e.g., values) that relates to the distance of objects in a scene from a viewpoint (e.g., a camera, an optical sensor, a depth camera sensor). In one embodiment of a depth map, each depth pixel defines the position in the viewpoint's Z-axis where its corresponding two-dimensional pixel is located. In some embodiments, a depth map is composed of pixels wherein each pixel is defined by a value (e.g., 0-255). For example, the "0" value represents pixels that are located at the most distant place in a "three dimensional" scene and the "255" value represents pixels that are located closest to a viewpoint (e.g., a camera, an optical sensor, a depth camera sensor) in the "three dimensional" scene. In other embodiments, a depth map represents the distance between an object in a scene and the plane of the viewpoint. In some embodiments, the depth map includes information about the relative depth of various features of an object of interest in view of the depth camera (e.g., the relative depth of eyes, nose, mouth, ears of a user's face). In some embodiments, the depth map includes information that enables the device to determine contours of the object of interest in a z direction.

Device 100 optionally also includes one or more contact intensity sensors 165. FIG. 1A shows a contact intensity sensor coupled to intensity sensor controller 159 in I/O subsystem 106. Contact intensity sensor 165 optionally includes one or more piezoresistive strain gauges, capacitive force sensors, electric force sensors, piezoelectric force sensors, optical force sensors, capacitive touch-sensitive surfaces, or other intensity sensors (e.g., sensors used to measure the force (or pressure) of a contact on a touch-sensitive surface). Contact intensity sensor 165 receives contact intensity information (e.g., pressure information or a proxy for pressure information) from the environment. In some embodiments, at least one contact intensity sensor is collocated with, or proximate to, a touch-sensitive surface (e.g., touch-sensitive display system 112). In some embodiments, at least one contact intensity sensor is located on the back of device 100, opposite touch screen display 112, which is located on the front of device 100.

Device 100 optionally also includes one or more proximity sensors 166. FIG. 1A shows proximity sensor 166 coupled to peripherals interface 118. Alternately, proximity sensor 166 is, optionally, coupled to input controller 160 in I/O subsystem 106. Proximity sensor 166 optionally performs as described in U.S. patent application Ser. No. 11/241,839, "Proximity Detector In Handheld Device"; Ser. No. 11/240,788, "Proximity Detector In Handheld Device"; Ser. No. 11/620,702, "Using Ambient Light Sensor To Augment Proximity Sensor Output"; Ser. No. 11/586,862, "Automated Response To And Sensing Of User Activity In Portable Devices"; and Ser. No. 11/638,251, "Methods And Systems For Automatic Configuration Of Peripherals," which are hereby incorporated by reference in their entirety.

In some embodiments, the proximity sensor turns off and disables touch screen 112 when the multifunction device is placed near the user's ear (e.g., when the user is making a phone call).

Device 100 optionally also includes one or more tactile output generators 167. FIG. 1A shows a tactile output generator coupled to haptic feedback controller 161 in I/O subsystem 106. Tactile output generator 167 optionally includes one or more electroacoustic devices such as speakers or other audio components and/or electromechanical devices that convert energy into linear motion such as a motor, solenoid, electroactive polymer, piezoelectric actuator, electrostatic actuator, or other tactile output generating component (e.g., a component that converts electrical signals into tactile outputs on the device). Contact intensity sensor 165 receives tactile feedback generation instructions from haptic feedback module 133 and generates tactile outputs on device 100 that are capable of being sensed by a user of device 100. In some embodiments, at least one tactile output generator is collocated with, or proximate to, a touch-sensitive surface (e.g., touch-sensitive display system 112) and, optionally, generates a tactile output by moving the touch-sensitive surface vertically (e.g., in/out of a surface of device 100) or laterally (e.g., back and forth in the same plane as a surface of device 100). In some embodiments, at least one tactile output generator sensor is located on the back of device 100, opposite touch screen display 112, which is located on the front of device 100.

Device 100 optionally also includes one or more accelerometers 168. FIG. 1A shows accelerometer 168 coupled to peripherals interface 118. Alternately, accelerometer 168 is, optionally, coupled to an input controller 160 in I/O subsystem 106. Accelerometer 168 optionally performs as described in U.S. Patent Publication No. 20050190059, "Acceleration-based Theft Detection System for Portable Electronic Devices," and U.S. Patent Publication No. 20060017692, "Methods And Apparatuses For Operating A Portable Device Based On An Accelerometer," both of which are incorporated by reference herein in their entirety. In some embodiments, information is displayed on the touch screen display in a portrait view or a landscape view based on an analysis of data received from the one or more accelerometers. Device 100 optionally includes, in addition to accelerometer(s) 168, a magnetometer and a GPS (or GLONASS or other global navigation system) receiver for obtaining information concerning the location and orientation (e.g., portrait or landscape) of device 100.

Figure 3:
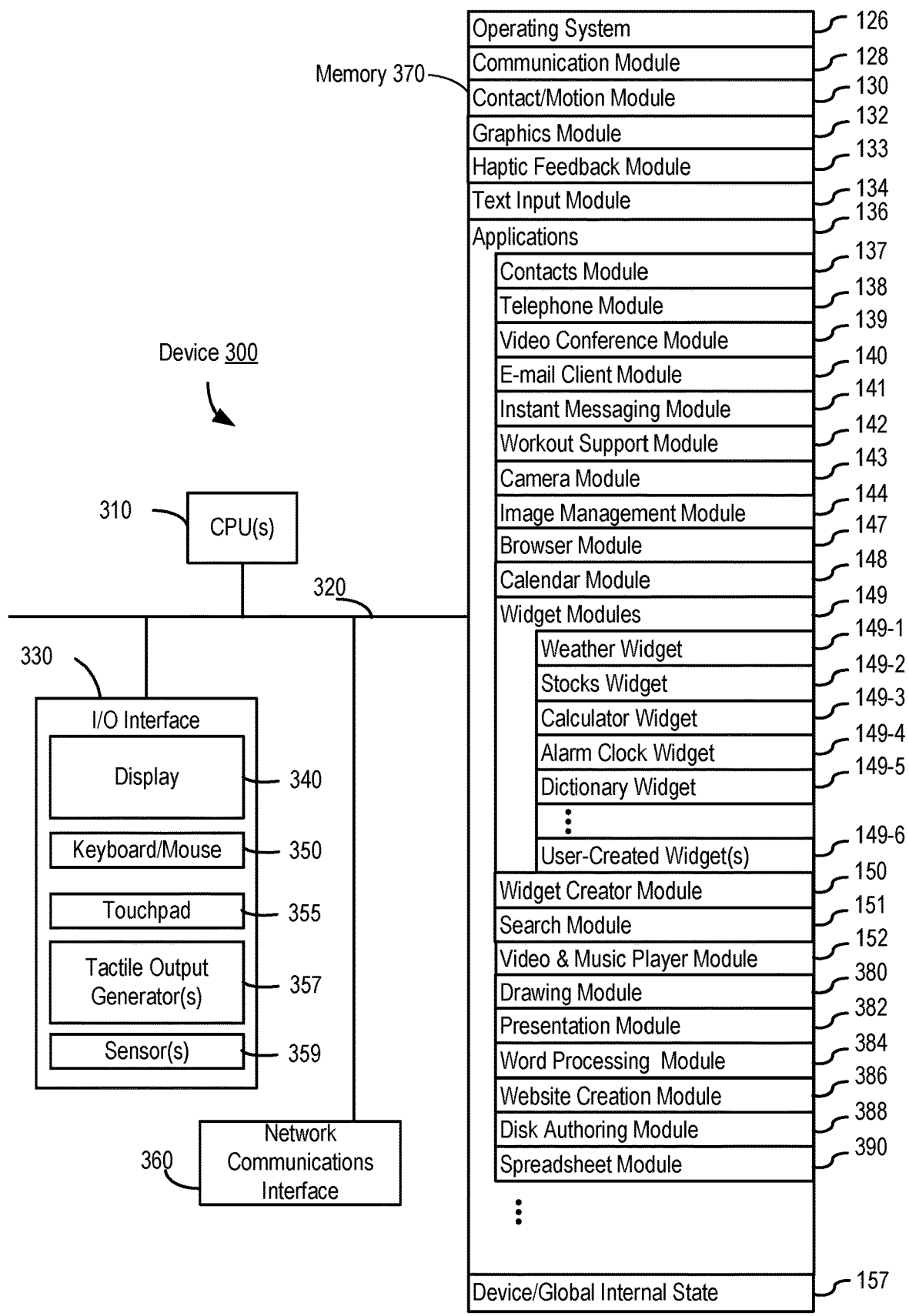
FIG. 3 is a block diagram of an exemplary multifunction device with a display and a touch-sensitive surface in accordance with some embodiments.

In some embodiments, the software components stored in memory 102 include operating system 126, communication module (or set of instructions) 128, contact/motion module (or set of instructions) 130, graphics module (or set of instructions) 132, text input module (or set of instructions) 134, Global Positioning System (GPS) module (or set of instructions) 135, and applications (or sets of instructions) 136. Furthermore, in some embodiments, memory 102 (FIG. 1A) or 370 (FIG. 3) stores device/global internal state 157, as shown in FIGS. 1A and 3. Device/global internal state 157 includes one or more of: active application state, indicating which applications, if any, are currently active; display state, indicating what applications, views or other information occupy various regions of touch screen display 112; sensor state, including information obtained from the device's various sensors and input control devices 116; and location information concerning the device's location and/or attitude.

Operating system 126 (e.g., Darwin, RTXC, LINUX, UNIX, OS X, iOS, WINDOWS, or an embedded operating system such as VxWorks) includes various software components and/or drivers for controlling and managing general system tasks (e.g., memory management, storage device control, power management, etc.) and facilitates communication between various hardware and software components.

Communication module 128 facilitates communication with other devices over one or more external ports 124 and also includes various software components for handling data received by RF circuitry 108 and/or external port 124. External port 124 (e.g., Universal Serial Bus (USB), FIREWIRE, etc.) is adapted for coupling directly to other devices or indirectly over a network (e.g., the Internet, wireless LAN, etc.). In some embodiments, the external port is a multi-pin (e.g., 30-pin) connector that is the same as, or similar to and/or compatible with, the 30-pin connector used on iPod® (trademark of Apple Inc.) devices.

Contact/motion module 130 optionally detects contact with touch screen 112 (in conjunction with display controller 156) and other touch-sensitive devices (e.g., a touchpad or physical click wheel). Contact/motion module 130 includes various software components for performing various operations related to detection of contact, such as determining if contact has occurred (e.g., detecting a finger-down event), determining an intensity of the contact (e.g., the force or pressure of the contact or a substitute for the force or pressure of the contact), determining if there is movement of the contact and tracking the movement across the touch-sensitive surface (e.g., detecting one or more finger-dragging events), and determining if the contact has ceased (e.g., detecting a finger-up event or a break in contact). Contact/motion module 130 receives contact data from the touch-sensitive surface. Determining movement of the point of contact, which is represented by a series of contact data, optionally includes determining speed (magnitude), velocity (magnitude and direction), and/or an acceleration (a change in magnitude and/or direction) of the point of contact. These operations are, optionally, applied to single contacts (e.g., one finger contacts) or to multiple simultaneous contacts (e.g., "multitouch"/multiple finger contacts). In some embodiments, contact/motion module 130 and display controller 156 detect contact on a touchpad.

In some embodiments, contact/motion module 130 uses a set of one or more intensity thresholds to determine whether an operation has been performed by a user (e.g., to determine whether a user has "clicked" on an icon). In some embodiments, at least a subset of the intensity thresholds are determined in accordance with software parameters (e.g., the intensity thresholds are not determined by the activation thresholds of particular physical actuators and can be adjusted without changing the physical hardware of device 100). For example, a mouse "click" threshold of a trackpad or touch screen display can be set to any of a large range of predefined threshold values without changing the trackpad or touch screen display hardware. Additionally, in some implementations, a user of the device is provided with software settings for adjusting one or more of the set of intensity thresholds (e.g., by adjusting individual intensity thresholds and/or by adjusting a plurality of intensity thresholds at once with a system-level click "intensity" parameter).

Contact/motion module 130 optionally detects a gesture input by a user. Different gestures on the touch-sensitive surface have different contact patterns (e.g., different motions, timings, and/or intensities of detected contacts). Thus, a gesture is, optionally, detected by detecting a particular contact pattern. For example, detecting a finger tap gesture includes detecting a finger-down event followed by detecting a finger-up (liftoff) event at the same position (or substantially the same position) as the finger-down event (e.g., at the position of an icon). As another example, detecting a finger swipe gesture on the touch-sensitive surface includes detecting a finger-down event followed by detecting one or more finger-dragging events, and subsequently followed by detecting a finger-up (liftoff) event.

Graphics module 132 includes various known software components for rendering and displaying graphics on touch screen 112 or other display, including components for changing the visual impact (e.g., brightness, transparency, saturation, contrast, or other visual property) of graphics that are displayed. As used herein, the term "graphics" includes any object that can be displayed to a user, including, without limitation, text, web pages, icons (such as user-interface objects including soft keys), digital images, videos, animations, and the like.

In some embodiments, graphics module 132 stores data representing graphics to be used. Each graphic is, optionally, assigned a corresponding code. Graphics module 132 receives, from applications etc., one or more codes specifying graphics to be displayed along with, if necessary, coordinate data and other graphic property data, and then generates screen image data to output to display controller 156.

Haptic feedback module 133 includes various software components for generating instructions used by tactile output generator(s) 167 to produce tactile outputs at one or more locations on device 100 in response to user interactions with device 100.

Text input module 134, which is, optionally, a component of graphics module 132, provides soft keyboards for entering text in various applications (e.g., contacts 137, e-mail 140, IM 141, browser 147, and any other application that needs text input).

GPS module 135 determines the location of the device and provides this information for use in various applications (e.g., to telephone 138 for use in location-based dialing; to camera 143 as picture/video metadata; and to applications that provide location-based services such as weather widgets, local yellow page widgets, and map/navigation widgets).

Applications 136 optionally include the following modules (or sets of instructions), or a subset or superset thereof:
  Contacts module 137 (sometimes called an address book or contact list);
  Telephone module 138;
  Video conference module 139;
  E-mail client module 140;
  Instant messaging (IM) module 141;
  Workout support module 142;
  Camera module 143 for still and/or video images;
  Image management module 144;
  Video player module;
  Music player module;
  Browser module 147;
  Calendar module 148;
  Widget modules 149, which optionally include one or more of: weather widget 149-1, stocks widget 149-2, calculator widget 149-3, alarm clock widget 149-4, dictionary widget 149-5, and other widgets obtained by the user, as well as user-created widgets 149-6;
  Widget creator module 150 for making user-created widgets 149-6;
  Search module 151;
  Video and music player module 152, which merges video player module and music player module;
  Notes module 153;
  Map module 154; and/or
  Online video module 155.

Examples of other applications 136 that are, optionally, stored in memory 102 include other word processing applications, other image editing applications, drawing applications, presentation applications, JAVA-enabled applications, encryption, digital rights management, voice recognition, and voice replication.

In conjunction with touch screen 112, display controller 156, contact/motion module 130, graphics module 132, and text input module 134, contacts module 137 are, optionally, used to manage an address book or contact list (e.g., stored in application internal state 192 of contacts module 137 in memory 102 or memory 370), including: adding name(s) to the address book; deleting name(s) from the address book; associating telephone number(s), e-mail address(es), physical address(es) or other information with a name; associating an image with a name; categorizing and sorting names; providing telephone numbers or e-mail addresses to initiate and/or facilitate communications by telephone 138, video conference module 139, e-mail 140, or IM 141; and so forth.

In conjunction with RF circuitry 108, audio circuitry 110, speaker 111, microphone 113, touch screen 112, display controller 156, contact/motion module 130, graphics module 132, and text input module 134, telephone module 138 are optionally, used to enter a sequence of characters corresponding to a telephone number, access one or more telephone numbers in contacts module 137, modify a telephone number that has been entered, dial a respective telephone number, conduct a conversation, and disconnect or hang up when the conversation is completed. As noted above, the wireless communication optionally uses any of a plurality of communications standards, protocols, and technologies.

In conjunction with RF circuitry 108, audio circuitry 110, speaker 111, microphone 113, touch screen 112, display controller 156, optical sensor 164, optical sensor controller 158, contact/motion module 130, graphics module 132, text input module 134, contacts module 137, and telephone module 138, video conference module 139 includes executable instructions to initiate, conduct, and terminate a video conference between a user and one or more other participants in accordance with user instructions.

In conjunction with RF circuitry 108, touch screen 112, display controller 156, contact/motion module 130, graphics module 132, and text input module 134, e-mail client module 140 includes executable instructions to create, send, receive, and manage e-mail in response to user instructions. In conjunction with image management module 144, e-mail client module 140 makes it very easy to create and send e-mails with still or video images taken with camera module 143.

In conjunction with RF circuitry 108, touch screen 112, display controller 156, contact/motion module 130, graphics module 132, and text input module 134, the instant messaging module 141 includes executable instructions to enter a sequence of characters corresponding to an instant message, to modify previously entered characters, to transmit a respective instant message (for example, using a Short Message Service (SMS) or Multimedia Message Service (MMS) protocol for telephony-based instant messages or using XMPP, SIMPLE, or IMPS for Internet-based instant messages), to receive instant messages, and to view received instant messages. In some embodiments, transmitted and/or received instant messages optionally include graphics, photos, audio files, video files and/or other attachments as are supported in an MMS and/or an Enhanced Messaging Service (EMS). As used herein, "instant messaging" refers to both telephony-based messages (e.g., messages sent using SMS or MMS) and Internet-based messages (e.g., messages sent using XMPP, SIMPLE, or IMPS).

In conjunction with RF circuitry 108, touch screen 112, display controller 156, contact/motion module 130, graphics module 132, text input module 134, GPS module 135, map module 154, and music player module, workout support module 142 includes executable instructions to create workouts (e.g., with time, distance, and/or calorie burning goals); communicate with workout sensors (sports devices); receive workout sensor data; calibrate sensors used to monitor a workout; select and play music for a workout; and display, store, and transmit workout data.

In conjunction with touch screen 112, display controller 156, optical sensor(s) 164, optical sensor controller 158, contact/motion module 130, graphics module 132, and image management module 144, camera module 143 includes executable instructions to capture still images or video (including a video stream) and store them into memory 102, modify characteristics of a still image or video, or delete a still image or video from memory 102.

In conjunction with touch screen 112, display controller 156, contact/motion module 130, graphics module 132, text input module 134, and camera module 143, image management module 144 includes executable instructions to arrange, modify (e.g., edit), or otherwise manipulate, label, delete, present (e.g., in a digital slide show or album), and store still and/or video images.

In conjunction with RF circuitry 108, touch screen 112, display controller 156, contact/motion module 130, graphics module 132, and text input module 134, browser module 147 includes executable instructions to browse the Internet in accordance with user instructions, including searching, linking to, receiving, and displaying web pages or portions thereof, as well as attachments and other files linked to web pages.

In conjunction with RF circuitry 108, touch screen 112, display controller 156, contact/motion module 130, graphics module 132, text input module 134, e-mail client module 140, and browser module 147, calendar module 148 includes executable instructions to create, display, modify, and store calendars and data associated with calendars (e.g., calendar entries, to-do lists, etc.) in accordance with user instructions.

In conjunction with RF circuitry 108, touch screen 112, display controller 156, contact/motion module 130, graphics module 132, text input module 134, and browser module 147, widget modules 149 are mini-applications that are, optionally, downloaded and used by a user (e.g., weather widget 149-1, stocks widget 149-2, calculator widget 149-3, alarm clock widget 149-4, and dictionary widget 149-5) or created by the user (e.g., user-created widget 149-6). In some embodiments, a widget includes an HTML (Hypertext Markup Language) file, a CSS (Cascading Style Sheets) file, and a JavaScript file. In some embodiments, a widget includes an XML (Extensible Markup Language) file and a JavaScript file (e.g., Yahoo! Widgets).

In conjunction with RF circuitry 108, touch screen 112, display controller 156, contact/motion module 130, graphics module 132, text input module 134, and browser module 147, the widget creator module 150 are, optionally, used by a user to create widgets (e.g., turning a user-specified portion of a web page into a widget).

In conjunction with touch screen 112, display controller 156, contact/motion module 130, graphics module 132, and text input module 134, search module 151 includes executable instructions to search for text, music, sound, image, video, and/or other files in memory 102 that match one or more search criteria (e.g., one or more user-specified search terms) in accordance with user instructions.

In conjunction with touch screen 112, display controller 156, contact/motion module 130, graphics module 132, audio circuitry 110, speaker 111, RF circuitry 108, and browser module 147, video and music player module 152 includes executable instructions that allow the user to download and play back recorded music and other sound files stored in one or more file formats, such as MP3 or AAC files, and executable instructions to display, present, or otherwise play back videos (e.g., on touch screen 112 or on an external, connected display via external port 124). In some embodiments, device 100 optionally includes the functionality of an MP3 player, such as an iPod (trademark of Apple Inc.).

In conjunction with touch screen 112, display controller 156, contact/motion module 130, graphics module 132, and text input module 134, notes module 153 includes executable instructions to create and manage notes, to-do lists, and the like in accordance with user instructions.

In conjunction with RF circuitry 108, touch screen 112, display controller 156, contact/motion module 130, graphics module 132, text input module 134, GPS module 135, and browser module 147, map module 154 are, optionally, used to receive, display, modify, and store maps and data associated with maps (e.g., driving directions, data on stores and other points of interest at or near a particular location, and other location-based data) in accordance with user instructions.

In conjunction with touch screen 112, display controller 156, contact/motion module 130, graphics module 132, audio circuitry 110, speaker 111, RF circuitry 108, text input module 134, e-mail client module 140, and browser module 147, online video module 155 includes instructions that allow the user to access, browse, receive (e.g., by streaming and/or download), play back (e.g., on the touch screen or on an external, connected display via external port 124), send an e-mail with a link to a particular online video, and otherwise manage online videos in one or more file formats, such as H.264. In some embodiments, instant messaging module 141, rather than e-mail client module 140, is used to send a link to a particular online video. Additional description of the online video application can be found in U.S. Provisional Patent Application No. 60/936,562, "Portable Multifunction Device, Method, and Graphical User Interface for Playing Online Videos," filed Jun. 20, 2007, and U.S. patent application Ser. No. 11/968,067, "Portable Multifunction Device, Method, and Graphical User Interface for Playing Online Videos," filed Dec. 31, 2007, the contents of which are hereby incorporated by reference in their entirety.

Each of the above-identified modules and applications corresponds to a set of executable instructions for performing one or more functions described above and the methods described in this application (e.g., the computer-implemented methods and other information processing methods described herein). These modules (e.g., sets of instructions) need not be implemented as separate software programs, procedures, or modules, and thus various subsets of these modules are, optionally, combined or otherwise rearranged in various embodiments. For example, video player module is, optionally, combined with music player module into a single module (e.g., video and music player module 152, FIG. 1A). In some embodiments, memory 102 optionally stores a subset of the modules and data structures identified above. Furthermore, memory 102 optionally stores additional modules and data structures not described above.

In some embodiments, device 100 is a device where operation of a predefined set of functions on the device is performed exclusively through a touch screen and/or a touchpad. By using a touch screen and/or a touchpad as the primary input control device for operation of device 100, the number of physical input control devices (such as push buttons, dials, and the like) on device 100 is, optionally, reduced.

The predefined set of functions that are performed exclusively through a touch screen and/or a touchpad optionally include navigation between user interfaces. In some embodiments, the touchpad, when touched by the user, navigates device 100 to a main, home, or root menu from any user interface that is displayed on device 100. In such embodiments, a "menu button" is implemented using a touchpad. In some other embodiments, the menu button is a physical push button or other physical input control device instead of a touchpad.

Figure 1B:
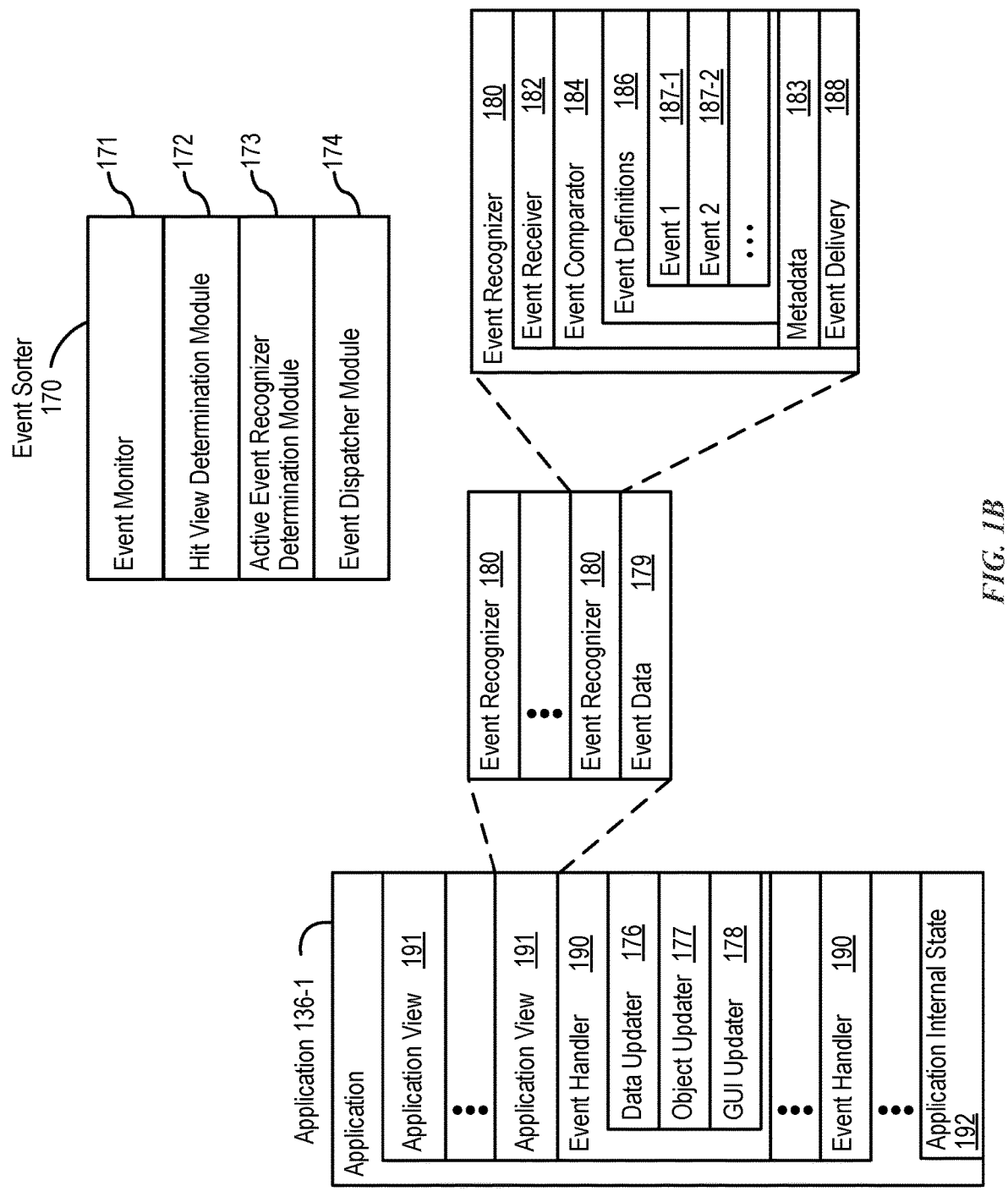
FIG. 1B is a block diagram illustrating exemplary components for event handling in accordance with some embodiments.

FIG. 1B is a block diagram illustrating exemplary components for event handling in accordance with some embodiments. In some embodiments, memory 102 (FIG. 1A) or 370 (FIG. 3) includes event sorter 170 (e.g., in operating system 126) and a respective application 136-1 (e.g., any of the aforementioned applications 137-151, 155, 380-390).

Event sorter 170 receives event information and determines the application 136-1 and application view 191 of application 136-1 to which to deliver the event information. Event sorter 170 includes event monitor 171 and event dispatcher module 174. In some embodiments, application 136-1 includes application internal state 192, which indicates the current application view(s) displayed on touch-sensitive display 112 when the application is active or executing. In some embodiments, device/global internal state 157 is used by event sorter 170 to determine which application(s) is (are) currently active, and application internal state 192 is used by event sorter 170 to determine application views 191 to which to deliver event information.

In some embodiments, application internal state 192 includes additional information, such as one or more of: resume information to be used when application 136-1 resumes execution, user interface state information that indicates information being displayed or that is ready for display by application 136-1, a state queue for enabling the user to go back to a prior state or view of application 136-1, and a redo/undo queue of previous actions taken by the user.

Event monitor 171 receives event information from peripherals interface 118. Event information includes information about a sub-event (e.g., a user touch on touch-sensitive display 112, as part of a multi-touch gesture). Peripherals interface 118 transmits information it receives from I/O subsystem 106 or a sensor, such as proximity sensor 166, accelerometer(s) 168, and/or microphone 113 (through audio circuitry 110). Information that peripherals interface 118 receives from I/O subsystem 106 includes information from touch-sensitive display 112 or a touch-sensitive surface.

In some embodiments, event monitor 171 sends requests to the peripherals interface 118 at predetermined intervals. In response, peripherals interface 118 transmits event information. In other embodiments, peripherals interface 118 transmits event information only when there is a significant event (e.g., receiving an input above a predetermined noise threshold and/or for more than a predetermined duration).

In some embodiments, event sorter 170 also includes a hit view determination module 172 and/or an active event recognizer determination module 173.

Hit view determination module 172 provides software procedures for determining where a sub-event has taken place within one or more views when touch-sensitive display 112 displays more than one view. Views are made up of controls and other elements that a user can see on the display.

Another aspect of the user interface associated with an application is a set of views, sometimes herein called application views or user interface windows, in which information is displayed and touch-based gestures occur. The application views (of a respective application) in which a touch is detected optionally correspond to programmatic levels within a programmatic or view hierarchy of the application. For example, the lowest level view in which a touch is detected is, optionally, called the hit view, and the set of events that are recognized as proper inputs are, optionally, determined based, at least in part, on the hit view of the initial touch that begins a touch-based gesture.

Hit view determination module 172 receives information related to sub-events of a touch-based gesture. When an application has multiple views organized in a hierarchy, hit view determination module 172 identifies a hit view as the lowest view in the hierarchy which should handle the sub-event. In most circumstances, the hit view is the lowest level view in which an initiating sub-event occurs (e.g., the first sub-event in the sequence of sub-events that form an event or potential event). Once the hit view is identified by the hit view determination module 172, the hit view typically receives all sub-events related to the same touch or input source for which it was identified as the hit view.

Active event recognizer determination module 173 determines which view or views within a view hierarchy should receive a particular sequence of sub-events. In some embodiments, active event recognizer determination module 173 determines that only the hit view should receive a particular sequence of sub-events. In other embodiments, active event recognizer determination module 173 determines that all views that include the physical location of a sub-event are actively involved views, and therefore determines that all actively involved views should receive a particular sequence of sub-events. In other embodiments, even if touch sub-events were entirely confined to the area associated with one particular view, views higher in the hierarchy would still remain as actively involved views.

Event dispatcher module 174 dispatches the event information to an event recognizer (e.g., event recognizer 180). In embodiments including active event recognizer determination module 173, event dispatcher module 174 delivers the event information to an event recognizer determined by active event recognizer determination module 173. In some embodiments, event dispatcher module 174 stores in an event queue the event information, which is retrieved by a respective event receiver 182.

In some embodiments, operating system 126 includes event sorter 170. Alternatively, application 136-1 includes event sorter 170. In yet other embodiments, event sorter 170 is a stand-alone module, or a part of another module stored in memory 102, such as contact/motion module 130.

In some embodiments, application 136-1 includes a plurality of event handlers 190 and one or more application views 191, each of which includes instructions for handling touch events that occur within a respective view of the application's user interface. Each application view 191 of the application 136-1 includes one or more event recognizers 180. Typically, a respective application view 191 includes a plurality of event recognizers 180. In other embodiments, one or more of event recognizers 180 are part of a separate module, such as a user interface kit or a higher level object from which application 136-1 inherits methods and other properties. In some embodiments, a respective event handler 190 includes one or more of: data updater 176, object updater 177, GUI updater 178, and/or event data 179 received from event sorter 170. Event handler 190 optionally utilizes or calls data updater 176, object updater 177, or GUI updater 178 to update the application internal state 192. Alternatively, one or more of the application views 191 include one or more respective event handlers 190. Also, in some embodiments, one or more of data updater 176, object updater 177, and GUI updater 178 are included in a respective application view 191.

A respective event recognizer 180 receives event information (e.g., event data 179) from event sorter 170 and identifies an event from the event information. Event recognizer 180 includes event receiver 182 and event comparator 184. In some embodiments, event recognizer 180 also includes at least a subset of: metadata 183, and event delivery instructions 188 (which optionally include sub-event delivery instructions).

Event receiver 182 receives event information from event sorter 170. The event information includes information about a sub-event, for example, a touch or a touch movement. Depending on the sub-event, the event information also includes additional information, such as location of the sub-event. When the sub-event concerns motion of a touch, the event information optionally also includes speed and direction of the sub-event. In some embodiments, events include rotation of the device from one orientation to another (e.g., from a portrait orientation to a landscape orientation, or vice versa), and the event information includes corresponding information about the current orientation (also called device attitude) of the device.

Event comparator 184 compares the event information to predefined event or sub-event definitions and, based on the comparison, determines an event or sub-event, or determines or updates the state of an event or sub-event. In some embodiments, event comparator 184 includes event definitions 186. Event definitions 186 contain definitions of events (e.g., predefined sequences of sub-events), for example, event 1 (187-1), event 2 (187-2), and others. In some embodiments, sub-events in an event (187) include, for example, touch begin, touch end, touch movement, touch cancellation, and multiple touching. In one example, the definition for event 1 (187-1) is a double tap on a displayed object. The double tap, for example, comprises a first touch (touch begin) on the displayed object for a predetermined phase, a first liftoff (touch end) for a predetermined phase, a second touch (touch begin) on the displayed object for a predetermined phase, and a second liftoff (touch end) for a predetermined phase. In another example, the definition for event 2 (187-2) is a dragging on a displayed object. The dragging, for example, comprises a touch (or contact) on the displayed object for a predetermined phase, a movement of the touch across touch-sensitive display 112, and liftoff of the touch (touch end). In some embodiments, the event also includes information for one or more associated event handlers 190.

In some embodiments, event definition 187 includes a definition of an event for a respective user-interface object. In some embodiments, event comparator 184 performs a hit test to determine which user-interface object is associated with a sub-event. For example, in an application view in which three user-interface objects are displayed on touch-sensitive display 112, when a touch is detected on touch-sensitive display 112, event comparator 184 performs a hit test to determine which of the three user-interface objects is associated with the touch (sub-event). If each displayed object is associated with a respective event handler 190, the event comparator uses the result of the hit test to determine which event handler 190 should be activated. For example, event comparator 184 selects an event handler associated with the sub-event and the object triggering the hit test.

In some embodiments, the definition for a respective event (187) also includes delayed actions that delay delivery of the event information until after it has been determined whether the sequence of sub-events does or does not correspond to the event recognizer's event type.

When a respective event recognizer 180 determines that the series of sub-events do not match any of the events in event definitions 186, the respective event recognizer 180 enters an event impossible, event failed, or event ended state, after which it disregards subsequent sub-events of the touch-based gesture. In this situation, other event recognizers, if any, that remain active for the hit view continue to track and process sub-events of an ongoing touch-based gesture.

In some embodiments, a respective event recognizer 180 includes metadata 183 with configurable properties, flags, and/or lists that indicate how the event delivery system should perform sub-event delivery to actively involved event recognizers. In some embodiments, metadata 183 includes configurable properties, flags, and/or lists that indicate how event recognizers interact, or are enabled to interact, with one another. In some embodiments, metadata 183 includes configurable properties, flags, and/or lists that indicate whether sub-events are delivered to varying levels in the view or programmatic hierarchy.

In some embodiments, a respective event recognizer 180 activates event handler 190 associated with an event when one or more particular sub-events of an event are recognized. In some embodiments, a respective event recognizer 180 delivers event information associated with the event to event handler 190. Activating an event handler 190 is distinct from sending (and deferred sending) sub-events to a respective hit view. In some embodiments, event recognizer 180 throws a flag associated with the recognized event, and event handler 190 associated with the flag catches the flag and performs a predefined process.

In some embodiments, event delivery instructions 188 include sub-event delivery instructions that deliver event information about a sub-event without activating an event handler. Instead, the sub-event delivery instructions deliver event information to event handlers associated with the series of sub-events or to actively involved views. Event handlers associated with the series of sub-events or with actively involved views receive the event information and perform a predetermined process.

In some embodiments, data updater 176 creates and updates data used in application 136-1. For example, data updater 176 updates the telephone number used in contacts module 137, or stores a video file used in video player module. In some embodiments, object updater 177 creates and updates objects used in application 136-1. For example, object updater 177 creates a new user-interface object or updates the position of a user-interface object. GUI updater 178 updates the GUI. For example, GUI updater 178 prepares display information and sends it to graphics module 132 for display on a touch-sensitive display.

In some embodiments, event handler(s) 190 includes or has access to data updater 176, object updater 177, and GUI updater 178. In some embodiments, data updater 176, object updater 177, and GUI updater 178 are included in a single module of a respective application 136-1 or application view 191. In other embodiments, they are included in two or more software modules.

It shall be understood that the foregoing discussion regarding event handling of user touches on touch-sensitive displays also applies to other forms of user inputs to operate multifunction devices 100 with input devices, not all of which are initiated on touch screens. For example, mouse movement and mouse button presses, optionally coordinated with single or multiple keyboard presses or holds; contact movements such as taps, drags, scrolls, etc. on touchpads; pen stylus inputs; movement of the device; oral instructions; detected eye movements; biometric inputs; and/or any combination thereof are optionally utilized as inputs corresponding to sub-events which define an event to be recognized.

Figure 2:
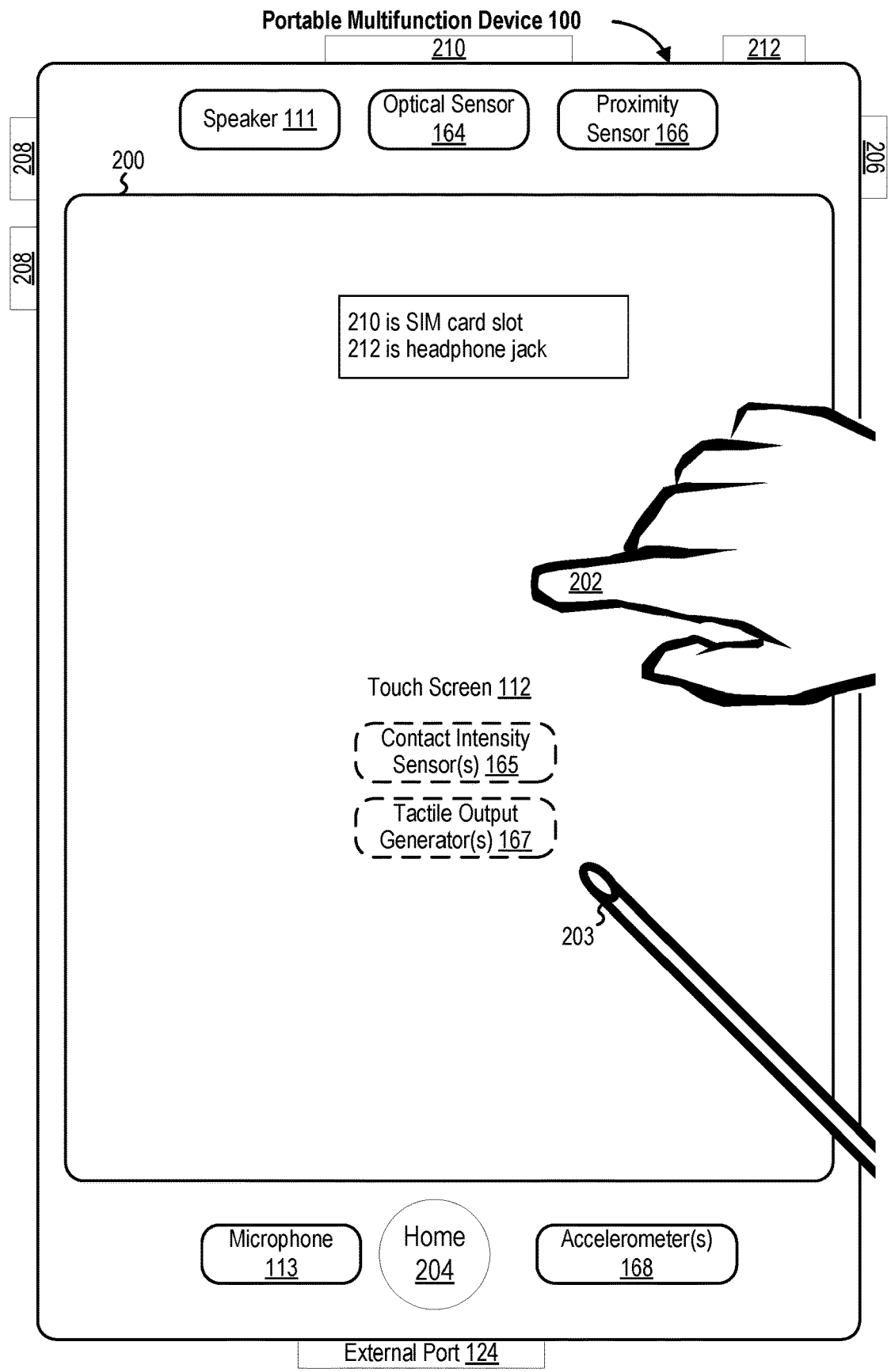
FIG. 2 illustrates a portable multifunction device having a touch screen in accordance with some embodiments.

FIG. 2 illustrates a portable multifunction device 100 having a touch screen 112 in accordance with some embodiments. The touch screen optionally displays one or more graphics within user interface (UI) 200. In this embodiment, as well as others described below, a user is enabled to select one or more of the graphics by making a gesture on the graphics, for example, with one or more fingers 202 (not drawn to scale in the figure) or one or more styluses 203 (not drawn to scale in the figure). In some embodiments, selection of one or more graphics occurs when the user breaks contact with the one or more graphics. In some embodiments, the gesture optionally includes one or more taps, one or more swipes (from left to right, right to left, upward and/or downward), and/or a rolling of a finger (from right to left, left to right, upward and/or downward) that has made contact with device 100. In some implementations or circumstances, inadvertent contact with a graphic does not select the graphic. For example, a swipe gesture that sweeps over an application icon optionally does not select the corresponding application when the gesture corresponding to selection is a tap.

Device 100 optionally also include one or more physical buttons, such as "home" or menu button 204. As described previously, menu button 204 is, optionally, used to navigate to any application 136 in a set of applications that are, optionally, executed on device 100. Alternatively, in some embodiments, the menu button is implemented as a soft key in a GUI displayed on touch screen 112.

In some embodiments, device 100 includes touch screen 112, menu button 204, push button 206 for powering the device on/off and locking the device, volume adjustment button(s) 208, subscriber identity module (SIM) card slot 210, headset jack 212, and docking/charging external port 124. Push button 206 is, optionally, used to turn the power on/off on the device by depressing the button and holding the button in the depressed state for a predefined time interval; to lock the device by depressing the button and releasing the button before the predefined time interval has elapsed; and/or to unlock the device or initiate an unlock process. In an alternative embodiment, device 100 also accepts verbal input for activation or deactivation of some functions through microphone 113. Device 100 also, optionally, includes one or more contact intensity sensors 165 for detecting intensity of contacts on touch screen 112 and/or one or more tactile output generators 167 for generating tactile outputs for a user of device 100.

FIG. 3 is a block diagram of an exemplary multifunction device with a display and a touch-sensitive surface in accordance with some embodiments. Device 300 need not be portable. In some embodiments, device 300 is a laptop computer, a desktop computer, a tablet computer, a multimedia player device, a navigation device, an educational device (such as a child's learning toy), a gaming system, or a control device (e.g., a home or industrial controller). Device 300 typically includes one or more processing units (CPUs) 310, one or more network or other communications interfaces 360, memory 370, and one or more communication buses 320 for interconnecting these components. Communication buses 320 optionally include circuitry (sometimes called a chipset) that interconnects and controls communications between system components. Device 300 includes input/output (I/O) interface 330 comprising display 340, which is typically a touch screen display. I/O interface 330 also optionally includes a keyboard and/or mouse (or other pointing device) 350 and touchpad 355, tactile output generator 357 for generating tactile outputs on device 300 (e.g., similar to tactile output generator(s) 167 described above with reference to FIG. 1A), sensors 359 (e.g., optical, acceleration, proximity, touch-sensitive, and/or contact intensity sensors similar to contact intensity sensor(s) 165 described above with reference to FIG. 1A). Memory 370 includes high-speed random access memory, such as DRAM, SRAM, DDR RAM, or other random access solid state memory devices; and optionally includes non-volatile memory, such as one or more magnetic disk storage devices, optical disk storage devices, flash memory devices, or other non-volatile solid state storage devices. Memory 370 optionally includes one or more storage devices remotely located from CPU(s) 310. In some embodiments, memory 370 stores programs, modules, and data structures analogous to the programs, modules, and data structures stored in memory 102 of portable multifunction device 100 (FIG. 1A), or a subset thereof. Furthermore, memory 370 optionally stores additional programs, modules, and data structures not present in memory 102 of portable multifunction device 100. For example, memory 370 of device 300 optionally stores drawing module 380, presentation module 382, word processing module 384, website creation module 386, disk authoring module 388, and/or spreadsheet module 390, while memory 102 of portable multifunction device 100 (FIG. 1A) optionally does not store these modules.

Each of the above-identified elements in FIG. 3 is, optionally, stored in one or more of the previously mentioned memory devices. Each of the above-identified modules corresponds to a set of instructions for performing a function described above. The above-identified modules or programs (e.g., sets of instructions) need not be implemented as separate software programs, procedures, or modules, and thus various subsets of these modules are, optionally, combined or otherwise rearranged in various embodiments. In some embodiments, memory 370 optionally stores a subset of the modules and data structures identified above. Furthermore, memory 370 optionally stores additional modules and data structures not described above.

Attention is now directed towards embodiments of user interfaces that are, optionally, implemented on, for example, portable multifunction device 100.

Figure 4A:
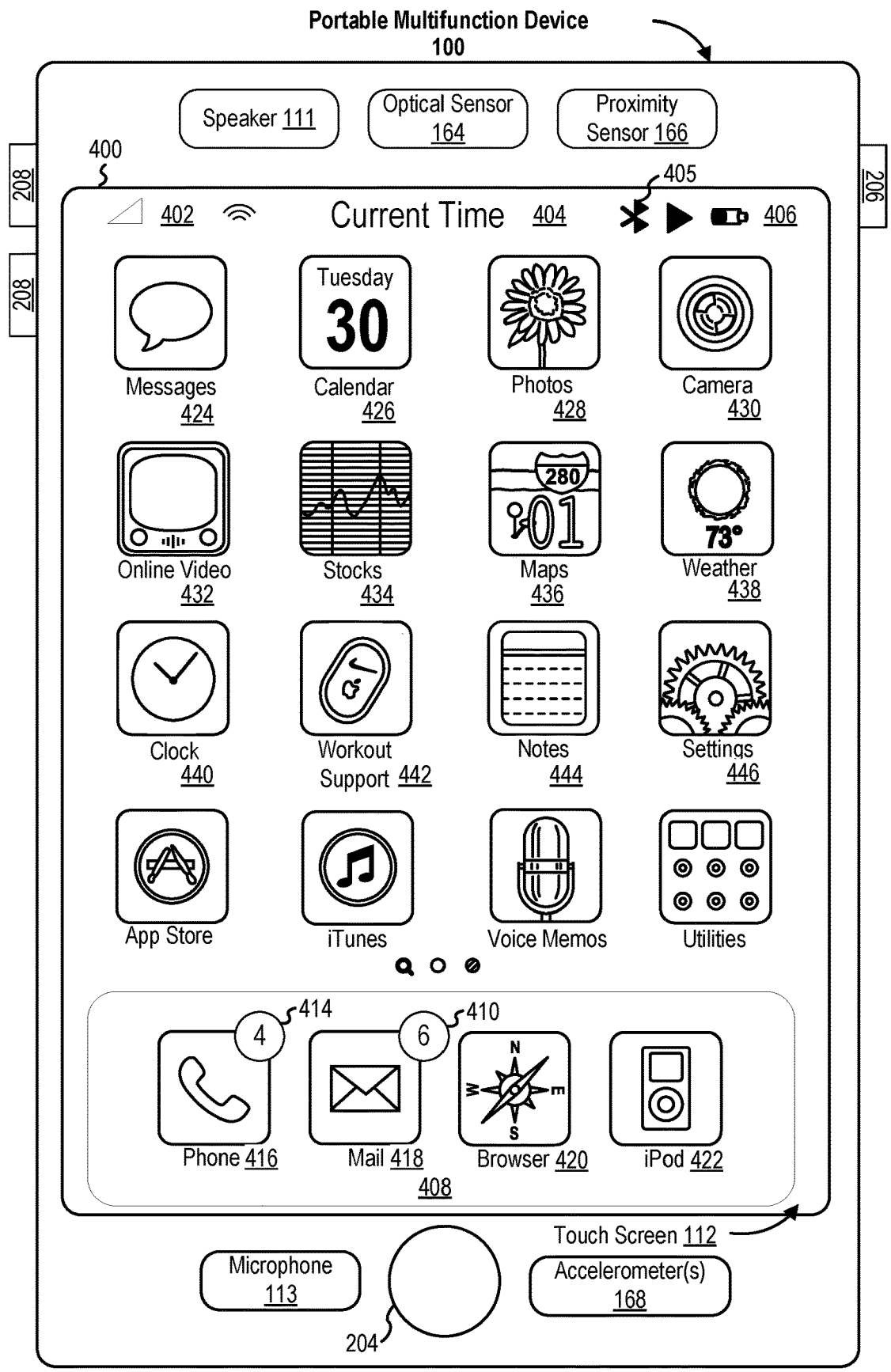
FIG. 4A illustrates an exemplary user interface for a menu of applications on a portable multifunction device in accordance with some embodiments.

FIG. 4A illustrates an exemplary user interface for a menu of applications on portable multifunction device 100 in accordance with some embodiments. Similar user interfaces are, optionally, implemented on device 300. In some embodiments, user interface 400 includes the following elements, or a subset or superset thereof:

- Signal strength indicator(s) 402 for wireless communication(s), such as cellular and Wi-Fi signals;
- Time 404;
- Bluetooth indicator 405;
- Battery status indicator 406;

Tray 408 with icons for frequently used applications, such as:

Icon 416 for telephone module 138, labeled "Phone," which optionally includes an indicator 414 of the number of missed calls or voicemail messages;

Icon 418 for e-mail client module 140, labeled "Mail," which optionally includes an indicator 410 of the number of unread e-mails;

Icon 420 for browser module 147, labeled "Browser;" and

Icon 422 for video and music player module 152, also referred to as iPod (trademark of Apple Inc.) module 152, labeled "iPod;" and Icons for other applications, such as:

Icon 424 for IM module 141, labeled "Messages;"

Icon 426 for calendar module 148, labeled "Calendar;"

Icon 428 for image management module 144, labeled "Photos;"

Icon 430 for camera module 143, labeled "Camera;"

Icon 432 for online video module 155, labeled "Online Video;"

Icon 434 for stocks widget 149-2, labeled "Stocks;"

Icon 436 for map module 154, labeled "Maps;"

Icon 438 for weather widget 149-1, labeled "Weather;"

Icon 440 for alarm clock widget 149-4, labeled "Clock;"

Icon 442 for workout support module 142, labeled "Workout Support;"

Icon 444 for notes module 153, labeled "Notes;" and

Icon 446 for a settings application or module, labeled "Settings," which provides access to settings for device 100 and its various applications 136.

It should be noted that the icon labels illustrated in FIG. 4A are merely exemplary. For example, icon 422 for video and music player module 152 is labeled "Music" or "Music Player." Other labels are, optionally, used for various application icons. In some embodiments, a label for a respective application icon includes a name of an application corresponding to the respective application icon. In some embodiments, a label for a particular application icon is distinct from a name of an application corresponding to the particular application icon.

FIG. 4B illustrates an exemplary user interface on a device (e.g., device 300, FIG. 3) with a touch-sensitive surface 451 (e.g., a tablet or touchpad 355, FIG. 3) that is separate from the display 450 (e.g., touch screen display 112). Device 300 also, optionally, includes one or more contact intensity sensors (e.g., one or more of sensors 359) for detecting intensity of contacts on touch-sensitive surface 451 and/or one or more tactile output generators 357 for generating tactile outputs for a user of device 300.

Although some of the examples that follow will be given with reference to inputs on touch screen display 112 (where the touch-sensitive surface and the display are combined), in some embodiments, the device detects inputs on a touch-sensitive surface that is separate from the display, as shown in FIG. 4B. In some embodiments, the touch-sensitive surface (e.g., 451 in FIG. 4B) has a primary axis (e.g., 452 in FIG. 4B) that corresponds to a primary axis (e.g., 453 in FIG. 4B) on the display (e.g., 450). In accordance with these embodiments, the device detects contacts (e.g., 460 and 462 in FIG. 4B) with the touch-sensitive surface 451 at locations that correspond to respective locations on the display (e.g., in FIG. 4B, 460 corresponds to 468 and 462 corresponds to 470). In this way, user inputs (e.g., contacts 460 and 462, and movements thereof) detected by the device on the touch-sensitive surface (e.g., 451 in FIG. 4B) are used by the device to manipulate the user interface on the display (e.g., 450 in FIG. 4B) of the multifunction device when the touch-sensitive surface is separate from the display. It should be understood that similar methods are, optionally, used for other user interfaces described herein.

Additionally, while the following examples are given primarily with reference to finger inputs (e.g., finger contacts, finger tap gestures, finger swipe gestures), it should be understood that, in some embodiments, one or more of the finger inputs are replaced with input from another input device (e.g., a mouse-based input or stylus input). For example, a swipe gesture is, optionally, replaced with a mouse click (e.g., instead of a contact) followed by movement of the cursor along the path of the swipe (e.g., instead of movement of the contact). As another example, a tap gesture is, optionally, replaced with a mouse click while the cursor is located over the location of the tap gesture (e.g., instead of detection of the contact followed by ceasing to detect the contact). Similarly, when multiple user inputs are simultaneously detected, it should be understood that multiple computer mice are, optionally, used simultaneously, or a mouse and finger contacts are, optionally, used simultaneously.

Figure 5A:
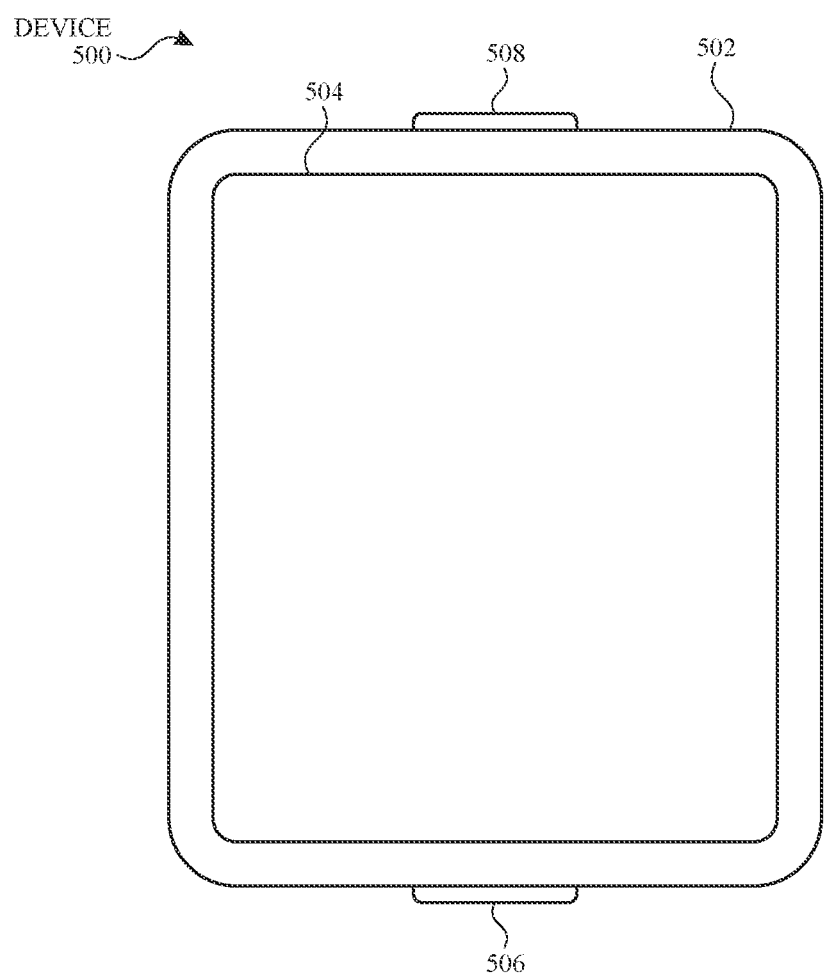
FIG. 5A illustrates a personal electronic device in accordance with some embodiments.
Figure 6A:
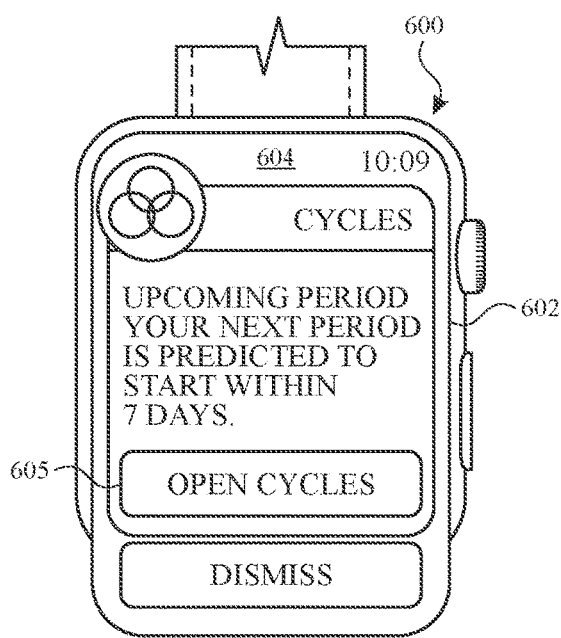
FIGS. 6A-6O illustrate exemplary user interfaces for cycle tracking, in accordance with some embodiments.

FIG. 5A illustrates exemplary personal electronic device 500. Device 500 includes body 502. In some embodiments, device 500 can include some or all of the features described with respect to devices 100 and 300 (e.g., FIGS. 1A-4B). In some embodiments, device 500 has touch-sensitive display screen 504, hereafter touch screen 504. Alternatively, or in addition to touch screen 504, device 500 has a display and a touch-sensitive surface. As with devices 100 and 300, in some embodiments, touch screen 504 (or the touch-sensitive surface) optionally includes one or more intensity sensors for detecting intensity of contacts (e.g., touches) being applied. The one or more intensity sensors of touch screen 504 (or the touch-sensitive surface) can provide output data that represents the intensity of touches. The user interface of device 500 can respond to touches based on their intensity, meaning that touches of different intensities can invoke different user interface operations on device 500.

Exemplary techniques for detecting and processing touch intensity are found, for example, in related applications: International Patent Application Serial No. PCT/US2013/040061, titled "Device, Method, and Graphical User Interface for Displaying User Interface Objects Corresponding to an Application," filed May 8, 2013, published as WIPO Publication No. WO/2013/169849, and International Patent Application Serial No. PCT/US2013/069483, titled "Device, Method, and Graphical User Interface for Transitioning Between Touch Input to Display Output Relationships," filed Nov. 11, 2013, published as WIPO Publication No. WO/2014/105276, each of which is hereby incorporated by reference in their entirety.

In some embodiments, device 500 has one or more input mechanisms 506 and 508. Input mechanisms 506 and 508, if included, can be physical. Examples of physical input mechanisms include push buttons and rotatable mechanisms. In some embodiments, device 500 has one or more attachment mechanisms. Such attachment mechanisms, if included, can permit attachment of device 500 with, for example, hats, eyewear, earrings, necklaces, shirts, jackets, bracelets, watch straps, chains, trousers, belts, shoes, purses, backpacks, and so forth. These attachment mechanisms permit device 500 to be worn by a user.

Figure 5B:
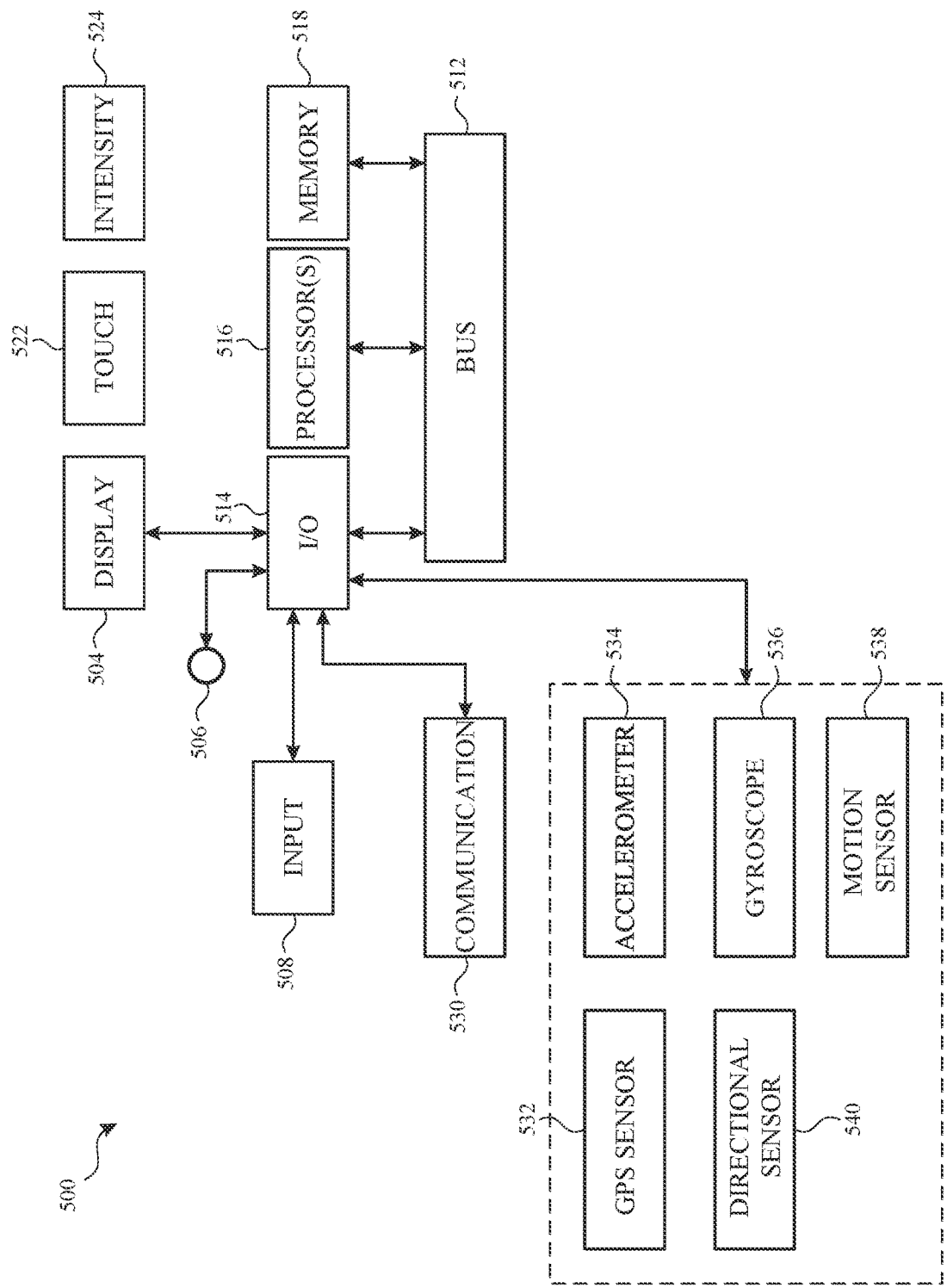
FIG. 5B is a block diagram illustrating a personal electronic device in accordance with some embodiments.

FIG. 5B depicts exemplary personal electronic device 500. In some embodiments, device 500 can include some or all of the components described with respect to FIGS. 1A, 1B, and 3. Device 500 has bus 512 that operatively couples I/O section 514 with one or more computer processors 516 and memory 518. I/O section 514 can be connected to display 504, which can have touch-sensitive component 522 and, optionally, intensity sensor 524 (e.g., contact intensity sensor). In addition, I/O section 514 can be connected with communication unit 530 for receiving application and operating system data, using Wi-Fi, Bluetooth, near field communication (NFC), cellular, and/or other wireless communication techniques. Device 500 can include input mechanisms 506 and/or 508. Input mechanism 506 is, optionally, a rotatable input device or a depressible and rotatable input device, for example. Input mechanism 508 is, optionally, a button, in some examples.

Input mechanism 508 is, optionally, a microphone, in some examples. Personal electronic device 500 optionally includes various sensors, such as GPS sensor 532, accelerometer 534, directional sensor 540 (e.g., compass), gyroscope 536, motion sensor 538, and/or a combination thereof, all of which can be operatively connected to I/O section 514.

Memory 518 of personal electronic device 500 can include one or more non-transitory computer-readable storage mediums, for storing computer-executable instructions, which, when executed by one or more computer processors 516, for example, can cause the computer processors to perform the techniques described below, including processes 700 and 900 (FIGS. 7A-7B and 9A-9B). A computer-readable storage medium can be any medium that can tangibly contain or store computer-executable instructions for use by or in connection with the instruction execution system, apparatus, or device. In some examples, the storage medium is a transitory computer-readable storage medium. In some examples, the storage medium is a non-transitory computer-readable storage medium. The non-transitory computer-readable storage medium can include, but is not limited to, magnetic, optical, and/or semiconductor storages. Examples of such storage include magnetic disks, optical discs based on CD, DVD, or Blu-ray technologies, as well as persistent solid-state memory such as flash, solid-state drives, and the like. Personal electronic device 500 is not limited to the components and configuration of FIG. 5B, but can include other or additional components in multiple configurations.

As used here, the term "affordance" refers to a user-interactive graphical user interface object that is, optionally, displayed on the display screen of devices 100, 300, and/or 500 (FIGS. 1A, 3, and 5A-5B). For example, an image (e.g., icon), a button, and text (e.g., hyperlink) each optionally constitute an affordance.

As used herein, the term "focus selector" refers to an input element that indicates a current part of a user interface with which a user is interacting. In some implementations that include a cursor or other location marker, the cursor acts as a "focus selector" so that when an input (e.g., a press input) is detected on a touch-sensitive surface (e.g., touchpad 355 in FIG. 3 or touch-sensitive surface 451 in FIG. 4B) while the cursor is over a particular user interface element (e.g., a button, window, slider, or other user interface element), the particular user interface element is adjusted in accordance with the detected input. In some implementations that include a touch screen display (e.g., touch-sensitive display system 112 in FIG. 1A or touch screen 112 in FIG. 4A) that enables direct interaction with user interface elements on the touch screen display, a detected contact on the touch screen acts as a "focus selector" so that when an input (e.g., a press input by the contact) is detected on the touch screen display at a location of a particular user interface element (e.g., a button, window, slider, or other user interface element), the particular user interface element is adjusted in accordance with the detected input. In some implementations, focus is moved from one region of a user interface to another region of the user interface without corresponding movement of a cursor or movement of a contact on a touch screen display (e.g., by using a tab key or arrow keys to move focus from one button to another button); in these implementations, the focus selector moves in accordance with movement of focus between different regions of the user interface. Without regard to the specific form taken by the focus selector, the focus selector is generally the user interface element (or contact on a touch screen display) that is controlled by the user so as to communicate the user's intended interaction with the user interface (e.g., by indicating, to the device, the element of the user interface with which the user is intending to interact). For example, the location of a focus selector (e.g., a cursor, a contact, or a selection box) over a respective button while a press input is detected on the touch-sensitive surface (e.g., a touchpad or touch screen) will indicate that the user is intending to activate the respective button (as opposed to other user interface elements shown on a display of the device).

As used in the specification and claims, the term "characteristic intensity" of a contact refers to a characteristic of the contact based on one or more intensities of the contact. In some embodiments, the characteristic intensity is based on multiple intensity samples. The characteristic intensity is, optionally, based on a predefined number of intensity samples, or a set of intensity samples collected during a predetermined time period (e.g., 0.05, 0.1, 0.2, 0.5, 1, 2, 5, 10 seconds) relative to a predefined event (e.g., after detecting the contact, prior to detecting liftoff of the contact, before or after detecting a start of movement of the contact, prior to detecting an end of the contact, before or after detecting an increase in intensity of the contact, and/or before or after detecting a decrease in intensity of the contact). A characteristic intensity of a contact is, optionally, based on one or more of: a maximum value of the intensities of the contact, a mean value of the intensities of the contact, an average value of the intensities of the contact, a top 10 percentile value of the intensities of the contact, a value at the half maximum of the intensities of the contact, a value at the 90 percent maximum of the intensities of the contact, or the like. In some embodiments, the duration of the contact is used in determining the characteristic intensity (e.g., when the characteristic intensity is an average of the intensity of the contact over time). In some embodiments, the characteristic intensity is compared to a set of one or more intensity thresholds to determine whether an operation has been performed by a user. For example, the set of one or more intensity thresholds optionally includes a first intensity threshold and a second intensity threshold. In this example, a contact with a characteristic intensity that does not exceed the first threshold results in a first operation, a contact with a characteristic intensity that exceeds the first intensity threshold and does not exceed the second intensity threshold results in a second operation, and a contact with a characteristic intensity that exceeds the second threshold results in a third operation. In some embodiments, a comparison between the characteristic intensity and one or more thresholds is used to determine whether or not to perform one or more operations (e.g., whether to perform a respective operation or forgo performing the respective operation), rather than being used to determine whether to perform a first operation or a second operation.

Figure 5D:
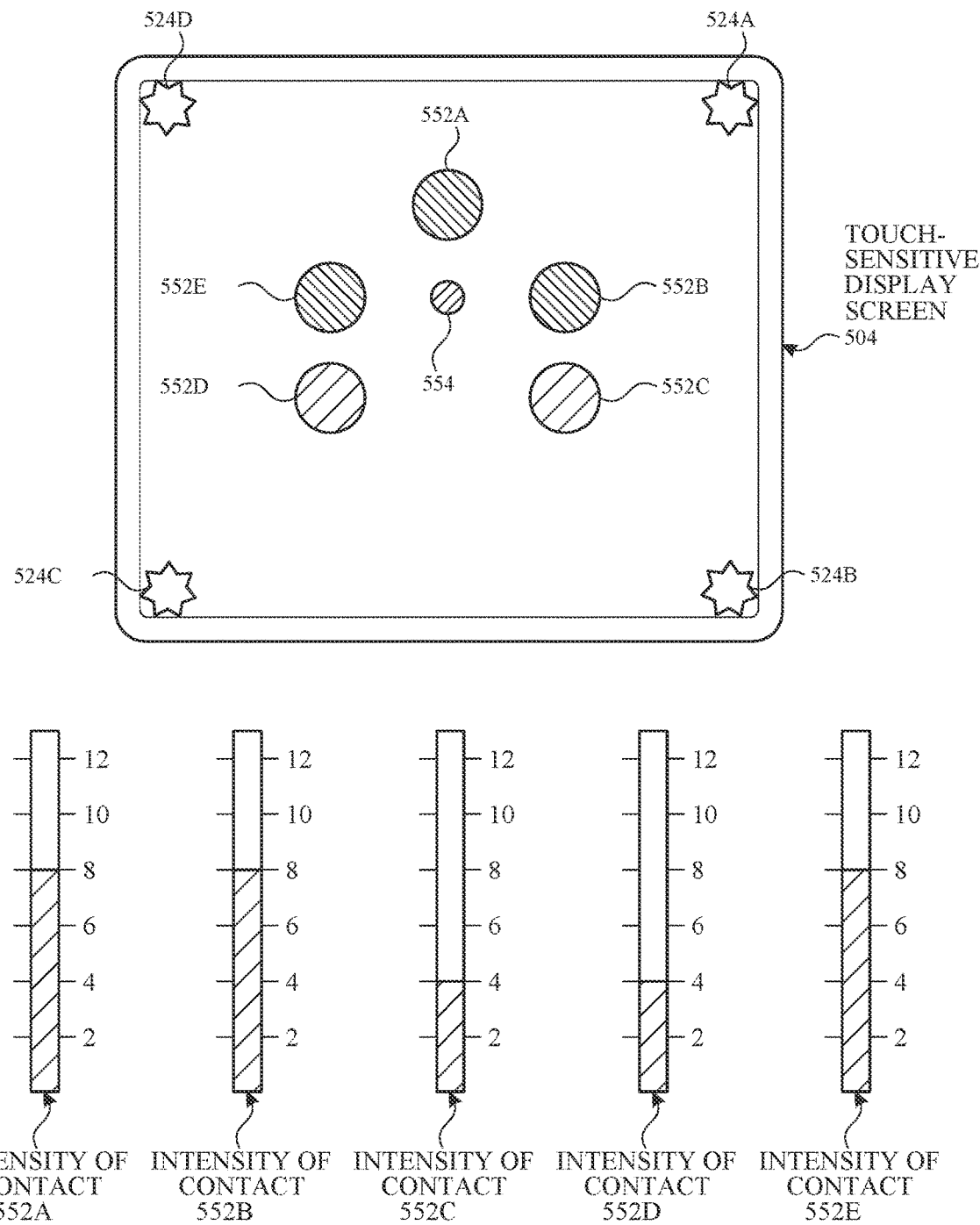

FIG. 5C illustrates detecting a plurality of contacts 552A-552E on touch-sensitive display screen 504 with a plurality of intensity sensors 524A-524D. FIG. 5C additionally includes intensity diagrams that show the current intensity measurements of the intensity sensors 524A-524D relative to units of intensity. In this example, the intensity measurements of intensity sensors 524A and 524D are each 9 units of intensity, and the intensity measurements of intensity sensors 524B and 524C are each 7 units of intensity. In some implementations, an aggregate intensity is the sum of the intensity measurements of the plurality of intensity sensors 524A-524D, which in this example is 32 intensity units. In some embodiments, each contact is assigned a respective intensity that is a portion of the aggregate intensity. FIG. 5D illustrates assigning the aggregate intensity to contacts 552A-552E based on their distance from the center of force 554. In this example, each of contacts 552A, 552B, and 552E are assigned an intensity of contact of 8 intensity units of the aggregate intensity, and each of contacts 552C and 552D are assigned an intensity of contact of 4 intensity units of the aggregate intensity. More generally, in some implementations, each contact j is assigned a respective intensity Ij that is a portion of the aggregate intensity, A, in accordance with a predefined mathematical function, $Ij=A \cdot (Dj/\Sigma Di)$, where Dj is the distance of the respective contact j to the center of force, and $\Sigma Di$ is the sum of the distances of all the respective contacts (e.g., i=1 to last) to the center of force. The operations described with reference to FIGS. 5C-5D can be performed using an electronic device similar or identical to device 100, 300, or 500. In some embodiments, a characteristic intensity of a contact is based on one or more intensities of the contact. In some embodiments, the intensity sensors are used to determine a single characteristic intensity (e.g., a single characteristic intensity of a single contact). It should be noted that the intensity diagrams are not part of a displayed user interface, but are included in FIGS. 5C-5D to aid the reader.

In some embodiments, a portion of a gesture is identified for purposes of determining a characteristic intensity. For example, a touch-sensitive surface optionally receives a continuous swipe contact transitioning from a start location and reaching an end location, at which point the intensity of the contact increases. In this example, the characteristic intensity of the contact at the end location is, optionally, based on only a portion of the continuous swipe contact, and not the entire swipe contact (e.g., only the portion of the swipe contact at the end location). In some embodiments, a smoothing algorithm is, optionally, applied to the intensities of the swipe contact prior to determining the characteristic intensity of the contact. For example, the smoothing algorithm optionally includes one or more of: an unweighted sliding-average smoothing algorithm, a triangular smoothing algorithm, a median filter smoothing algorithm, and/or an exponential smoothing algorithm. In some circumstances, these smoothing algorithms eliminate narrow spikes or dips in the intensities of the swipe contact for purposes of determining a characteristic intensity.

The intensity of a contact on the touch-sensitive surface is, optionally, characterized relative to one or more intensity thresholds, such as a contact-detection intensity threshold, a light press intensity threshold, a deep press intensity threshold, and/or one or more other intensity thresholds. In some embodiments, the light press intensity threshold corresponds to an intensity at which the device will perform operations typically associated with clicking a button of a physical mouse or a trackpad. In some embodiments, the deep press intensity threshold corresponds to an intensity at which the device will perform operations that are different from operations typically associated with clicking a button of a physical mouse or a trackpad. In some embodiments, when a contact is detected with a characteristic intensity below the light press intensity threshold (e.g., and above a nominal contact-detection intensity threshold below which the contact is no longer detected), the device will move a focus selector in accordance with movement of the contact on the touch-sensitive surface without performing an operation associated with the light press intensity threshold or the deep press intensity threshold. Generally, unless otherwise stated, these intensity thresholds are consistent between different sets of user interface figures.

An increase of characteristic intensity of the contact from an intensity below the light press intensity threshold to an intensity between the light press intensity threshold and the deep press intensity threshold is sometimes referred to as a "light press" input. An increase of characteristic intensity of the contact from an intensity below the deep press intensity threshold to an intensity above the deep press intensity threshold is sometimes referred to as a "deep press" input. An increase of characteristic intensity of the contact from an intensity below the contact-detection intensity threshold to an intensity between the contact-detection intensity threshold and the light press intensity threshold is sometimes referred to as detecting the contact on the touch-surface. A decrease of characteristic intensity of the contact from an intensity above the contact-detection intensity threshold to an intensity below the contact-detection intensity threshold is sometimes referred to as detecting liftoff of the contact from the touch-surface. In some embodiments, the contact-detection intensity threshold is zero. In some embodiments, the contact-detection intensity threshold is greater than zero.

In some embodiments described herein, one or more operations are performed in response to detecting a gesture that includes a respective press input or in response to detecting the respective press input performed with a respective contact (or a plurality of contacts), where the respective press input is detected based at least in part on detecting an increase in intensity of the contact (or plurality of contacts) above a press-input intensity threshold. In some embodiments, the respective operation is performed in response to detecting the increase in intensity of the respective contact above the press-input intensity threshold (e.g., a "down stroke" of the respective press input). In some embodiments, the press input includes an increase in intensity of the respective contact above the press-input intensity threshold and a subsequent decrease in intensity of the contact below the press-input intensity threshold, and the respective operation is performed in response to detecting the subsequent decrease in intensity of the respective contact below the press-input threshold (e.g., an "up stroke" of the respective press input).

FIGS. 5E-5H illustrate detection of a gesture that includes a press input that corresponds to an increase in intensity of a contact 562 from an intensity below a light press intensity threshold (e.g., "ITL") in FIG. 5E, to an intensity above a deep press intensity threshold (e.g., "ITD") in FIG. 5H. The gesture performed with contact 562 is detected on touch-sensitive surface 560 while cursor 576 is displayed over application icon 572B corresponding to App 2, on a displayed user interface 570 that includes application icons 572A-572D displayed in predefined region 574. In some embodiments, the gesture is detected on touch-sensitive display 504. The intensity sensors detect the intensity of contacts on touch-sensitive surface 560. The device determines that the intensity of contact 562 peaked above the deep press intensity threshold (e.g., "ITD"). Contact 562 is maintained on touch-sensitive surface 560. In response to the detection of the gesture, and in accordance with contact 562 having an intensity that goes above the deep press intensity threshold (e.g., "ITD") during the gesture, reduced-scale representations 578A-578C (e.g., thumbnails) of recently opened documents for App 2 are displayed, as shown in FIGS. 5F-5H. In some embodiments, the intensity, which is compared to the one or more intensity thresholds, is the characteristic intensity of a contact. It should be noted that the intensity diagram for contact 562 is not part of a displayed user interface, but is included in FIGS. 5E-5H to aid the reader.

In some embodiments, the display of representations 578A-578C includes an animation. For example, representation 578A is initially displayed in proximity of application icon 572B, as shown in FIG. 5F. As the animation proceeds, representation 578A moves upward and representation 578B is displayed in proximity of application icon 572B, as shown in FIG. 5G. Then, representations 578A moves upward, 578B moves upward toward representation 578A, and representation 578C is displayed in proximity of application icon 572B, as shown in FIG. 5H. Representations 578A-578C form an array above icon 572B. In some embodiments, the animation progresses in accordance with an intensity of contact 562, as shown in FIGS. 5F-5G, where the representations 578A-578C appear and move upwards as the intensity of contact 562 increases toward the deep press intensity threshold (e.g., "ITD"). In some embodiments, the intensity, on which the progress of the animation is based, is the characteristic intensity of the contact. The operations described with reference to FIGS. 5E-5H can be performed using an electronic device similar or identical to device 100, 300, or 500.

In some embodiments, the device employs intensity hysteresis to avoid accidental inputs sometimes termed "jitter," where the device defines or selects a hysteresis intensity threshold with a predefined relationship to the press-input intensity threshold (e.g., the hysteresis intensity threshold is X intensity units lower than the press-input intensity threshold or the hysteresis intensity threshold is 75%, 90%, or some reasonable proportion of the press-input intensity threshold). Thus, in some embodiments, the press input includes an increase in intensity of the respective contact above the press-input intensity threshold and a subsequent decrease in intensity of the contact below the hysteresis intensity threshold that corresponds to the press-input intensity threshold, and the respective operation is performed in response to detecting the subsequent decrease in intensity of the respective contact below the hysteresis intensity threshold (e.g., an "up stroke" of the respective press input). Similarly, in some embodiments, the press input is detected only when the device detects an increase in intensity of the contact from an intensity at or below the hysteresis intensity threshold to an intensity at or above the press-input intensity threshold and, optionally, a subsequent decrease in intensity of the contact to an intensity at or below the hysteresis intensity, and the respective operation is performed in response to detecting the press input (e.g., the increase in intensity of the contact or the decrease in intensity of the contact, depending on the circumstances).

For ease of explanation, the descriptions of operations performed in response to a press input associated with a press-input intensity threshold or in response to a gesture including the press input are, optionally, triggered in response to detecting either: an increase in intensity of a contact above the press-input intensity threshold, an increase in intensity of a contact from an intensity below the hysteresis intensity threshold to an intensity above the press-input intensity threshold, a decrease in intensity of the contact below the press-input intensity threshold, and/or a decrease in intensity of the contact below the hysteresis intensity threshold corresponding to the press-input intensity threshold. Additionally, in examples where an operation is described as being performed in response to detecting a decrease in intensity of a contact below the press-input intensity threshold, the operation is, optionally, performed in response to detecting a decrease in intensity of the contact below a hysteresis intensity threshold corresponding to, and lower than, the press-input intensity threshold.

As used herein, an "installed application" refers to a software application that has been downloaded onto an electronic device (e.g., devices 100, 300, and/or 500) and is ready to be launched (e.g., become opened) on the device. In some embodiments, a downloaded application becomes an installed application by way of an installation program that extracts program portions from a downloaded package and integrates the extracted portions with the operating system of the computer system.

As used herein, the terms "open application" or "executing application" refer to a software application with retained state information (e.g., as part of device/global internal state 157 and/or application internal state 192). An open or executing application is, optionally, any one of the following types of applications:
  an active application, which is currently displayed on a display screen of the device that the application is being used on;
  a background application (or background processes), which is not currently displayed, but one or more processes for the application are being processed by one or more processors; and
  a suspended or hibernated application, which is not running, but has state information that is stored in memory (volatile and non-volatile, respectively) and that can be used to resume execution of the application.

As used herein, the term "closed application" refers to software applications without retained state information (e.g., state information for closed applications is not stored in a memory of the device). Accordingly, closing an application includes stopping and/or removing application processes for the application and removing state information for the application from the memory of the device. Generally, opening a second application while in a first application does not close the first application. When the second application is displayed and the first application ceases to be displayed, the first application becomes a background application.

Attention is now directed towards embodiments of user interfaces ("UI") and associated processes that are implemented on an electronic device, such as portable multifunction device 100, device 300, or device 500.

FIGS. 6A-6O illustrate exemplary user interfaces for cycle tracking, in accordance with some embodiments. While the following user interfaces relate to menstrual cycle tracking, it should be recognized that techniques described here can relate to tracking different thing, such as weight, food, exercise, projects, etc. The user interfaces in these figures are used to illustrate the processes described below, including the processes in FIGS. 7A-7B.

FIG. 6A depicts electronic device 600 displaying notification 604 via touch-sensitive display device 602 at a first time. In some examples, electronic device 600 includes one or more features of devices 100, 300, or 500.

In some examples, notification 604 is a notification that was issued (e.g., caused to be displayed by electronic device 600) from a process executing on electronic device 600. For example, the process can be a tracking process associated with a tracking application. In some examples, notification 604 is issued in response to a determination that a user associated with electronic device 600 is going to have a predicted menstrual period in the next 7 days. Such a prediction can be determined in a number of different ways, including based on previous periods and other information (including user interactions with electronic device 600) provided to the tracking application.

As depicted in FIG. 6A, notification 604 includes open affordance 605 and a dismiss affordance. Selection of open affordance 605 causes electronic device 600 to display a user interface corresponding to the tracking application, such as depicted in FIG. 6N and further discussed below with regard to FIG. 6N. Selection of the dismiss affordance causes electronic device 600 to cease display of notification 604.

Figure 6B:
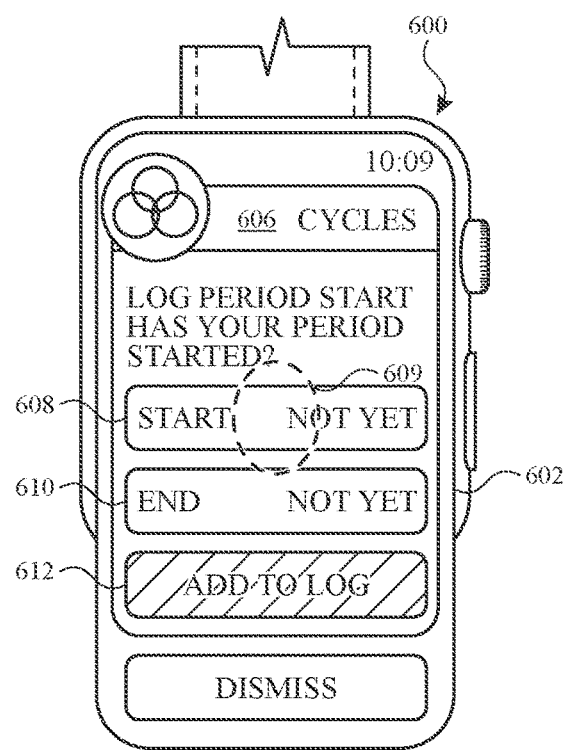

FIG. 6B depicts electronic device 600 displaying notification 606 via touch-sensitive display device 602 at a second time after the first time. In some examples, notification 606 is a notification that was issued (e.g., caused to be displayed by electronic device 600) from a process (e.g., the tracking process discussed above) executing on electronic device 600.

In some examples, notification 606 is issued in response to a determination that a user associated with electronic device 600 will likely begin or has likely begun their period. Such a prediction can be determined in a number of different ways, including based on previous periods and other information (including user interactions with electronic device 600) provided to the tracking application. In some examples, notification 606 is issued a predefined amount of time before a predicted beginning of a period, at the predicted beginning of the period, or after a predefined amount of time has passed since the predicted beginning of the period.

As depicted in FIG. 6B, notification 604 includes start affordance 608. In some examples, start affordance 608, by default, includes the text "NOT YET," indicating that no date for the beginning of the period has been set. In other examples, start affordance 608 is populated with a predicted start of the period (e.g., a current day). In some examples, start affordance 608 is used to identify a start date for the period, as further discussed below.

As depicted in FIG. 6B, notification 604 includes end affordance 610. In some examples, end affordance 610, by default, includes the text "NOT YET," indicating that no date for the end of the period has been set). In other examples, start affordance 608 is populated with a predicted end of the period (e.g., a current day). In some examples, end affordance 610 is used to identify an end date for the period, as further discussed below.

As depicted in FIG. 6B, notification 604 includes a dismiss affordance. In some examples, selection of the dismiss affordance causes electronic device 600 to cease display of notification 606.

Figure 6C:
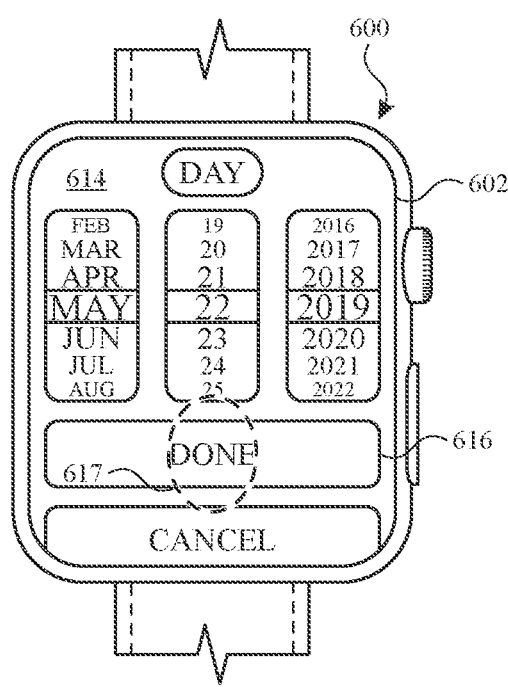

FIG. 6B depicts electronic device 600 receiving user input 609 corresponding to start affordance 608. In some examples, user input 609 is received via touch-sensitive display device 602 and corresponds to a selection gesture (e.g., tap) on start affordance 608. In other examples, other forms of selection may be used, such as a click using a mouse. In some examples, user input 609 causes a different user interface to be displayed via touch-sensitive display device 602, such as display of date-picking user interface 614 as depicted in FIG. 6C. In some examples, instead of causing a different user interface to be displayed, selection of start affordance 608 causes a process to be initiated for inserting a start date into start affordance 608. In some examples, the process includes displaying an insertion marker in start affordance 608 to allow a user to enter the start date using user input (e.g., via a keyboard, either virtual or physical). In some examples, the process includes detecting, via a sound sensor of electronic device 600, sound to identify the start date in the sound (e.g., a user speaking the start date).

FIG. 6C depicts electronic device 600 displaying date-picking user interface 614 via touch-sensitive display device 602 at a third time after the second time. As discussed above, date-picking user interface 614 is displayed in response to electronic device 600 receiving user input corresponding to start affordance 608 in notification 606.

In some examples, date-picking user interface 614 allows a user to identify a date to insert into start affordance 608 of notification 606, which is depicted in FIG. 6B. As depicted in FIG. 6C, date-picking user interface 614 includes three lists of values (e.g., a month list, a day list, and a year list), done affordance 616, and a cancel affordance (e.g., to cease display of date-picking user interface 614 and display notification 606 without identifying a date). A date can be identified by translating each list until a particular value for each list is selected. For example, a gesture to move each list in an upward or downward direction can change a value selected for each list.

While FIG. 6C depicts three lists of values, other techniques for selecting a date can be used. For example, date-picking user interface 614 can include a text box for which a user can enter the date using an input device, such as a keyboard or microphone. For another example, start affordance 608 of notification 606 may include an element to pick a date directly from notification 606 (e.g., a text box for which a user can enter the date using an input device, such as a keyboard or microphone).

FIG. 6C depicts electronic device 600 receiving user input 617 corresponding to done affordance 616. In some examples, user input 617 is received via touch-sensitive display device 602 and corresponds to a selection gesture (e.g., tap) on done affordance 616. In other examples, other forms of selection may be used, such as a click using a mouse. In some examples, user input 617 causes a different user interface to be displayed via touch-sensitive display device 602, such as re-display of notification 606 with a date included in start affordance 608 as depicted in FIG. 6D.

Figure 6D:
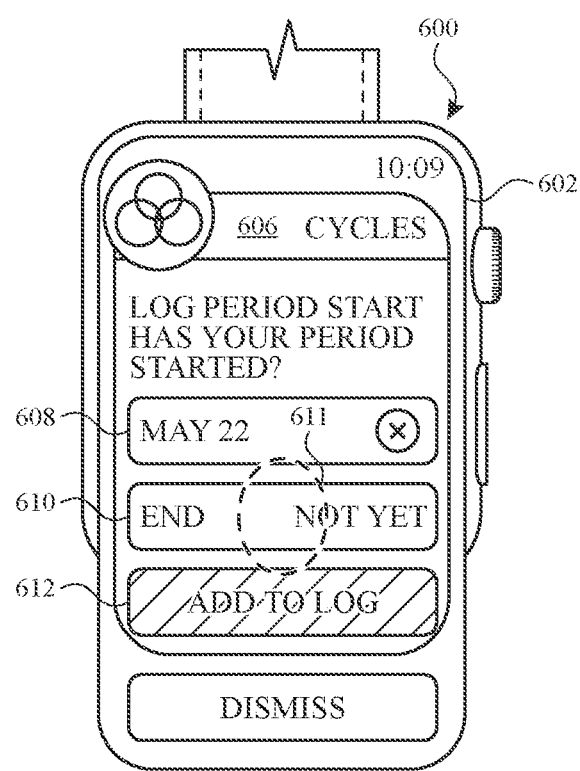

FIG. 6D depicts electronic device 600 displaying notification 606 via touch-sensitive display device 602 at a fourth time after the third time. Notification 606, in some examples, is displayed in response to user input corresponding to date-picking user interface 614 (e.g., selection of done affordance 616).

As depicted in FIG. 6D, notification 606 still includes start affordance 608, end affordance 610, add affordance 612, and a dismiss affordance; however, start affordance 608 has been updated based on a date selected using date-picking user interface 614. In particular, start affordance 608, at the fourth time, includes "MAY 22" to indicate that a user has identified the start of the period as May 22nd.

FIG. 6D depicts electronic device 600 receiving user input 611 corresponding to end affordance 610. In some examples, user input 611 is received via touch-sensitive display device 602 and corresponds to a selection gesture (e.g., tap) on end affordance 610. In other examples, other forms of selection can be used, such as a click using a mouse. In some examples, user input 611 causes a different user interface to be displayed via touch-sensitive display device 602, such as display of date-picking user interface 618 as depicted in FIG. 6E. In some examples, instead of causing a different user interface to be displayed, selection of end affordance 610 causes a process to be initiated for inserting an end date into end affordance 610. In some examples, the process includes displaying an insertion marker in end affordance 610 to allow a user to enter the end date using user input (e.g., via a keyboard, either virtual or physical). In some examples, the process includes detecting, via a sound sensor of electronic device 600, sound to identify the end date in the sound (e.g., a user speaking the end date).

FIG. 6E depicts electronic device 600 displaying date-picking user interface 618 via touch-sensitive display device 602 at a fifth time after the fourth time. As discussed above, date-picking user interface 618 is displayed in response to electronic device 600 receiving user input corresponding to end affordance 610 in notification 606.

In some examples, date-picking user interface 618 has the same functionality as date-picking user interface 614. To show such functionality, FIG. 6E depicts electronic device 600 receiving upward gesture 623 (e.g., a finger gesture beginning at a first location and moving upward to a second location before lifting off from touch-sensitive display device 602) corresponding to day picker 622. Before upward gesture 623, day picker 622 indicates that 22 is selected. Upward gesture 623 causes day picker 622 to change such that a different day (e.g., 28) is selected using day picker 622, as depicted in FIG. 6F.

FIG. 6F depicts electronic device 600 displaying date-picking user interface 618 via touch-sensitive display device 602 at a sixth time after the fifth time. In FIG. 6F, day picker 622 is indicating that 28 has been selected so that date-picking user interface 618 is indicating that May 28, 2019 is currently selected.

FIG. 6F depicts electronic device 600 receiving user input 621 corresponding to done affordance 620 in date-picking user interface 618. In some examples, user input 621 is received via touch-sensitive display device 602 and corresponds to a selection gesture (e.g., tap) on done affordance 620. In other examples, other forms of selection can be used, such as a click using a mouse. In some examples, user input 621 causes a different user interface to be displayed via touch-sensitive display device 602, such as re-display of notification 606 with a date included in end affordance 610 as depicted in FIG. 6G.

Figure 6G:
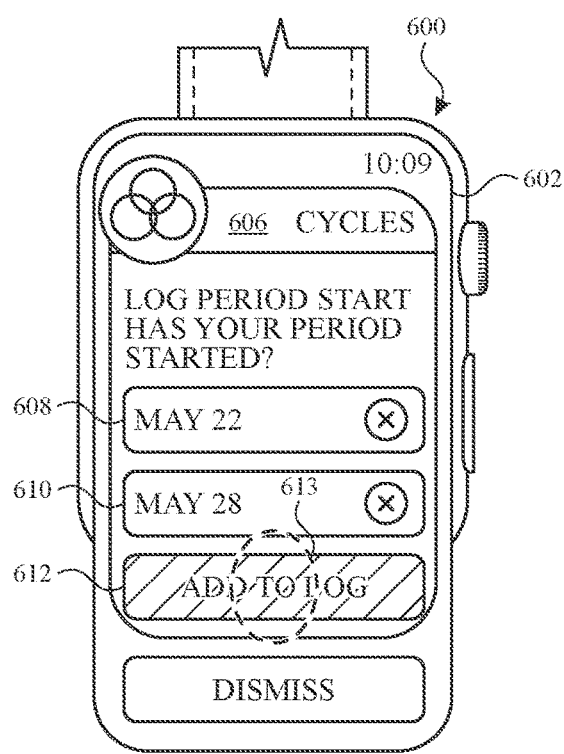

FIG. 6G depicts electronic device 600 displaying notification 606 via touch-sensitive display device 602 at a seventh time after the sixth time. Notification 606, in some examples, is displayed in response to user input corresponding to date-picking user interface 618 (e.g., selection of done affordance 620).

As depicted in FIG. 6G, notification 606 still includes start affordance 608, end affordance 610, add affordance 612, and a dismiss affordance (as depicted in FIG. 6D); however, end affordance 610 has been updated based on a date selected using date-picking user interface 618. In particular, end affordance 610, at the seventh time, includes "MAY 28" to indicate that a user has identified the end of the period as May 28th.

FIG. 6G depicts electronic device 600 receiving user input 613 corresponding to add affordance 612. In some examples, user input 613 is received via touch-sensitive display device 602 and corresponds to a selection gesture (e.g., tap) on add affordance 612. In other examples, other forms of selection can be used, such as a click using a mouse. In some examples, user input 613 causes a period to be logged with a start date of May 22nd and an end date of May 28th. In some examples, logging the period causes indications of the period to be added to a user interface that can be viewed at a later time, such as depicted in FIG. 6N. In some examples, logging the period causes predictions for future periods to be updated based on this logged period. In some examples, user input 613 also causes electronic device 600 to cease display of notification 606.

Figure 6H:
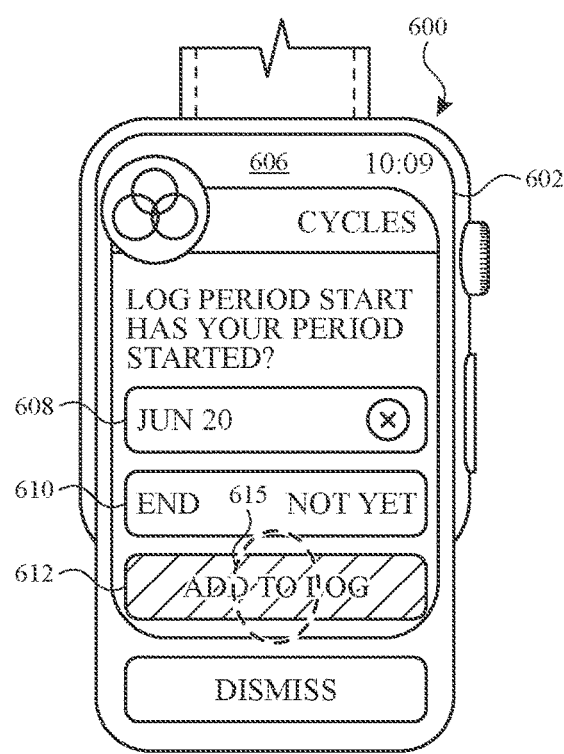

FIG. 6H depicts electronic device 600 displaying notification 606 via touch-sensitive display device 602 at an eighth time after the seventh time. In some examples, notification 606 (as depicted in FIG. 6H) is a notification that was issued (e.g., caused to be displayed by electronic device 600) from a process (e.g., the tracking process discussed above) executing on electronic device 600.

In some examples, notification 606 is issued in response to a determination that a user associated with electronic device 600 has likely begun their next period after the period logged in FIG. 6G. Similar to as described above, such a prediction can be determined in a number of different ways, including based on previous periods and other information (including user interactions with electronic device 600) provided to the tracking application.

As depicted in FIG. 6H, notification 604 includes start affordance 608, end affordance 610 (which, by default, includes the text "NOT YET," indicating that no date for the end of the period has been set), add affordance 612, and a dismiss affordance. Unlike as depicted in FIG. 6B, FIG. 6H depicts start affordance 608 as beginning with a date already selected for the start of the period (e.g., start affordance 608 includes the text "JUNE 20"). FIG. 6H is depicting that start affordance 608 can be pre-filled with a start date based on a prediction or a current day, instead of beginning with default text of "NOT YET."

FIG. 6H depicts electronic device 600 receiving user input 615 corresponding to add affordance 612. In some examples, user input 615 is received via touch-sensitive display device 602 and corresponds to a selection gesture (e.g., tap) on add affordance 612. In other examples, other forms of selection can be used, such as a click using a mouse. In some examples, user input 615 causes a period to be logged with a start date of June 20th and no end date (e.g., end affordance 610 does not have a selected day, indicated by the text "NOT YET"). In some examples, logging the period causes an indication of the start of the period to be added to a user interface that can be viewed at a later time, such as depicted in FIG. 6N. In some examples, logging the beginning of the period causes predictions for the rest of the period and future periods to be updated based on this logging. In some examples, user input 615 also causes electronic device 600 to cease display of notification 606.

Figure 6I:
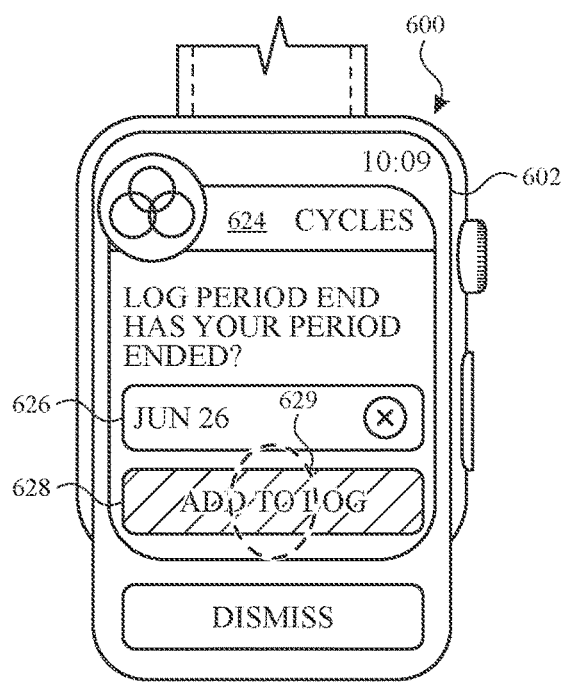

FIG. 6I depicts electronic device 600 displaying notification 624 via touch-sensitive display device 602 at a ninth time after the eighth time. In some examples, notification 606 is a notification that was issued (e.g., caused to be displayed by electronic device 600) from a process (e.g., the tracking process discussed above) executing on electronic device 600.

In some examples, notification 624 is issued in response to a determination that a user associated with electronic device 600 has previously entered a start of a period and has not entered an end date for the period. In some examples, notification 624 is issued in further response to a criterion based on a predicted end date for the period. Similar to as described above, such a prediction can be determined in a number of different ways, including based on previous periods and other information (including user interactions with electronic device 600) provided to the tracking application. In some examples, notification 624 is issued a predefined amount of time before a predicted end of a period, at the predicted end of the period, or after a predefined amount of time has passed since the predicted end of the period.

As depicted in FIG. 6I, notification 624 includes end affordance 626, add affordance 628, and a dismiss affordance. End affordance 626 includes a date for the end of the period (e.g., "JUNE 26"). FIG. 6I is depicting that end affordance 626 can be pre-filled with an end date based on a prediction or a current day; however, in some examples, end affordance 626 begins with default text of "NOT YET," indicating that no date for the end of the period has been set. In such examples, a user might need to select the end of the period, similarly to as described above in FIGS. 6D-6G.

FIG. 6I depicts electronic device 600 receiving user input 629 corresponding to add affordance 628. In some examples, user input 629 is received via touch-sensitive display device 602 and corresponds to a selection gesture (e.g., tap) on add affordance 628. In other examples, other forms of selection can be used, such as a click using a mouse. In some examples, user input 629 causes a period to be logged with an end date of June 29th. In such examples, user input 629 can also cause a period to be logged on each day between the start date of the period (e.g., June 20th) and the end date of June 29th. In some examples, logging the period causes an indication of the end of the period to be added to a user interface that can be viewed at a later time, such as depicted in FIG. 6N. In some examples, user input 615 also causes electronic device 600 to cease display of notification 624.

Figure 6J:
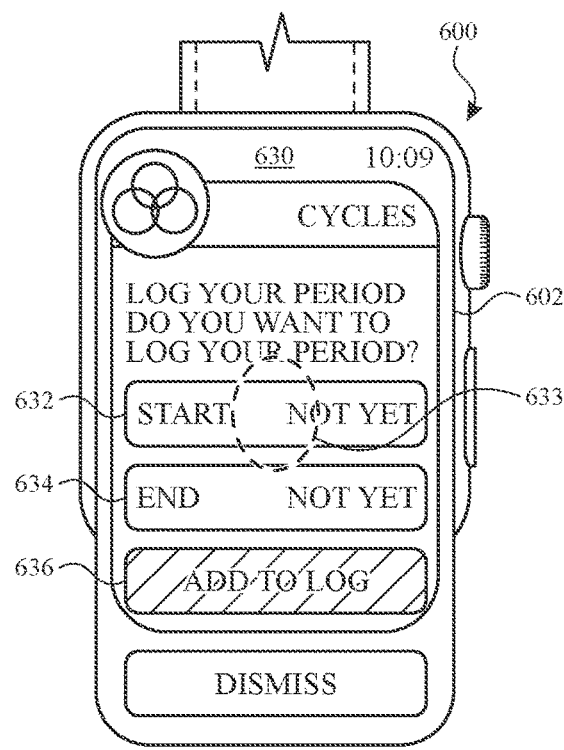

FIG. 6J depicts electronic device 600 displaying notification 630 via touch-sensitive display device 602 at a tenth time after the ninth time. In some examples, notification 630 (as depicted in FIG. 6J) is a notification that was issued (e.g., caused to be displayed by electronic device 600) from a process (e.g., the tracking process discussed above) executing on electronic device 600.

In some examples, notification 630 is issued in response to a determination that a user associated with electronic device 600 has not entered a start of a period and has not entered an end date for the period. In some examples, notification 630 is issued in further response to a criterion based on a predicted end date for the period. Similar to as described above, such a prediction can be determined in a number of different ways, including based on previous periods and other information (including user interactions with electronic device 600) provided to the tracking application.

As depicted in FIG. 6J, notification 604 includes start affordance 632 (which, by default, includes the text "NOT YET," indicating that no date for the end of the period has been set), end affordance 634 (which, by default, includes the text "NOT YET," indicating that no date for the end of the period has been set), add affordance 636, and a dismiss affordance. Similar to FIG. 6B, in some examples, start affordance 632 is populated with a predicted start of the period and/or end affordance 634 is populated with a predicted end of the period.

FIG. 6J depicts electronic device 600 receiving user input 633 corresponding to start affordance 632. In some examples, user input 608 is received via touch-sensitive display device 602 and corresponds to a selection gesture (e.g., tap) on start affordance 632. In other examples, other forms of selection can be used, such as a click using a mouse. In some examples, user input 633 causes a different user interface to be displayed via touch-sensitive display device 602, such as display of date-picking user interface 614 as depicted in FIG. 6C. In some examples, instead of causing a different user interface to be displayed, selection of start affordance 632 causes a process to be initiated for inserting a start date into start affordance 632. In some examples, the process includes displaying an insertion marker in start affordance 632 to allow a user to enter the start date using user input (e.g., via a keyboard, either virtual or physical). In some examples, the process includes detecting, via a sound sensor of electronic device 600, sound to identify the start date in the sound (e.g., a user speaking the start date).

Figure 6K:
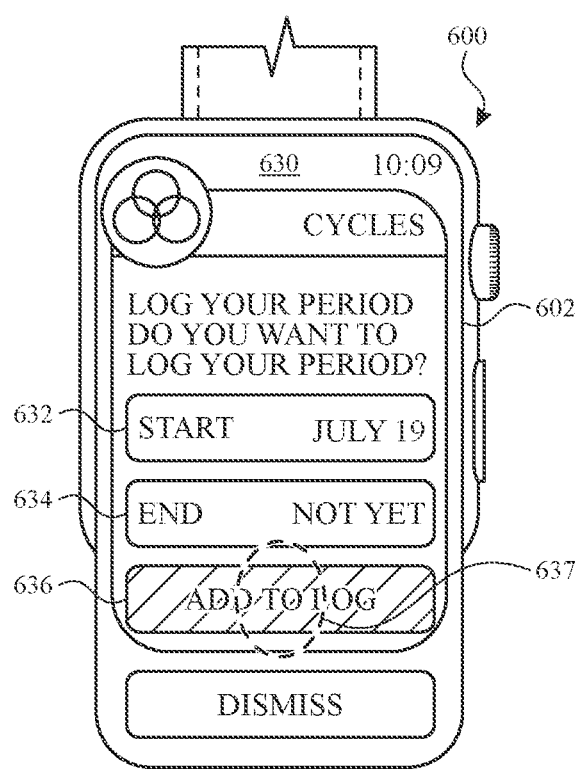

FIG. 6K depicts electronic device 600 displaying notification 630 via touch-sensitive display device 602 at an eleventh time after the tenth time. As depicted in FIG. 6K, notification 630 still includes start affordance 632, end affordance 634, add affordance 636, and a dismiss affordance; however, start affordance 632 has been updated based on an identified date. In particular, start affordance 632, at the eleventh time, includes "JULY 19" to indicate that a user has identified the start of the period as July 19.

FIG. 6K depicts electronic device 600 receiving user input 637 corresponding to add affordance 636. In some examples, user input 637 is received via touch-sensitive display device 602 and corresponds to a selection gesture (e.g., tap) on add affordance 636. In other examples, other forms of selection can be used, such as a click using a mouse. In some examples, user input 637 causes a period to be logged with a start date of July 19th and no end date (e.g., end affordance 634 does not have a selected day, indicated by the text "NOT YET"). In some examples, logging the period causes an indication of the start of the period to be added to a user interface that can be viewed at a later time, such as depicted in FIG. 6N. In some examples, logging the beginning of the period causes predictions for the rest of the period and future periods to be updated based on this logging. In some examples, user input 637 also causes electronic device 600 to cease display of notification 630.

Figure 6L:
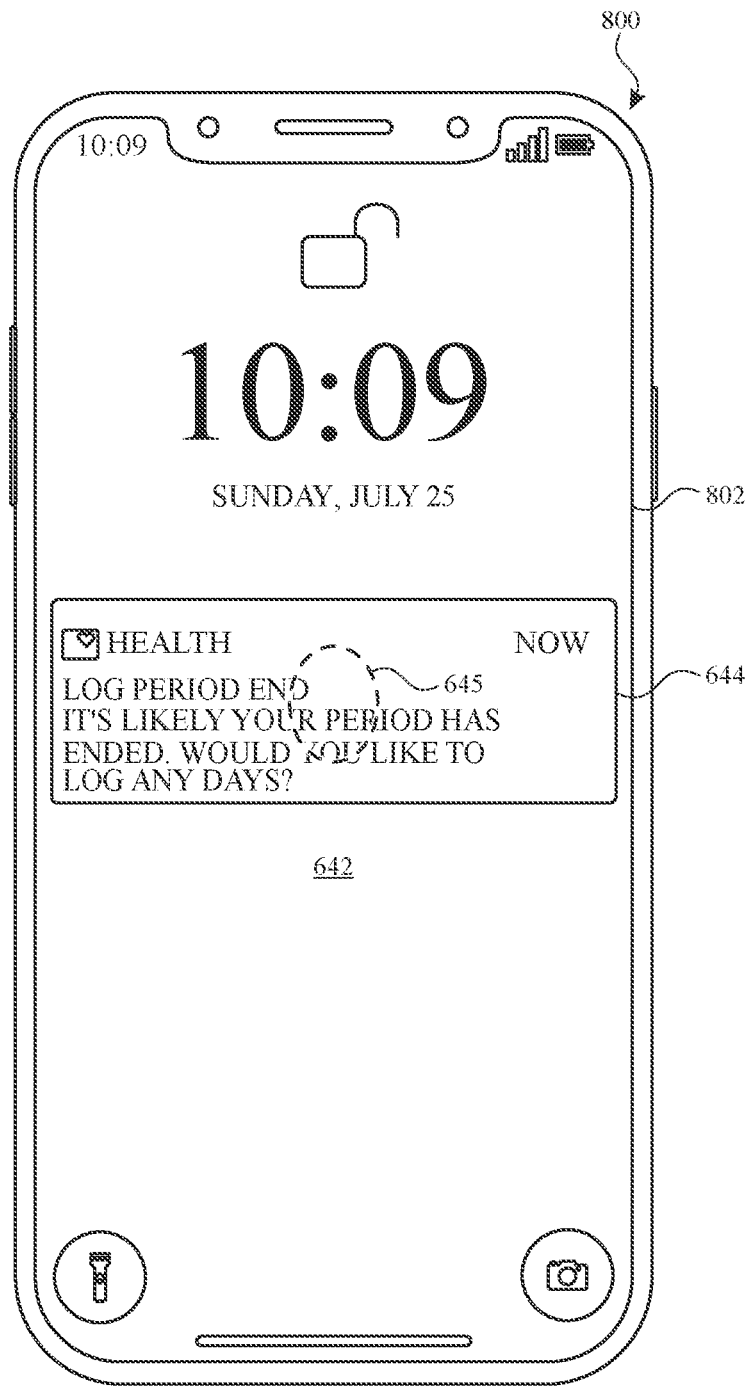

FIG. 6L depicts electronic device 800 displaying notification 644 via touch-sensitive display device 802 at a twelfth time after the eleventh time. In some examples, electronic device 600 includes one or more features of devices 100, 300, 500, or 600.

In some examples, notification 644 is displayed at least partially on top of another user interface of electronic device 800, such as lock screen user interface 642 (as depicted in FIG. 6L). Notification 644 is a notification that was issued (e.g., caused to be displayed by electronic device 600) from a process executing on electronic device 800. For example, the process can be a tracking process associated with a tracking application. In some examples, notification 644 is issued in response to a determination that a user associated with electronic device 800 has previously entered a start of a period (e.g., as depicted in FIG. 6K) and has not entered an end date for the period. In some examples, notification 644 is issued in further response to a criterion based on a predicted end date for the period. Similar to as described above, such a prediction can be determined in a number of different ways, including based on previous periods and other information (including user interactions with electronic device 600 and/or electronic device 800) provided to the tracking application. In some examples, notification 644 is issued a predefined amount of time before a predicted end of a period, at the predicted end of the period, or after a predefined amount of time has passed since the predicted end of the period.

FIG. 6L depicts electronic device 800 receiving user input 645 corresponding to notification 644. In some examples, user input 645 is received via touch-sensitive display device 802 and corresponds to a hold gesture (e.g., a finger gesture on notification 644 that exceeds a threshold amount of time) on notification 644. In other examples, other forms of a hold gesture can be used, such as holding a mouse button on a mouse. In some examples, user input 645 causes a different user interface to be displayed via touch-sensitive display device 802, such as display of calendar user interface depicted in FIG. 6M.

Figure 6M:
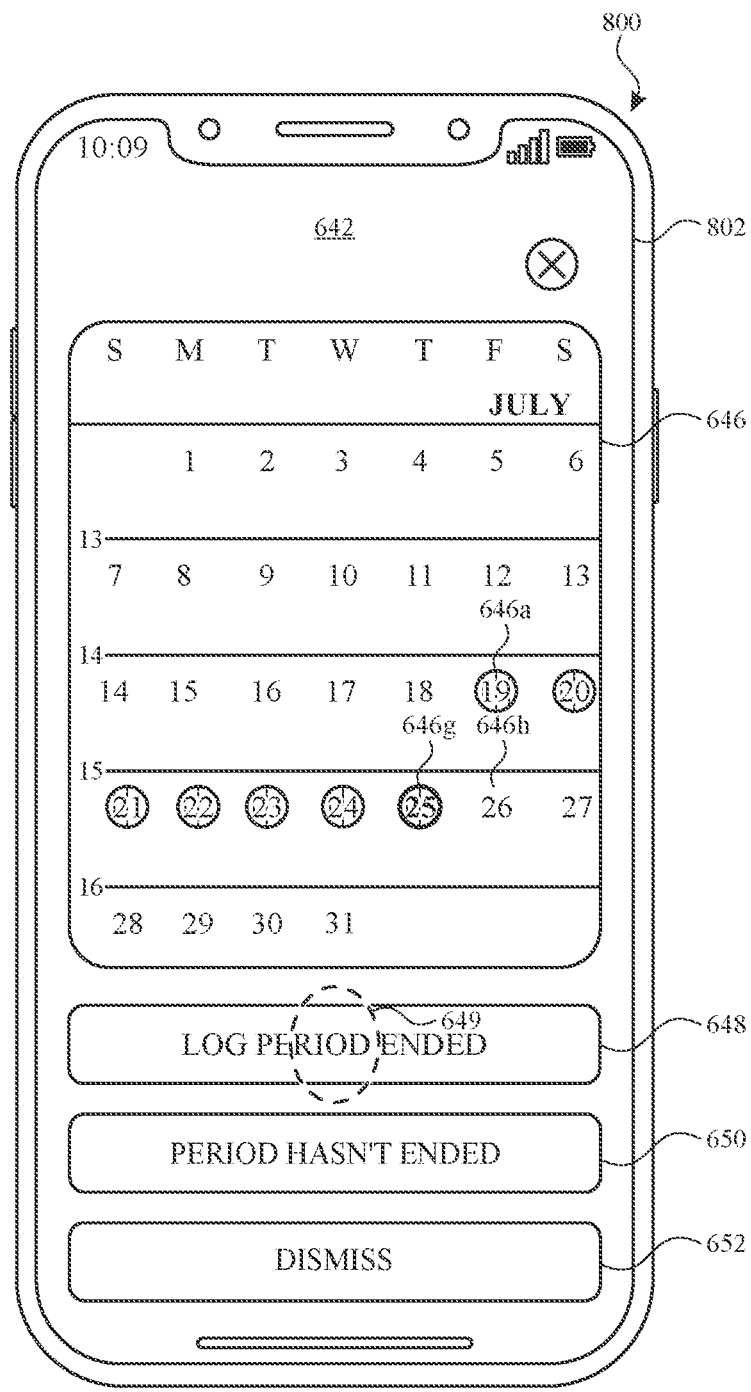
Figures 6N, 6O:
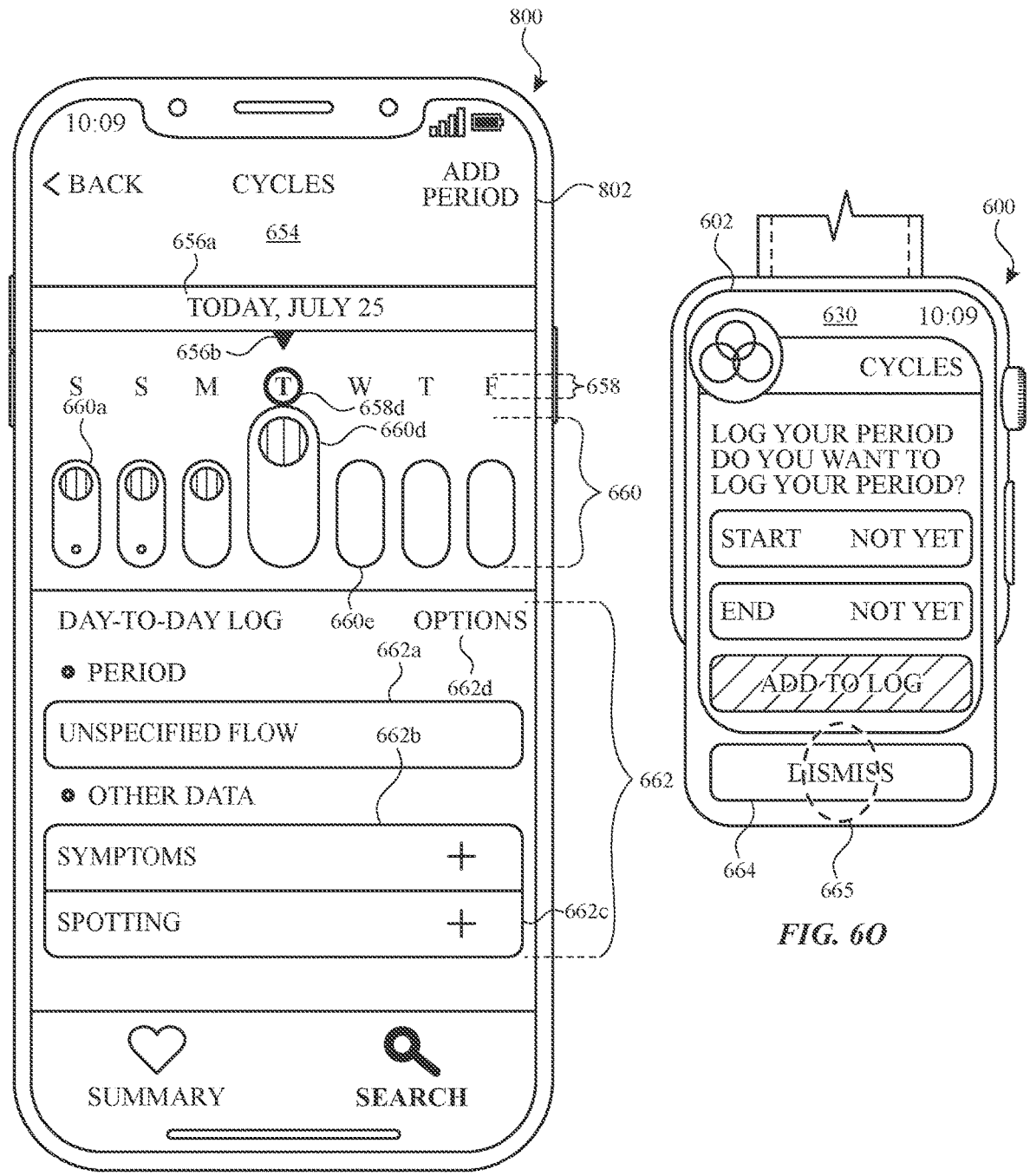

FIG. 6M depicts electronic device 800 displaying a calendar user interface on top of lock screen user interface 642 (e.g., where at least a portion of lock screen user interface 642 is still visible) via touch-sensitive display device 802 at a thirteenth time after the twelfth time. The calendar user interface includes calendar representation 646, end affordance 648, continuing affordance 650 (e.g., for indicating that the current period has not ended), and dismiss affordance 652.

In some examples, calendar representation 646 includes a graphical representation of a month, including day representations for each day (e.g., a number for each day) in a format corresponding to a calendar. An example of a day representation in FIG. 6M is 646h (e.g., "26"). As depicted in FIG. 6M, calendar representation 646 corresponds to the month of July. In some examples, a current day is visually distinguished in calendar representation 646. For example, in FIG. 6M, the current day is July 25th, which corresponds to a day representation that is bolded as compared to other day representations.

In some examples, calendar representation 646 is configured to receive selections of day representations (e.g., a finger tap on a day representation). Selecting a day representation causes a period indication to be displayed associated with the day representation. In some examples, the period indication is displayed on calendar representation 646 in response to (e.g., without another user input) selection of the day representation. In some examples, the period indication indicates that a period occurred on the day corresponding to the day representation. As depicted in FIG. 6M, the period indication includes a circle around the day representation, with the inside of the circle visually distinct from outside of the circle (e.g., the circle is red inside). An example of a day representation with a period indication in FIG. 6M is 646a (e.g., a circle around the "19" with the inside of the circle visually distinguished from outside of the circle). It should be recognized that a day representation can include a period indication without user input on calendar representation 646. For example, such a day representation can have been indicated to have a period occurred using a user interface different from the calendar user interface depicted in FIG. 6M (e.g., a previous calendar user interface or a different user interface). For another example, such a day representation can have been indicated to have a period by the tracking application (e.g., a prediction).

In some examples, end affordance 648, when selected, causes a period to be logged based on selections performed on day representations in calendar representation 646. In one example, end affordance 648 is not selectable unless at least one day representation includes a period indication. In some examples, selection of end affordance 648 causes electronic device 800 to cease display of the calendar user interface and, in some examples, notification 644. In other examples, selection of end affordance 648 causes electronic device 800 to display a user interface corresponding to the tracking application, such as depicted in FIG. 6N.

In some examples, continuing affordance 650, when selected, causes a period to be logged for a current day. In some examples, continuing affordance 650, when selected, causes a period to be logged from a start date of a period to the current day. In some examples, continuing affordance 650, when selected, causes a period to be logged based on selections performed on day representations in calendar representation 646 and the current day. In one example, end affordance 648 is not selectable unless at least one day representation includes a period indication. In some examples, selection of continuing affordance 650 causes electronic device 800 to cease display of the calendar user interface and, in some examples, notification 644. In other examples, selection of continuing affordance 650 causes electronic device 800 to display a user interface corresponding to the tracking application, such as depicted in FIG. 6N.

In some examples, selection of dismiss affordance 652 causes electronic device 800 to cease display of the calendar user interface and, in some examples, notification 644.

FIG. 6N depicts electronic device 800 displaying tracking home user interface 654 via touch-sensitive display device 802 at a fourteenth time after the thirteenth time. Tracking home user interface 654 allows a user to view and add information regarding periods.

Tracking home user interface 654 includes bottom portion 662. Bottom portion 662 includes detailed information regarding periods for a selected day. For example, bottom portion 662 includes period representation 662a, which indicates (1) whether a period is logged for the selected day and (2), if a period is logged for the selected day, detail about the period that was logged. Examples of possible details include light flow, medium flow, heavy flow, unspecified flow, and no flow. In FIG. 6N, period representation 662a indicates that a period was logged and that the period had an unspecified flow.

As depicted in FIG. 6N, bottom portion 662 includes a region for other data, including symptoms representation 662b and spotting representation 662c. Symptoms representation 662b includes one or more symptoms logged by a user for the selected day. Examples of possible symptoms include cramps, mood changes, low back pain, aches, bloating, constipation, and headache. Spotting representation 662c indicates whether the user indicated that spotting occurred on the selected day.

Tracking home user interface 654 includes a top portion (e.g., 656a, 656b, 658, and 660). The top portion indicates summary information regarding each day of a week, identifies a selected day, and provides a technique to select a different day such that when a different day is selected the bottom portion is modified to correspond to the selected day. For example, the top portion includes identification information 656a, which indicates a selected day. In FIG. 6N, identification information 656a includes "TODAY, JULY 25", indicating that a current day is selected and that the current day is July 25th. The top portion also includes multiple day representations 660 aligned along an axis (e.g., a horizontal axis). Each of multiple day representations 660 do not overlap each other and a selected day is centered in the middle of multiple day representations 660.

Each day representation in multiple day representations 660 (e.g., day representation 660a) includes summary information for that day. The summary information indicates whether a period has been logged for the day and whether other data has been logged for the day. As depicted in FIG. 6N, day representation 660a indicates that (1) a period occurred on a day corresponding to day representation 660a (e.g., by the large circle at the top of day representation 660a that is visually distinguished (e.g., red)) and (2) other data has been logged for the day (e.g., by the small circle at the bottom of day representation 660a). For another example, day representation 660d indicates that (1) a period occurred on a day corresponding to day representation 660d (e.g., by the large circle at the top of day representation 660d that is visually distinguished (e.g., red)) and (2) no other data has been logged for the day (e.g., by the lack of a small circle at the bottom of day representation 660d).

Above each day representation of multiple day representations 660 is an indication of which day the day representation corresponds. For example, day representation 660a has an "S" above itself, indicating that day representation 660a corresponds to Saturday. For another example, day representation 660d has a "T" above itself, indicating that day representation 660d corresponds to Tuesday. The indications above each day representation also indicate which day is a current day. In particular, day indication 658d has a circle around itself, indicating that day indication 658d is the current day. In some examples, the day representation corresponding to a selected day (e.g., day representation 660d) is a different size (e.g., bigger than) other day representations. In regards to a selected day, the top portion also includes arrow 656b to provide an indication of multiple day representations 660 corresponds to the selected day.

In some examples, the top portion of tracking home user interface 654 is configured to receive user input along the first axis to change a selected day to an adjacent day. For example, a left swipe would change the selected day to the day to one day ahead of a currently selected day. Similarly, a right swipe would change the selected day to one day behind a currently selected day.

FIG. 6O depicts electronic device 600 displaying notification 630 via touch-sensitive display device 602 at a fifteenth time after the fourteenth time. In some examples, notification 630 (as depicted in FIG. 6O) is a notification that was issued (e.g., caused to be displayed by electronic device 600) from a process (e.g., the tracking process discussed above) executing on electronic device 600.

In some examples, notification 630 is issued in response to a determination that a user associated with electronic device 600 has not entered a start for a period and has not entered an end date for the period. In some examples, notification 630 is issued in further response to a criterion based on a predicted end date for the period. Similar to as described above, such a prediction can be determined in a number of different ways, including based on previous periods and other information (including user interactions with electronic device 600) provided to the tracking application.

As depicted in FIG. 6O, notification 604 includes dismiss affordance 664. FIG. 6O depicts electronic device 600 receiving user input 665 corresponding to dismiss affordance 664. In some examples, user input 665 is received via touch-sensitive display device 602 and corresponds to a selection gesture (e.g., tap) on dismiss affordance 664. In other examples, other forms of selection can be used, such as a click using a mouse.

In some examples, user input 665 causes electronic device 600 to cease display of notification 630. In some examples, when a minimum number of notifications have been dismissed without logging any information related to periods, the tracking application can determine to suspend future notifications until notification criteria are met (e.g., a criterion that is based on whether a user interaction has been received associated with the tracking application).

FIGS. 7A-7B are a flow diagram illustrating a method for cycle tracking using an electronic device in accordance with some embodiments. Method 700 is performed at a device (e.g., 100, 300, 500, 600) (e.g., a smartphone, a smartwatch) with a display device (e.g., a touch-sensitive display). Some operations in method 700 are, optionally, combined, the orders of some operations are, optionally, changed, and some operations are, optionally, omitted.

As described below, method 700 provides an intuitive way for cycle tracking. The method reduces the cognitive burden on a user for cycle tracking, thereby creating a more efficient human-machine interface. For battery-operated computing devices, enabling a user to track cycles faster and more efficiently conserves power and increases the time between battery charges.

At a first time (e.g., a specific time (e.g., 12:00 PM) of the current date; a time that has a predetermined relationship to a predicted or recorded start or end date for a respective recurrence of a recurring event), the electronic device (e.g., 600) displays (702), via the display device, in accordance with a determination that a first set of criteria is met, the first set of criteria including a criterion that is met when a current date (e.g., a specific time of the current date (e.g., 12:00 AM; 12:00 PM)) corresponds (e.g., is at the predicted start date; is a predetermined period of time before the predicted start date; is a predetermined period of time after the predicted start date) to a predicted start date (e.g., a date that is determined based on historical information about past occurrences of the recurring event) of a recurring event, a first notification (704) (e.g., 606, 630, 642) that includes a first affordance (e.g., 612, 636, 650) (e.g., an add to log affordance) that, when selected, initiates a process to record (e.g., to log, to store) a start date (e.g., to associate a date (e.g., the current date, a date other than the current date) with the current recurrence) for a respective recurrence (e.g., a current occurrence) of the recurring event. In some embodiments, the first set of criteria includes a second criterion that is met when a start date for the respective recurrence has not been identified (e.g., a user has not entered or otherwise indicated the start date for the occurrence).

At the first time (e.g., a specific time (e.g., 12:00 PM) of the current date; a time that has a predetermined relationship to a predicted or recorded start or end date for a respective recurrence of a recurring event), the electronic device (e.g., 600) displays (702), via the display device, in accordance with a determination that a second set of criteria is met, the second set of criteria including a criterion that is met when the current date (e.g., a specific time of the current date (e.g., 12:00 AM; 12:00 PM)) corresponds (e.g., is at the predicted end date; is a predetermined period of time before the predicted end date; is a predetermined period of time after the predicted end date) to a predicted end date (e.g., a date that is determined based on historical information about past occurrences of the recurring event) of the recurring event, a second notification (706) (e.g., 624, 630) that includes a second affordance (e.g., 628, 636) (e.g., an add to log affordance; the first affordance) that, when selected, initiates a process to record an end date (e.g., to associate a date (e.g., the current date, a date other than the current date) with the current recurrence) for the respective recurrence of the recurring event.

The technique displays different notifications that initiate different processes based on whether the first or second set of criteria is met. Performing an operation when a set of conditions has been met without requiring further user input enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the recurring event corresponds to a recurring menstrual period (e.g., FIG. 6G and next period FIG. 6H).

In some embodiments, while displaying a respective notification selected from the group consisting of the first notification and the second notification, the electronic device (e.g., 600) receives (708) a first set of one or more inputs. In some embodiments, in response to (710) receiving the first set of one or more inputs, in accordance with a determination that the first set of one or more inputs includes a first input corresponding to selection of the first affordance, the electronic device (e.g., 600) records (712) a start date for the respective recurrence of the recurring event. In some embodiments, in response to (710) receiving the first set of one or more inputs, in accordance with a determination that the first set of one or more inputs includes a second input corresponding to selection of the second affordance, the electronic device (e.g., 600) records (714) an end date for the respective recurrence of the recurring event.

In some embodiments, the first time is after the predicted start date of the recurring event. In some embodiments, the first notification includes an indication of a suggested start date for the respective recurrence of the recurring event (e.g., FIG. 6H). In some embodiments, the indication is an affordance (e.g., 608) that, when selected, initiates a process for selecting a start date for the respective recurrence of the recurring event. In some embodiments, as part of the process for recording the start date for the respective recurrence of the recurring event, the electronic device (e.g., 600) (or another device) records the suggested start date as the start date for the respective recurrence of the recurring event.

Including the indication of a suggested start date in the first notification provides the user about feedback about a date that can be recorded for the recurrence of the recurring event. Providing improved visual feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the first time is after the predicted end date of the recurring event. In some embodiments, the second notification includes a first indication (e.g., 626) of a suggested end date for the respective recurrence of the recurring event (e.g., FIG. 6I). In some embodiments, the indication is an affordance (e.g., 610) that, when selected, initiates a process for selecting an end date for the respective recurrence of the recurring event. In some embodiments, as part of the process for recording the end date for the respective recurrence of the recurring event, the electronic device (e.g., 600) (or another device) records the suggested end date as the end date for the respective recurrence of the recurring event.

Including the indication of a suggested start date in the first notification provides the user about feedback about a date that can be recorded for the recurrence of the recurring event. Providing improved visual feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the first notification is displayed at a predetermined time (e.g., 1 day, 3 days, 5 days) before the predicted start date of the recurring event.

Displaying the notification before the predicted start date provides the user with feedback about the recurring event before the event is expected to occur. Providing improved visual feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the second notification includes a third affordance (e.g., 632, 650) that, when selected, initiates a process for selecting a start date for the respective recurrence of the recurring event. In some embodiments, the third affordance is initially displayed when a suggested start date.

In some embodiments, the second notification (e.g., 624) is displayed after the predicted start date of the recurring event. In some embodiments, the second set of criteria includes a criterion that is met when a start date has not been recorded (e.g., previously recorded) for the current recurrence of the recurring event. In some embodiments, the notification includes both start-of-event and end-of-event affordances (e.g., 632 and 634 of notification 630) when the predicted start date has passed a start date has not been recorded.

In some embodiments, prior to displaying the second notification, the electronic device (e.g., 600) receives data corresponding to recording of a start date for the current occurrence of the recurring event (e.g., data from inputs at the electronic device corresponding to recording of the start date; data from an external device corresponding to recording of a start date). In some embodiments, the predicted end date (e.g., June 26 in FIG. 6I) of the recurring event is based on the data corresponding to recording of a start date for the current occurrence of the recurring event. In some embodiments, the second notification includes a second indication of a suggested end date for the respective recurrence of the recurring event that is based on the predicted end date. In some embodiments, the indication is an affordance that, when selected, initiates a process for selecting an end date for the respective recurrence of the recurring event. In some embodiments, the second notification (e.g., 624) does not include an indication of a start date for the current occurrence of the recurring event. In some embodiments, the process to record an end date for the respective recurrence of the recurring event does not include recording a start date for the respective recurrence of the recurring event.

In some embodiments, the first set of criteria includes a second criterion that is met when, for the respective recurrence of the recurring event, less than a predetermined number of notifications (e.g., notifications similar to the first notification (e.g., relating to the first set of criteria); notifications similar to either the first notification or the second notification (e.g., relating to the first set of criteria or the second set of criteria)) corresponding to (e.g., relating to, based on a start date or end date prediction for the respective recurrence) the respective recurrence of the recurring event have been displayed (e.g., FIG. 6O) (e.g., issued, outputted).

In some embodiments, a notification is issued and/or displayed only if a permissible number of previous notifications has not been exceeded.

In some embodiments, while displaying a respective notification selected from the group consisting of the first notification and the second notification, the electronic device (e.g., 600) receives a second set of one or more inputs (e.g., 645, an input that includes an input of a first type (e.g., a tap, a tap having a characteristic intensity greater than a threshold intensity)). In some embodiments, in response to receiving the second set of one or more inputs, the electronic device (e.g., 600) displays a calendar user interface (e.g., 642) that includes a first set of one or more graphical indications of dates corresponding the respective recurrence of the recurring event (e.g., dates that correspond to predicted dates corresponding to the respective recurrence; dates that correspond to recorded dates corresponding to the respective recurrence).

Displaying a calendar user interface that includes graphical indications of dates corresponding the respective recurrence of the recurring event provides the user with feedback about the event so that the user can take an appropriate action, if desired. Providing improved visual feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

Note that details of the processes described above with respect to method 700 (e.g., FIGS. 7A-7B) are also applicable in an analogous manner to the methods described below. For example, method 900 optionally includes one or more of the characteristics of the various methods described above with reference to method 700. For another example, the recurring event described with respect to method 700 can be the same event as that described with respect to method 900. For another example, devices 600 and 800 can include features of the other respective device. For brevity, these details are not repeated below.

FIGS. 8A-8S illustrate exemplary user interfaces for cycle tracking, in accordance with some embodiments. While the following user interfaces relate to cycle tracking, it should be recognized that techniques described here can relate to tracking other things, such as weight, food, exercise, projects, etc. The user interfaces in these figures are used to illustrate the processes described below, including the processes in FIGS. 9A-9B.

FIG. 8A depicts electronic device 800 displaying home user interface 804 via touch-sensitive display device 802 at a first time. In some examples, electronic device 800 includes one or more features of devices 100, 300, 500, or 600.

Home user interface 804 includes multiple icons, each icon corresponding to a different application. For example, home user interface 804 includes health icon 806 to initiate a health application and/or display a user interface of the health application.

FIG. 8A depicts electronic device 800 receiving user input 807 corresponding to health icon 806. In some examples, user input 807 is received via touch-sensitive display device 802 and corresponds to a selection of health icon 806 (e.g., a tap gesture on health icon 806). In other examples, other forms of input can be used, such as a click via a mouse. In some examples, user input 807 causes a different user interface to be displayed via touch-sensitive display device 802, such as display of a user interface of the health application, as depicted in FIG. 8B.

Figure 8B:
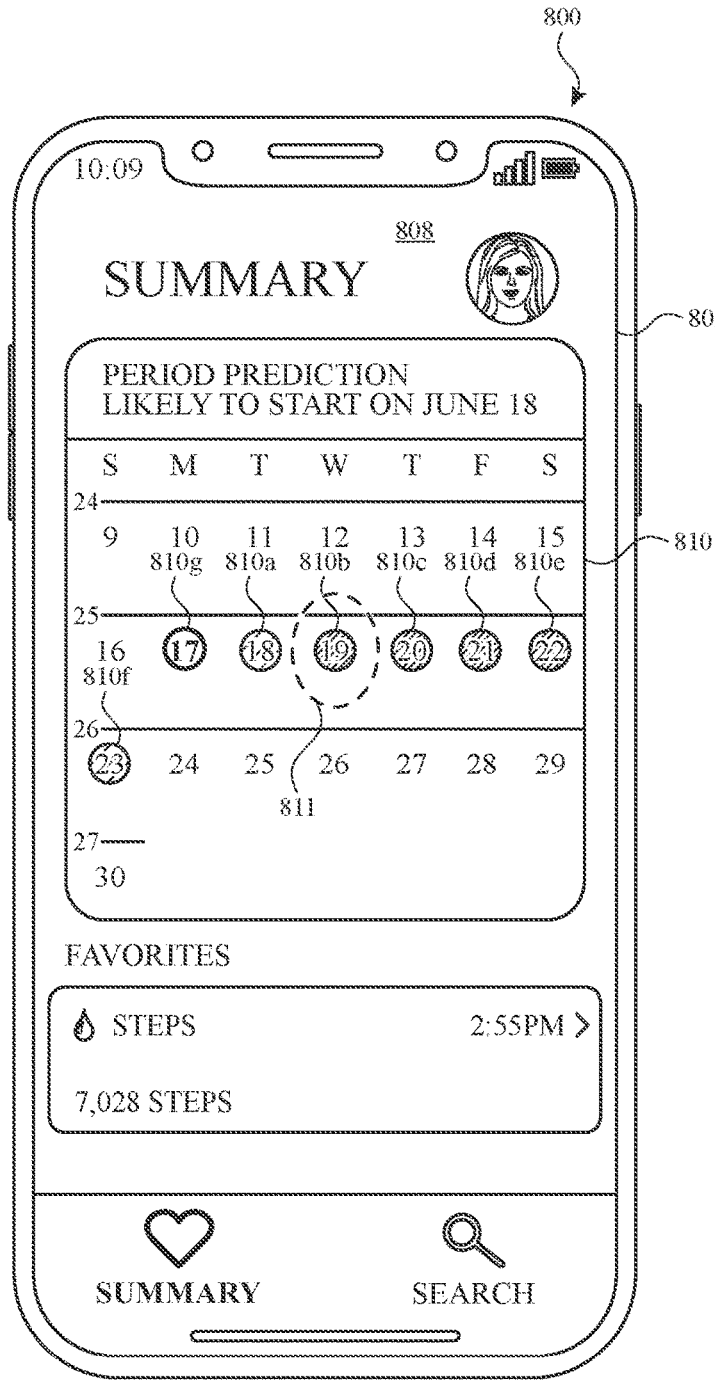

FIG. 8B depicts electronic device 800 displaying summary user interface 808 via touch-sensitive display device 802 at a second time after the first time. In some examples, summary user interface 808 is a user interface of a health application.

Summary user interface 808 includes affordance 810 corresponding to a tracking application. Affordance 810 indicates that a period is predicted to start on June 18th. Such a prediction can be determined in a number of different ways, including based on previous periods and other information (including user interactions with electronic device 800) provided to the tracking application.

Affordance 810 includes a graphical representation of a month, including day representations for each day (e.g., a number corresponding to the day of the month for each day) in a format corresponding to a calendar. An example of a day representation in FIG. 8B is day representation 810*g* (e.g., "17," indicating that representation 810*g* corresponds to the 18th day of June). As depicted in FIG. 8B, the graphical representation corresponds to the month of June. In some examples, a current day is visually distinguished in the graphical representation. For example, in FIG. 8B, the current day is June 17th, which corresponds to day representation 810*g*, which is bolded and outlined. It should be recognized that day representation 810*g* can be visually distinguished in other ways, such as by color.

The graphical representation in FIG. 8B includes predicted period indications corresponding to day representations. In some examples, a predicted period indication indicates that a period is predicted to occur on the day corresponding to the day representation. As depicted in FIG. 8B, a predicted period indication includes a circle around a respective day representation, with the inside of the circle visually distinct from outside of the circle (e.g., the circle is light red inside). In some examples, different shades of a color (e.g., red) indicate a confidence level that a user will have their period on a particular day (e.g., the more confident that a period will occur, the closer the color to the color corresponding to a logged period (e.g., red)). An example of a day representation with a predicted period indication in FIG. 8B is 810*a* (e.g., a circle around the "18" with the inside of the circle visually distinguished from outside of the circle). It should be noted that predicted period indications (as depicted in FIG. 8B) are visually distinguished from period indications (as depicted in FIG. 6N). In some examples, period indications are a darker red while predicted period indications are a lighter red.

FIG. 8B depicts electronic device 800 receiving user input 811 corresponding to affordance 810. In some examples, user input 811 is received via touch-sensitive display device 802 and corresponds to selection of affordance 810 (e.g., a tap gesture on affordance 810). In other examples, other forms of an input can be used, such as a click via a mouse. In some examples, user input 811 causes a different user interface to be displayed via touch-sensitive display device 802, such as display of a user interface of the tracking application, as depicted in FIG. 8D.

Figure 8C:
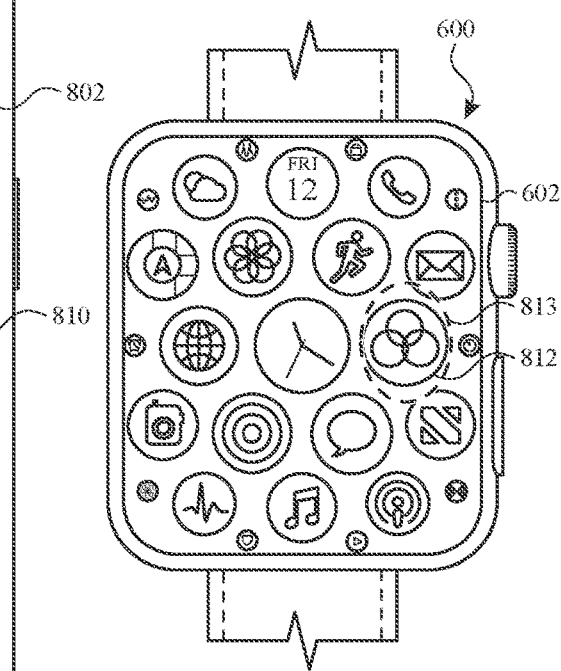

FIG. 8C depicts electronic device 600 displaying a springboard user interface (e.g., home user interface) via touch-sensitive display device 602 at a third time after the second time. The springboard user interface includes multiple icons, each icon corresponding to a different application. For example, the springboard user interface includes tracking icon 812 to initiate a tracking application and/or display a user interface of the tracking application.

FIG. 8C depicts electronic device 600 receiving user input 813 corresponding to tracking icon 812. In some examples, user input 813 is received via touch-sensitive display device 802 and corresponds to selection of tracking icon 812 (e.g., a tap gesture on tracking icon 812). In other examples, other forms of an input can be used, such as a click via a mouse. In some examples, user input 813 causes a different user interface to be displayed via touch-sensitive display device 802, such as display of a user interface of the tracking application, as depicted in FIG. 8E.

Figures 8D, 8E:
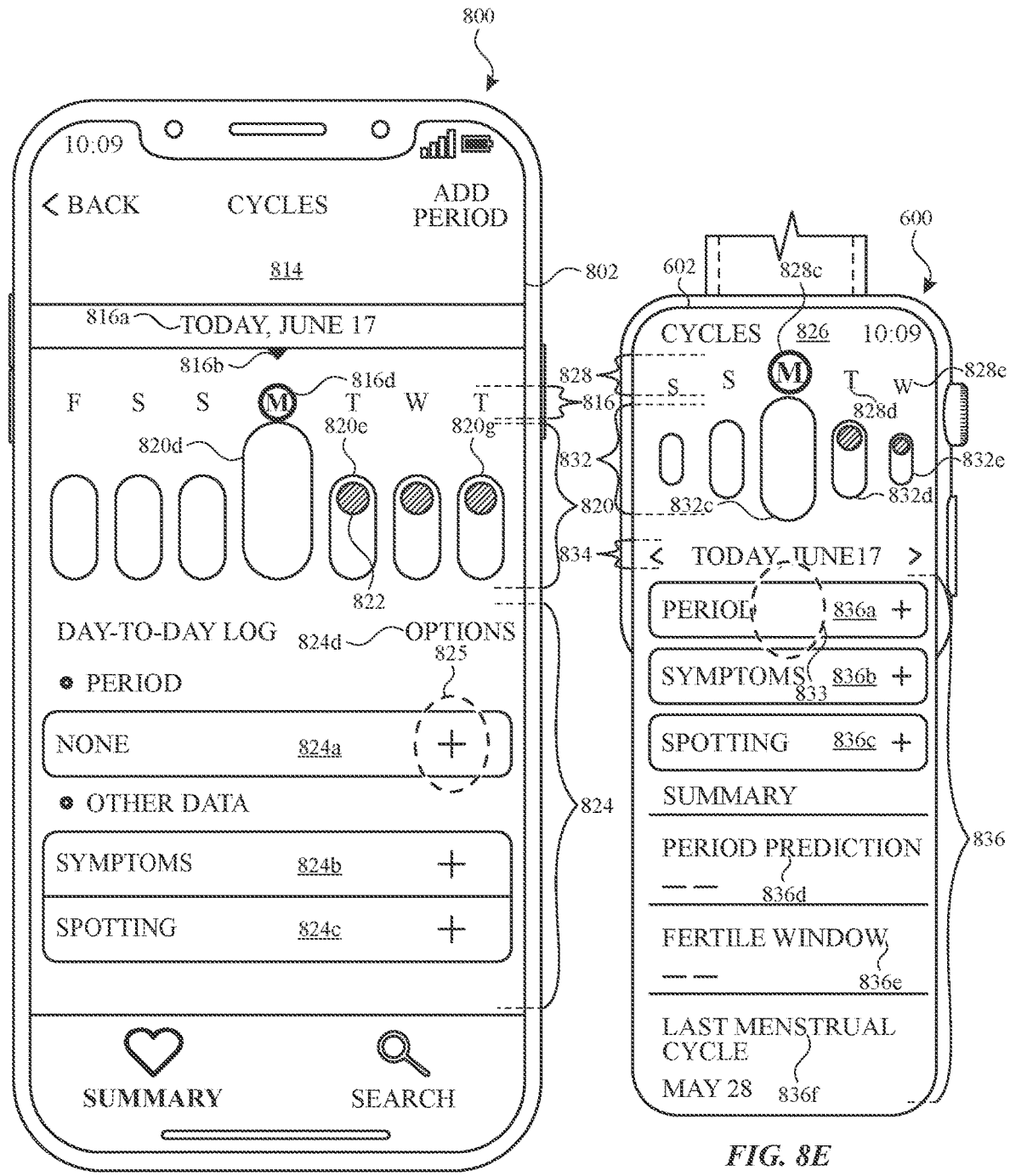

FIG. 8D depicts electronic device 800 displaying tracking home user interface 814 via touch-sensitive display device 802 at a fourth time after the third time. Tracking home user interface 814 has the same functionality as tracking home user interface 654, as described in FIG. 6N.

As depicted in FIG. 8D, tracking home user interface 814 corresponds to the situation depicted in FIG. 8C. In particular, the current day is June 17th, as indicated (1) in identification information 816a (e.g., "TODAY, JUNE 17th") and (2) by the circle around day indication 816d. The day representation for June 17th (e.g., 820d) does not include any indication of a period occurring, as also shown in FIG. 8C. In addition, the day representations depicted in FIG. 8D (e.g., June 18th-June 20th) following the current day each include a predicted period indication with a pattern matching what is depicted in FIG. 8C.

In FIG. 8D, bottom portion 824 includes: (1) period representation 824a, indicating that no period has been logged for the current day; (2) symptoms representation 824b, indicating that no symptoms have been logged for the current day; and (3) and spotting representation 824c, indicating that no spotting has been logged for the current day. Each of period representation 824a, symptoms representation 824b, and spotting representation 824c are configured to be selected to cause a user interface to select information for the respective representation to be displayed.

Figure 8F:
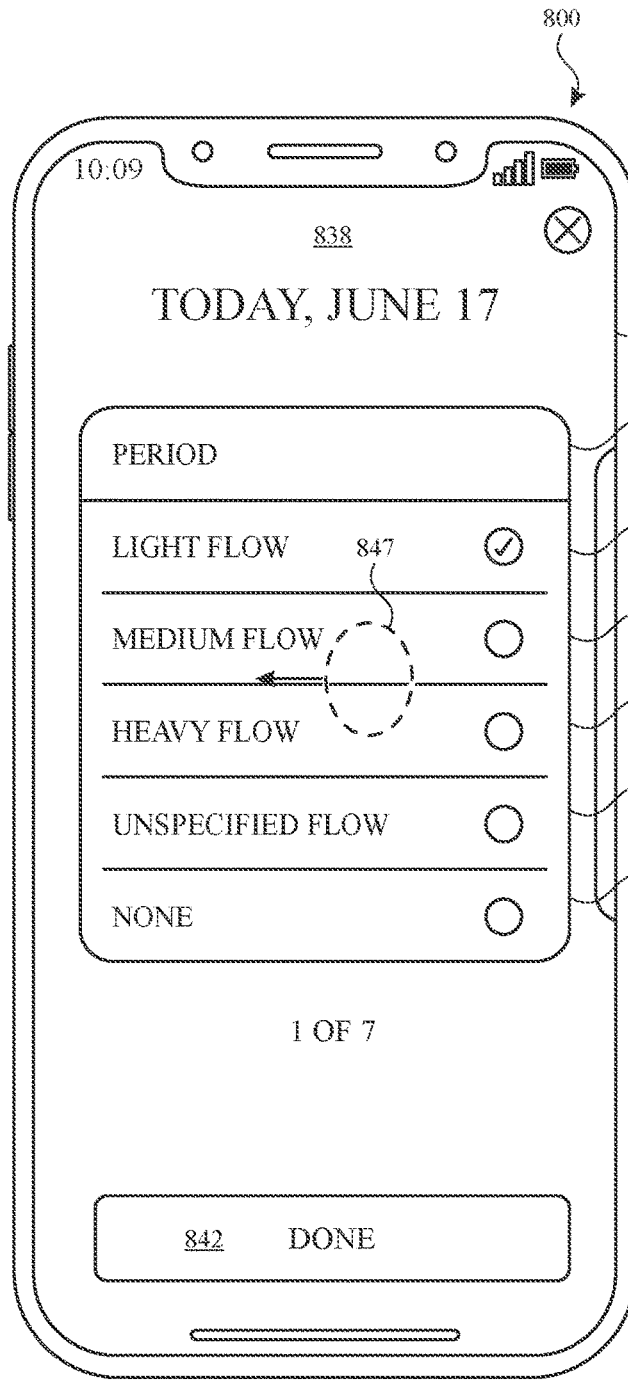

FIG. 8D depicts electronic device 800 receiving user input 825 corresponding to period representation 824a. In some examples, user input 825 is received via touch-sensitive display device 802 and corresponds to a selection of period representation 824a (e.g., a tap gesture on period representation 824a). In other examples, other forms of an input can be used, such as a click via a mouse. In some examples, user input 825 causes a different user interface to be displayed via touch-sensitive display device 802, such as display of a different user interface of the tracking application, as depicted in FIG. 8F.

FIG. 8E depicts electronic device 600 displaying tracking home user interface 826 via touch-sensitive display device 602 at a fifth time after the fourth time. Tracking home user interface 826 has similar functionality as tracking home user interface 814, as described in FIG. 8D. Some differences in tracking home user interface 826 and tracking home user interface 814 are discussed below.

As depicted in FIG. 8E, identification information 834 (e.g., "TODAY, JUNE 17") is below day representations instead of above day representations (e.g., FIG. 8D depicts identification information 816a above day representations 820). As depicted in FIG. 8E, tracking home user interface 826 does not include an arrow pointing to day representations 820 while tracking home user interface 814 includes arrow 816b. As depicted in FIG. 8E, there are 5 day representations 832 in tracking home user interface 826 while there are 8 day representations 820 tracking home user interface 814. As depicted in FIG. 8E, day representations 832 become progressively smaller as they get farther from a selected day (e.g., day representation 832c is bigger than day representation 832d, which is bigger than day representation 832e). Similarly, day indications in tracking home user interface 826 as depicted in FIG. 8E become progressively smaller as they get farther from a selected day (e.g., day indication 828c is bigger than day indication 828d, which is bigger than day indication 828e). As depicted in FIG. 8E, tracking home user interface 826 includes a summary section, including period prediction 836d, fertile window 836e, and last menstrual cycle 836f. While such a section is not depicted in FIG. 8D, it should be recognized that tracking home user interface 814 can include a summary section similar to the summary section in tracking home user interface 826.

As depicted in FIG. 8E, tracking home user interface 814 corresponds to the situation depicted in FIG. 8C. In particular, the current day is June 17th, as indicated (1) in identification information 834 (e.g., "TODAY, JUNE 17") and (2) by the circle around day indication 832c. The day representation for June 17th (e.g., 832c) does not include any indication of a period occurring, as also shown in FIG. 8C. In addition, the day representations depicted in FIG. 8E (e.g., June 18th-June 20th) following the current day each include a predicted period indication with a pattern matching what is depicted in FIG. 8C.

FIG. 8E depicts electronic device 600 receiving user input 833 corresponding to period representation 836a. In some examples, user input 833 is received via touch-sensitive display device 602 and corresponds to a selection of period representation 836a (e.g., a tap gesture on period representation 836a). In other examples, other forms of an input can be used, such as a click via a mouse. In some examples, user input 833 causes a different user interface to be displayed via touch-sensitive display device 602, such as display of a different user interface of the tracking application, as depicted in FIG. 8G.

Figure 8G:
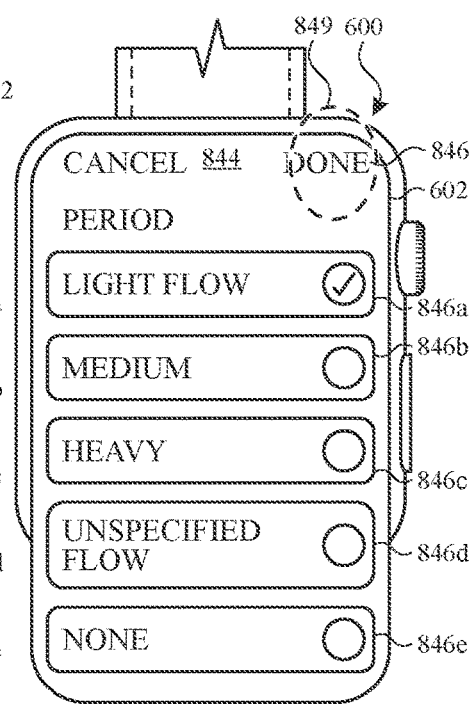

FIGS. 8F and 8G depict user interfaces (e.g., period user interface 838 in FIG. 8F and period user interface 844 in FIG. 8G) allowing a user to select whether the user had a period on the selected day and, if the user did have a period, an amount of flow for the period. In both FIGS. 8F and 8G, the user interfaces depict that a user has selected that they have had a period and that it had a light flow. Navigating from the user interfaces depicted in FIGS. 8F and 8G is different, as is described below.

Figures 8H, 8I:
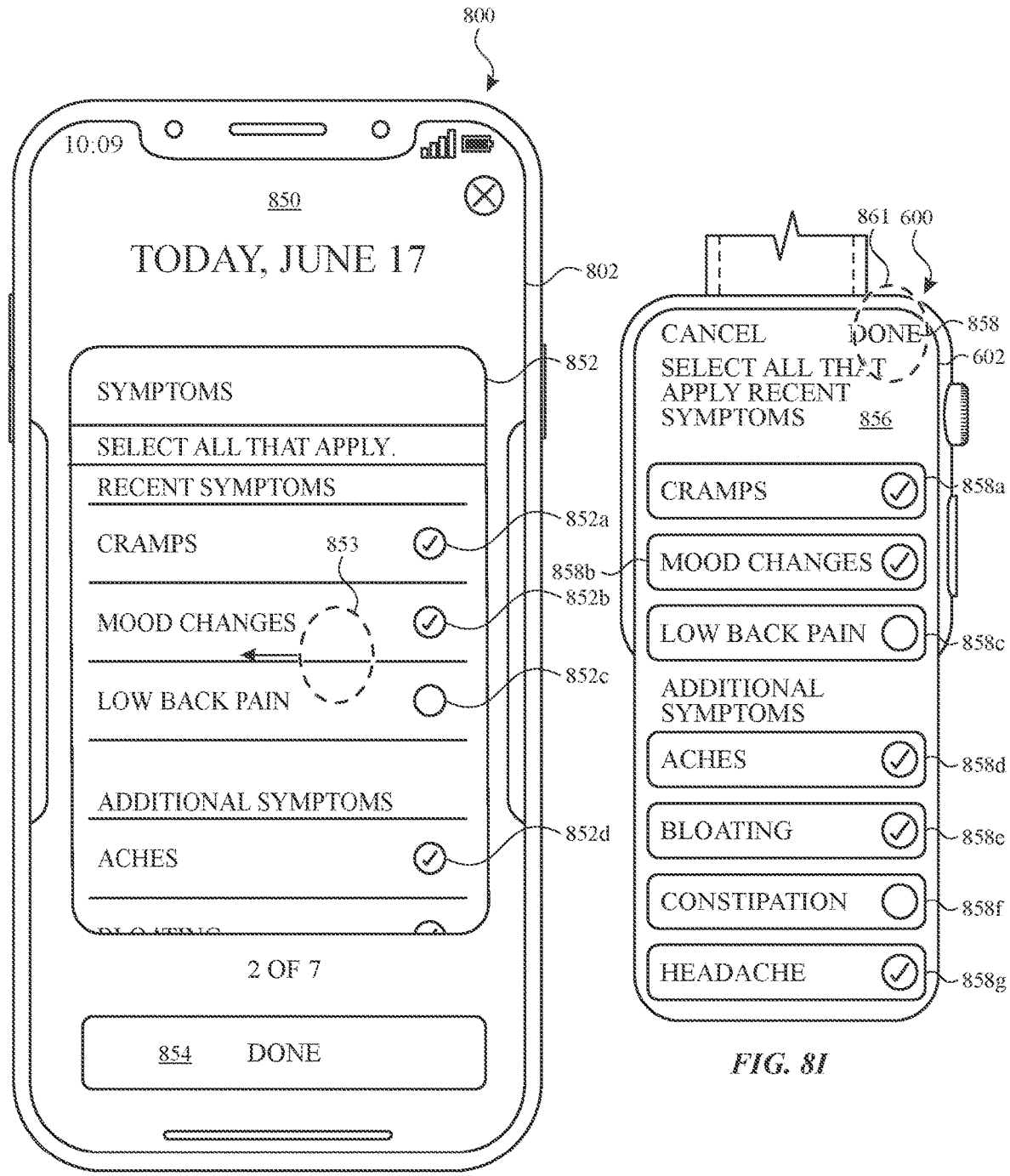

FIG. 8F depicts electronic device 800 receiving user input 847 via touch-sensitive display device 802 at a sixth time after the fifth time. As depicted in FIG. 8F, user input 847 corresponds to a swipe gesture (e.g., a touch gesture beginning at a first location and traveling to a second location along an axis before liftoff). In some examples, a left swipe gesture (as depicted in FIG. 8F) causes a next information user interface in a list of information user interfaces to be displayed, as depicted in FIG. 8H. If there is not a next information user interface, a first information user interface is displayed (e.g., period user interface 838). In some examples, a right swipe gesture causes a previous information user interface in a list of information user interfaces to be displayed (not depicted). If there is not a previous information user interface, a final information user interface is displayed (as depicted in 8J). In some examples, period user interface 838 is configured to allow a swipe in a horizontal direction. Once selecting all of the desired information, a user can select done affordance 842 to cause electronic device 800 to display a home user interface of the tracking application, as depicted in FIG. 8L.

In the alternative to the functionality of period user interface 838, period user interface 844 requires a user to hit done affordance 846 to proceed serially to the next user interface (e.g., the user interface depicted in FIG. 8I) until the user has provided an input on each of the remaining information user interfaces. FIG. 8G depicts electronic device 600 receiving user input 849 corresponding to done affordance 846 via touch-sensitive display device 602 at the sixth time.

FIGS. 8H and 8I depict user interfaces (e.g., symptoms user interface 850 in FIG. 8H and symptoms user interface 856 in FIG. 8I) allowing a user to select whether the user had one of a number of symptoms on the selected day. In both FIGS. 8H and 8I, the user interfaces depict that a user has selected that they have had cramps, mood changes, and aches. In symptoms user interface 856 in FIG. 8G, it is further illustrated that the user has selected headache. Navigating from the user interfaces depicted in FIGS. 8H and 8I is similar to as described above for the user interfaces depicted in FIGS. 8F and 8G respectively.

FIG. 8H depicts electronic device 800 receiving user input 853 via touch-sensitive display device 802 at a seventh time after the sixth time. As depicted in FIG. 8H, user input 853 corresponds to a swipe gesture (e.g., a touch gesture beginning at a first location and traveling to a second location along an axis before liftoff). In some examples, a left swipe gesture (as depicted in FIG. 8H) causes a next information user interface in a list of information user interfaces to be displayed, as depicted in FIG. 8J.

Similar to period user interface 844, symptoms user interface 856 requires a user to hit done affordance 858 to proceed serially to the next user interface (e.g., the user interface depicted in FIG. 8K) until the user has provided an input on each of the remaining information user interfaces. FIG. 8I depicts electronic device 600 receiving user input 861 corresponding to done affordance 858 via touch-sensitive display device 602 at the seventh time.

Figures 8J, 8K:
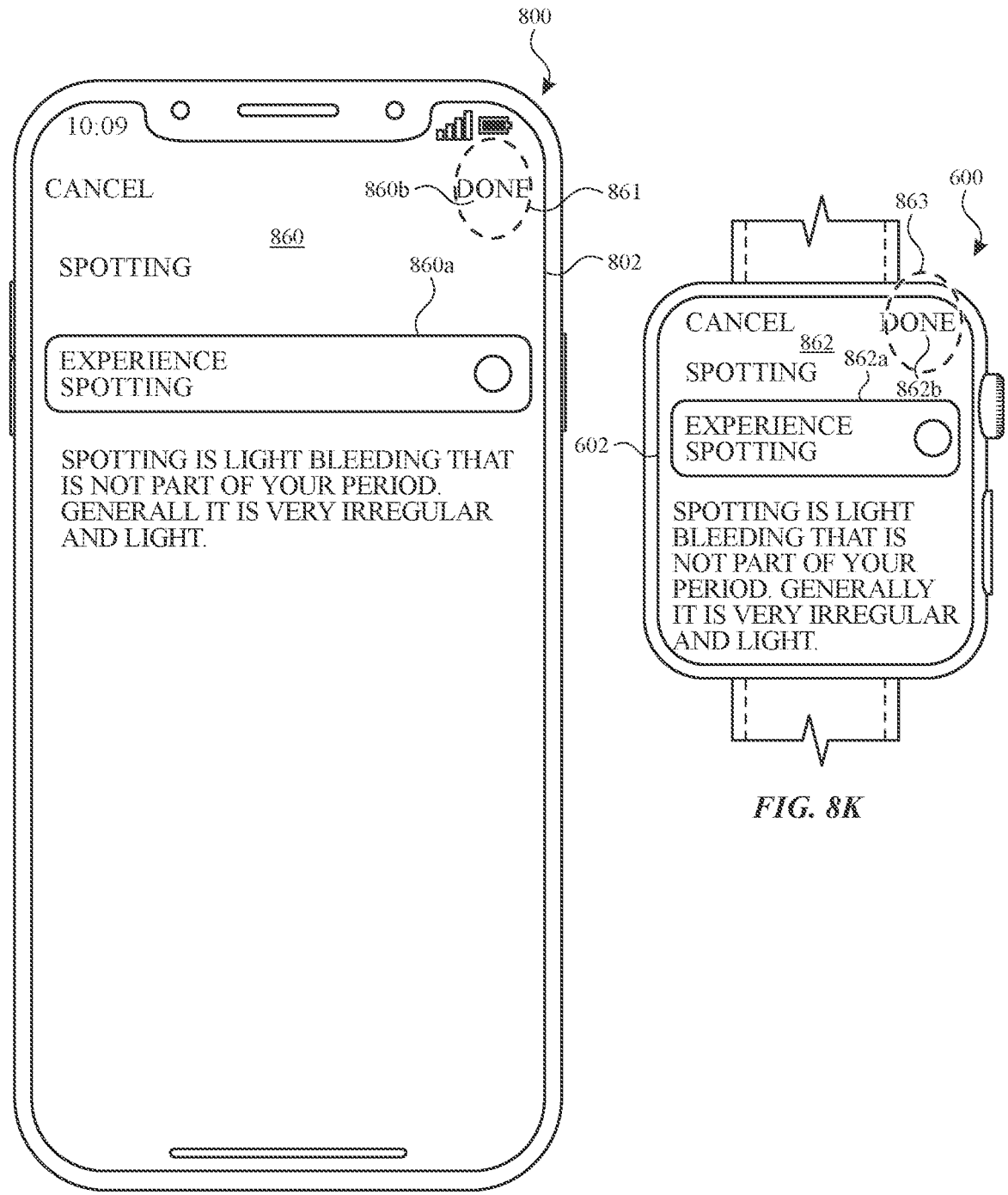

FIGS. 8J and 8K depict user interfaces (e.g., spotting user interface 860 in FIG. 8J and spotting user interface 862 in FIG. 8K) allowing a user to select whether the user experienced spotting on the selected day. In both FIGS. 8H and 8I, the user interfaces depict that a user has selected that they have not experienced spotting. Navigating from the user interfaces depicted in FIGS. 8J and 8K is similar to as described above for the user interfaces depicted in FIGS. 8H and 8I respectively.

FIG. 8J depicts electronic device 800 receiving user input 861 corresponding to done affordance 860b via touch-sensitive display device 802 at an eighth time after the seventh time. As depicted in FIG. 8J, user input 861 corresponds to selection of done affordance 860b (e.g., a tap gesture), causing a tracking home user interface to be displayed (as depicted in FIG. 8L). Similarly, FIG. 8K depicts electronic device 600 receiving user input 863 corresponding to done affordance 862b via touch-sensitive display device 602 at the eighth time. As depicted in FIG. 8K, user input 863 corresponds to selection of done affordance 862b (e.g., a tap gesture), causing a tracking home user interface to be displayed (as depicted in FIG. 8M).

FIGS. 8L and 8M depict tracking home user interfaces (e.g., tracking home user interface 814 in FIG. 8L and tracking home user interface 826 in FIG. 8M) at a ninth time after the eighth time. In both FIGS. 8L and 8M, the user interfaces depict the selected information in the respective bottom portions from the previous user interfaces (e.g., light flow, cramps, and no spotting). For example, as depicted in FIG. 8L, tracking home user interface 814 includes the text "LIGHT FLOW" in period representation 824a and the "+" sign in period representation 824a has been removed. In some examples, the "+" sign is not removed (not illustrated). Similarly, as depicted in FIG. 8M, tracking home user interface 826 includes the text "LIGHT FLOW" in period representation 836a. For another example, as depicted in FIG. 8L, tracking home user interface 814 includes the text "CRAMPS+4 MORE" in symptoms representation 824b. Similarly, as depicted in FIG. 8M, tracking home user interface 826 includes the text "CRAMPS, MOOD CHANGES+3 MORE" in symptoms representation 836b.

Tracking home user interface 814 in FIG. 8L and tracking home user interface 826 in FIG. 8M also depict that their respective day representations have been updated based on the information added. For example, day representation 820d in tracking home user interface 814 indicates that (1) a period occurred on the day corresponding to day representation 820d (e.g., by the large circle at the top of day representation 820d that is visually distinguished (e.g., red)) (e.g., the light flow) and (2) other data has been logged for the day (e.g., by the small circle at the bottom of day representation 820d) (e.g., cramps, mood changes, low back pain, aches, bloating, and headache). Similarly, day representation 832c in tracking home user interface 826 indicates that (1) a period occurred on the day corresponding to day representation 832c (e.g., by the large circle at the top of day representation 832c that is visually distinguished (e.g., red)) (e.g., the light flow) and (2) other data has been logged for the day (e.g., by the small circle at the bottom of day representation 832c) (e.g., cramps, mood changes, low back pain, aches, bloating, and headache).

In FIG. 8L, day representation 820g in tracking home user interface 814 no longer includes a predicted period indication (see FIG. 8D where tracking home user interface 814 includes a predicted period indication), indicating that the prediction was updated in response to adding the information.

Referring to FIG. 8M, the summary section (e.g., period prediction 836d, fertile window 836e, and last menstrual cycle 836f) has been updated as compared to the summary section depicted in FIG. 8D. In particular, period prediction 836d did not have a value in FIG. 8E and now has a value of July 19th in FIG. 8M and fertile window 836e did not have a value in FIG. 8D and now has a value of June 25th in FIG. 8M. In some examples, the updates are due to logging a period.

FIG. 8M depicts electronic device 600 receiving user input 865 corresponding to the top portion of tracking home user interface 826 via touch-sensitive display device 602. As depicted in FIG. 8M, user input 865 corresponds to a left swipe gesture (e.g., a touch gesture beginning at a first location within the top portion of tracking home user interface 826 and traveling to a second location within the top portion of tracking home user interface 826 along an axis (e.g., a horizontal axis) before liftoff). In some examples, user input 865 causes tracking home user interface 826 to be updated to a different day, as depicted in FIG. 8N. In particular, the left swipe gesture corresponding to the top portion causes the selected day to change to the next adjacent day (e.g., Tuesday, June 18th).

FIG. 8N depicts electronic device 600 displaying tracking home user interface 826 via touch-sensitive display device 802 at a tenth time after the ninth time. Tracking home user interface 826 has been updated relative to FIG. 8M to show bottom portion 836 for day representation 832d. In some examples, because day representation 832d is a day in the future (e.g., tomorrow), period representation 836a, symptoms representation 836b, and spotting representation 836c are all visually distinguished to indicate that such representations are not able to be used. In such examples, the tracking application does not allow a user to add data for a day in the future.

FIG. 8N depicts electronic device 600 receiving user input 867 corresponding to the top portion of tracking home user interface 826 via touch-sensitive display device 602. As depicted in FIG. 8N, user input 867 corresponds to a right swipe gesture (e.g., a touch gesture beginning at a first location within the top portion of tracking home user interface 826 and traveling to a second location within the top portion of tracking home user interface 826 along an axis (e.g., a horizontal axis) before liftoff). In some examples, user input 867 causes tracking home user interface 826 to be updated to a different day, as depicted in FIG. 8O. In particular, the right swipe gesture corresponding to the top portion causes the selected day to change to the previous adjacent day (e.g., Monday, June 17th).

FIG. 8O depicts electronic device 600 displaying tracking home user interface 826 via touch-sensitive display device 802 at a eleventh time after the tenth time. Tracking home user interface 826 has been updated relative to FIG. 8N to show bottom portion 836 for day representation 832c, as depicted in FIG. 8M.

Figure 8P:
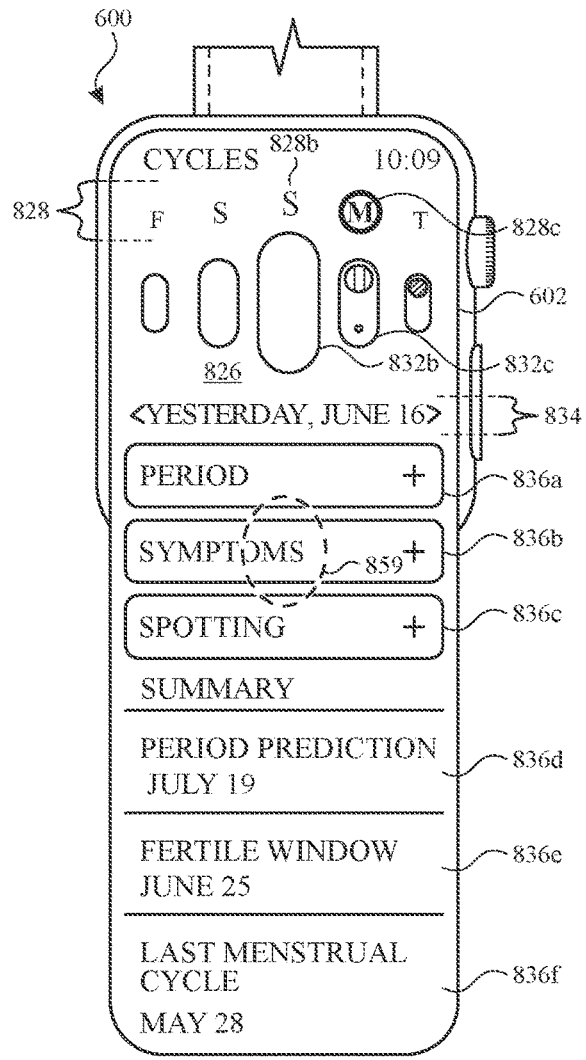

FIG. 8O depicts electronic device 600 receiving user input 869 corresponding to the top portion of tracking home user interface 826 via touch-sensitive display device 602. As depicted in FIG. 8O, user input 869 corresponds to a right swipe gesture (e.g., a touch gesture beginning at a first location within the top portion of tracking home user interface 826 and traveling to a second location within the top portion of tracking home user interface 826 along an axis (e.g., a horizontal axis) before liftoff). In some examples, user input 869 causes tracking home user interface 826 to be updated to a different day, as depicted in FIG. 8P. In particular, the right swipe gesture corresponding to the top portion causes the selected day to change to the previous adjacent day (e.g., Sunday, June 16th).

FIG. 8P depicts electronic device 600 displaying tracking home user interface 826 via touch-sensitive display device 802 at a twelfth time after the eleventh time. Tracking home user interface 826 has been updated relative to FIG. 8O to show bottom portion 836 for day representation 832b, which does not include any indications as depicted in FIG. 8P.

FIG. 8P depicts electronic device 600 receiving user input 859 corresponding to period representation 836a. In some examples, user input 859 is received via touch-sensitive display device 602 and corresponds to a selection of symptoms representation 836b (e.g., a tap gesture on symptoms representation 836b). In other examples, other forms of an input can be used, such as a click via a mouse. In some examples, user input 859 causes a different user interface to be displayed via touch-sensitive display device 602, such as display of a different user interface of the tracking application, as depicted in FIG. 8Q.

Figure 8Q:
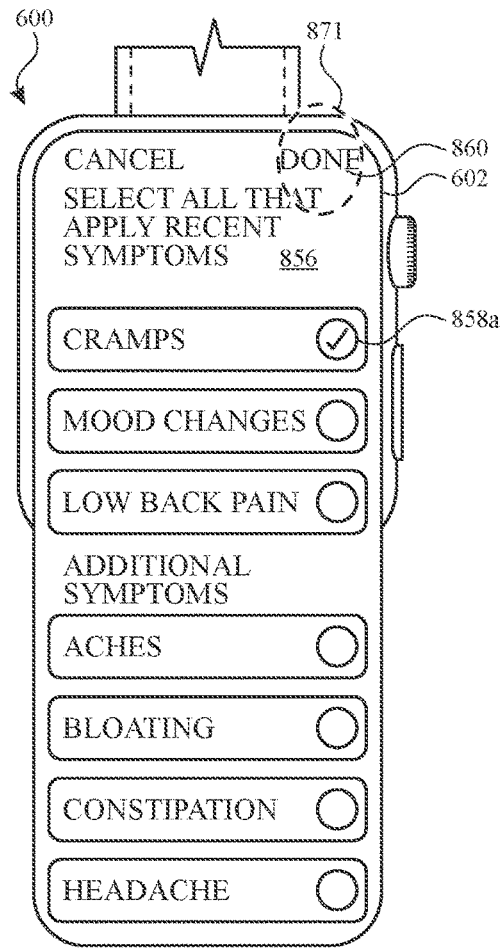

FIG. 8Q depicts electronic device 600 displaying symptoms user interface 856 via touch-sensitive display device 802 at a thirteenth time after the twelfth time. Symptoms user interface 856 depicts that a user has selected that they have had cramps. FIG. 8Q depicts electronic device 600 receiving user input 871 corresponding to done affordance 860 via touch-sensitive display device 602. In response to user input 871, spotting user interface 862 is displayed.

Figure 8R:
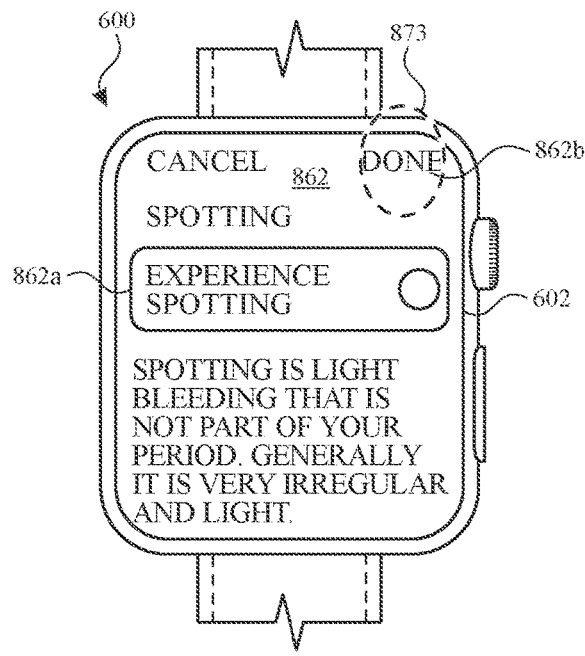

FIG. 8R depicts electronic device 600 displaying spotting user interface 862 via touch-sensitive display device 802 at a fourteenth time after the thirteenth time. Spotting user interface 862 depicts that a user has selected that they have not experience spotting on June 16th. FIG. 8R depicts electronic device 600 receiving user input 873 corresponding to done affordance 862b via touch-sensitive display device 602. In response to user input 873, a tracking home user interface to be displayed (as depicted in FIG. 8S).

FIG. 8S depicts electronic device 600 displaying tracking home user interface 826 via touch-sensitive display device 802 at a fifteenth time after the fourteenth time. In FIG. 8M, tracking home user interface 826 includes the text "CRAMPS" in symptoms representation 836b, corresponding to selection made in FIG. 8Q. This update causes day representation 832b to include a dot at the bottom of day representation 832b, indicating that symptoms have been added to the day corresponding to day representation 832b.

FIGS. 9A-9B are a flow diagram illustrating a method for cycle tracking using an electronic device in accordance with some embodiments. Method 900 is performed at a device (e.g., 100, 300, 500) (e.g., a smartphone, a smartwatch) with a display device (e.g., a touch-sensitive display). Some operations in method 900 are, optionally, combined, the orders of some operations are, optionally, changed, and some operations are, optionally, omitted.

As described below, method 900 provides an intuitive way for cycle tracking. The method reduces the cognitive burden on a user for cycle tracking, thereby creating a more efficient human-machine interface. For battery-operated computing devices, enabling a user to track cycles faster and more efficiently conserves power and increases the time between battery charges.

The electronic device (e.g., 800) displays (902) a first user interface (e.g., 814, 826) (e.g., in response to an input corresponding to a request to display the first user interface).

As part of displaying the first user interface, the electronic device (e.g., 800) displays a first region (e.g., 820, 832) (904) (e.g., portion, area) that includes a plurality of representations of dates, including a first representation corresponding to a first date (e.g., Jan. 1, 2019) (e.g., 820d, 832c) and a second representation corresponding to a second date (e.g., Jan. 2, 2019) (e.g., 820e, 832d).

As part of displaying the first user interface, the electronic device (e.g., 800) displays a second region (e.g., 824, 836) (906). As part of displaying the second region, in accordance with (908) a determination that the first representation occupies a first predetermined position (e.g., a location at the middle of the first portion; a location that indicates a currently selected representation) in the first region, the electronic device (e.g., 800) displays a first affordance (e.g., 824a, 824b, 824c, 836a, 836b, 836c) that, when selected, initiates a process for recording (e.g., logging, storing) information (e.g., health information (e.g., menstrual cycle information)) corresponding to the first date. As part of displaying the second region, in accordance with (910) a determination that the second representation occupies the first predetermined position (e.g., 820d is in middle position, 832c is in middle position) (e.g., a location at the middle of the first portion; a location that indicates a currently selected representation) in the first region, the electronic device (e.g., 800) displays a second affordance (e.g., 824a, 824b, 824c, 836a, 836b, 836c when a different date is selected) that, when selected, initiates a process for recording information (e.g., health information (e.g., menstrual cycle information)) corresponding to the second date. In some embodiments, in accordance with a determination that the second representation occupies the first predetermined position in the first portion, the second portion does not include the first affordance (e.g., or any affordance corresponding to the first date).

Displaying different affordances in the second region and initiating different processes based on the respective positions of the representations provides the user with feedback for which process will be initiated (e.g., which date will be used for recording of information). Providing improved visual feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, while the first representation occupies the first predetermined position (and/or while the second affordance is not displayed in the second region), the electronic device (e.g., 800) receives (912) a first input (e.g., 825, 833, 865) (e.g., a swipe gesture corresponding to the first region; a tap gesture corresponding to the second representation).

In some embodiments, in response to (914) the first input, the electronic device (e.g., 800) displays (916) the second representation at the first predetermined position. In some embodiments, in response to (914) the first input, the electronic device (e.g., 800) ceases (918) to display the first affordance in the second region. In some embodiments, in response to (914) the first input, the electronic device (e.g., 800) displays (920) the second affordance in the second region.

Changing which affordance is in the first predetermined position provides the user with the ability to change which process to initiate. Display of the affordance at the first predetermined position also provides the user with feedback for which process will be initiated (e.g., which date will be used for recording of information). Providing improved visual feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

Figure 10L:
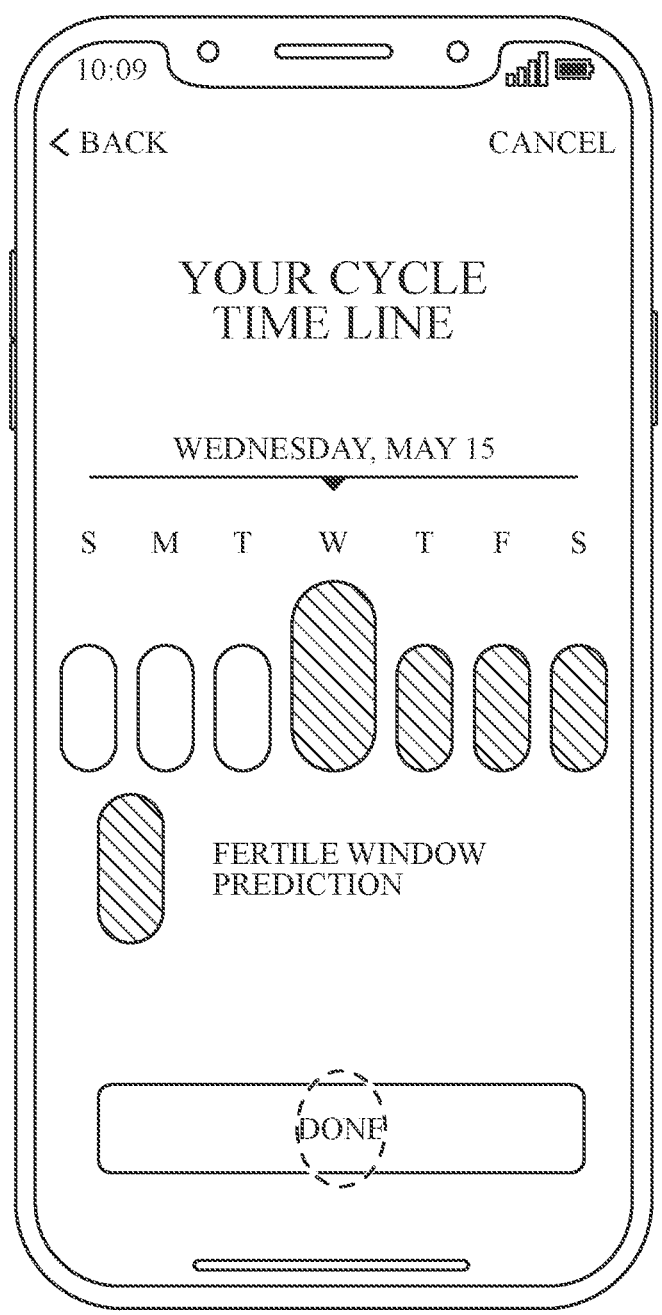

In some embodiments, in accordance with a determination that the first date is associated with recorded information (e.g., information recorded at the electronic device; information recorded at an external device and transmitted to the electronic device) of a first type (e.g., information indicating that the date corresponds to a respective recurrence of a recurring event (e.g., a menstruation period)), the first representation includes a first indication (e.g., big circle at top of 820d, 822, circle at bottom of 820d in FIG. 8L, shading shown in FIG. 10L) (e.g., an icon; a graphical object, a respective visual appearance (e.g., a background color, a foreground color)). In some embodiments, in accordance with a determination that the first date is not associated with recorded information of the first type, the first representation does not include the first indication. In some embodiments, in accordance with a determination that the first date is associated with recorded information of a second type different from the first type (e.g., information indicating that the date corresponds to a respective recurrence of a second type of recurring event (e.g., a fertile period, an ovulation period)), the first representation includes a second indication (e.g., big circle at top of 820d, 822, circle at bottom of 820d in FIG. 8L, e.g., shading shown in FIG. 10L) (e.g., an icon; a graphical object, a respective visual appearance (e.g., a background color, a foreground color)) different from the first indication. In some embodiments, at least a portion of the second indication overlaps (e.g., big circle at top of 820d, 822) at least a portion of the first indication (e.g., shading shown in FIG. 10L), when both indications are displayed. In some embodiments, in accordance with a determination that the first date is not associated with recorded information of the second type; the first representation does not include the second indication. In some embodiments, the first representation visually indicates whether the first date is associated with recorded information relating to menstruation and/or fertility.

Displaying a first indication as part of the first representation based on the state of the device (whether the date is or is not associated with recorded information) provides the user feedback about whether recorded information is available for a particular date. Providing improved visual feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, in accordance with a determination that the first date is associated with recorded information of the first type and of a third type (e.g., big circle at top of 820d, 822, circle at bottom of 820d in FIG. 8L, shading shown in FIG. 10L) (e.g., information that is affiliated with the first type of information; information that is only recordable when information of the first type is also recorded; information relating to one or more symptoms related to or correlated to menstruation), the first representation includes a third indication (e.g., an icon; a graphical object, a respective visual appearance (e.g., a background color, a foreground color)) different from the first indication and different from the second representation. In some embodiments, at least a portion of the third indication overlaps at least a portion of the first indication, when both indications are displayed. In some embodiments, no portion of the third indication overlaps any portion of the second indication, when both indications are displayed. In some embodiments, in accordance with a determination that the first date is not associated with recorded information of the third type, the first representation does not include the third indication.

In some embodiments, in accordance with a determination that the first date is associated with (e.g., falls within a predicted period for the event) a prediction of a first recurring event (e.g., a menstruation period)(and, optionally, not associated with recorded information of the first type), the first representation includes a fourth indication (e.g., 822) (e.g., an icon; a graphical object, a respective visual appearance (e.g., a background color, a foreground color)) different from the first indication.

Including display of the fourth indication as part of the first representation provides the user with feedback about whether the first date corresponds to a prediction of the first recurring event. Providing improved visual feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the first affordance, when selected, initiates a process for recording information of a first kind (e.g., 850) (e.g., a first kind of health information (e.g., menstruation information, symptom information)) corresponding to the first date. In some embodiments, while displaying the first affordance, the electronic device (e.g., 800) displays, in the second portion of the first user interface, a third affordance (e.g., 824a, 824b, 824c, 836a, 836b, 836c) that, when selected, initiates a process for recording information of a second kind, different than the first kind, corresponding to the first date.

In some embodiments, as part of the process for recording information of the first kind, the electronic device (e.g., 800) displays a second user interface (e.g., 838, 844, 850, 856, 860, 862) (e.g., an information entry interface) that includes a plurality of lists of information affordances. In some embodiments, as part of displaying the second user interface, the electronic device (e.g., 800) displays a first list including a plurality of affordances corresponding to information of the first kind. In some embodiments, selection of the first affordance displays the second user interface with the first list centered on the display device. In some embodiments, as part of displaying the second user interface, the electronic device (e.g., 800) displays a second list including a plurality of affordances corresponding to information of the second kind. In some embodiments, selection of the first affordance displays the second user interface with the second list not centered on the display device (e.g., partially on the display or not included on the display). In some embodiments, the electronic device centers the second list in response to one or more inputs (e.g., swipe gestures) received on the second user interface.

In some embodiments, the plurality of representations of dates are displayed along a first axis of the electronic device (e.g., a horizontal axis, an axis running along the width of the device). In some embodiments, the plurality of representations of dates are scrollable along the first axis. In some embodiments, the plurality of affordances of the first list are displayed along a second axis (e.g., a vertical axis; an axis running along the length of the device) of the electronic device different from the first axis. In some embodiments, the plurality of affordances of the first list are scrollable along the second axis.

In some embodiments, in accordance with the determination that the first representation occupies the first predetermined position, the first representation is displayed at a first size. In some embodiments, in accordance with the determination that the first representation does not occupy the first predetermined position, the first representation is displayed at a second size that is smaller than the first size. In some embodiments, a respective representation is displayed at a larger size when it occupies the predetermined position and is therefore selected and/or in focus (e.g., 820, 832).

Changing a size of the representations indicates to the user which representation is selected. Providing improved visual feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, in accordance with a determination that the first representation is occupying a second predetermined position (e.g., a position immediately next to the first predetermined position) that is a first distance from the first predetermined position, the first representation is displayed at a third size. In some embodiments, in accordance with a determination that the first representation is occupying a third predetermined position (e.g., a position that is at least two positions away from the first predetermined position) that is a second distance, greater than the first distance, from the first predetermined position, the first representation is displayed at a fourth size that is smaller than the third size. In some embodiments, the first representation is displayed at progressive smaller sizes, as its position is further away from the first predetermined position.

Note that details of the processes described above with respect to method 900 (e.g., FIGS. 9A-9B) are also applicable in an analogous manner to the methods described above. For example, method 700 optionally includes one or more of the characteristics of the various methods described above with reference to method 900. For example, the recurring event described with respect to method 700 can be the same event as that described with respect to method 900. For another example, devices 600 and 800 can include features of the other respective device. For brevity, these details are not repeated below.

FIGS. 10A-10AK illustrate exemplary user interfaces for cycle tracking, in accordance with some embodiments. While the following user interfaces relate to cycle tracking, it should be recognized that techniques described here can relate to different areas, such as any tracking mechanism (e.g., weight, food, exercise, projects, etc.). The user interfaces in these figures are used to supplement the user interfaces discussed above.

Figure 10M:
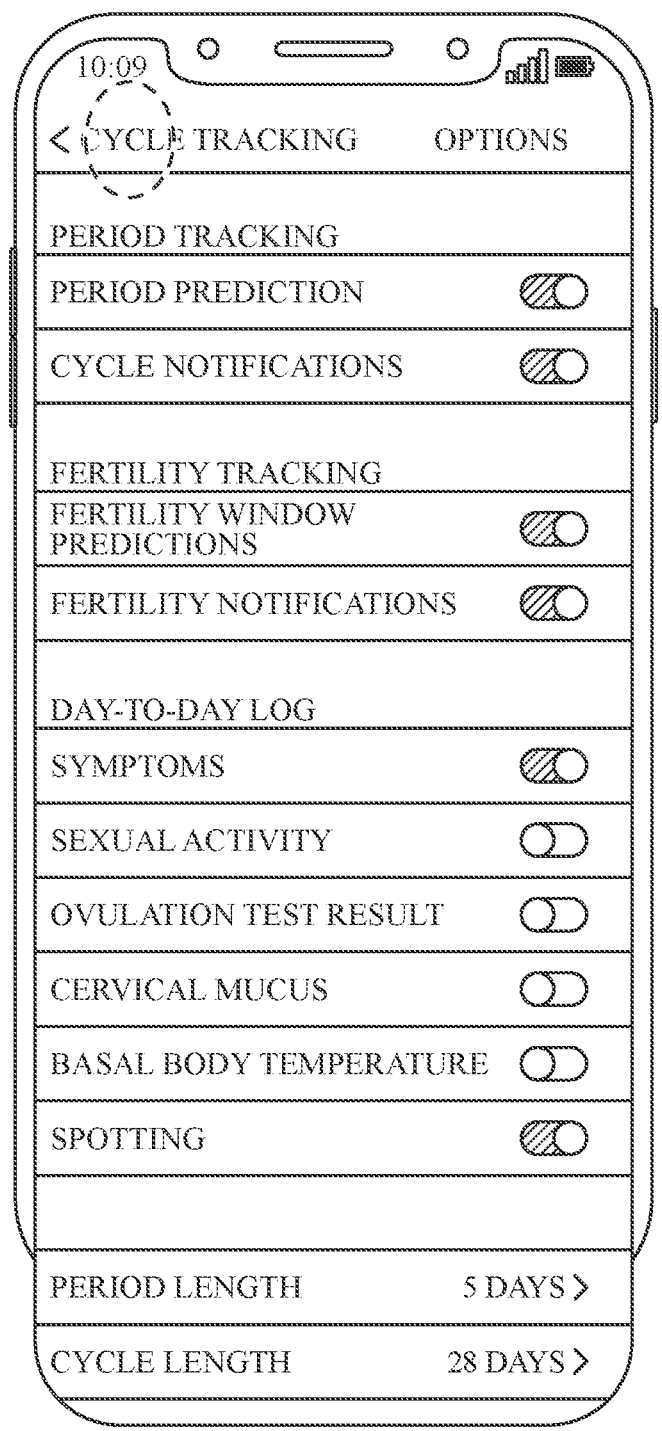
Figure 10N:
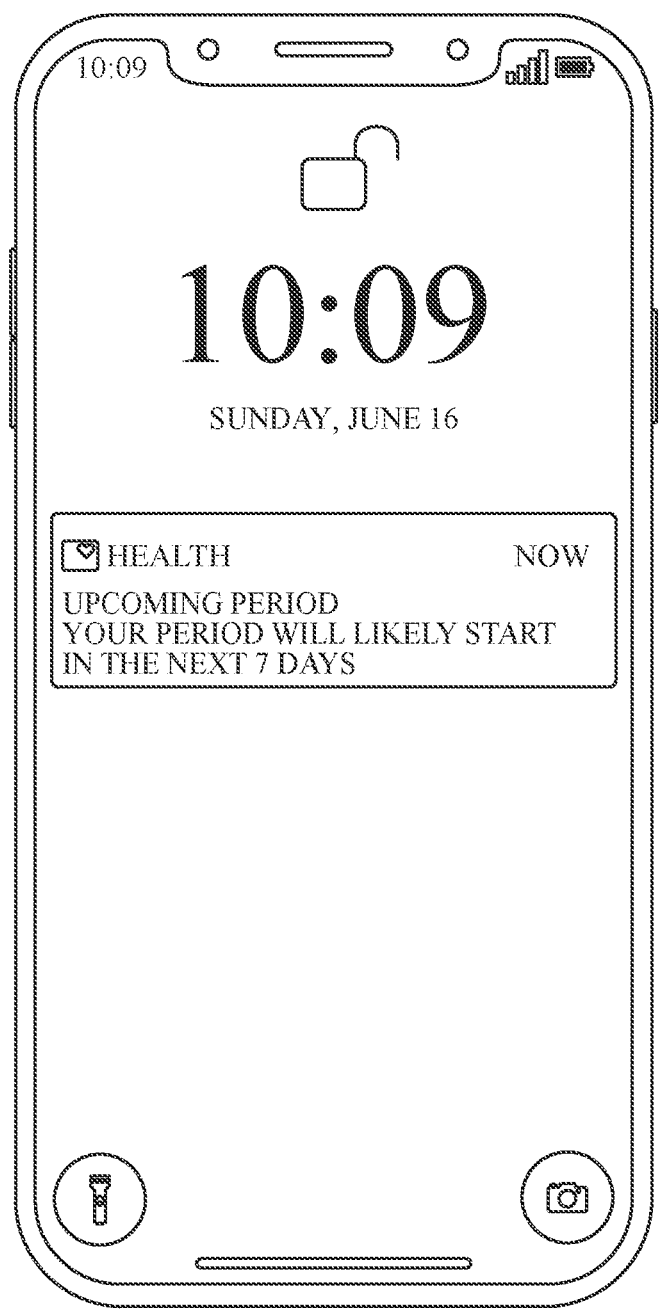
Figure 10O:
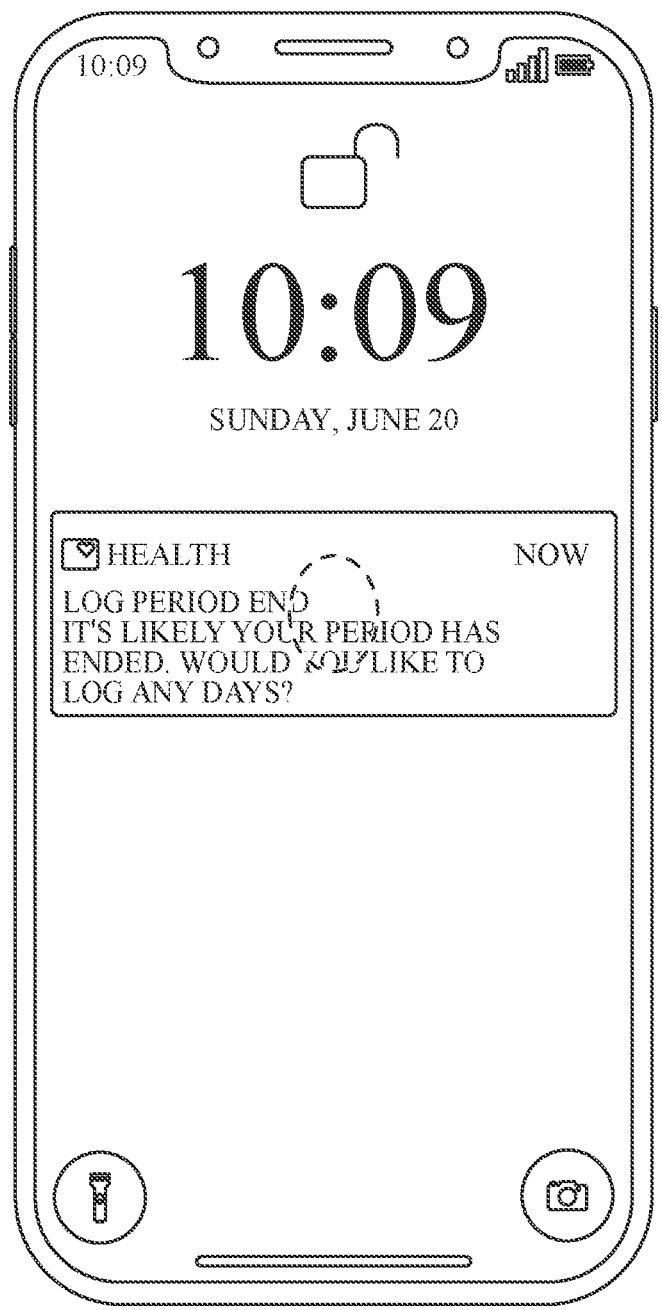
Figure 10P:
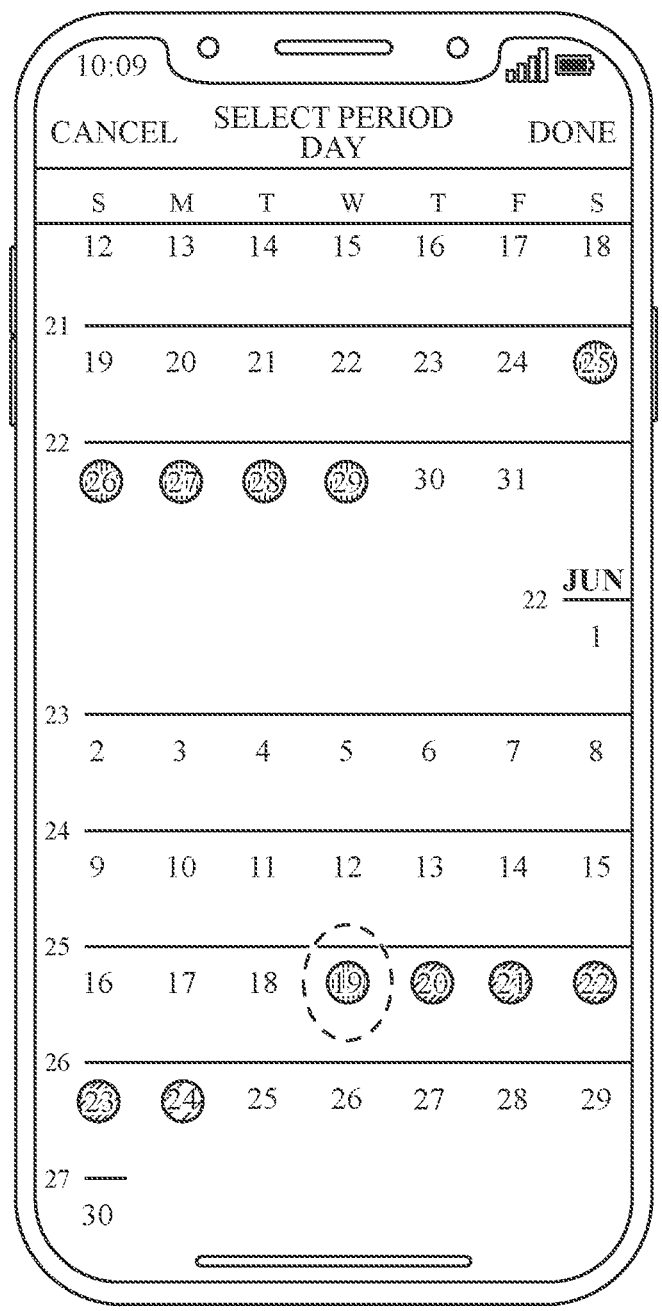
Figure 10Q:
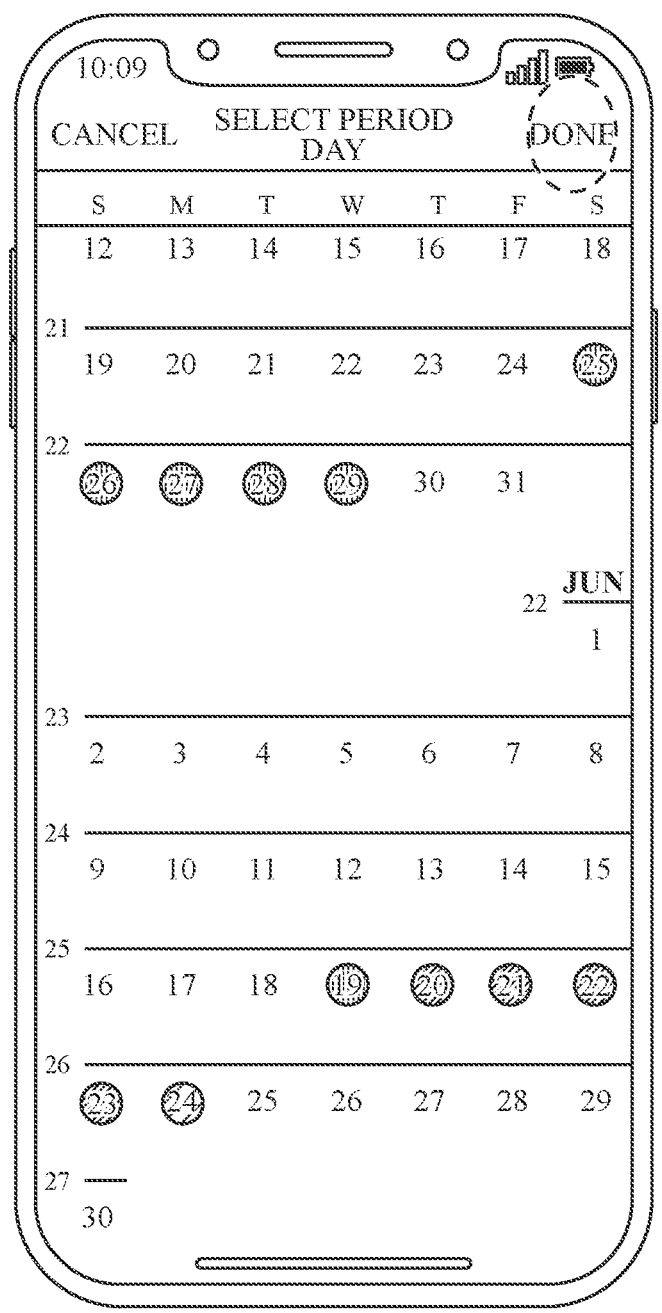
Figure 10R:
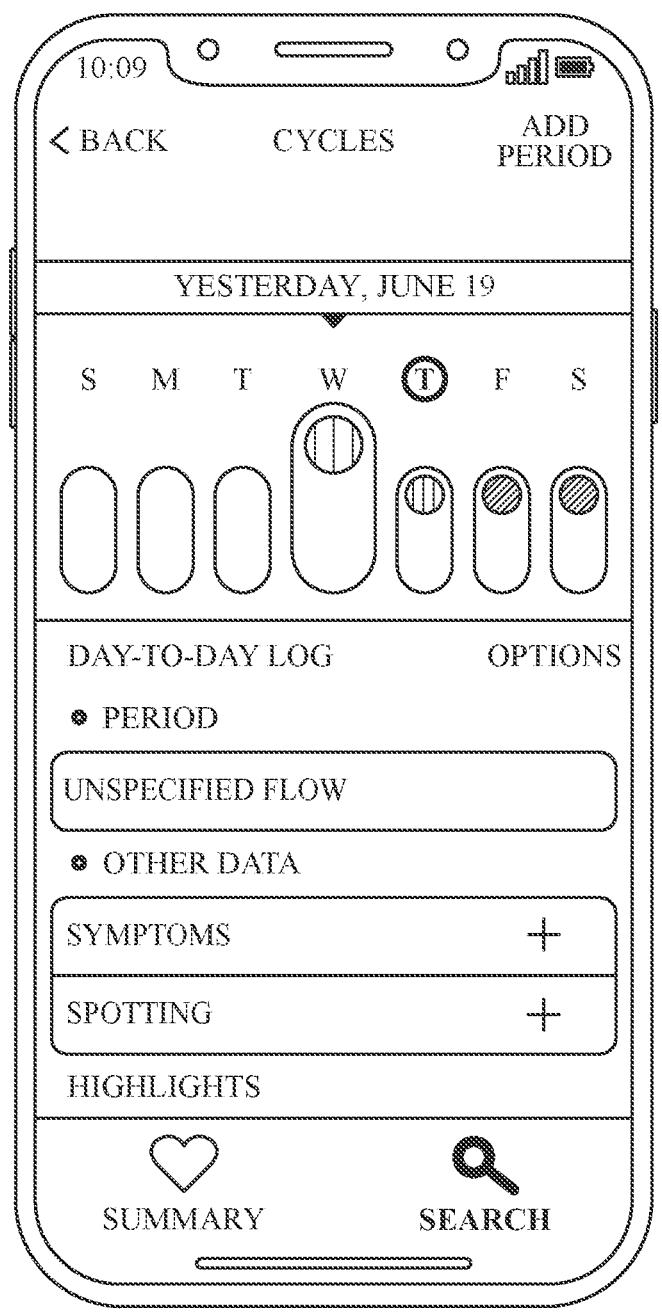
Figure 10S:
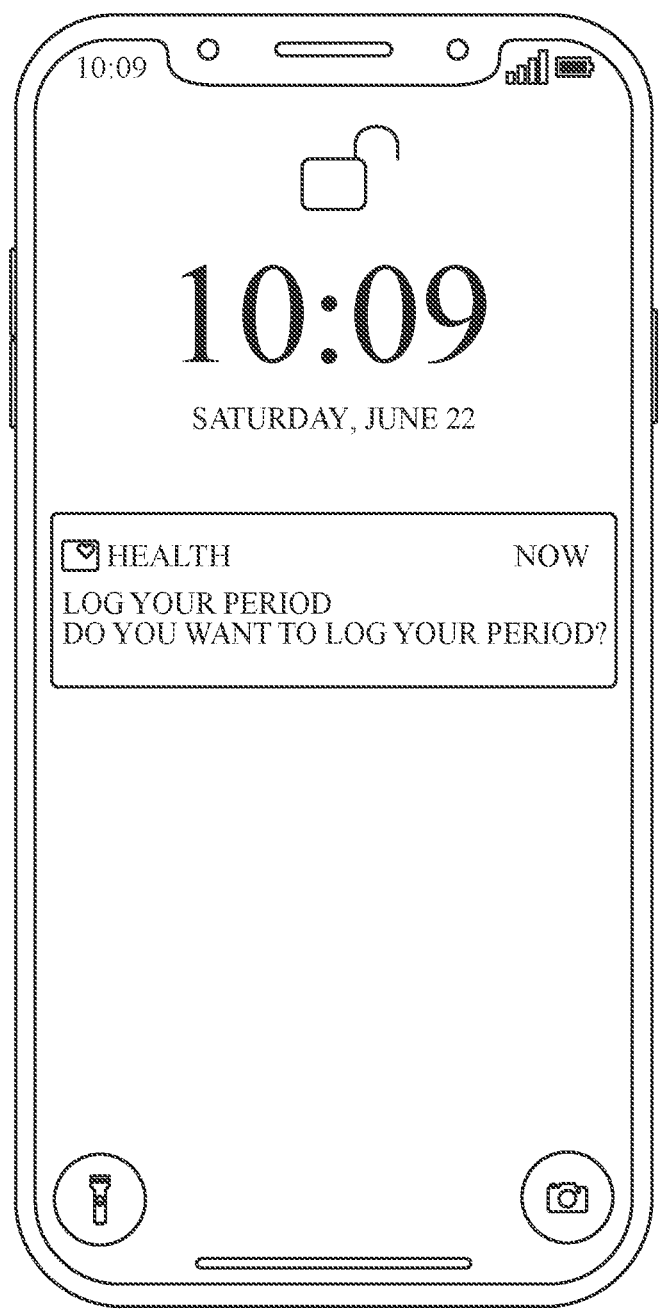
Figure 10T:
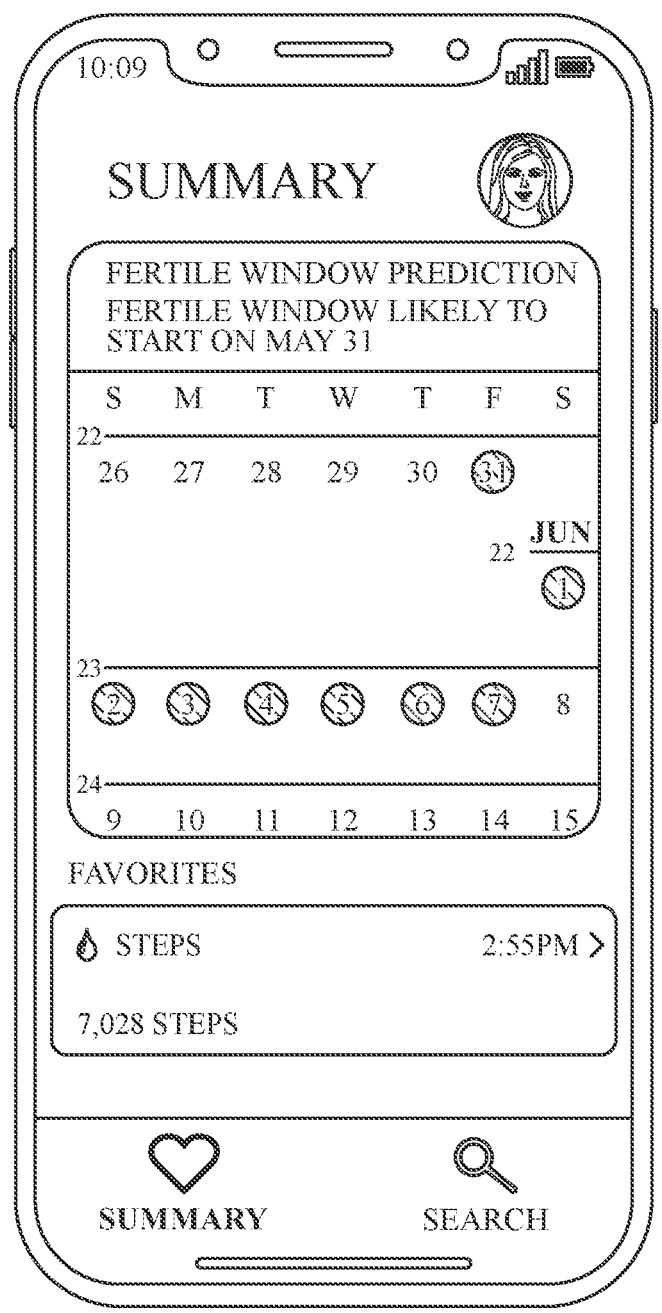
Figure 10U:
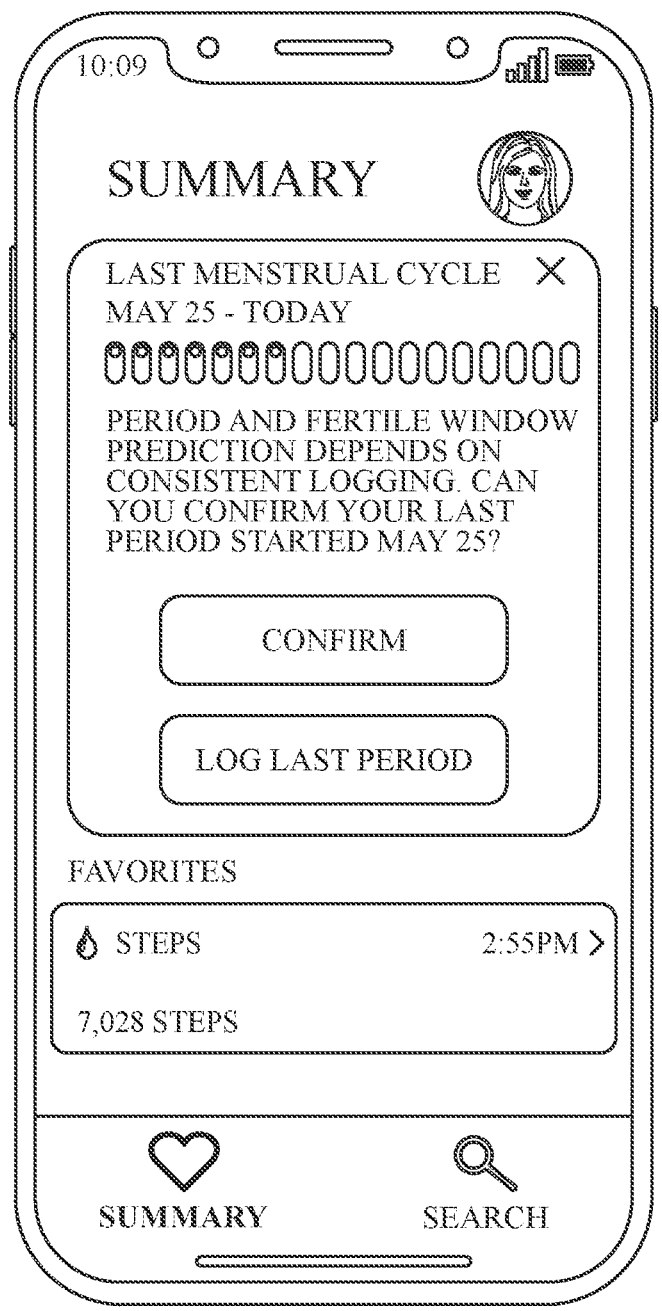
Figure 10V:
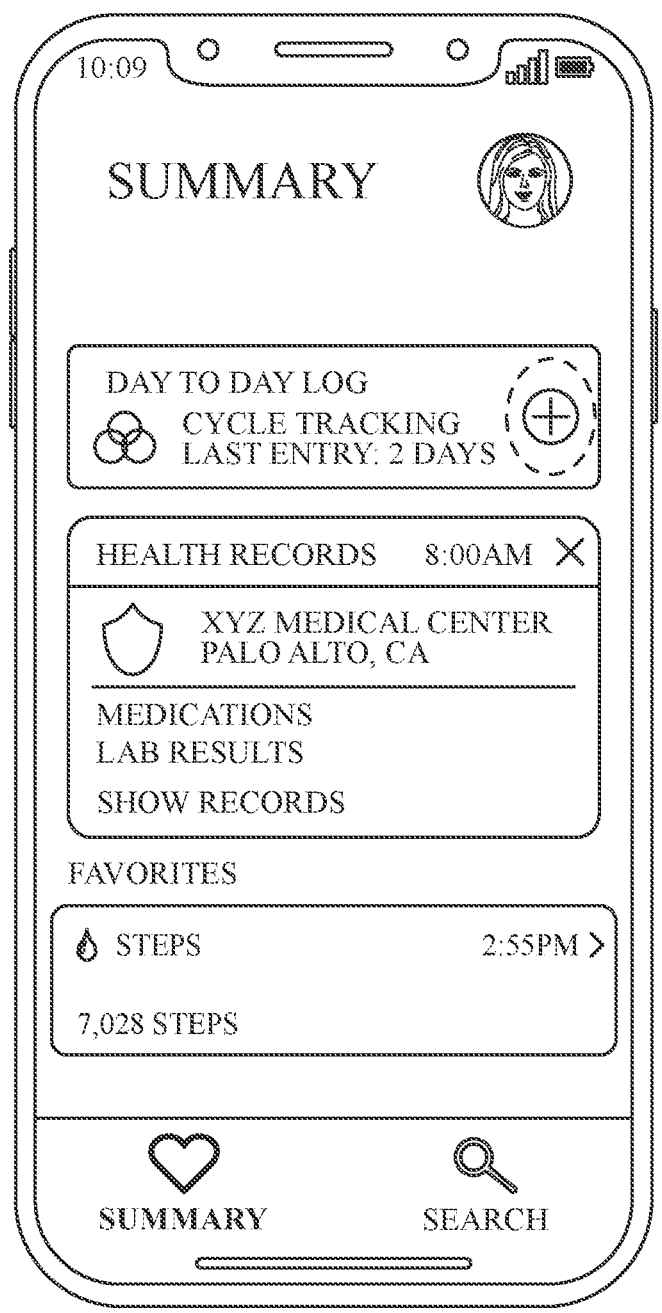
Figure 10W:
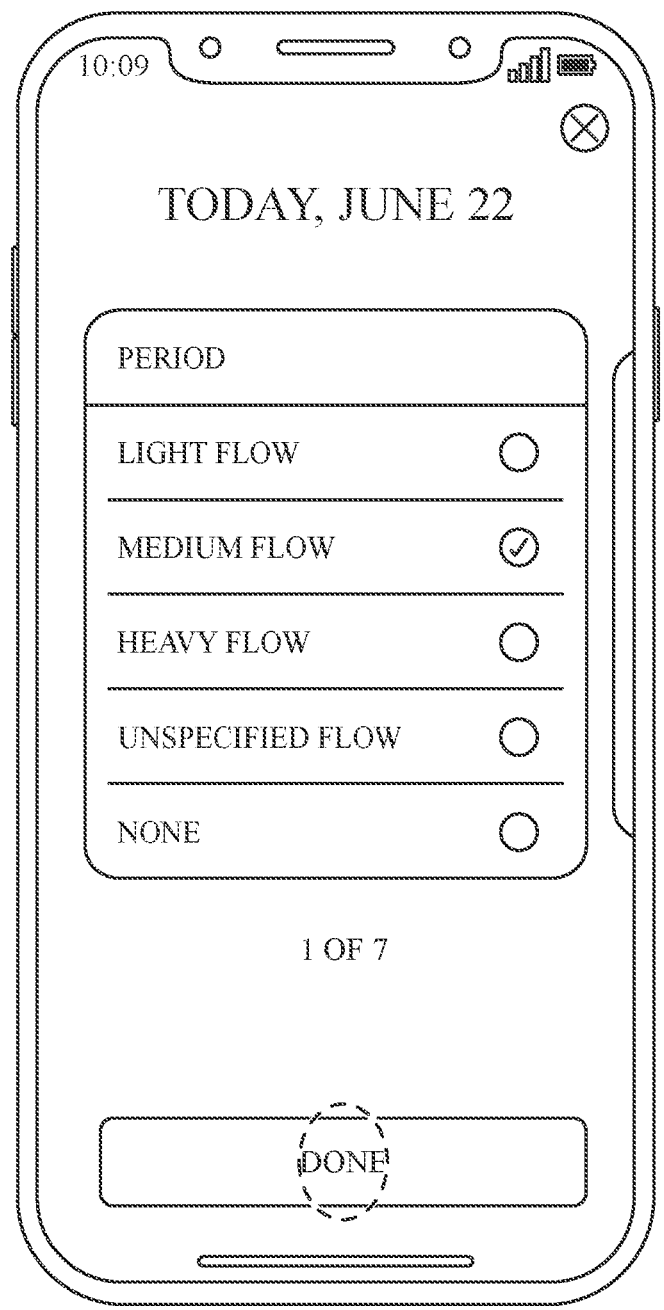
Figure 10X:
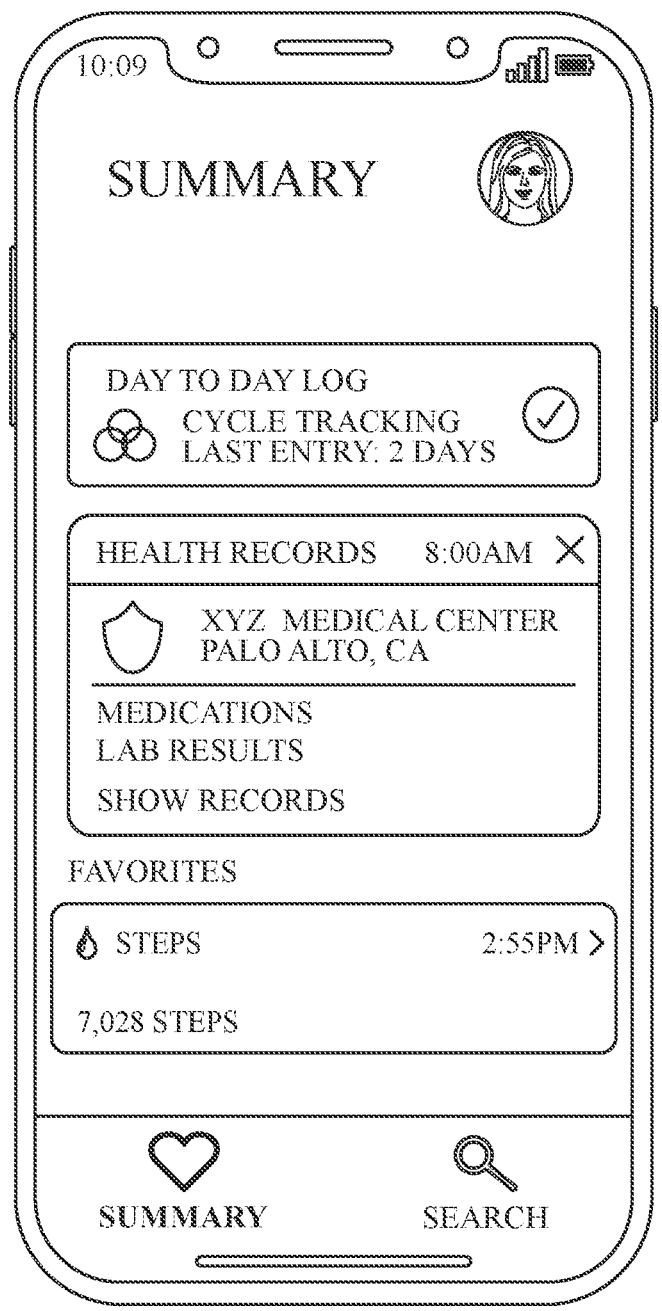
Figure 10Y:
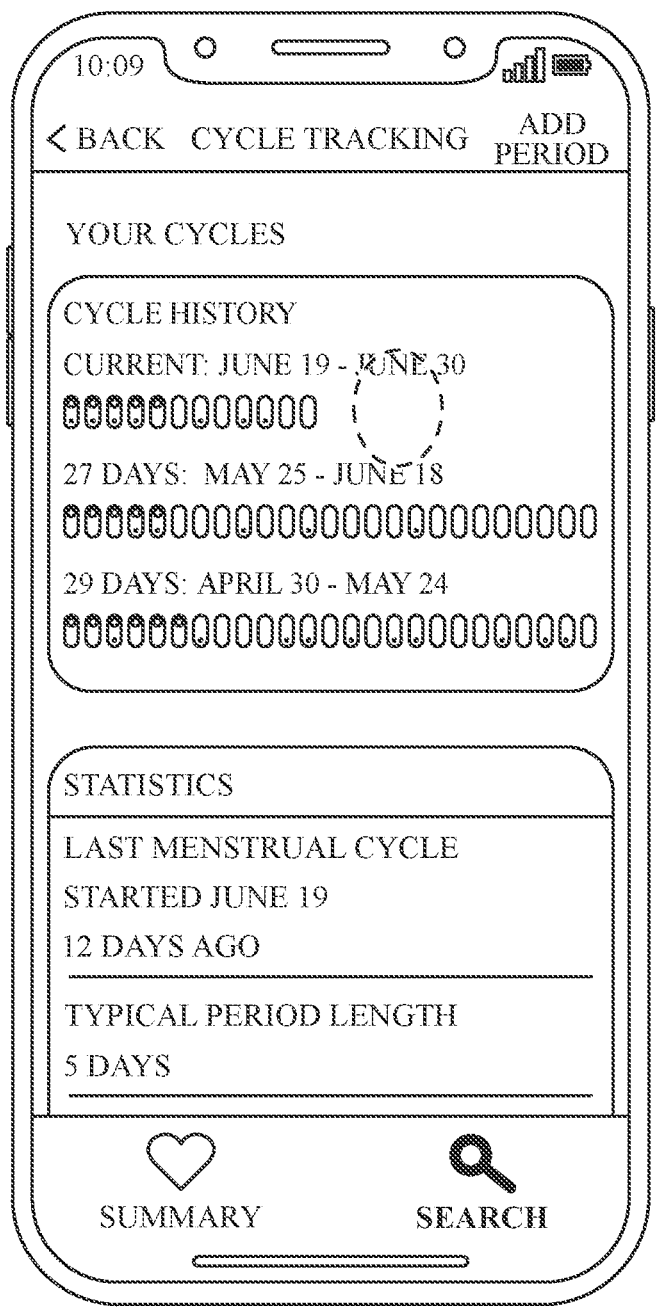
Figure 10Z:
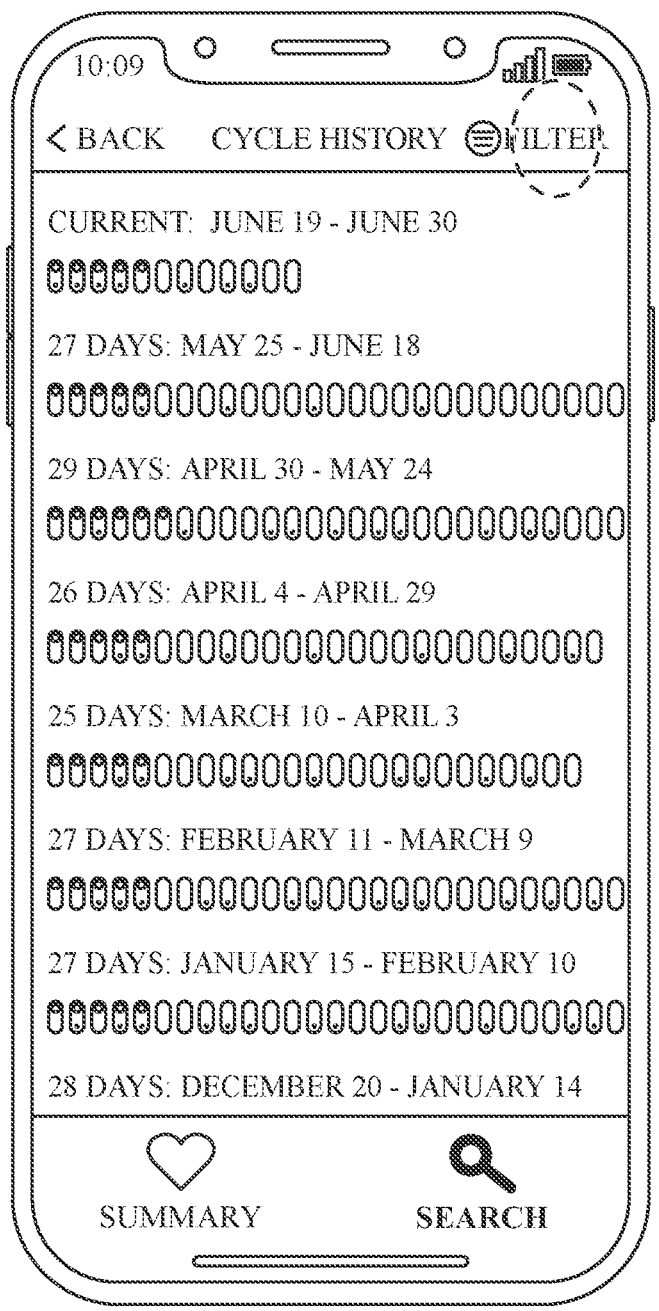
Figure 10A:
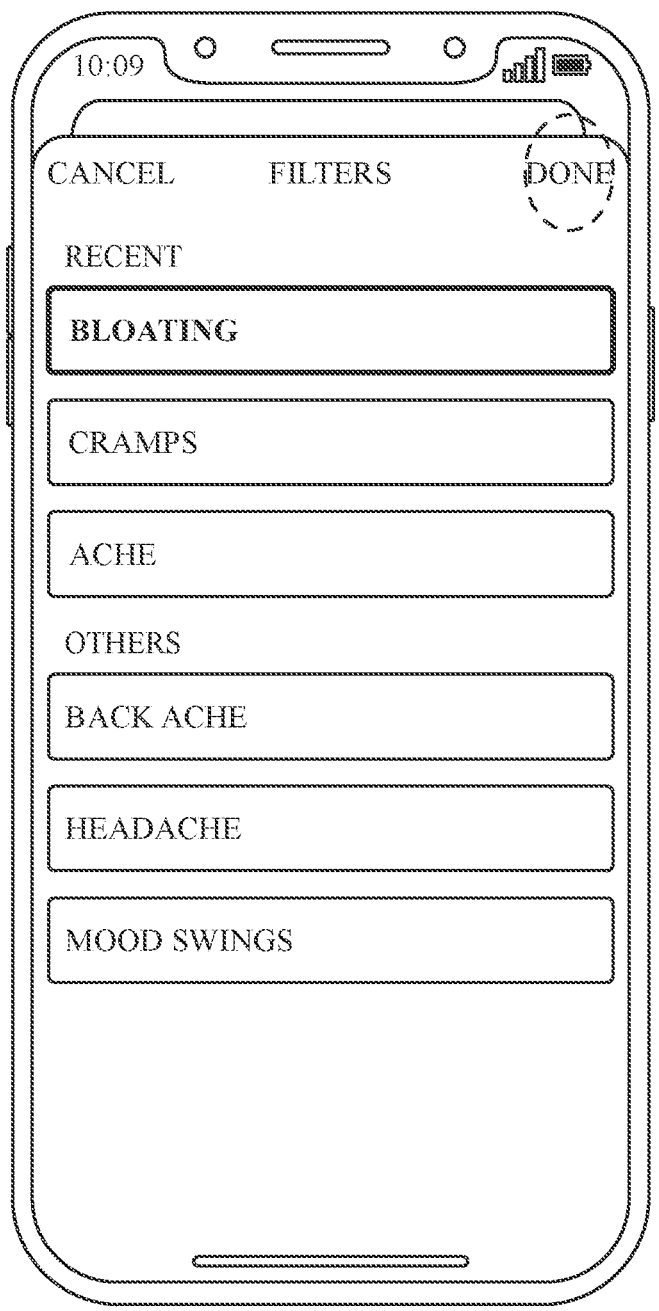
Figure 10A:
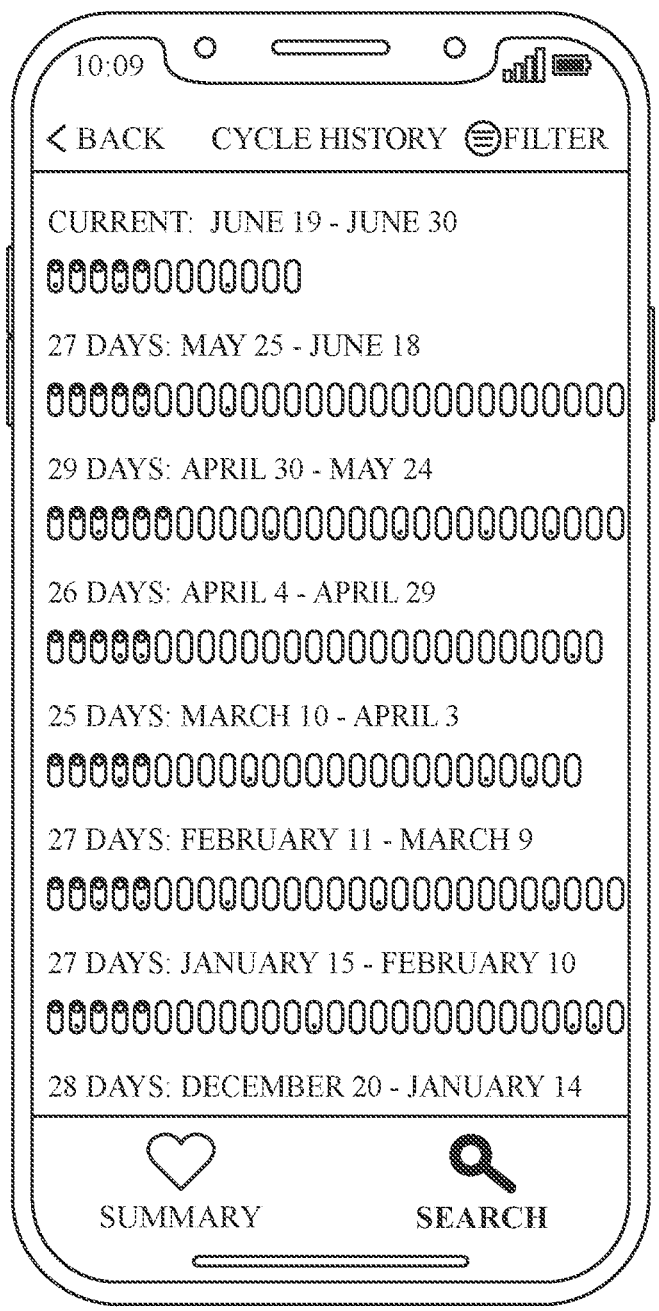
Figure 10A:
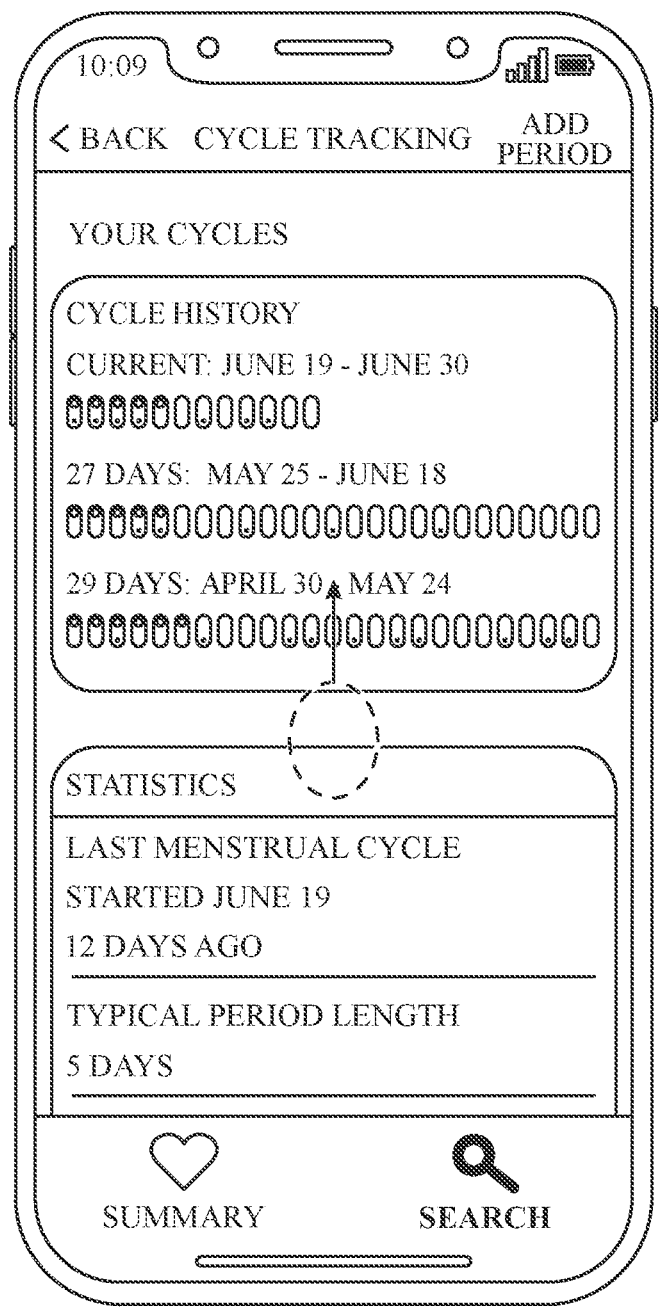
Figure 10A:
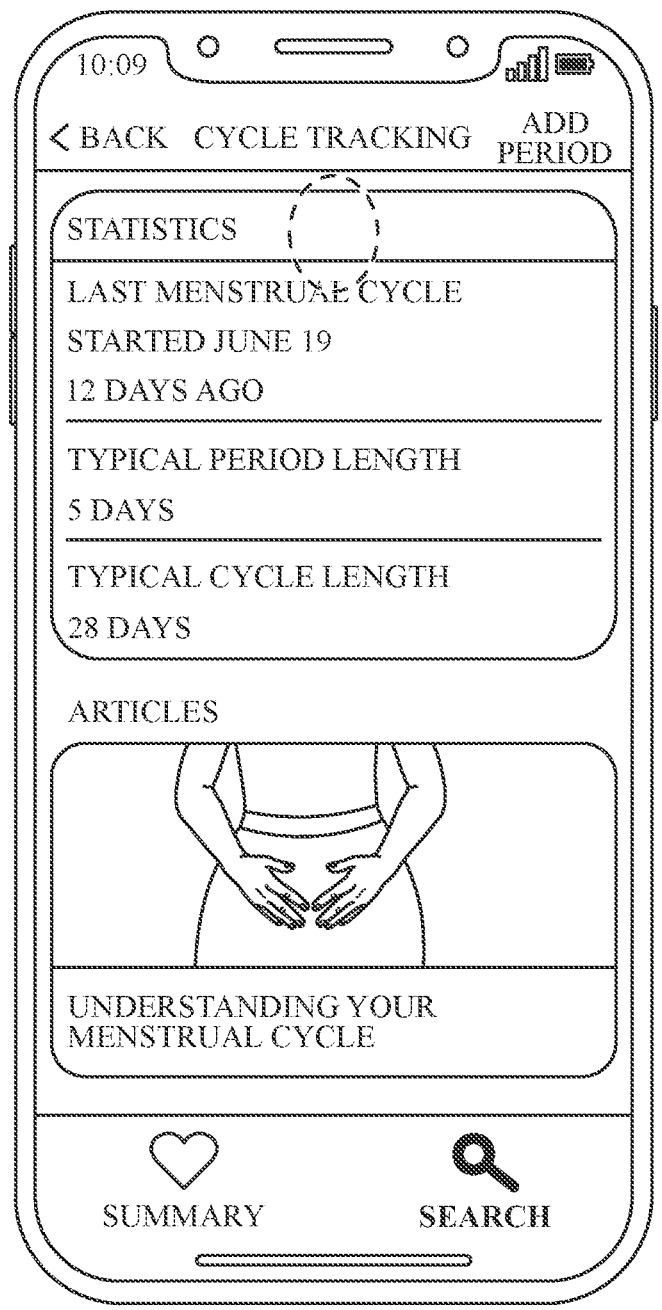
Figure 10A:
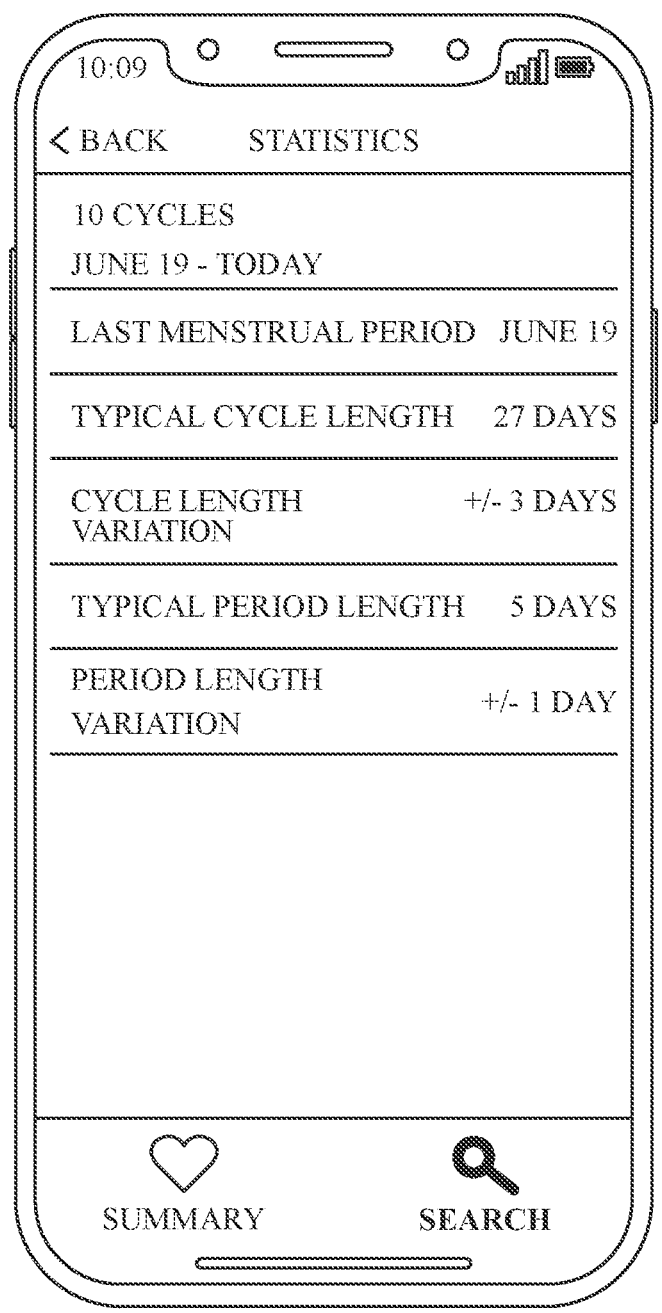
Figure 10A:
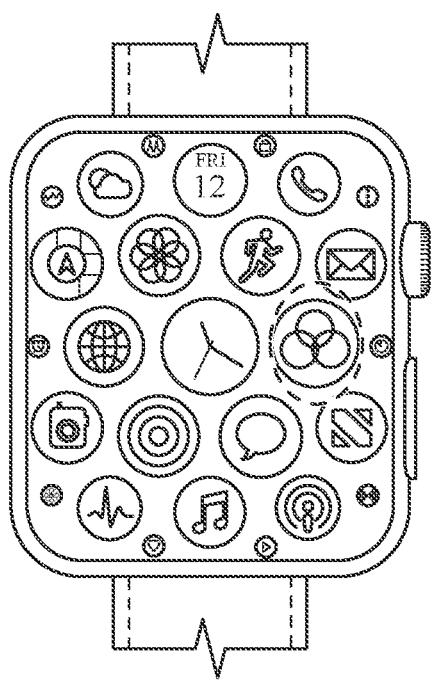
Figure 10A:
Figure 10A:
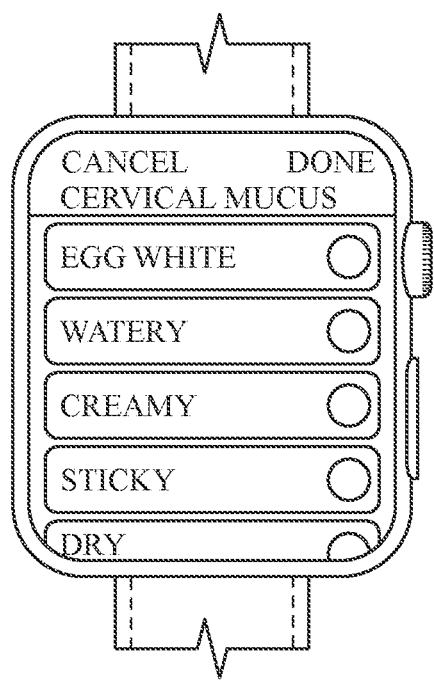
Figure 10A:
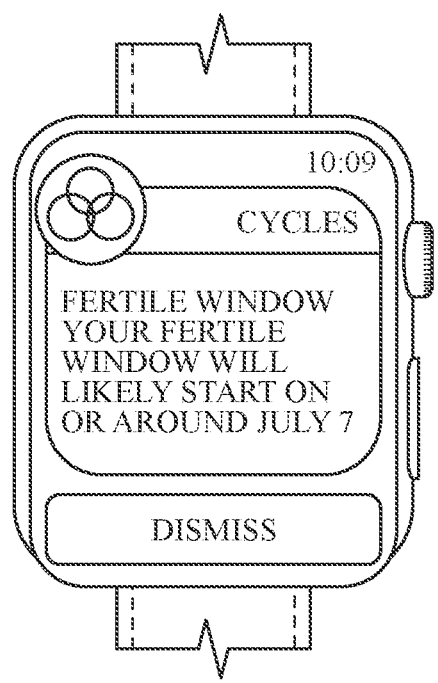

FIGS. 10A-10L and LOAF-10AG depict a flow for setting up the tracking application. The flow would occur before FIGS. 6A and 8A. FIG. 10M depicts an options user interface that would be displayed in response to selection of options 662d in FIG. 6N. FIGS. 10N-10X and 10AK depicts various notifications that can be received on device 800 and corresponding flows from the notifications. As can be seen on the bottom of FIG. 10M, the options user interface includes defined numbers (e.g., period length and cycle length). While these numbers can be initially defined by a user (e.g., using set up flow depicted in FIGS. 10A-10L and LOAF-10AG), in some examples, these numbers are updated as the user logs periods so that the numbers are based on previous periods. FIGS. 10Y-10AE depicts various user interfaces for viewing cycle history and statistics and filtering the cycle history. In some examples, cycle history for periods of time are not shown when there is no logged information for those periods of time. In some examples, when a filter results in no logged information for a period of time, the period of time is not illustrated in the cycle history. In other examples, when a filter results in no logged information for a period of time, the period of time is still illustrated in the cycle history. FIGS. 10AH-10AJ depict various user interfaces for logging sexual activity, ovulation tests, and cervical mucus.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the techniques and their practical applications. Others skilled in the art are thereby enabled to best utilize the techniques and various embodiments with various modifications as are suited to the particular use contemplated.

Although the disclosure and examples have been fully described with reference to the accompanying drawings, it is to be noted that various changes and modifications will become apparent to those skilled in the art. Such changes and modifications are to be understood as being included within the scope of the disclosure and examples as defined by the claims.

As described above, one aspect of the present technology is the gathering and use of data available from various sources to improve cycle tracking and prediction. The present disclosure contemplates that in some instances, this gathered data can include personal information data that uniquely identifies or can be used to contact or locate a specific person. Such personal information data can include demographic data, location-based data, telephone numbers, email addresses, twitter IDs, home addresses, data or records relating to a user's health or level of fitness (e.g., menstrual information, vital signs measurements, medication information, exercise information), date of birth, or any other identifying or personal information.

The present disclosure recognizes that the use of such personal information data, in the present technology, can be used to the benefit of users. For example, the personal information data can be used to track cycles and provide the user with upcoming predicted cycle dates. Accordingly, use of such personal information data enables users to better monitor and track health-related cycles. Further, other uses for personal information data that benefit the user are also contemplated by the present disclosure. For instance, health and fitness data can be used to provide insights into a user's general wellness, or can be used as positive feedback to individuals using technology to pursue wellness goals.

The present disclosure contemplates that the entities responsible for the collection, analysis, disclosure, transfer, storage, or other use of such personal information data will comply with well-established privacy policies and/or privacy practices. In particular, such entities should implement and consistently use privacy policies and practices that are generally recognized as meeting or exceeding industry or governmental requirements for maintaining personal information data private and secure. Such policies should be easily accessible by users, and should be updated as the collection and/or use of data changes. Personal information from users should be collected for legitimate and reasonable uses of the entity and not shared or sold outside of those legitimate uses. Further, such collection/sharing should occur after receiving the informed consent of the users. Additionally, such entities should consider taking any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices. In addition, policies and practices should be adapted for the particular types of personal information data being collected and/or accessed and adapted to applicable laws and standards, including jurisdiction-specific considerations. For instance, in the US, collection of or access to certain health data may be governed by federal and/or state laws, such as the Health Insurance Portability and Accountability Act (HIPAA); whereas health data in other countries may be subject to other regulations and policies and should be handled accordingly. Hence different privacy practices should be maintained for different personal data types in each country.

Despite the foregoing, the present disclosure also contemplates embodiments in which users selectively block the use of, or access to, personal information data. That is, the present disclosure contemplates that hardware and/or software elements can be provided to prevent or block access to such personal information data. For example, in the case cycle tracking, the present technology can be configured to allow users to select to "opt in" or "opt out" of participation in the collection of personal information data during registration for services or anytime thereafter. In another example, users can select not to provide certain health related information. In addition to providing "opt in" and "opt out" options, the present disclosure contemplates providing notifications relating to the access or use of personal information. For instance, a user may be notified upon downloading an app that their personal information data will be accessed and then reminded again just before personal information data is accessed by the app.

Moreover, it is the intent of the present disclosure that personal information data should be managed and handled in a way to minimize risks of unintentional or unauthorized access or use. Risk can be minimized by limiting the collection of data and deleting data once it is no longer needed. In addition, and when applicable, including in certain health related applications, data de-identification can be used to protect a user's privacy. De-identification may be facilitated, when appropriate, by removing specific identifiers (e.g., date of birth, etc.), controlling the amount or specificity of data stored (e.g., collecting location data a city level rather than at an address level), controlling how data is stored (e.g., aggregating data across users), and/or other methods.

Therefore, although the present disclosure broadly covers use of personal information data to implement one or more various disclosed embodiments, the present disclosure also contemplates that the various embodiments can also be implemented without the need for accessing such personal information data. That is, the various embodiments of the present technology are not rendered inoperable due to the lack of all or a portion of such personal information data. For example, certain health-related information can be provided to the user without tracking (or with limited tracking) of the user's health events.

What is claimed is:

1. An electronic device, comprising:
a display;
one or more processors; and
memory storing one or more programs configured to be executed by the one or more processors, the one or more programs including instructions for:
while a cycle tracking interface is not launched:
in accordance with a determination that a first set of criteria is met, the first set of criteria including a criterion that is met when a current date corresponds to a predetermined amount of time before or after a predicted start date of a recurring event, displaying, concurrently and separately, on the display:
a first notification that includes an indication of the predicted start date of the recurring event, and
a first affordance that, when selected, launches the cycle tracking interface for recording a start date for a respective recurrence of the recurring event; and
in accordance with a determination that a second set of criteria is met, the second set of criteria including a criterion that is met when the current date corresponds to a predetermined amount of time after the predicted start date of the recurring event, displaying, concurrently and separately, on the display:

a second notification, and
a second affordance that, when selected, launches the cycle tracking interface for recording an end date for the respective recurrence of the recurring event.

2. The electronic device of claim 1, wherein the recurring event corresponds to a recurring menstrual period.

3. The electronic device of claim 1, the one or more programs further including instructions for:
while displaying a respective notification selected from a group consisting of the first notification and the second notification, receiving a first set of one or more inputs;
in response to receiving the first set of one or more inputs:
in accordance with a determination that the first set of one or more inputs includes a first input corresponding to selection of the first affordance, recording a start date for the respective recurrence of the recurring event; and
in accordance with a determination that the first set of one or more inputs includes a second input corresponding to selection of the second affordance, recording an end date for the respective recurrence of the recurring event.

4. The electronic device of claim 1, wherein:
the predetermined amount of time is after the predicted start date of the recurring event; and
the first notification includes an indication of a suggested start date for the respective recurrence of the recurring event; and
the cycle tracking interface for recording the start date for the respective recurrence of the recurring event includes one or more graphical objects for recording the suggested start date as the start date for the respective recurrence of the recurring event.

5. The electronic device of claim 1, wherein:
the predetermined amount of time is after a predicted end date of the recurring event;
the second notification includes a first indication of a suggested end date for the respective recurrence of the recurring event; and
the cycle tracking interface for recording the end date for the respective recurrence of the recurring event includes one or more graphical objects for recording the suggested end date as the end date for the respective recurrence of the recurring event.

6. The electronic device of claim 1, wherein the first notification is displayed at a predetermined time before the predicted start date of the recurring event.

7. The electronic device of claim 1, wherein the second notification includes a third affordance that, when selected, launches the cycle tracking interface for selecting a start date for the respective recurrence of the recurring event.

8. The electronic device of claim 7, wherein:
the second notification is displayed after the predicted start date of the recurring event; and
the second set of criteria includes a criterion that is met when a start date has not been recorded for a current recurrence of the recurring event.

9. The electronic device of claim 1, the one or more programs further including instructions for:
prior to displaying the second notification, receiving data corresponding to recording of a start date for a current recurrence of the recurring event; and
wherein:
a predicted end date of the recurring event is based on the data corresponding to recording of a start date for the current recurrence of the recurring event; and
the second notification includes a second indication of a suggested end date for the respective recurrence of the recurring event that is based on the predicted end date.

10. The electronic device of claim 1, wherein:
the first set of criteria includes a second criterion that is met when, for the respective recurrence of the recurring event, less than a predetermined number of notifications corresponding to the respective recurrence of the recurring event have been displayed.

11. The electronic device of claim 1, the one or more programs further including instructions for:
while displaying a respective notification selected from a group consisting of the first notification and the second notification, receiving a second set of one or more inputs; and
in response to receiving the second set of one or more inputs, displaying a calendar user interface that includes a first set of one or more graphical indications of dates corresponding the respective recurrence of the recurring event.

12. A non-transitory computer-readable storage medium storing one or more programs configured to be executed by one or more processors of an electronic device with a display, the one or more programs including instructions for:
while a cycle tracking interface is not launched:
in accordance with a determination that a first set of criteria is met, the first set of criteria including a criterion that is met when a current date corresponds to a predetermined amount of time before or after a predicted start date of a recurring event, displaying, concurrently and separately, on the display:
a first notification that includes an indication of the predicted start date of the recurring event, and
a first affordance that, when selected, launches the cycle tracking interface for recording a start date for a respective recurrence of the recurring event; and
in accordance with a determination that a second set of criteria is met, the second set of criteria including a criterion that is met when the current date corresponds to a predetermined amount of time after the predicted start date of the recurring event, displaying, concurrently and separately, on the display:
a second notification, and
a second affordance that, when selected, launches the cycle tracking interface for recording an end date for the respective recurrence of the recurring event.

13. The non-transitory computer-readable storage medium of claim 12, wherein the recurring event corresponds to a recurring menstrual period.

14. The non-transitory computer-readable storage medium of claim 12, the one or more programs further including instructions for:
while displaying a respective notification selected from a group consisting of the first notification and the second notification, receiving a first set of one or more inputs;
in response to receiving the first set of one or more inputs:
in accordance with a determination that the first set of one or more inputs includes a first input corresponding to selection of the first affordance, recording a start date for the respective recurrence of the recurring event; and
in accordance with a determination that the first set of one or more inputs includes a second input corresponding to selection of the second affordance, recording an end date for the respective recurrence of the recurring event.

15. The non-transitory computer-readable storage medium of claim 12, wherein:
the predetermined amount of time is after the predicted start date of the recurring event; and
the first notification includes an indication of a suggested start date for the respective recurrence of the recurring event; and
the cycle tracking interface for recording the start date for the respective recurrence of the recurring event includes one or more graphical objects for recording the suggested start date as the start date for the respective recurrence of the recurring event.

16. The non-transitory computer-readable storage medium of claim 12, wherein:
the predetermined amount of time is after a predicted end date of the recurring event;
the second notification includes a first indication of a suggested end date for the respective recurrence of the recurring event; and
the cycle tracking interface for recording the end date for the respective recurrence of the recurring event includes one or more graphical objects for recording the suggested end date as the end date for the respective recurrence of the recurring event.

17. The non-transitory computer-readable storage medium of claim 12, wherein the first notification is displayed at a predetermined time before the predicted start date of the recurring event.

18. The non-transitory computer-readable storage medium of claim 12, wherein the second notification includes a third affordance that, when selected, launches the cycle tracking interface for selecting a start date for the respective recurrence of the recurring event.

19. The non-transitory computer-readable storage medium of claim 18, wherein:
the second notification is displayed after the predicted start date of the recurring event; and
the second set of criteria includes a criterion that is met when a start date has not been recorded for a current recurrence of the recurring event.

20. The non-transitory computer-readable storage medium of claim 12, the one or more programs further including instructions for:
prior to displaying the second notification, receiving data corresponding to recording of a start date for a current recurrence of the recurring event; and
wherein:
a predicted end date of the recurring event is based on the data corresponding to recording of a start date for the current recurrence of the recurring event; and
the second notification includes a second indication of a suggested end date for the respective recurrence of the recurring event that is based on the predicted end date.

21. The non-transitory computer-readable storage medium of claim 12, wherein:
the first set of criteria includes a second criterion that is met when, for the respective recurrence of the recurring event, less than a predetermined number of notifications corresponding to the respective recurrence of the recurring event have been displayed.

22. The non-transitory computer-readable storage medium of claim 12, the one or more programs further including instructions for:

while displaying a respective notification selected from a group consisting of the first notification and the second notification, receiving a second set of one or more inputs; and
in response to receiving the second set of one or more inputs, displaying a calendar user interface that includes a first set of one or more graphical indications of dates corresponding the respective recurrence of the recurring event.

23. A method, comprising:
at an electronic device including a display:
while a cycle tracking interface is not launched:
in accordance with a determination that a first set of criteria is met, the first set of criteria including a criterion that is met when a current date corresponds to a predetermined amount of time before or after a predicted start date of a recurring event, displaying, concurrently and separately, on the display:
a first notification that includes an indication of the predicted start date of the recurring event,
a first affordance that, when selected, launches the cycle tracking interface for recording a start date for a respective recurrence of the recurring event; and
in accordance with a determination that a second set of criteria is met, the second set of criteria including a criterion that is met when the current date corresponds to a predetermined amount of time after the predicted start date of the recurring event, displaying, concurrently and separately, on the display:
a second notification, and
a second affordance that, when selected, launches the cycle tracking interface for recording an end date for the respective recurrence of the recurring event.

24. The method of claim 23, wherein the recurring event corresponds to a recurring menstrual period.

25. The method of claim 23, further comprising:
while displaying a respective notification selected from a group consisting of the first notification and the second notification, receiving a first set of one or more inputs;
in response to receiving the first set of one or more inputs:
in accordance with a determination that the first set of one or more inputs includes a first input corresponding to selection of the first affordance, recording a start date for the respective recurrence of the recurring event; and
in accordance with a determination that the first set of one or more inputs includes a second input corresponding to selection of the second affordance, recording an end date for the respective recurrence of the recurring event.

26. The method of claim 23, wherein:
the predetermined amount of time is after the predicted start date of the recurring event; and
the first notification includes an indication of a suggested start date for the respective recurrence of the recurring event; and
the cycle tracking interface for recording the start date for the respective recurrence of the recurring event includes one or more graphical objects for recording the suggested start date as the start date for the respective recurrence of the recurring event.

27. The method of claim 23, wherein:
the predetermined amount of time is after a predicted end date of the recurring event;
the second notification includes a first indication of a suggested end date for the respective recurrence of the recurring event; and
the cycle tracking interface for recording the end date for the respective recurrence of the recurring event includes one or more graphical objects for recording the suggested end date as the end date for the respective recurrence of the recurring event.

28. The method of claim 23, wherein the first notification is displayed at a predetermined time before the predicted start date of the recurring event.

29. The method of claim 23, wherein the second notification includes a third affordance that, when selected, launches the cycle tracking interface for selecting a start date for the respective recurrence of the recurring event.

30. The method of claim 29, wherein:
the second notification is displayed after the predicted start date of the recurring event; and
the second set of criteria includes a criterion that is met when a start date has not been recorded for a current recurrence of the recurring event.

31. The method of claim 23, further comprising:
prior to displaying the second notification, receiving data corresponding to recording of a start date for a current recurrence of the recurring event; and
wherein:
a predicted end date of the recurring event is based on the data corresponding to recording of a start date for the current recurrence of the recurring event; and
the second notification includes a second indication of a suggested end date for the respective recurrence of the recurring event that is based on the predicted end date.

32. The method of claim 23, wherein:
the first set of criteria includes a second criterion that is met when, for the respective recurrence of the recurring event, less than a predetermined number of notifications corresponding to the respective recurrence of the recurring event have been displayed.

33. The method of claim 23, further comprising:
while displaying a respective notification selected from a group consisting of the first notification and the second notification, receiving a second set of one or more inputs; and
in response to receiving the second set of one or more inputs, displaying a calendar user interface that includes a first set of one or more graphical indications of dates corresponding the respective recurrence of the recurring event.

* * * * *

UNITED STATES PATENT AND TRADEMARK OFFICE
CERTIFICATE OF CORRECTION

PATENT NO. : 11,209,957 B2  
APPLICATION NO. : 16/586154  
DATED : December 28, 2021  
INVENTOR(S) : Allison Dryer et al.

Page 1 of 1

It is certified that error appears in the above-identified patent and that said Letters Patent is hereby corrected as shown below:

In the Claims

In Column 62, Line 22, Claim 23, after "event," insert -- and --.

Signed and Sealed this  
Twenty-second Day of February, 2022

Drew Hirshfeld  
*Performing the Functions and Duties of the*  
*Under Secretary of Commerce for Intellectual Property and*  
*Director of the United States Patent and Trademark Office*